US008865182B2

(12) United States Patent
Mayall et al.

(10) Patent No.: US 8,865,182 B2
(45) Date of Patent: Oct. 21, 2014

(54) ADENOVIRAL-BASED VECTORS

(75) Inventors: Timothy P. Mayall, Encinitas, CA (US); Jeff Alexander, San Diego, CA (US)

(73) Assignee: Paxvax, Inc., San Diego, CA (US)

( * ) Notice: Subject to any disclaimer, the term of this patent is extended or adjusted under 35 U.S.C. 154(b) by 603 days.

(21) Appl. No.: 12/847,767

(22) Filed: Jul. 30, 2010

(65) Prior Publication Data

US 2011/0123564 A1     May 26, 2011

Related U.S. Application Data

(60) Provisional application No. 61/230,617, filed on Jul. 31, 2009.

(51) Int. Cl.
| | | |
|---|---|---|
| *A61K 39/12* | (2006.01) | |
| *A61K 39/235* | (2006.01) | |
| *A61K 39/295* | (2006.01) | |
| *C12N 15/86* | (2006.01) | |
| *A61K 39/145* | (2006.01) | |
| *A61K 31/713* | (2006.01) | |
| *C12N 7/00* | (2006.01) | |
| *A61K 39/00* | (2006.01) | |

(52) U.S. Cl.
CPC ....... *A61K 31/713* (2013.01); *A61K 2039/5256* (2013.01); *C12N 15/86* (2013.01); *A61K 39/145* (2013.01); *C12N 2760/16134* (2013.01); *C12N 7/00* (2013.01); *C12N 2710/10343* (2013.01)
USPC .................. 424/199.1; 424/201.1; 424/233.1

(58) Field of Classification Search
None
See application file for complete search history.

(56) References Cited

U.S. PATENT DOCUMENTS

| | | | |
|---|---|---|---|
| 4,920,209 | A | 4/1990 | Davis et al. |
| 6,083,716 | A | 7/2000 | Wilson et al. |
| 6,127,525 | A | 10/2000 | Crystal et al. |
| 7,144,712 | B2 | 12/2006 | Milich et al. |
| 7,261,885 | B2 | 8/2007 | Falck-Pedersen et al. |
| 7,879,602 | B2 | 2/2011 | Tucker |
| 2002/0034519 | A1* | 3/2002 | Tikoo et al. ............ 424/233.1 |
| 2003/0157688 | A1 | 8/2003 | Von Seggern et al. |
| 2005/0032045 | A1* | 2/2005 | Tikoo et al. .................. 435/5 |
| 2006/0002893 | A1 | 1/2006 | Vigne et al. |
| 2006/0115456 | A1 | 6/2006 | Peng et al. |
| 2006/0246092 | A1 | 11/2006 | Neirynck et al. |
| 2006/0257371 | A1 | 11/2006 | Hermiston et al. |
| 2006/0292682 | A1* | 12/2006 | Hawkins et al. .......... 435/235.1 |
| 2007/0003576 | A1 | 1/2007 | Gambotto et al. |
| 2007/0207166 | A1 | 9/2007 | Nabel et al. |
| 2007/0249043 | A1 | 10/2007 | Mayall |
| 2008/0112929 | A1 | 5/2008 | Kovesdi et al. |
| 2009/0175897 | A1 | 7/2009 | Tang et al. |
| 2010/0104600 | A1* | 4/2010 | Hammond et al. ........ 424/233.1 |
| 2011/0123564 | A1* | 5/2011 | Mayall et al. ............. 424/199.1 |

FOREIGN PATENT DOCUMENTS

| | | |
|---|---|---|
| CN | 101358202 A | 2/2009 |
| CN | 101404927 A | 4/2009 |
| EP | 0996717 B1 | 12/2005 |
| WO | WO 94/17832 | 8/1994 |
| WO | WO 99/07839 | 2/1999 |
| WO | WO 02/074795 | 9/2002 |
| WO | WO 2007/095056 | 8/2007 |
| WO | WO 2008/010864 | 1/2008 |
| WO | WO 2008/039267 | 4/2008 |
| WO | WO 2008/054540 | 5/2008 |
| WO | WO 2011/014794 | 2/2011 |

OTHER PUBLICATIONS

International Search Report and Written Opinion for International Application No. PCT/US2010/043951, mailed Sep. 21, 2010.
Almanzar, G. et al., "Immunodominant peptides from conserved influenza proteins—a tool for more efficient vaccination in the elderly?" Wiener Medizinische Wochenschrift, 157/5-6:116-121 (2007).
Assarsson, E. et al., "Immunomic analysis of the repertoire of t-cell specificities for influenza A virus in humans," Journal of Virology, 82(24):12241-12251 (2008).
Ballay, A. et al., "In vitro and in vivo synthesis of the hepatitus B virus surface antigen and of the receptor for polymerized human serum albumin from recombinant human adenoviruses," The EMBO Journal. 4(13B):3861-3865 (1985).
Bangari, D. S. et al., "Development of nonhuman adenoviruses as vaccine vectors," Vaccine, 24(7):849-862 (2006).
Barouch, D. H. et al., "Mosaic HIV-1 vaccines expand the breadth and depth of cellular immune responses in rhesus monkeys," Nature Medince, 16(3):319-324 (2010).
Berg, M. et al., "HPV 16 L1 capsid protein expressed from viable adenovirus recombinants elicits neutralizing antibody in mice," Vaccine, 25:3501-3510 (2007).
Berg, M. et al., "Viable adenovirus vaccine prototypes: High-level production of a papillomavirus capsid antigen from the major late transcriptional unit," PNAS, 102(12):4590-4595 (2005).
Berkner, K. L. et al., "Generation of adenovirus by transfection of plasmids," Nucleic Acids Research, 11(17):6003-6020 (1983).
Bhat, B. M. et al., "Adenovirus mutants with splice-enhancing mutations in the E3 complex transcription unit are also defective in E3A RNA 3'-end formation," Journal of Virology, 57(3):1155-1158 (1986).
Bhat, B. M. et al., "Genetic analysis of mRNA synthesis in adenovirus region E3 at different stages of productive infection by RNA-processing mutants," Journal of Virology, 60(1):54-63 (1986).
Boon, A. C. M. et al., "The magnitude and specificity of influenza A virus-specific cytotoxic T-lymphocyte responses in humans is related to HLA-A and -B phenotype," Journal of Virology, 76(2):582-590 (2002).

(Continued)

*Primary Examiner* — Shanon A Foley

(74) *Attorney, Agent, or Firm* — Cooley LLP

(57) ABSTRACT

The present invention provides replication competent adenoviral vectors capable of expressing antigens from infectious pathogens, such as influenza virus. The adenoviral vectors can be used to vaccinate subjects against the infectious pathogens. The adenoviral vectors comprise heterologous sequences encoding the antigens. The heterologous sequences can be inserted into various locations in the adenoviral vectors, including in or near specific E3 deletions and/or integrated into the adenoviral hexon coding region. The adenoviral vectors can be derived from any adenoviral serotype, particularly an Ad4 or Ad7 serotype.

35 Claims, 36 Drawing Sheets

(56) References Cited

OTHER PUBLICATIONS

Brett, S. J. et al., "Selection of the same major T cell determinants of influenza nucleoprotein after vaccination or exposure to infectious virus," The Journal of Immunology, 147(5):1647-1652 (1991).
Brett, S. J. et al., "Human T cell recognition of influenza A nucleoprotein," The Journal of Immunology, 147(3):984-991 (1991).
Carette, J. E. et al., "Replication-dependent transgene expression from a conditionally replicating adenovirus via alternative splicing to a heterologous splice-acceptor site," The Journal of Gene Medicine, 7:1053-1062 (2005).
Crompton, J. et al., "Expression of a foreign epitope on the surface of the adenovirus hexon," Journal of General Virology, 75:133-139 (1994).
De Bouteiller, O. et al., "Recognition of double-stranded RNA by human toll-like receptor 3 and downstream receptor signaling requires multimerization and an acidic pH," The Journal of Biological Chemistry, 280(46):38133-38145 (2005).
De Filette, M. et al., "Improved design and intranasal delivery of an M2e-based human influenza A vaccine," Vaccine, 24(44-46):6597-6601 (2006).
De Filette, M. et al., "An influenza A vaccine based on tetrameric ectodomain of matrix protein 2," The Journal of Biological Chemistry, 283(17):11382-11387 (2008).
De Filette, M. et al., "Universal influenza A vaccine: Optimization of M2-based constructs," Virology, 337:149-161 (2005).
Deng, Y. et al., "MHC affinity, peptide liberation, T cell repertoire, and immunodominance all contribute to the paucity of MHC class I-restricted peptides recognized by antiviral CTL," The Journal of Immunology, 158:1507-1515 (1997).
Dewar, R. L. et al., "Synthesis and processing of human immunodeficiency virus type 1 envelope proteins encoded by a recombinant human adenovirus," Journal of Virology, 63(1):129-136 (1989).
DiBrino, M. et al., "HLA-A1 and HLA-A3 T cell epitopes derived from influenza virus proteins predicted from peptide binding motifs," The Journal of Immunology, 151(11):5930-5935 (1993).
Doytchinova, I. A. et al., "In silico identification of supertypes for class II MHCs," The Journal of Immunology, 174:7085-7095 (2005).
Fiers, W. et al., "A 'universal' human influenza A vaccine," Virus Research, 103:173-176 (2004).
Fiers, W. et al., "Soluble recombinant influenza vaccines," Philos. Trans. R. Soc. Lond. B., 356(1416)1961-1963 (2001).
Forrest, B. D. et al., "Correlation of cellular immune responses with protection against culture-confirmed influenza virus in young children," Clinical and Vaccine Immunology, 15(7):1042-1053 (2008).
Gall, J. et al, "Adenovirus type 5 and 7 capsid chimera: fiber replacement alters receptor tropism without affecting primary immune neutralization epitopes," Journal of Virology, 70(4):2116-2123 (1996).
Gao, W. et al., "Protection of mice and poultry from lethal H5N1 avian influenza virus through adenovirus-based immunization," Journal of Virology, 80(4):1959-1964 (2006).
Gao, X-M et al., "Identification and characterization of T helper epitopes in the nucleoprotein of influenza A virus," The Journal of Immunology, 143(9):3007-3014 (1989).
GenBank Sequence AY594254, Human adenovirus type 4 vaccine strain, complete genome (2005).
Gianfrani, C. et al., "Human memory CTL response specific for influenza A virus is broad and multispecific," Human Immunology, 61:438-452 (2000).
Gotch, F. et al., "Cytotoxic T lymphocytes recognize a fragment of influenza virus matrix protein in association with HLA-A2," Nature, 326:881-882 (1987).
Haj-Ahmad, Y. et al., "Development of helper-independent human adenovirus vector and its use in the transfer of the herpes simplex virus thymidine kinase gene," Journal of Virology, 57(1):267-274 (1986).
Hawkins, L. K. et al., "A 12,500 MW protein is coded by region E3 of adenovirus," Virology, 188:486-494 (1992).
He, T-C et al., "A simplified system for generating recombinant adenoviruses," Proc. Natl. Acad. Sci. USA, 95:2509-2514 (1998).
Hoelscher, M. A. et al., "Development of adenoviral-vector-based pandemic influenza vaccine against antigenically distinct human H5N1 strains in mice," Lancet, 367:475-481 (2006).
Jacobson, E. L. et al., "Interleukin-2 infusions in HIV-infected patients," The New England Journal of Medicine, 336(17):1260-1261 (1997).
Jin, F. et al, "Identification of novel insertion sites in the Ad5 genome that utilize the ad splicing machinery for therapeutic gene expression," Molecular Therapy, 12(6):1052-1063 (2005).
Kalyuzhnly, O. et al., "Adenovirus serotype 5 hexon is critical for virus infection of hepatocytes in vivo," PNAS, 105(14):5483-5488 (2008).
Kozak, M., "An analysis of 5'-noncoding sequences from 699 vertebrate messenger RNAs," Nucleic Acid Res., 15(20):8125-8148 (1987).
Krause, A. et al., "Epitopes expressed in different adenovirus capsid proteins induce different levels of epitope-specific immunity," Journal of Virology, 80(11):5523-5530 (2006).
Lalvani, A. et al., "Rapid effector function in $CD8^+$ memory T cells," J. Exp. Med., 186(6):859-865 (1997).
Li, S. et al., "Recombinant influenza A virus vaccines for the pathogenic human A/Hong Kong/97 (H5N1) viruses," The Journal of Infectious Diseases, 179:1132-1138 (1999).
Li, H. et al., "Standardized, mathematical model-based and validated in vitro analysis of anthrax lethal toxin neutralization," Journal of Immunological Methods, 333(1-2):89-106 (2008).
Lubeck, M. D. et al., "Immunogenicity and efficacy testing in chimpanzees of an oral hepatitis B vaccine based on live recombinant adenovirus," Proc. Natl. Acad. Sci. USA, 86:6763-6767 (1989).
Lunn, D. P. et al., "Antibody responses to DNA vaccination of horses using the influenza virus hemagglutinin gene," Vaccine, 17:2245-2258 (1999).
Malkevitch, N. et al., "A replication competent adenovirus 5 host range mutant-simian immunodeficiency virus (SIV) recombinant priming/subunit protein boosting vaccine regimen induces broad, persistent SIV-specific cellular immunity to dominant and subdominant epitopes in Mamu-A*01 rhesus macaques," The Journal of Immunology, 170(8):4281-4289 (2003).
Man, S. et al., "Definition of a human T cell epitope from influenza A non-structural protein 1 using HLA-A2.1 transgenic mice," International Immunology, 7(4):597-605 (1995).
Marshall, G. S. et al., "An adenovirus recombinant that expresses the human cytomegalovirus major envelope glycoprotein and induces neutralizing antibodies," The Journal of Infectious Diseases, 162:1177-1181 (1990).
Massie, B. et al., "Improved adenovirus vector provides herpes simplex virus ribonucleotide reductase R1 and R2 subunits very efficiently," Biotechnology, 13(6):602-608 (1995).
Matsumoto, M. et al., "Establishment of a monoclonal antibody against human toll-like receptor 3 that blocks double-stranded RNA-mediated signaling," Biochemical and Biophysical Research Communications, 293(5):1364-1369 (2002).
Matthews, Q. L. et al., "Optimization of capsid-incorporated antigens for a novel adenovirus vaccine approach," Virology Journal, 5:98 (2008).
McConnell, M. J. et al., "Characterization of a permissive epitope insertion site in adenovirus hexon," Journal of Virology, 80(11):5361-5370 (2006).
McElhaney, J. E. et al., "T cell responses are better correlates of vaccine protection in the elderly," The Journal of Immunology, 176:6333-6339 (2006).
McMichael, A. J. et al., "Cytotoxic t-cell immunity to influena," New England Journal of Medicine, 309(1):13-17 (1983).
Morin, J. E. et al., "Recombinant adenovirus induces antibody response to hepatitis B virus surface antigen in hamsters," Proc. Natl. Acad. Sci. USA, 84:4626-4630 (1987).
Muhlemann, O. et al., "Enhanced splicing of nonconsensus 3' splice sites late during adenovirus infection," Journal of Virology, 69(11):7324-7327 (1995).
Neirynck, S. et al., "A universal influenza A vaccine based on the extracellular domain of the M2 protein," Nature Medicine, 5(10):1157-1163 (1999).

(56) References Cited

OTHER PUBLICATIONS

NCT00695877 Study, "A phase I randomized, double-blind, placebo controlled dose escalation clinical trial to evaluate the safety and immunogenicity of recombinant adenovirus serotype 5 HVR48 HIV-1 vaccine (Ad5HVR48.ENVA.01) in health, HIV-1 uninfected adults," [online]. Last updated on Oct. 30, 2008. National Institute of Allergy and Infectious Diseases (NIAID). [Retrieved on Dec. 9, 2008]. URL: http://www.clinicaltrials.gov/ct2/show/record/NCT00695877?term=adenovirus+AND+hiv . . . >.
Purkayastha, A. et al., "Genomic and bioinformatics analysis of HAdV-4, a human adenovirus causing acute respiratory disease: implications for gene therapy and vaccine vector development," Journal of Virology, 79(4):2559-2572 (2005).
Roberts, D. M. et al., "Hexon-chimaeric adenovirus serotype 5 vectors circumvent pre-existing anti-vector immunity," Nature, 441:239-243 (2006).
Robinson, M. et al., "Comparison of the E3 and L3 regions for arming oncolytic adenoviruses to achieve a high level of tumor-specific transgene expression," Cancer Gene Therapy, 15:9-17 (2008).
Roti, M. et al., "Healthy human subjects have CD4$^+$ T cells directed against H5N1 influenza virus," The Journal of Immunology, 180:1758-1768 (2008).
Saito, I. et al., "Construction of nondefective adenovirus type 5 bearing a 2.8-kilobase hepatitis B virus DNA near the right end of its genome," Journal of Virology, 54(3):711-719 (1985).
Schoggins, J. W. et al., "Subgroup B and F fiber chimeras eliminate normal adenovirus type 5 vector transduction in vitro and in vivo," Journal of Virology, 77(2):1039-1048 (2003).
Shi, C. et al., "Cloning and sequencing of adenovirus type 7 vaccine strain 76.5-87 mu fragment," Zhonghua Shi Yan He Lin Chuang Bing Du Xue Za Zhi, 12(3):201-206 (1998) Abstract.
Sidney, J. et al., "HLA class I supertypes: a revised and updated classification," BMC Immunology, 9:1-15 (2008).
Skog, J., "The quest for new improved adenovirus gene therapy vectors against glioma tumours," Department of Clinical Microbiology, Virology, Faculty of Medicine, Umeå University, Sweden, pp. 1-80 (2005).
Smith, K. A., "Rational interleukin-2 therapy," Cancer J. Sci. Am., 3(1):S137-S140 (1997).
Smith, T. J. et al., "Experimental respiratory infection with type 4 adenovirus vaccine in volunteers: clinical and immunological responses," The Journal of Infectious Diseases, 122(4):239-248 (1970).
Sonoguchi, T. et al., "Cross-subtype protection in humans during sequential, overlapping, and/or concurrent epidemics caused by H3N2 and H1N1 influenza viruses," The Journal of Infectious Diseases, 151(1):81-88 (1985).
Southwood, S. et al., "Several common HLA-DR types share largely overlapping peptide binding repertoires," The Journal of Immunology, 160:3363-3373 (1998).
Tang, M. et al., "Recombinant adenovirus encoding the HA gene from swine H3N2 influenza virus partially protects mice from challenge with heterologous virus: A/HK/1/68 (H3N2)," Archives of Virology, 147:2125-2141 (2002).
Top, F. H., Jr. et al., "Immunization with live types 7 and 4 adenovirus vaccines. I. Safety, infectivity, antigenicity, and potency of adenovirus type 7 vaccine in humans," Journal of Infectious Diseases, 124(2):148-154 (1971).
Toth, K. et al., "Adenovirus immunoregulatory E3 proteins prolong transplants of human cells in immunocompetent mice," Virus Research, 108:149-159 (2005).

Vigant, F. et al., "Substitution of hexon hypervariable region 5 of adenovirus serotype 5 abrogates blood factor binding and limits gene transfer to liver," Molecular Therapy, 16(8):1474-1480 (2008).
Vogels, R. et al., "Replication-deficient human adenovirus type 35 vectors for gene transfer and vaccination: efficient human cell infection and bypass of preexisting adenovirus immunity," Journal of Virology, 77(15):8263-8271 (2003).
Waddington, S. N. et al., "Adenovirus serotype 5 hexon mediates liver gene transfer," Cell, 132:397-409 (2008).
Worgall, S. et al., "Protective immunity to *Pseudomonas aeruginosa* induced with a capsid-modified adenovirus expressing *P. aeruginosa* OprF," Journal of Virology, 81(24):13801-13808 (2007).
Worgall, S. et al., "Protection against *P. aeruginosa* with an adenovirus vector containing an OprF epitope in the capsid," The Journal of Clinical Investigation, 115(5):1281-1289 (2005).
Wu, H. et al., "Identification of sites in adenovirus hexon for foreign peptide incorporation," Journal of Virology, 79(6):3382-3390 (2005).
Yang, J. et al., "Multiplex mapping of CD4 T cell epitopes using class II tetramers," Clinical Immunology, pp. 1-12 (2006).
Zebedee, S. L. et al., "Influenza A virus M2 protein: monoclonal antibody restriction of virus growth and detection of M2 in virions," Journal of Virology, 62(8):2762-2772 (1988).
Zhu, M. et al., "Linked tumor-selective virus replication and transgene expression from E3-containing oncolytic adenvirues," Journal of Virology, 79(9):5455-5465 (2005).
Chengalvala et al., "Immunogenicity of High Expression Adenovirus-Hepatitis B Virus Recombinant Vaccines in Dogs," Journal of General Virology, vol. 75: 125-131, 1994.
Patterson et al., "Insertion of HIV-1 Genes into Ad4ΔE3 Vector Abrogates Increased Pathogenesis in Cotton Rats Due to E3 Deletion," Virology, vol. 292:107-113, 2002.
Vernon et al., "Ultrastructural Characterization of Human Immunodeficiency Virus Type 1 Gag-Containing Particles Assembled in a Recombinant Adenovirus Vector System," Journal of General Virology, vol. 72: 1243-1251, 1991.
Chanda et al., "High Level of Expression of the Envelope Glycoproteins of Human Immunodeficiency Virus Type 1 in Presence of Rev Gene Using Helper-Independent Adenovirus Type 7 Recombinants," Virology, vol. 175: 535-547, 1990.
Mason et al., "Adenovirus Vaccine Vectors Expressing Hepatitis B Surface Antigen: Importance of Regulatory Elements in the Adenovirus Major Late Intron," Virology, vol. 177: 452-461, 1990.
Jacobs et al., "Characterization and Manipulation of the Human Adenovirus 4 genome," Journal of General Virology, vol. 85: 3361-3366, 2004.
Horton et al., "A Protein Serologically and Functionally Related to the Group C E3 14,700-Kilodalton Protein Is Found in Multiple Adenovirus Serotypes," Journal of Virology, vol. 64: 1250-1255, 1990.
Chengalvala et al., "Adenovirus vectors for gene expression," Current Opinion in Biotechnology, vol. 2: 718-722, 1991.
Rutz, European Supplementary Search Report for EP Application No. 10805122.8, mailed May 17, 2013.
Johnson et al., "Delivery of avian cytokines by adenovirus vectors," Dev Comp Immunol, vol. 24: 343-354, 2000.
Johnson et al., "A recombinant fowl adenovirus expressing the S1 gene of infectious bronchitis virus protects against challenge with infectious bronchitis virus," Vaccine, vol. 21: 2730-2736, 2003.
Examination Report for Chinese Application No. 201080044581.9, issued May 14, 2014.

* cited by examiner

Epitope Sequences

H5 M2e

L G S   S L L T E V E T P T R N E W E C R C S D S S D   L G S   (1)
CTGGGCAGC AGCCTGCTGACCGAGGTGGAGACCCCCACCCGGAACGAGTGGGAGTGCCGCTGCAGCGACAGCAGCGACGAC CTGGGCAGC (2)
CTGGGCAGC AGTTTGTTAACCGAAGTCGAGACTCCAACCAGAAATGAATGGGAATGCAGATGCAGCGATTCAAGTGAT CTGGGCAGC

H7 M2e

L G S   S L L T E V E T P T T K G N E C K C S D S S D   L G S
CTGGGCAGC AGCCTGCTGACCGAGGTGGAGACTCCAACCACCAAGGGCAATGAGTGCAAGTGCAGTGACAGCAGCGAC CTGGGCAGC

H9 M2e

L G S   S L L T E V E T L T R K G N E R C S G S S D   L G S
CTGGGCAGC AGCCTGCTGACCGAAGTGGAGACCCTGACCCGCAAGGGCAATGAACGCTGCAGCGGCAGCAGCGAC CTGGGCAGC

Human M2e

L G S   S L L T E V E T P I R N E W G C R C N D S S D   L G S
CTGGGCAGC AGCCTGCTGACCGAAGTGGAGACCCCTATCCGCAACGAGTGGGGCTGCCGTTGTAACGACAGCAGCGAC CTGGGCAGC

NP

L G S   L E L R S R Y W A I R T R S G G N T Q Q R A S   L G S
CTGGGCAGC CTTGAACTGAGAAGCAGATACTGGGCTATAAGAACCAGAAGCGGAAGTAACACCCAGCAGAGGGCATCT CTGGGCAGC

Matrix CTL 58-66

L G R   G A A A   G I L G F V F T L   N A A   L G S
CTGGGCAGG GGCGCGGCGGCC GGGATTTTGGGATTTGTATTCACGCTG AACGCGGCC CTGGGCAGC

Legend:
Each peptide is flanked by LGS as a flexible spacer to improve stability
The matrix CTL is also flanked directly by sequences known to improve the processing of CTL peptides

FIGURE 12

Purified PXVX0103 and PXVX0116 Induce HA-Specific Antibody Responses in Mice

Study 3 - H5 ELISA and HAI Endpoints

FIGURE 14

ADENOVIRAL-BASED VECTORS

CROSS-REFERENCE TO RELATED APPLICATIONS

This application claims the benefit of U.S. Provisional Application No. 61/230,617, filed Jul. 31, 2009, which is herein incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PAXV_004_01US_SeqList_ST25.txt, date recorded: Jul. 30, 2010, file size 62 kilobytes).

BACKGROUND OF THE INVENTION

Adenoviruses have been widely studied as infectious agents, as a subject for basic research, and for their potential use in gene therapy and vaccines. Forty-nine human adenoviral serotypes have been identified and they are categorized into six subgenera (A through F) based on nucleic acid comparisons, fiber protein characteristics, and biological properties. For example, group A includes serotypes 12 and 31, group B includes serotypes 3 and 7, group C includes serotypes 2 and 5, group D includes serotypes 8 and 30, group E includes serotype 4, and group F includes serotypes 40 and 41.

In terms of general structure, all adenoviruses examined to date are nonenveloped, regular icosahedrons of about 80 nanometers in diameter. Adenoviruses contain linear, double-stranded DNA that is complexed with core proteins and surrounded by the adenoviral capsid. Individual virions contain about 11 different proteins designated by Roman numerals (II-XII), in order of their decreasing size on SDS gels.

The capsid is composed of seven structural proteins: II (hexon), III (penton), IIIa, IV (fiber), VI, VII, and IX. The capsid comprises 252 capsomeres, of which 240 are hexon capsomeres and 12 are penton capsomeres. Hexon capsomeres, which are trimers of the hexon protein, make up about 75% of the protein of the capsid. Penton capsomeres, which are pentamers of the penton protein, are situated at each of the 12 vertices of the virion. Each penton capsomer is bound to six adjacent hexon capsomeres and a fiber. The fiber, which is usually a trimer of the fiber protein, projects from the penton capsomer. The hexon protein and, to a lesser extent, the fiber protein comprise the main antigenic determinants of an adenovirus and also determine serotype specificity.

Researchers have examined and compared the structure of the capsid proteins of different adenoviral serotypes, and in particular hexon proteins, in an effort to define the regions of the proteins against which neutralizing antibodies are elicited. The predominant regions in hexon protein against which neutralizing antibodies are directed appear to be in loops 1 and 2 (i.e., LI or l1, and LII or l2, respectively), which project outward from the base of the hexon capsomere. Analysis of loops 1 and 2 from different adenovirus hexon proteins has revealed the presence of seven discrete hypervariable regions (HVR1 to HVR7) corresponding to locations where the hexon proteins differ considerably between serotypes.

The core of an adenoviral virion contains the linear double-stranded DNA genome and associated proteins V, VII, X (mu), IVa2, and terminal protein (TP). The genome organization of different adenoviruses is conserved and has been proposed to have a timing function, wherein the ends of the genome are transcribed first (the immediate early genes E1 and E4 are located at opposite ends of the linear genome). Early transcription of E1 and E4 leads to the opening of the central region of the genome, allowing transcription of the central region.

Adenoviral genomes typically comprise eight RNA polymerase II transcriptional units: five early units, E1A, E1B, E2A-E2B, E3, and E4; two delayed early units, IX and IVa2; and the Major Late transcriptional unit. The Major Late transcriptional unit is further subdivided into L1-L5 regions based upon the use of alternative splicing sites. The transcriptional units often express proteins of similar function. For example, the E1A unit codes for two proteins responsible for activation of transcription and induction of S-phase upon cellular infection; the E1B transcription unit encodes two proteins that inhibit cellular apoptosis; the E3 transcriptional unit is involved in evasion of the immune response; and the Major Late transcriptional unit encodes structural proteins necessary for assembly of the capsid.

For the purpose of gene therapy and vaccination, recombinant adenoviral vectors have been designed to encode and express heterologous genes and antigens. The Ad2 and Ad5 serotypes have been used most extensively in this context. Heterologous sequences have been inserted into the adenoviral genomes, including in the early transcriptional units and in the coding regions of various structural proteins, such as hexon, penton, and fiber. In many cases, deletions in the adenoviral genome (e.g., in the E1 regions) have been used to create replication-defective adenoviral vectors, which have generally been considered safer for administration to human subjects. Despite such extensive research and development, there remains a need in the art for new recombinant adenoviral vectors suitable, for example, as vaccines for infectious diseases.

SUMMARY OF THE INVENTION

The present invention is directed to recombinant adenoviral vectors that find use as effective vaccines. The invention is based, in part, on the development of novel recombinant adenoviral vectors that express heterologous sequences at high levels. The invention is also based, in part, on the development of novel recombinant adenoviral vectors designed to improve host immune response and circumvent pre-existing neutralizing antibodies. The invention is also based, in part, on the development of novel recombinant adenoviral vectors to be used as antigen-specific and/or universal influenza vaccines.

Accordingly, in one aspect, the invention provides a vaccine comprising an adenoviral vector comprising a first heterologous sequence, wherein the adenoviral vector is replication competent and has a partial E3 deletion. In certain embodiments, the adenoviral vector is derived from an Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, or Ad50 adenovirus. In other embodiments, the adenoviral vector is derived from a chimpanzee adenovirus, for instance, Ad C1, Ad C3, Ad C6, Ad C7, or Ad68. In certain embodiments, the first heterologous sequence is integrated into a location containing the partial E3 deletion. In certain embodiments, the first heterologous sequence is under the control of or operably linked to an adenoviral transcriptional and/or translational control sequence. For example, the first heterologous sequence can be under the control of or operably linked to an adenoviral Major Late Promoter (MLP), an adenoviral tripartite leader (TPL) sequence, an adenoviral splice acceptor sequence, and/or an adenoviral poly-adenylation signal sequence. In certain embodiments, the first heterologous sequence comprises and/or is under the control of an non-adenoviral transcriptional and/or translational control sequence, such as an enhancer, promoter, intron sequence, and/or leader sequence from cytomegalovirus (CMV), rous sarcoma virus (RSV), or simian virus 40 (SV40), or any combination of such elements. In certain embodiments, the first heterologous sequence is modified to increase expression. For example, the first heterologous sequence can be codon optimized and/or modified to include a consensus Kozak sequence. In certain embodiments, the first heterologous sequence encodes an immunogenic polypeptide from an infectious pathogen, such as influenza virus, human papilloma virus (HPV), human immunodeficiency virus (HIV), *Bacillus, Shigella, Mycobacterium, Plasmodium*, etc. In certain embodiments, the first heterologous sequence encodes at least two separate polypeptides and/or a multimer of immunogenic epitopes from an infectious pathogen.

In another aspect, the invention provides a vaccine comprising an adenoviral vector comprising a first heterologous sequence, wherein the adenoviral vector is replication competent and has a full E3 deletion. In certain embodiments, the adenoviral vector is derived from an Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, or Ad50 adenovirus. In other embodiments, the adenoviral vector is derived from a chimpanzee adenovirus, for instance, Ad C1, Ad C3, Ad C6, Ad C7, or Ad68. In certain embodiments, the first heterologous sequence is integrated into a location containing the full E3 deletion. In certain embodiments, the first heterologous sequence is under the control of or operably linked to an adenoviral transcriptional and/or translational control sequence. For example, the first heterologous sequence can be under the control of or operably linked to an adenoviral Major Late Promoter (MLP), an adenoviral tripartite leader (TPL) sequence, an adenoviral splice acceptor sequence, and/or an adenoviral poly-adenylation signal sequence. In certain embodiments, the first heterologous sequence comprises and/or is under the control of a non-adenoviral transcriptional and/or translational control sequence, such as an enhancer, promoter, intron sequence, and/or leader sequence from cytomegalovirus (CMV), rous sarcoma virus (RSV), or simian virus 40 (SV40), or any combination of such elements. In certain embodiments, the first heterologous sequence is modified to increase expression. For example, the first heterologous sequence can be codon optimized and/or modified to include a consensus Kozak sequence. In certain embodiments, the first heterologous sequence encodes an immunogenic polypeptide from an infectious pathogen, such as influenza virus, human papilloma virus (HPV), human immunodeficiency virus (HIV), *Bacillus, Shigella, Mycobacterium, Plasmodium*, etc. In certain embodiments, the first heterologous sequence encodes at least two separate polypeptides and/or a multimer of immunogenic epitopes from an infectious pathogen.

In another aspect, the invention provides a vaccine comprising an adenoviral vector comprising a first heterologous sequence, wherein said adenoviral vector is replication competent, and wherein expression of the first heterologous sequence is under the control of an adenoviral transcriptional and/or translation control sequence. In certain embodiments, the adenoviral vector is derived from an Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, or Ad50 adenovirus. In other embodiments, the adenoviral vector is derived from a chimpanzee adenovirus, for instance, Ad C1, Ad C3, Ad C6, Ad C7, or Ad68. In certain embodiments, the adenovirus has a full or partial E3 deletion. In certain embodiments, the first heterologous sequence is integrated into a location containing a full or partial E3 deletion. In certain embodiments, the first heterologous sequence is under the control of or operably linked to an adenoviral MLP. In certain embodiments, the first heterologous sequence is under the control of or operably linked to an adenoviral MLP and an adenoviral TPL sequence. In certain embodiments, the first heterologous sequence is further under the control of or operably linked to an adenoviral splice acceptor sequence and/or an adenoviral poly-adenylation signal sequence. In certain embodiments, the first heterologous sequence is modified to increase expression. For example, the first heterologous sequence can be codon optimized and/or modified to include a consensus Kozak sequence. In certain embodiments, the first heterologous sequence encodes an immunogenic polypeptide from an infectious pathogen, such as influenza virus, human papilloma virus (HPV), human immunodeficiency virus (HIV), Dengue Fever virus, *Streptococcus, Bacillus, Shigella, Mycobacterium, Plasmodium*, etc. In certain embodiments, the first heterologous sequence encodes at least two separate polypeptides or a multimer of immunogenic epitopes from an infectious pathogen.

In another aspect, the invention provides a vaccine comprising an adenoviral vector comprising a first heterologous sequence and a second heterologous sequence, wherein the second heterologous sequence is integrated into an adenoviral hexon region, wherein the first heterologous sequence is integrated into an adenoviral non-hexon region, and wherein the adenoviral vector is replication competent. In certain embodiments, the adenoviral vector is derived from an Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, or Ad50 adenovirus. In other embodiments, the adenoviral vector is derived from a chimpanzee adenovirus, for instance, Ad C1, Ad C3, Ad C6, Ad C7, or Ad68. In certain embodiments, the adenovirus has a full or partial E3 deletion. In certain embodiments, the first heterologous sequence is integrated into a location containing a full or partial E3 deletion. In certain embodiments, the first heterologous sequence is under the control of or operably linked to an adenoviral transcriptional and/or translational control sequence. For example, the first heterologous sequence can be under the control of or operably linked to an adenoviral Major Late Promoter (MLP), an adenoviral tripartite leader (TPL) sequence, an adenoviral splice acceptor sequence, and/or an adenoviral poly-adenylation signal sequence.

In certain embodiments, the second heterologous sequence is integrated into one or more hypervariable regions of the hexon region. For example, the second heterologous sequence can be integrated into a hexon HVR1, HVR2, HVR4, or HVR5 sequence, or a combination thereof. In certain embodiments, the second heterologous sequence encodes a portion of a viral membrane protein (e.g., an integral membrane protein or peripheral membrane protein). For example, the second heterologous sequence can encode an extracellular portion of a conserved viral membrane protein. In certain embodiments, the second heterologous sequence encodes a portion of an influenza M2 protein, an influenza matrix protein, an influenza NP protein, or a hexon hypervariable region from an adenovirus having a different serotype. In certain embodiments, the second heterologous sequence encodes two or more copies of a protein, such as a viral membrane protein, or a fragment thereof.

In certain embodiments, the adenoviral vector comprises one or more additional heterologous sequences, wherein each additional heterologous sequence is integrated into a hexon region and is different from the second heterologous sequence. For example, the additional heterologous sequences can be all of the hypervariable regions from an adenovirus having a different serotype.

In another aspect, the invention provides a vaccine comprising an adenoviral vector comprising a second heterologous sequence, wherein the second heterologous sequence encodes a region of a membrane protein of a virus and is integrated into a hexon region of the adenoviral vector. In certain embodiments, the adenoviral vector is derived from an Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, or Ad50 adenovirus. In other embodiments, the adenoviral vector is derived from a chimpanzee adenovirus, for instance, Ad C1, Ad C3, Ad C6, Ad C7, or Ad68. In certain embodiments, the second heterologous sequence is adjacent to an endogenous adenoviral sequence. In other embodiments, the second heterologous sequence is flanked by a spacer. In certain embodiments, the spacer encodes the peptide sequence "LGS." In certain embodiments, the second heterologous sequence is from an influenza virus. For example, the second heterologous sequence can encode an influenza M2, influenza matrix, or influenza NP polypeptide, or fragment thereof.

In yet another aspect, the invention provides methods of vaccination using a recombinant adenoviral vector-based vaccine described herein. In certain embodiments, the vaccination is for influenza, human papilloma virus (HPV), human immunodeficiency virus (HIV), Dengue Fever virus, *Streptococcus, Bacillus, Shigella, Mycobacterium*, or *Plasmodium*.

BRIEF DESCRIPTION OF THE DRAWINGS

FIG. 12 depicts various influenza epitope sequences that can be used to replace hexon HVR sequences. H5 M2e (SEQ ID NOs: 339-341), H7 M2e (SEQ ID NOs: 342-343); H9 M2e (SEQ ID NOs: 344-345); Human M2e (SEQ ID NOs: 346-347); NP (SEQ ID NOs: 348-349); Matrix CTL 58-66 (SEQ ID NOs: 350-351).

FIG. 14 depicts HA-specific antibody responses in mice induced by PXVX0103 and PXVX0116 recombinant adenoviruses.

DETAILED DESCRIPTION

Figure 1:
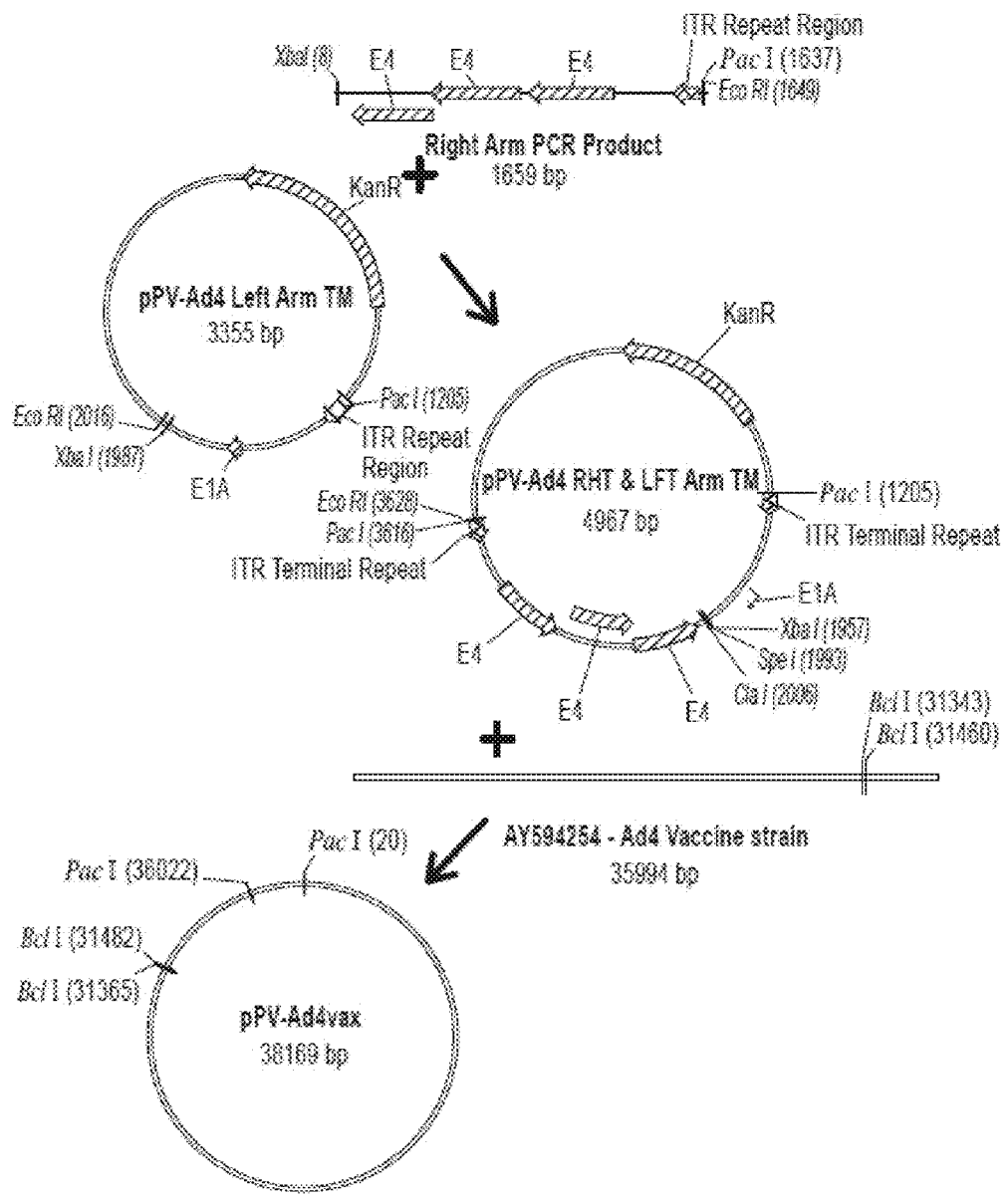
FIG. 1 is a diagram of various cloning steps involved in production of the pPV-Ad4vax recombinant adenoviral vector.

As used herein, the following terms shall have the following meanings.

The term "adenoviral vector" refers to a wild-type, mutant, and/or recombinant adenoviral genome, as well as adenoviruses comprising such a genome. An adenoviral vector can comprise all or part of the genome of any adenoviral serotype, as well as combinations thereof (i.e., hybrid genomes).

The term "infectious pathogen" refers to any agent capable of infecting humans and causing deterioration in health and/or triggering an immune response. In certain embodiments, the infectious pathogen is a virus, such as an influenza virus, retrovirus (e.g., HIV, Rous Sarcoma Virus (RSV), human endogenous retrovirus K (HERV-K)), human endogenous retrovirus K (HERV-K), papillomavirus (e.g., human papilloma virus), picornavirus (e.g., Hepatitis A, Poliovirus), hepadnavirus (e.g., Hepatitis B), flavivirus (e.g., Hepatitis C, Yellow Fever virus, Dengue Fever virus, Japanese encephalitis virus, West Nile virus), togavirus (e.g., chikungunya virus, Eastern equine encephalitis (EEE) virus, Western equine encephalitis (WEE) virus, Venezuelan equine encephalitis (VEE) virus,), herpesvirus (e.g., Cytomegalovirus), paramyxovirus (Parainfluenza virus, Pneumonia virus, Bronchiolitis virus, common cold virus, Measles virus, Mumps virus), rhabdovirus (e.g., Rabies virus), Filovirus (e.g., Ebola virus), bunyavirus (e.g., Hantavirus, Rift Valley Fever virus), calicivirus (e.g., Norovirus), or reovirus (e.g., Rotavirus, Epstein-Barr virus, Herpes simplex virus types 1 & 2).

In other embodiments, the infectious pathogen is a prokaryotic organism such as a gram-negative bacterium, gram-positive bacterium, or other type of bacterium. Such prokaryotic organisms include, but are not limited to, *Bacillus* (e.g., *Bacillus anthracis*), *Mycobacterium* (e.g., *Mycobacterium tuberculosis, Mycobacterium Leprae*), *Shigella* (e.g., *Shigella sonnei, Shigella dysenteriae, Shigella flexneri*), *Helicobacter* (e.g., *Helicobacter pylori*), *Salmonella* (e.g., *Salmonella enterica, Salmonella typhi, Salmonella typhimurium*), *Neisseria* (e.g., *Neisseria gonorrhoeae, Neisseria meningitidis*), *Moraxella* (e.g., *Moraxella catarrhalis*), *Haemophilus* (e.g., *Haemophilus influenzae*), *Klebsiella* (e.g., *Klebsiella pneumoniae*), *Legionella* (e.g., *Legionella pneumophila*), *Pseudomonas* (e.g., *Pseudomonas aeruginosa*), *Acinetobacter* (e.g., *Acinetobacter baumannii*), *Listeria* (e.g., *Listeria monocytogenes*), *Staphylococcus* (e.g., methicillin-resistant, multidrug-resistant, or oxacillin-resistant *Staphylococcus aureus*), *Streptococcus* (e.g., *Streptococcus pneumoniae, Streptococcus pyogenes, Streptococcus agalactiae*), *Corynebacterium* (e.g., *Corynebacterium diphtheria*), *Clostridium* (e.g., *Clostridium botulinum, Clostridium tetani, Clostridium difficile*), *Chlamydia* (e.g., *Chlamydia pneumonia, Chlamydia trachomatis*), *Camphylobacter* (e.g., *Camphylobacter jejuni*), *Bordetella* (e.g., *Bordetella pertussis*), *Enterococcus* (e.g., *Enterococcus faecalis, Enterococcus faecum*, Vancomycin-resistant enterococcus (VRE)), *Vibrio* (e.g., *Vibrio cholerae*), *Yersinia* (e.g., *Yersinia pestis*), *Burkholderia* (e.g., *Burkholderia cepacia* complex), *Coxiella* (e.g., *Coxiella burnetti*), *Francisella* (e.g., *Francisella tularensis*), and *Escherichia* (e.g., enterotoxigenic, enterohemorrhagic or Shiga toxin-producing *E. coli*, such as ETEC, EHEC, EPEC, EIEC, and EAEC)).

In still other embodiments, the infectious pathogen is a eukaryotic organism. Examples of eukaryotic organisms include, but are not limited to protists, such as a *Plasmodium* (e.g., *Plasmodium falciparum, Plasmodium vivax, Plasmodium ovale, Plasmodium malariae Plasmodium* diarrhea), and fungi such as *Candida* (e.g., *Candida albicans*), *Aspergillus* (e.g., *Aspergillus fumigatus*), *Cryptococcus* (e.g., *Cryptococcus neoformans*), *Histoplasma* (e.g., *Histoplasma capsulatum*), *Pneumocystis* (e.g., *Pneumocystis jirovecii*), and *Coccidioides* (e.g., *Coccidioides immitis*).

The term "cancer" refers to a medical condition characterized by an abnormal increase in the proliferation of particular population of cells. The cancerous cells can be derived from any tissue or organ including, e.g., skin, muscle, lung, heart, liver, kidney, neural tissue, etc. In certain embodiments, the cancer is benign (e.g., a benign tumor). In other embodiments, the cancer is malignant (e.g., a malignant tumor). In certain embodiments, the cancer is metastatic (i.e., the cancer cells are able to migrate from their place of origin to another tissue or organ).

Additional terms shall be defined, as needed, throughout the specification.

The present invention is directed to recombinant adenoviral vaccines. The invention is based, in part, on the development of novel recombinant adenoviral vectors that express heterologous sequences at high levels. The invention is also based, in part, on the development of novel recombinant adenoviral vectors designed to improve host immune response and circumvent pre-existing neutralizing antibodies. The invention is also based, in part, on the development of novel recombinant adenoviral vectors to be used as antigen-specific and/or universal influenza vaccines.

Accordingly, in one aspect, the invention provides an adenoviral vector comprising a first heterologous sequence. As used herein, a "heterologous sequence" is a nucleic acid sequence that, upon integration into an adenoviral vector, creates a non-naturally occurring juxtaposition of adenoviral sequences with the nucleic acid sequence. Typically, a heterologous sequence will comprise nucleic acid sequence that is non-adenoviral in origin. For example, the heterologous sequence can be entirely, mostly, or partially non-adenoviral (e.g., a mosaic of adenoviral and non-adenoviral sequences) in origin. In some instances, however, a heterologous sequence can be entirely adenoviral in origin, e.g., an adenoviral sequence from one type of adenovirus can be integrated into an adenoviral vector generated from a different type of adenovirus. For instance, an adenoviral sequence encoding a hexon or fiber protein from one type of adenovirus can be integrated into an adenoviral vector generated from a different type of adenovirus to produce recombinant adenovirus with fiber proteins from different serotypes and/or adenovirus with chimeric hexon and fiber proteins. Adenoviral vectors comprising a first heterologous sequence can be useful, e.g., as vaccines against infectious pathogens or cancerous cells. Thus, the first heterologous sequence can encode an antigen from an infectious pathogen. Alternatively, the first heterologous sequence can encode an antigen associated with cancerous cells.

In certain embodiments, the first heterologous sequence encodes all or part of a protein produced by an infectious pathogen. The protein, or fragment thereof (e.g., cleavage product, structural domain, unit(s) of secondary structure, B-cell epitope, cytotoxic T lymphocyte (CTL) epitope, helper T lymphocyte (HTL) epitope, etc.), can be located on the surface of the infectious pathogen. For example, the protein or fragment thereof can be highly antigenic, involved in cellular targeting, and/or involved in cellular entry. Alternatively, the protein, or fragment thereof (e.g., cleavage product, structural domain, unit(s) of secondary structure, HTL or CTL epitope, etc.), can be located internal to the infectious pathogen. For example, the protein or fragment thereof can be an intracellular protein, a capsid or core protein of an enveloped virus, a core protein of a non-enveloped virus, etc.

In certain embodiments, the epitope, structural domain, or unit of secondary structure is evolutionarily conserved. As used herein, the term "evolutionarily conserved" means that a sequence is at least about 50% conserved among a diverse set of strains of a particular infectious pathogen. For viruses, a diverse set of strains includes at least one isolate from each identified subclassification (e.g., serotype) capable of infecting and thereby causing disease or illness in the target population for the vaccine, or a representative number of infectious isolates encompassing the known diversity in such strains. For example, in certain embodiments, a diverse set of influenza strains includes representative strains that are associated with disease in man, swine, and/or birds, including H1N1 strains (e.g., A/Wilson-Smith/33, A/New Calcdonia/20/99, A/Swine Korea/S10/2004, A/Brevig Mission/1/1918, A/Pureto Rico/8/34/Mount Sinai, A/California/7/2009, A/California/05/2009, A/California/08/2009, A/Texas/04/2009, A/swine/Saskatchewan/18789/02, A/mallard/Alberta/130/2003, A/mallard/Alberta/2001, A/swine/Cotes d'Armor/1482/99, A/swine/Betzig/2/2001, and/or A/turkey/Germany/3/91), H3N2 strains (e.g., A/Perth/16/2009), H2N2 strains (e.g., A/Japan/305/57, A/Ann Arbor/6/60, A/Canada/720/05, A/mallard/NY/6750/78, A/mallard/Potsdam/177-4/83, and/or A/duck/Hokkaido/95/2001), N3N2 strains (e.g., A/Hong Kong/1/66, A/Charlottesville/03/2004, A/Canterbury/129/2005, A/Fujian/411/01-like, A/duck/Korea/S9/2003, A/swine/Texas/4199-2/98, A/turkey/Ohio/313053/2004, and/or A/turkey/North Carolina/12344/03), H5N1 strains (e.g., A/swine/Shandong/2/03, A/goose/Guangdong/1/96, A/duck/Hunan/114/05, A/VietNam/1203/2004, A/VietNam/DT-036/2005, A/Vietnam/1194/2004, A/Vietnam/1203/2004, A/Anhui/1/2005, A/Egypt/2321/2007, A/Egypt/3300-NAMRU3/2008, A/grebe/Novosibirsk/29/2005, A/Bar-headed goose/Mondolia/1/05, A/cat/Thailand/KU-02/04, A/Hong Kong/213/03, A/chicken/Guangdong/174/04, and/or A/HK/159/97), H6N1 strains (e.g., A/teal/Hong Kong/1073/99), H6N2 strains (e.g., A/chicken/California/0139/2001, and/or A/guillemot/Sweden/3/2000), H6N9 strains (e.g., A/goose/Hong Kong/W217/97), H7N1 strains (e.g., A/FPV/Rostock/34), H7N3 strains (e.g., A/chicken/British Columbia/04, and/or A/turkey/Italy/220158/2002), H7N7 strains (e.g., A/chicken/Netherlands/1/2003, A/Netherlands/219/03, A/FPV/Dobson/27, and/or A/chicken/FPV/Weybridge), H9N2 strains (e.g., A/shorebird/Delaware/9/96, A/swine/Korea/S452/2004, A/duck/Hong Kong/Y439/97, A/Hong Kong/1073/99, A/HK/2108/2003, A/quail/Hong Kong/G1/97, A/duck/Hong Kong/Y280/97, A/chicken HK/FY23/03, and/or A/chicken HK/G9/97), and B influenza strains (e.g., B/Brisbane/60/2008). In certain embodiments, a diverse set of influenza strains includes all of the foregoing strains as well as additional influenza strains known to be associated with disease in man, swine, or birds. For cellular pathogens, such as bacteria, protists, fungi, etc., a diverse set of strains includes at least one isolate from each species capable of infecting and thereby causing disease or illness in the target population for the vaccine, or a representative number of infectious isolates encompassing the know diversity in such strains. In certain embodiments, the epitope and/or structural motif is at least 60%, 70%, 75%, 80%, 85%, 90%, 95%, or more conserved.

In certain embodiments, the first heterologous sequence encodes a plurality of epitopes (e.g., B cell, CTL, or HTL epitopes) and/or structural motifs (e.g., protein domains or units of secondary structure) present in proteins produced by the infectious pathogen. In certain embodiments, one or more of the plurality of epitopes and/or structural motifs is evolutionarily conserved. In certain embodiments, the first heterologous sequence encodes at least 5, 10, 15, 20, 25, 30, 35, 40, or more epitopes and/or structural motifs. The plurality of epitopes and/or structural motifs can be from a single protein or from multiple proteins. In certain embodiments, the plurality of epitopes and/or structural motifs consists of or comprises a multimer of a single epitope or structural motif. In other embodiments, the plurality of epitopes and/or structural motifs comprises a multimer of different epitopes and/or structural motifs. For example, the multimer can include two or more epitopes and/or structural motifs from a single protein or one or more epitopes and/or structural motifs from each of two or more proteins. As used herein, a "multimer" is a protein sequence that comprises a series of discrete polypeptides that have been linked together to form a single, larger polypeptide. In certain embodiments, a linker sequence is used to connect adjacent discrete polypeptides in a multimer. Persons skilled in the art can readily identify short peptide sequences capable of acting as a linker in a multimer.

In certain embodiments, the plurality of epitopes comprises a plurality of HTL epitopes, wherein each HTL epitope comprises a HLA class II-binding peptide. As used herein, a "HLA class II-binding peptide" is a peptide that binds to a HLA class II molecule with an $IC_{50}$<1000 nM. In general, a HLA class II-binding peptide is about 6 to about 25 amino acids, or about 13 to about 21 amino acids in length. In certain embodiments, one or more of said plurality of HTL epitopes comprises a HLA class II-binding peptide that binds to a HLA class II molecule selected from the group consisting of HLA-DRB1*0101, HLA-DRB1*0301, HLA-DRB1*0401, HLA-DRB1*0402, HLA-DRB1*0404, HLA-DRB1*0405, HLA-DRB1*0701, HLA-DRB1*0801, HLA-DRB1*0802, HLA-DRB1*0901, HLA-DRB1*1001, HLA-DRB1*1101, HLA-DRB1*1107, HLA-DRB1*1201, HLA-DRB1*1301, HLA-DRB1*1302, HLA-DRB1*1333, HLA-DRB1*1401, HLA-DRB1*1403, HLA-DRB1*1447, HLA-DRB1*1501, HLA-DRB1*1601, HLA-DRB3*0101, HLA-DRB3*0201, HLA-DRB3*0215, HLA-DRB3*0301, HLA-DRB4*0101 and HLA-DRB5*0101, HLA-DRB5-0202. In certain embodiments, one or more of said plurality of HTL epitopes comprises a HLA class II-binding peptide that binds to a HLA class II molecule selected from the group consisting of HLA-DR1, HLA-DR3, HLA-DR4, HLA-DR5, HLA-DR9 supertype variants as described, e.g., in Doytchinova and Flower (2005) J Immunol 174:7085 and/or Southwood et al. (1998) J Immunol 160:3363. In certain embodiments, one or more of said plurality of HTL epitopes comprises a HLA class II-binding peptide that binds to a plurality of HLA class II molecules (e.g., at least 2, 3, 4, 5, 6, 7, 8, 9, 10, or more). The plurality of HLA class II molecules can be selected, for example, from the group consisting of HLA-DRB1*0101, HLA-DRB1*0301, HLA-DRB1*0401, HLA-DRB1*0402, HLA-DRB1*0404, HLA-DRB1*0405, HLA-DRB1*0701, HLA-DRB1*0801, HLA-DRB1*0802, HLA-DRB1*0901, HLA-DRB1*1001, HLA-DRB1*1101, HLA-DRB1*1107, HLA-DRB1*1201, HLA-DRB1*1301, HLA-DRB1*1302, HLA-DRB1*1333, HLA-DRB1*1401, HLA-DRB1*1403, HLA-DRB1*1447, HLA-DRB1*1501, HLA-DRB1*1601, HLA-DRB3*0101, HLA-DRB3*0201, HLA-DRB3*0215, HLA-DRB3*0301, HLA-DRB4*0101 and HLA-DRB5*0101, HLA-DRB5-0202. In certain embodiments, one or more of said plurality of HTL epitopes comprises a HLA class II-binding peptide that binds to a HLA class II molecule selected from the group consisting of HLA-DR1, HLA-DR3, HLA-DR4, HLA-DR5, HLA-DR9 supertype variants as described, e.g., in Doytchinova and Flower (2005) J Immunol 174:7085 and/or Southwood et al. (1998) J Immunol 160:3363. In certain embodiments, the plurality of HTL epitopes comprise HLA class II-binding peptides that collectively bind to each HLA class II molecule in the group consisting of HLA-DRB1*0101, HLA-DRB1*0301, HLA-DRB1*0401, HLA-DRB1*0402, HLA-DRB1*0404, HLA-DRB1*0405, HLA-DRB1*0701, HLA-DRB1*0801, HLA-DRB1*0802, HLA-DRB1*0901, HLA-DRB1*1001, HLA-DRB1*1101, HLA-DRB1*1107, HLA-DRB1*1201, HLA-DRB1*1301, HLA-DRB1*1302, HLA-DRB1*1333, HLA-DRB1*1401, HLA-DRB1*1403, HLA-DRB1*1447, HLA-DRB1*1501, HLA-DRB1*1601, HLA-DRB3*0101, HLA-DRB3*0201, HLA-DRB3*0215, HLA-DRB3*0301, HLA-DRB4*0101 and HLA-DRB5*0101, HLA-DRB5-0202. In certain embodiments, one or more of said plurality of HTL epitopes comprises a HLA class II-binding peptide that binds to a HLA class II molecule selected from the group consisting of HLA-DR1, HLA-DR3, HLA-DR4, HLA-DR5, HLA-DR9 supertype variants as described, e.g., in Doytchinova and Flower (2005) J Immunol 174:7085 and/or Southwood et al. (1998) J Immunol 160:3363.

In certain embodiments, the plurality of epitopes comprises a plurality of CTL epitopes, wherein each CTL epitope comprises a HLA class I-binding peptide. As used herein, a "HLA class I-binding peptide" is a peptide that binds to a HLA class II molecule with an $IC_{50}$<500 nM. In general, a HLA class I-binding peptide is about 8 to about 13 amino acids, or about 8, 9, 10, or 11 amino acids in length. In certain embodiments, one or more of said plurality of CTL epitopes comprises a HLA class I-binding peptide that binds to a HLA class 1 molecule selected from the group consisting of HLA-A01, HLA-A02, HLA-A03, HLA-A24, HLA-B07, HLA-B08, HLA-B27, HLA-B58, HLA-B62 and HLA-B44 supertype variants as described, e.g., in Sidney et al. (2008) BMC Immunol 9:1. In certain embodiments, one or more of said plurality of CTL epitopes comprises a HLA class I-binding peptide that binds to a plurality of HLA class I molecules (e.g., at least 2, 3, 4, 5, or 6). For example, the CTL epitope can bind to: a plurality of HLA-A01 supertype variants (e.g., selected from the group consisting of A*0101, A*2601, A*2602, A*2603, A*2902, A*3001, A*3002, A*3003, A*3004, and A*3201); a plurality of HLA-A02 supertype variants (e.g., selected from the group consisting of A*0201, A*0202, A*0203, A*0204, A*0205, A*0206, A*0207, A*0214, A*0217, A*6802, and A*6901); a plurality of HLA-A03 supertype variants (e.g., selected from the group consisting of A*0301, A*1101, A*3101, A*3301, A*6601, A*6801, and A*7401); a plurality of HLA-A24 supertype variants (e.g., selected from the group consisting of A*2301, A*2402, and A*2902); a plurality of HLA-B07 supertype variants (e.g., selected from the group consisting of B*0702, B*0703, B*0705, B*1508, B*3501, B*3503, B*4201, B*5101, B*5102, B*5103, B*5301, B*5401, B*5501, B*5502, B*5601, B*6701, and B*7801); a plurality of HLA-B08 supertype variants (e.g., selected from the group consisting of B*0801 and B*0802); a plurality of HLA-B27 supertype variants (e.g., selected from the group consisting of B*1402, B*1503, B*1509, B*1510, B*1518, B*2702, B*2703, B*2704, B*2705, B*2706, B*2707, B*2709, B*3801, B*3901, B*3902, B*3909, B*4801, and B*7301); a plurality of HLA-B44 supertype variants (e.g., selected from the group consisting of B*1801, B*3701 B*4001, B*4002, B*4006, B*4402, B*4403, and B*4501); a plurality of HLA-B58 supertype variants (e.g., selected from the group consisting of B*1516, B*1517, B*5701, B*5702, B*5801, and B*5802); or a plurality of HLA-B62 supertype variants (e.g., selected from the group consisting of B*1501, B*1502, B*1512, B*1513, B*4601, and B*5201). In certain embodiments, the plurality of CTL epitopes comprise HLA class I-binding peptides that collectively bind to at least one HLA class I molecule from each of the HLA-A01, HLA-A02, HLA-A03, HLA-A24, HLA-B07, HLA-B08, HLA-B58, HLA-B62 and HLA-B44 supertypes.

Human studies have indicated that cellular immune responses play a role in controlling influenza infection. See, e.g., McMichael et al. (1983), New England J. Med. 309(1): 13; Sonoguchi et al. (1985), J Infect. Disease 151(1):81. The protective effect of cellular immune responses may be particularly relevant in the elderly (see, e.g., Almanzar et al. (2007), Wien. Med. Wochenschr 157/5-6:116, McElhaney et al. (2006), J. Immunol. 176:6333) and also young children (see, e.g., Forest et al. (2008) Clin. Vaccine Immunol. 15(7): 1042). In order to evaluate immunogenicity specific for identified epitopes, recall responses can be performed using human donor peripheral blood mononuclear cells (PBMCs)

and peptides. It can be assumed that epitope-specific recall responses are a result of previous influenza virus infection and the presence of such T cells indicates the epitopes are generated naturally and are therefore excellent choices for vaccine inclusion. In certain embodiments, a CTL or HTL epitope encoded by the first heterologous sequence has the capacity to generate a human interferon gamma (IFN-γ) response (specifically, Spot Forming Cells (SFC) per $1\times10^6$ cells) of at least two times above background responses, e.g., 300, 400, 500, 600, 700, 800, 900, 1000, 1100, 1200, 1300, 1400, 1500, 2000, 2500, 3000, or more upon ELISPOT assay analysis. The selected CTL or HTL peptides can be tested two ways: (1) directly ex vivo where the PBMC are thawed, rested 5 days in media, and responses measured by IFN-γ ELISPOT assay, and (2) following a culture step with peptides to increase sensitivity. Significant responses from the indicated epitopes can be defined as responses greater than the mean of background responses plus (2.0×Std. Dev.). It is critical to determine background responses for this method. Background responses can be determined using supertype CTL and HTL binding peptides from pathogens to which donors were not exposed, such as HIV, HBV, HCV and *Plasmodium falciparum*. In certain embodiments, a CTL or HTL epitope encoded by the first heterologous sequence is evolutionarily conserved and has the capacity to generate a human IFN-γ response of at least two times above background responses, e.g., 300, 400, 500, 600, 700, 800, 900, 1000, 1100, 1200, 1300, 1400, 1500, 2000, 2500, 3000, or more upon ELISPOT assay analysis. In certain embodiments, a CTL or HTL epitope encoded by the first heterologous sequence is evolutionarily conserved, has the capacity to generate a human IFN-γ response of at least two times above background responses, e.g., 300, 400, 500, 600, 700, 800, 900, 1000, 1100, 1200, 1300, 1400, 1500, 2000, 2500, 3000, or more upon ELISPOT assay analysis, and exhibits degenerate binding to (i.e., binds to more than one) HLA class I or class II molecules, respectively. Methods for testing CTL or HTL epitopes for their ability to bind HLA class I and class II molecules and to generate a human IFN-γ response are known in the art and have been described, e.g., in WO 2008/054540 (Alexander et al.), filed May 18, 2007, WO 2008/039267 (Alexander et al.), filed Jul. 23, 2007, and Assarsson et al. (2008), J Virol 82:12241, the contents of each of which are hereby incorporated by reference.

In certain embodiments, the first heterologous sequence encodes an antigen from an influenza virus. A suitable influenza antigen can be a surface antigen, such as hemagglutinin (HA), neuraminidase (NA), M2, or a fragment thereof (e.g., one or more HTL or CTL epitopes). Other suitable influenza antigens include M1, NP, NS1, NS2, PA, PB1, and PB2, or fragments thereof (e.g., one or more HTL or CTL epitopes).

In certain embodiments, the first heterologous sequence encodes a full-length influenza HA protein, or a portion thereof, such as an external portion (i.e., a portion located on the external surface of an influenza virus), HA1 fragment, HA2 fragment, or one or more epitopes (e.g., B-cell, HTL, or CTL epitope). In certain embodiments, the portion, fragment, or epitope is from an evolutionarily conserved sequence. In certain embodiments, the epitope is a HTL or CTL epitope that exhibits degenerate binding to HLA class I or class II molecules, respectively, and/or has the capacity to generate a human interferon gamma (IFN-γ) response upon ELISPOT assay analysis using human donor PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more HA HTL epitopes selected from the group shown in Table 1 (i.e., SEQ ID NOs:1-12). In other embodiments, the first heterologous sequence encodes one or more HA CTL epitopes selected from the group shown in Table 2 (i.e., SEQ ID NOs: 62-67).

TABLE 1

| Influenza Protein | HTL Peptide | SEQ ID NO: | Cons. (%)[a] | # Alleles Bound[b] | Recall[c] |
|---|---|---|---|---|---|
| HA | MEKIVLLFAIVSLVKSD | SEQ ID NO: 1 | n/a | 6 | n/a |
| HA | KSSFFRNVVWLIKKN | SEQ ID NO: 2 | n/a | 12 | n/a |
| HA | VVWLIKKNSTYPTIKR | SEQ ID NO: 3 | n/a | 9 | n/a |
| HA | PTTYISVGTSTLNQRL | SEQ ID NO: 4 | n/a | 9 | n/a |
| HA | RMEFFWTILKPNDAI | SEQ ID NO: 5 | n/a | 10 | n/a |
| HA | WTILKPNDAINFESN | SEQ ID NO: 6 | n/a | 8 | n/a |
| HA | CPKYVKSNRLVLATGL | SEQ ID NO: 7 | n/a | 12 | n/a |
| HA | NRLVLATGLRNSPQR | SEQ ID NO: 8 | n/a | 10 | n/a |
| HA | ELLVLMENERTLDFHDS | SEQ ID NO: 9 | n/a | 8 | n/a |
| HA | ISGVKLESIGIYQILSI | SEQ ID NO: 10 | n/a | 10 | n/a |
| HA | IYQILSIYSTVASSLA | SEQ ID NO: 11 | n/a | 13 | n/a |
| HA | ILSIYSTVASSLALAI | SEQ ID NO: 12 | n/a | 12 | n/a |
| M1 | KGILGFVFTLTVPSE | SEQ ID NO: 13 | 94 | 11 | 6 |
| M1 | YRKLKREITFHGAKE | SEQ ID NO: 14 | 61 | 11 | 10 |
| M1 | MGTVTTEVALGLVCA | SEQ ID NO: 15 | 22 | 7 | 5 |
| M1 | NPLIRHENRMVLAST | SEQ ID NO: 16 | 98 | 11 | 5 |

TABLE 1-continued

| Influenza Protein | HTL Peptide | SEQ ID NO: | Cons. (%)[a] | # Alleles Bound[b] | Recall[c] |
|---|---|---|---|---|---|
| M1 | AMEVASQARQMVQAM | SEQ ID NO: 17 | 75 | 8 | 3 |
| M2 | DPLVVAASIIGILHL | SEQ ID NO: 18 | 47 | 6 | 2 |
| NA | SLMLQIGNMISIWVSHS | SEQ ID NO: 19 | n/a | 13 | 1 |
| NP | IGRFYIQMCTELKLSDYEG | SEQ ID NO: 20 | 67 | 12 | 4 |
| NP | QNSITIERMVLSAFD | SEQ ID NO: 21 | 69 | 8 | 5 |
| NP | VGTMVMELIRMIKRG | SEQ ID NO: 22 | 73 | 10 | 8 |
| NP | DLIFLARSALILRGS | SEQ ID NO: 23 | 92 | 12 | 4 |
| NP | RSALILRGSVAHKSC | SEQ ID NO: 24 | 100 | 12 | 2 |
| NP | KSQLVWMACHSAAFE | SEQ ID NO: 25 | 71 | 11 | 2 |
| NP | AGQISVQPTFSVQRN | SEQ ID NO: 26 | 61 | 10 | 5 |
| NS1 | SLCIRMDQAIMDKDI | SEQ ID NO: 27 | n/a | 7 | 1 |
| NS1 | EGAIVGEISPLPSLPGHTD | SEQ ID NO: 28 | 27 | 8 | 5 |
| NS1 | VGEISPLPSLPGHTD | SEQ ID NO: 29 | n/a | 9 | 3 |
| NS2 | SLKLYRDSLGEAVMR | SEQ ID NO: 30 | 46 | 8 | 3 |
| NS2 | IRWLIEEVRHRLRIT | SEQ ID NO: 31 | 8 | 7 | 4 |
| NS2 | FEQITFMQALQLLLE | SEQ ID NO: 32 | 58 | 10 | 1 |
| NS2 | ITFMQALQLLLEVEQ | SEQ ID NO: 33 | 58 | 10 | 1 |
| PA | RREVHIYYLEKANKI | SEQ ID NO: 34 | 76 | 11 | 4 |
| PA | LFTIRQEMASRGLWD | SEQ ID NO: 35 | 71 | 11 | 3 |
| PA | EPFLKTTPRPLRLPD | SEQ ID NO: 36 | 35 | 10 | 2 |
| PA | RSKFLLMDALKLSIED | SEQ ID NO: 37 | 90 | 13 | 2 |
| PA | VAPIEHIASMRRNYF | SEQ ID NO: 38 | 75 | 11 | 4 |
| PA | EYIMKGVYINTALLN | SEQ ID NO: 39 | 98 | 7 | 4 |
| PA | RPMFLYVRTNGTSKI | SEQ ID NO: 40 | 90 | 12 | 3 |
| PB1 | PTLLFLKVPAQNAIST | SEQ ID NO: 41 | 71 | 11 | 2 |
| PB1 | SYLIRALTLNTMTKD | SEQ ID NO: 42 | 88 | 12 | 2 |
| PB1 | FLAMITYITRNQPEW | SEQ ID NO: 43 | 76 | 11 | 3 |
| PB1 | QPEWFRNVLSIAPIMF | SEQ ID NO: 44 | 76 | 12 | 2 |
| PB1 | FRNVLSIAPIMFSNKM | SEQ ID NO: 45 | 76 | 12 | 1 |
| PB1 | IAPIMFSNKMARLGK | SEQ ID NO: 46 | 84 | 10 | 1 |
| PB1 | KGYMFESKSMKLRTQI | SEQ ID NO: 47 | 76 | 13 | 2 |
| PB1 | IRPLLVEGTASLSPG | SEQ ID NO: 48 | n/a | 10 | 1 |
| PB1 | MMGMFNMLSTVLGVS | SEQ ID NO: 49 | 100 | 12 | 10 |
| PB1 | DFALIVNAPNHEGIQ | SEQ ID NO: 50 | 84 | 11 | 3 |
| PB1 | YGFVANFSMELPSFG | SEQ ID NO: 51 | 90 | 9 | 3 |
| PB1 | GVTVIKNNMINNDLGP | SEQ ID NO: 52 | 92 | 8 | 2 |
| PB1 | PNLYNIRNLHIPEVC | SEQ ID NO: 53 | 80 | 9 | 2 |
| PB1 | ISSMVEAMVSRARID | SEQ ID NO: 54 | 78 | 8 | 1 |
| PB2 | KWMMAMKYPITADKR | SEQ ID NO: 55 | 82 | 8 | 1 |

TABLE 1-continued

| Influenza Protein | HTL Peptide | SEQ ID NO: | Cons. (%)[a] | # Alleles Bound[b] | Recall[c] |
|---|---|---|---|---|---|
| PB2 | GARILTSESQLTITK | SEQ ID NO: 56 | 82 | 8 | 2 |
| PB2 | KAAMGLRISSSFSFG | SEQ ID NO: 57 | 78 | 13 | 3 |
| PB2 | IKAVRGDLNFVNRAN | SEQ ID NO: 58 | 90 | 9 | 4 |
| PB2 | LRHFQKDAKVLFQNW | SEQ ID NO: 59 | 88 | 8 | 1 |
| PB2 | QWIIRNWETVKIQWS | SEQ ID NO: 60 | 76 | 11 | 3 |
| PB2 | RMQFSSLTVNVRGSG | SEQ ID NO: 61 | 96 | 11 | 2 |

[a]% Conservation is based on sequence analysis from 51 influenza strains (H1N1, H2N2, H3N2, H5N1, H7N7, H9N2, etc.)
[b]# Alleles bound refers to number of HLA class II molecules from the group consisting of HLA-DRB1*0101, HLA-DRB1*0301, HLA-DRB1*0401, HLA-DRB1*0404, HLA-DRB1*0405, HLA-DRB1*0701, HLA-DRB1*0802, HLA-DRB1*0901, HLA-DRB1*1101, HLA-DRB1*1302, HLA-DRB1*1501, HLA-DRB4*0101 and HLA-DRB5*0101 bound by the peptide.
[c]Recall refers to the number of human donors exhibiting IFN-γ responses > two times background responses upon ELISPOT assay analysis.

TABLE 2

| Influenza Protein | CTL Peptide | SEQ ID NO. | HLA Supertype | # Alleles Bound[a] |
|---|---|---|---|---|
| HA | LTIGECPKY | SEQ ID NO: 62 | HLA-A1 | 3 |
| HA | GMIDGWYGY | SEQ ID NO: 63 | HLA-A1 | 2 |
| HA | GLFGAIAGFI | SEQ ID NO: 64 | HLA-A2 | 3 |
| HA | FLDIWTYNA | SEQ ID NO: 65 | HLA-A2 | 4 |
| HA | TIGECPKYVK | SEQ ID NO: 66 | HLA-A3 | 1 |
| HA | LPFHNVHPL | SEQ ID NO: 67 | HLA-B7 | 5 |

[a]# Alleles bound refers to number of HLA class I molecules from a particular HLA supertype bound by the peptide. For HLA-A1, A*101, A*2601, A*2902, and A*3002 were tested; for HLA-A2, A*0201, A*0202, A*0203, A*0206, and A*6802 were tested; for HLA-A3, A*0301, A*1101, A*3101, A*3301, and A*6801 were tested; for HLA-A24, A*2301, A*2402, A*2902, and A*3002 were tested; for HLA-B7, B*0702, B*3501, B*5101, B*5301, and B*5401 were tested; and for HLA-B44, B*1801, B*4001, B*4002, B*4403, and B*4501 were tested.

In certain embodiments, the first heterologous sequence encodes a full-length influenza NA protein, or a portion thereof, such as an external portion (i.e., a portion located on the external surface of an influenza virus), fragment, or epitope (e.g., one or more B-cell, HTL, or CTL epitopes). In certain embodiments, the portion, fragment, or epitope is from an evolutionarily conserved sequence. In certain embodiments, the epitope is a HTL or CTL epitope that exhibits degenerate binding to HLA class I or class II molecules, respectively, and/or has the capacity to generate a human interferon gamma (IFN-γ) response upon ELISPOT assay analysis using human PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more copies of SEQ ID NO: 19 (see Table 1). In other embodiments, the first heterologous sequence encodes one or more NA CTL epitopes selected from the group shown in Table 3 (i.e., SEQ ID NOs: 86-109).

TABLE 3

| Protein | CTL Peptide | SEQ ID NO. | HLA Supertype | # Alleles Bound[a] |
|---|---|---|---|---|
| NA | GTVKDRSPY | SEQ ID NO: 86 | HLA-A1 | 2 |
| NA | VSFDQNLDY | SEQ ID NO: 87 | HLA-A1 | 2 |
| NA | IVAITDWSGY | SEQ ID NO: 88 | HLA-A1 | 1 |
| NA | KSCINRCFY | SEQ ID NO: 89 | HLA-A1 | 1 |
| NA | ALSTLCLLI | SEQ ID NO: 90 | HLA-A2 | 4 |
| NA | HLECRTFFL | SEQ ID NO: 91 | HLA-A2 | 4 |
| NA | CINGSCFTV | SEQ ID NO: 92 | HLA-A2 | 4 |
| NA | ITGFAPFSK | SEQ ID NO: 93 | HLA-A3 | 3 |
| NA | ITGWAIFSK | SEQ ID NO: 94 | HLA-A3 | 3 |
| NA | ASYKIFKIEK | SEQ ID NO: 95 | HLA-A3 | 2 |
| NA | VVFCGTSGTY | SEQ ID NO: 96 | HLA-A3 | 2 |
| NA | VFVIREPFI | SEQ ID NO: 97 | HLA-A24 | 2 |
| NA | FFLTQGALL | SEQ ID NO: 98 | HLA-A24 | 3 |
| NA | WWTSNSIIVF | SEQ ID NO: 99 | HLA-A24 | 2 |
| NA | SWPDGANIPF | SEQ ID NO: 100 | HLA-A24 | 2 |
| NA | SWPDGANINF | SEQ ID NO: 101 | HLA-A24 | 2 |
| NA | APFSKDNSI | SEQ ID NO: 102 | HLA-B7 | 1 |
| NA | APSPYNSRF | SEQ ID NO: 103 | HLA-B7 | 2 |
| NA | SPYNSRFESV | SEQ ID NO: 104 | HLA-B7 | 3 |
| NA | RPWVSFNQNL | SEQ ID NO: 105 | HLA-B7 | 1 |
| NA | RPCFWVELI | SEQ ID NO: 106 | HLA-B7 | 1 |
| NA | EECSCYPDY | SEQ ID NO: 107 | HLA-B44 | 3 |
| NA | EECSCYPRY | SEQ ID NO: 108 | HLA-B44 | 4 |
| NA | FEMIWDPNG | SEQ ID NO: 109 | HLA-B44 | 3 |

[a]See footnote (a) to Table 2.

In certain embodiments, the first heterologous sequence encodes a full-length influenza M2 protein, or a portion thereof, such as an external portion (i.e., M2e, a portion located on the external surface of an influenza virus), fragment, or epitope (e.g., one or more B-cell, HTL, or CTL epitopes). In certain embodiments, the portion, fragment, or epitope is from an evolutionarily conserved sequence. For example, in certain embodiments, the external M2 portion has a sequence shown in Table 4. The first heterologous sequence can encode a concatamer of two or more M2 fragments or portions (e.g., two or more repeats of a single M2e sequence shown in Table 4 or two or more M2e sequences shown in Table 4). In certain embodiments, the first heterologous sequence encodes a repeating sequence that includes SEQ ID NO: 312, SEQ ID NO: 318, SEQ ID NO: 321, SEQ ID NO: 327, or any combination thereof (e.g., at least one copy of all four sequences). In certain embodiments, the M2 epitope is a HTL or CTL epitope that exhibits degenerate binding to HLA class I or class II molecules, respectively, and/or has the capacity to generate a human interferon gamma (IFN-γ) response upon peptide restimulation of ELISPOT assay analysis using human PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more copies of SEQ ID NO: 18 (see Table 1). In other embodiments, the first heterologous sequence encodes one or more M2 CTL epitopes selected from the group shown in Table 5 (i.e., SEQ ID NOs: 80-85).

TABLE 4

| Influenza Protein | Influenza Strain | Peptide Sequence | SEQ ID NO. |
|---|---|---|---|
| M2 | A/New Caledonia/20/1999(H1N1)) | SLLTEVETPIRNEWGCRCNDSSD | SEQ ID NO: 312 |
| M2 | A/Brevig Mission/1/1918 (H1N1) | SLLTEVETPTRNEWGCRCNDSSD | SEQ ID NO: 313 |
| M2 | A/Puerto Rico/8/34/Mount Sinai (H1N1) | SLLTEVETPIRNEWGCRCNGSSD | SEQ ID NO: 314 |
| M2 | A/Fort Monmouth/1/47 (H1N1) | SLLTEVETPTKNEWECRCNDSSD | SEQ ID NO: 315 |
| M2 | A/Albany/1/76 (H3N2) | SLLTEVETPIRSEWGCRCNDSSD | SEQ ID NO: 316 |
| M2 | A/Hong Kong/1774/99 (H3N2) | SLLTEVETPTRNGWECRCSGSSD | SEQ ID NO: 317 |
| M2 | A/Viet Nam/1203/2004 (H5N1) clade 1 | SLLTEVETPTRNEWECRCSDSSD | SEQ ID NO: 318 |
| M2 | A/goose/Guangdong/1/96 (H5N1) | SLLTEVETPTKNEWECKCSDSSD | SEQ ID NO: 319 |
| M2 | A/HK/156/97 (H5N1) | SLLTEVETLTRNGWGCRCSDSSD | SEQ ID NO: 320 |
| M2 | A/chicken/Italy/2335/2000 (H7N1) | SLLTEVETPTRNGWECKCSDSSD | SEQ ID NO: 321 |
| M2 | A/turkey/Italy/3675/99 (H7N1) | SLLTEVETPTRNGWVCKCSDSSD | SEQ ID NO: 322 |
| M2 | A/chicken/New York/21211-2/05 (H7N2) | SLLTEVETPIRKGWECNCSDSSD | SEQ ID NO: 323 |
| M2 | A/equine/San Paulo/4/76 (H7N7) | SLLTEVETPTKSEWECRCNDSSD | SEQ ID NO: 324 |
| M2 | A/seal/Mass/1/1980 (H7N7) | SLLTEVETPIRNGWECKCSDSSD | SEQ ID NO: 325 |
| M2 | A/chicken/Netherlands/2586/2003(H7N7) | SLLTEVETPTRNGWECKCNDSSD | SEQ ID NO: 326 |
| M2 | A/Hong Kong/2108/2003 (H9N2) | SLLTEVETLTRNGWECRCSGSSD | SEQ ID NO: 327 |
| M2 | A/chicken/Beijing/1/94 (H9N2) | SLLTEVETPTRNGWGCRCSDSSD | SEQ ID NO: 328 |
| M2 | A/quail/Hong Kong/G1/1997 (H9N2) | SLLTEVETLTRNGWGCRCSDSSD | SEQ ID NO: 329 |
| M2 | A/Korea/KBNP-0028/2000 (H9N2) | SLLTEVETPTRDGWECKCNDSND | SEQ ID NO: 330 |

TABLE 4-continued

| Influenza Protein | Influenza Strain | Peptide Sequence | SEQ ID NO. |
|---|---|---|---|
| M2 | A/chicken/Hong Kong/G9/97 (H9N2) | SLLTEVETPTRNGWGCRCSGSSD | SEQ ID NO: 331 |
| M2 | A/chicken/Hong Kong/CSW153/2003 (H9N2) | SLLTEVETHTRNGWGCRCSDSSD | SEQ ID NO: 332 |
| M2 | A/chicken/Shantou/ 6781/2005 (H9N2) | SLLTEVETPTRNGWECKCSDSSD | SEQ ID NO: 333 |
| M2 | A/Hong Kong/1073/99 (H9N2) | SLLTEVETLTRNGWECKCRDSSD | SEQ ID NO: 334 |
| M2 | A/chicken/Zibo/L2/2008 (H9N2) | SLLTEVETLTRNGWECNCSDSSD | SEQ ID NO: 335 |

TABLE 5

| Protein | CTL Peptide | SEQ ID NO. | HLA Supertype | # Alleles Bound[a] |
|---|---|---|---|---|
| M2 | SIIGILHLI | SEQ ID NO: 80 | HLA-A2 | 5 |
| M2 | RLFFKCIYR | SEQ ID NO: 81 | HLA-A3 | 5 |
| M2 | RLFFKCIYRR | SEQ ID NO: 82 | HLA-A3 | 5 |
| M2 | LFFKCIYRR | SEQ ID NO: 83 | HLA-A3 | 4 |
| M2 | LWILDRLFF | SEQ ID NO: 84 | HLA-A24 | 3 |
| M2 | IYRRFKYGL | SEQ ID NO: 85 | HLA-A24 | 2 |

[a]See footnote (a) to Table 2.

In certain embodiments, the first heterologous sequence encodes a full-length influenza M1 protein, or a portion thereof, such as an epitope (e.g., one or more HTL or CTL epitopes). In certain embodiments, the portion or epitope is from an evolutionarily conserved sequence. In certain embodiments, the epitope is a HTL or CTL epitope that exhibits degenerate binding to HLA class I or class II molecules, respectively, and/or has the capacity to generate a human interferon gamma (IFN-γ) response upon ELISPOT assay analysis using human PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more M1 HTL epitopes selected from the group shown in Table 1 (i.e., SEQ ID NOs:13-17). In other embodiments, the first heterologous sequence encodes one or more M1 CTL epitopes selected from the group shown in Table 6 (i.e., SEQ ID NOs: 68-79).

TABLE 6

| Protein | CTL Peptide | SEQ ID NO. | HLA Supertype | # Alleles Bound[a] |
|---|---|---|---|---|
| M1 | NMDRAVKLY | SEQ ID NO: 68 | HLA-A1 | 3 |
| M1 | LLTEVETYV | SEQ ID NO: 69 | HLA-A2 | 5 |
| M1 | GILGFVFTL | SEQ ID NO: 70 | HLA-A2 | 4 |
| M1 | ILGFVFTLTV | SEQ ID NO: 71 | HLA-A2 | 4 |

TABLE 6-continued

| Protein | CTL Peptide | SEQ ID NO. | HLA Supertype | # Alleles Bound[a] |
|---|---|---|---|---|
| M1 | RMGTVTTEV | SEQ ID NO: 72 | HLA-A2 | 4 |
| M1 | ALMEWLKTR | SEQ ID NO: 73 | HLA-A3 | 5 |
| M1 | ASCMGLIYNR | SEQ ID NO: 74 | HLA-A3 | 4 |
| M1 | EWLKTRPIL | SEQ ID NO: 75 | HLA-A24 | 2 |
| M1 | TEVETYVLSI | SEQ ID NO: 76 | HLA-B44 | 4 |
| M1 | HENRMVLAST | SEQ ID NO: 77 | HLA-B44 | 4 |
| M1 | SEQAAEAMEV | SEQ ID NO: 78 | HLA-B44 | 6 |
| M1 | MEVASQARQM | SEQ ID NO: 79 | HLA-B44 | 5 |

[a]See footnote (a) to Table 2.

In certain embodiments, the first heterologous sequence encodes a full-length influenza NP protein, or a portion thereof, such as an epitope (e.g., one or more HTL or CTL epitopes). In certain embodiments, the portion or epitope is from an evolutionarily conserved sequence. In certain embodiments, the epitope is a HTL or CTL epitope that exhibits degenerate binding to HLA class I or class II molecules, respectively, and/or has the capacity to generate a human interferon gamma (IFN-γ) response upon ELISPOT assay analysis using human PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more NP HTL epitopes selected from the group shown in Table 1 (i.e., SEQ ID NOs:20-26). In other embodiments, the first heterologous sequence encodes one or more NP CTL epitopes selected from the group shown in Table 7 (i.e., SEQ ID NOs: 110-139). In still other embodiments, the first heterologous sequence encodes one or more copies of the NP sequence of SEQ ID NO: 337 (i.e., LELRSRYWAIRTRSGGNTNQQRAS).

TABLE 7

| Protein | CTL Peptide | SEQ ID NO. | HLA Supertype | # Alleles Bound[a] |
|---|---|---|---|---|
| NP | ASQGTKRS | SEQ ID NO: 110 | HLA-A1 | 1 |
| NP | CTELKLSDY | SEQ ID NO: 111 | HLA-A1 | 1 |
| NP | HSNLNDATY | SEQ ID NO: 112 | HLA-A1 | 2 |
| NP | KSCLPACVY | SEQ ID NO: 113 | HLA-A1 | 2 |
| NP | CLPACVYGL | SEQ ID NO: 114 | HLA-A2 | 4 |
| NP | LQNSQVFSL | SEQ ID NO: 115 | HLA-A2 | 4 |
| NP | FQGRGVFEL | SEQ ID NO: 116 | HLA-A2 | 4 |
| NP | IQNSITIER | SEQ ID NO: 117 | HLA-A3 | 2 |
| NP | MVLSAFDER | SEQ ID NO: 118 | HLA-A3 | 4 |
| NP | SLMQGSTLPR | SEQ ID NO: 119 | HLA-A3 | 4 |
| NP | MQGSTLPRR | SEQ ID NO: 120 | HLA-A3 | 2 |
| NP | GTMVMELIR | SEQ ID NO: 121 | HLA-A3 | 3 |
| NP | MVMELIRMIK | SEQ ID NO: 122 | HLA-A3 | 4 |
| NP | AVASGYDFER | SEQ ID NO: 123 | HLA-A3 | 3 |
| NP | SVQPTFSVQR | SEQ ID NO: 124 | HLA-A3 | 4 |
| NP | VQPTFSVQR | SEQ ID NO: 125 | HLA-A3 | 3 |
| NP | SVQRNLPFER | SEQ ID NO: 126 | HLA-A3 | 4 |
| NP | GVFELSDEK | SEQ ID NO: 127 | HLA-A3 | 2 |
| NP | FYIQMCTEL | SEQ ID NO: 128 | HLA-A24 | 2 |
| NP | HMMIWHSNL | SEQ ID NO: 129 | HLA-A24 | 3 |
| NP | IFLARSALI | SEQ ID NO: 130 | HLA-A24 | 2 |
| NP | WMACHSAAF | SEQ ID NO: 131 | HLA-A24 | 2 |
| NP | LPRRSGAAGA | SEQ ID NO: 132 | HLA-B7 | 2 |
| NP | LPACVYGLAV | SEQ ID NO: 133 | HLA-B7 | 4 |
| NP | LPFERATIM | SEQ ID NO: 134 | HLA-B7 | 5 |
| NP | GERQNATEI | SEQ ID NO: 135 | HLA-B44 | 4 |
| NP | RESRNPGNA | SEQ ID NO: 136 | HLA-B44 | 4 |
| NP | FEDLRVSSF | SEQ ID NO: 137 | HLA-B44 | 5 |
| NP | FERATIMAA | SEQ ID NO: 138 | HLA-B44 | 4 |
| NP | FERATIMAAF | SEQ ID NO: 139 | HLA-B44 | 5 |

[a]See footnote (a) to Table 2.

In certain embodiments, the first heterologous sequence encodes a full-length influenza NS1 protein, or a portion thereof, such as an epitope (e.g., one or more HTL or CTL epitopes). In certain embodiments, the portion or epitope is from an evolutionarily conserved sequence. In certain embodiments, the epitope is a HTL or CTL epitope that exhibits degenerate binding to HLA class I or class II molecules, respectively, and/or has the capacity to generate a human interferon gamma (IFN-γ) response upon ELISPOT assay analysis using human PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more NS1 HTL epitopes selected from the group shown in Table 1 (i.e., SEQ ID NOs: 27-29). In other embodiments, the first heterologous sequence encodes one or more NS1 CTL epitopes selected from the group shown in Table 8 (i.e., SEQ ID NOs: 140-152).

TABLE 8

| Protein | CTL Peptide | SEQ ID NO. | HLA Supertype | # Alleles Bound[a] |
|---|---|---|---|---|
| NS1 | TIASVPAPRY | SEQ ID NO: 140 | HLA-A1 | 2 |
| NS1 | FQVDCFLWHV | SEQ ID NO: 141 | HLA-A2 | 5 |
| NS1 | QVDCFLWHV | SEQ ID NO: 142 | HLA-A2 | 5 |
| NS1 | FLWHVRKQV | SEQ ID NO: 143 | HLA-A2 | 5 |
| NS1 | IILKANFSV | SEQ ID NO: 144 | HLA-A2 | 3 |
| NS1 | KQIVERILK | SEQ ID NO: 145 | HLA-A3 | 2 |
| NS1 | AIMDKNIILK | SEQ ID NO: 146 | HLA-A3 | 3 |
| NS1 | VPASRYLTDM | SEQ ID NO: 147 | HLA-B7 | 2 |
| NS1 | DEALKMTIA | SEQ ID NO: 148 | HLA-B44 | 4 |
| NS1 | LEEMSRDWLM | SEQ ID NO: 149 | HLA-B44 | 4 |
| NS1 | LETLILLRAF | SEQ ID NO: 150 | HLA-B44 | 4 |
| NS1 | GEISPLPSL | SEQ ID NO: 151 | HLA-B44 | 6 |
| NS1 | SETLQRFAW | SEQ ID NO: 152 | HLA-B44 | 3 |

[a]See footnote (a) to Table 2.

In certain embodiments, the first heterologous sequence encodes a full-length influenza NS2 protein, or a portion thereof, such as an epitope (e.g., one or more HTL or CTL epitopes). In certain embodiments, the portion or epitope is from an evolutionarily conserved sequence. In certain embodiments, the epitope is a HTL or CTL epitope that exhibits degenerate binding to HLA class I or class II molecules, respectively, and/or has the capacity to generate a human interferon gamma (IFN-γ) response upon ELISPOT assay analysis using human PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more NS2 HTL epitopes selected from the group shown in Table 1 (i.e., SEQ ID NOs: 30-33). In other embodiments, the first heterologous sequence encodes one or more NS2 CTL epitopes selected from the group shown in Table 9 (i.e., SEQ ID NOs: 153-163).

TABLE 9

| Protein | CTL Peptide | SEQ ID NO. | HLA Supertype | # Alleles Bound[a] |
|---|---|---|---|---|
| NS2 | ITQFESLKLY | SEQ ID NO: 153 | HLA-A1 | 1 |
| NS2 | FMQALQLLL | SEQ ID NO: 154 | HLA-A2 | 4 |
| NS2 | MQALQLLLEV | SEQ ID NO: 155 | HLA-A2 | 5 |
| NS2 | MITQFESLK | SEQ ID NO: 156 | HLA-A3 | 3 |

TABLE 9-continued

| Protein | CTL Peptide | SEQ ID NO. | HLA Supertype | # Alleles Bound[a] |
|---|---|---|---|---|
| NS2 | TQFESLKLYR | SEQ ID NO: 157 | HLA-A3 | 3 |
| NS2 | KFEEIRWLI | SEQ ID NO: 158 | HLA-A24 | 2 |
| NS2 | FMQALQLLF | SEQ ID NO: 159 | HLA-A24 | 3 |
| NS2 | EEVRHRLKI | SEQ ID NO: 160 | HLA-B44 | 5 |
| NS2 | FEQITFMQA | SEQ ID NO: 161 | HLA-B44 | 5 |
| NS2 | LEVEQEIRT | SEQ ID NO: 162 | HLA-B44 | 4 |
| NS2 | QEIRTFSFQLS | SEQ ID NO: 163 | HLA-B44 | 4 |

[a]See footnote (a) to Table 2.

In certain embodiments, the first heterologous sequence encodes a full-length influenza PA protein, or a portion thereof, such as an epitope (e.g., one or more HTL or CTL epitopes). In certain embodiments, the portion or epitope is from an evolutionarily conserved sequence. In certain embodiments, the epitope is a HTL or CTL epitope that exhibits degenerate binding to HLA class I or class II molecules, respectively, and/or has the capacity to generate a human interferon gamma (IFN-γ) response upon ELISPOT assay analysis using human PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more PA HTL epitopes selected from the group shown in Table 1 (i.e., SEQ ID NOs: 34-40). In other embodiments, the first heterologous sequence encodes one or more PA CTL epitopes selected from the group shown in Table 10 (i.e., SEQ ID NOs: 164-205).

TABLE 10

| Protein | CTL Peptide | SEQ ID NO. | HLA Supertype | # Alleles Bound[a] |
|---|---|---|---|---|
| PA | CTHLEVCFMYS | SEQ ID NO: 164 | HLA-A1 | 2 |
| PA | VTRREVHIY | SEQ ID NO: 165 | HLA-A1 | 1 |
| PA | SSLENFRAY | SEQ ID NO: 166 | HLA-A1 | 1 |
| PA | YVDGFEPNGYS | SEQ ID NO: 167 | HLA-A1 | 2 |
| PA | HIASMRRNY | SEQ ID NO: 168 | HLA-A1 | 1 |
| PA | VSHCRATEY | SEQ ID NO: 169 | HLA-A1 | 1 |
| PA | FMYSDFHFI | SEQ ID NO: 170 | HLA-A2 | 5 |
| PA | ALLKHRFEI | SEQ ID NO: 171 | HLA-A2 | 4 |
| PA | MAWTVVNSI | SEQ ID NO: 172 | HLA-A2 | 5 |
| PA | LLMDALKLSIS | SEQ ID NO: 173 | HLA-A2 | 5 |
| PA | LLAWKQVLA | SEQ ID NO: 174 | HLA-A2 | 3 |
| PA | YINTALLNA | SEQ ID NO: 175 | HLA-A2 | 5 |
| PA | SICNTTGVEKS | SEQ ID NO: 176 | HLA-A3 | 4 |
| PA | KFLPDLYDYKS | SEQ ID NO: 177 | HLA-A3 | 2 |
| PA | HIYYLEKANKS | SEQ ID NO: 178 | HLA-A3 | 4 |
| PA | KFLLMDALK | SEQ ID NO: 179 | HLA-A3 | 2 |
| PA | RTFFGWKEPYS | SEQ ID NO: 180 | HLA-A3 | 3 |
| PA | KIPKTKNMKKS | SEQ ID NO: 181 | HLA-A3 | 2 |
| PA | FQLIPMISK | SEQ ID NO: 182 | HLA-A3 | 2 |
| PA | KTNLYGFIIKS | SEQ ID NO: 183 | HLA-A3 | 4 |
| PA | NLYGFIIKGRS | SEQ ID NO: 184 | HLA-A3 | 4 |
| PA | SVKEKDMTK | SEQ ID NO: 185 | HLA-A3 | 2 |
| PA | MTKEFFENK | SEQ ID NO: 186 | HLA-A3 | 5 |
| PA | KVCRTLLAK | SEQ ID NO: 187 | HLA-A3 | 3 |
| PA | KLLLIVQALRS | SEQ ID NO: 188 | HLA-A3 | 3 |
| PA | KFAAICTHL | SEQ ID NO: 189 | HLA-A24 | 2 |
| PA | CFMYSDFHF | SEQ ID NO: 190 | HLA-A24 | 3 |
| PA | YYLEKANKI | SEQ ID NO: 191 | HLA-A24 | 2 |
| PA | EYIMKGVYI | SEQ ID NO: 192 | HLA-A24 | 2 |
| PA | FFENKSETW | SEQ ID NO: 193 | HLA-A24 | 2 |
| PA | LYASPQLEGFS | SEQ ID NO: 194 | HLA-A24 | 2 |
| PA | APIEHIASM | SEQ ID NO: 195 | HLA-B7 | 4 |
| PA | SPQLEGFSA | SEQ ID NO: 196 | HLA-B7 | 2 |
| PA | SEKTHIHIF | SEQ ID NO: 197 | HLA-B44 | 4 |
| PA | GEETIEERF | SEQ ID NO: 198 | HLA-B44 | 5 |
| PA | PELRSLSSWIS | SEQ ID NO: 199 | HLA-B44 | 4 |
| PA | SEFNKACELTS | SEQ ID NO: 200 | HLA-B44 | 5 |
| PA | MEFSLTDPRLS | SEQ ID NO: 201 | HLA-B44 | 6 |
| PA | WEKYCVLEI | SEQ ID NO: 202 | HLA-B44 | 5 |
| PA | AESRKLLLI | SEQ ID NO: 203 | HLA-B44 | 4 |
| PA | AESRKLLLIVS | SEQ ID NO: 204 | HLA-B44 | 3 |
| PA | YEAIEECLI | SEQ ID NO: 205 | HLA-B44 | 4 |

[a]See footnote (a) to Table 2.

In certain embodiments, the first heterologous sequence encodes a full-length influenza PB1 protein, or a portion thereof, such as an epitope (e.g., one or more HTL or CTL epitopes). In certain embodiments, the portion or epitope is from an evolutionarily conserved sequence. In certain embodiments, the epitope is a HTL or CTL epitope that exhibits degenerate binding to HLA class I or class II molecules, respectively, and/or has the capacity to generate a human interferon gamma (IFN-γ) response upon ELISPOT assay analysis using human PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more PB1 HTL epitopes selected from the group shown in Table 1 (i.e., SEQ ID NOs: 41-54). In other embodiments, the first heterologous sequence encodes one or more PB1 CTL epitopes selected from the group shown in Table 11 (i.e., SEQ ID NOs: 206-264).

TABLE 11

| Protein | CTL Peptide | SEQ ID NO. | HLA Supertype | # Alleles Bound[a] |
|---|---|---|---|---|
| PB1 | YSHGTGTGY | SEQ ID NO: 206 | HLA-A1 | 4 |
| PB1 | GMQIRGFVY | SEQ ID NO: 207 | HLA-A1 | 2 |
| PB1 | RMFLAMITY | SEQ ID NO: 208 | HLA-A1 | 2 |
| PB1 | KMARLGKGY | SEQ ID NO: 209 | HLA-A1 | 1 |
| PB1 | MLANIDLKY | SEQ ID NO: 210 | HLA-A1 | 3 |
| PB1 | MLASIDLKY | SEQ ID NO: 211 | HLA-A1 | 4 |
| PB1 | TFEFTSFFY | SEQ ID NO: 212 | HLA-A1 | 3 |
| PB1 | LVSDGGPNLY | SEQ ID NO: 213 | HLA-A1 | 3 |
| PB1 | AQTDCVLEA | SEQ ID NO: 214 | HLA-A2 | 4 |
| PB1 | CVLEAMAFL | SEQ ID NO: 215 | HLA-A2 | 4 |
| PB1 | RLIDFLKDV | SEQ ID NO: 216 | HLA-A2 | 4 |
| PB1 | QIRGFVYFV | SEQ ID NO: 217 | HLA-A2 | 4 |
| PB1 | FVYFVETLA | SEQ ID NO: 218 | HLA-A2 | 5 |
| PB1 | RMFLAMITYI | SEQ ID NO: 219 | HLA-A2 | 4 |
| PB1 | LLIDGTASL | SEQ ID NO: 220 | HLA-A2 | 5 |
| PB1 | NMLSTVLGV | SEQ ID NO: 221 | HLA-A2 | 4 |
| PB1 | FVANFSMEL | SEQ ID NO: 222 | HLA-A2 | 5 |
| PB1 | AQMALQLFI | SEQ ID NO: 223 | HLA-A2 | 4 |
| PB1 | RLCNPLNPFV | SEQ ID NO: 224 | HLA-A2 | 4 |
| PB1 | QTYDWTLNR | SEQ ID NO: 225 | HLA-A3 | 4 |
| PB1 | ALANTIEVFR | SEQ ID NO: 226 | HLA-A3 | 3 |
| PB1 | MVTQRTIGK | SEQ ID NO: 227 | HLA-A3 | 4 |
| PB1 | MVTQRTIGKK | SEQ ID NO: 228 | HLA-A3 | 3 |
| PB1 | ALTLNTMTK | SEQ ID NO: 229 | HLA-A3 | 2 |
| PB1 | TLARSICEK | SEQ ID NO: 230 | HLA-A3 | 3 |
| PB1 | SIAPIMFSNK | SEQ ID NO: 231 | HLA-A3 | 4 |
| PB1 | IQAGVDRFYR | SEQ ID NO: 232 | HLA-A3 | 4 |
| PB1 | KLVGINMSK | SEQ ID NO: 233 | HLA-A3 | 2 |
| PB1 | KLVGINMSKK | SEQ ID NO: 234 | HLA-A3 | 2 |
| PB1 | GTFEFTSFFY | SEQ ID NO: 235 | HLA-A3 | 4 |
| PB1 | TFEFTSFFYR | SEQ ID NO: 236 | HLA-A3 | 4 |
| PB1 | AQMALQLFIK | SEQ ID NO: 237 | HLA-A3 | 2 |
| PB1 | LQLFIKDYR | SEQ ID NO: 238 | HLA-A3 | 3 |
| PB1 | ATTHSWIPK | SEQ ID NO: 239 | HLA-A3 | 4 |
| PB1 | ATTHSWIPKR | SEQ ID NO: 240 | HLA-A3 | 2 |
| PB1 | YQKCCTLFEK | SEQ ID NO: 241 | HLA-A3 | 2 |
| PB1 | YQKCCNLFEK | SEQ ID NO: 242 | HLA-A3 | 2 |
| PB1 | KFFPSSSYR | SEQ ID NO: 243 | HLA-A3 | 4 |
| PB1 | SYLIRALTL | SEQ ID NO: 244 | HLA-A24 | 2 |
| PB1 | MFLAMITYI | SEQ ID NO: 245 | HLA-A24 | 2 |
| PB1 | RYTKTTYWW | SEQ ID NO: 246 | HLA-A24 | 2 |
| PB1 | SYINRTGTF | SEQ ID NO: 247 | HLA-A24 | 3 |
| PB1 | FYRGFVANF | SEQ ID NO: 248 | HLA-A24 | 2 |
| PB1 | LYNIRNLHI | SEQ ID NO: 249 | HLA-A24 | 2 |
| PB1 | MYQKCCNLF | SEQ ID NO: 250 | HLA-A24 | 2 |
| PB1 | MYQKCCTLF | SEQ ID NO: 251 | HLA-A24 | 3 |
| PB1 | NPRMFLAMI | SEQ ID NO: 252 | HLA-B7 | 1 |
| PB1 | QPEWFRNVL | SEQ ID NO: 253 | HLA-B7 | 1 |
| PB1 | APIMFSNKM | SEQ ID NO: 254 | HLA-B7 | 2 |
| PB1 | IPAEMLASI | SEQ ID NO: 255 | HLA-B7 | 4 |
| PB1 | SPGMMMGMF | SEQ ID NO: 256 | HLA-B7 | 1 |
| PB1 | GPATAQMAL | SEQ ID NO: 257 | HLA-B7 | 2 |
| PB1 | MPAHGPAKSM | SEQ ID NO: 258 | HLA-B7 | 4 |
| PB1 | IPKRNRSIL | SEQ ID NO: 259 | HLA-B7 | 1 |
| PB1 | FPSSSYRRPV | SEQ ID NO: 260 | HLA-B7 | 4 |
| PB1 | RPVGISSMV | SEQ ID NO: 261 | HLA-B7 | 1 |
| PB1 | CEKLEQSGL | SEQ ID NO: 262 | HLA-B44 | 4 |
| PB1 | IEKIRPLLI | SEQ ID NO: 263 | HLA-B44 | 5 |
| PB1 | IESVNNAVV | SEQ ID NO: 264 | HLA-B44 | 6 |

[a]See footnote (a) to Table 2.

In certain embodiments, the first heterologous sequence encodes a full-length influenza PB2 protein, or a portion thereof, such as an epitope (e.g., one or more HTL or CTL epitopes). In certain embodiments, the portion or epitope is from an evolutionarily conserved sequence. In certain embodiments, the epitope is a HTL or CTL epitope that exhibits degenerate binding to HLA class I or class II molecules, respectively, and/or has the capacity to generate a human interferon gamma (IFN-γ) response upon ELISPOT assay analysis using human PBMC. As discussed above, the HTL or CTL epitopes can form a concatamer wherein a single HTL or CTL epitope is repeated and/or wherein a plurality of HTL and/or CTL epitopes are joined together. In certain embodiments, the first heterologous sequence encodes one or more PB2 HTL epitopes selected from the group shown in Table 1 (i.e., SEQ ID NOs: 55-61). In other embodiments, the first heterologous sequence encodes one or more PB2 CTL epitopes selected from the group shown in Table 12 (i.e., SEQ ID NOs: 265-309).

TABLE 12

| Protein | CTL Peptide | SEQ ID NO. | HLA Supertype | # Alleles Bound[a] |
|---|---|---|---|---|
| PB2 | STVHYPKVY | SEQ ID NO: 265 | HLA-A1 | 2 |
| PB2 | KISPLMVAY | SEQ ID NO: 266 | HLA-A1 | 2 |
| PB2 | RVSKMGVDEY | SEQ ID NO: 267 | HLA-A1 | 1 |
| PB2 | GTEKLTITY | SEQ ID NO: 268 | HLA-A1 | 1 |
| PB2 | QWSQEPTMLY | SEQ ID NO: 269 | HLA-A1 | 2 |
| PB2 | WSQDPTMLY | SEQ ID NO: 270 | HLA-A1 | 4 |
| PB2 | LQDCKIAPL | SEQ ID NO: 271 | HLA-A2 | 4 |
| PB2 | FQNWGIEHI | SEQ ID NO: 272 | HLA-A2 | 4 |
| PB2 | FQNWGIEPI | SEQ ID NO: 273 | HLA-A2 | 4 |
| PB2 | RMQFSSLTV | SEQ ID NO: 274 | HLA-A2 | 4 |
| PB2 | TTVDHMAIIK | SEQ ID NO: 275 | HLA-A3 | 2 |
| PB2 | TVDHMAIIK | SEQ ID NO: 276 | HLA-A3 | 2 |
| PB2 | RIMEMIPER | SEQ ID NO: 277 | HLA-A3 | 4 |
| PB2 | TTSTVHYPK | SEQ ID NO: 278 | HLA-A3 | 5 |
| PB2 | STVHYPKVYK | SEQ ID NO: 279 | HLA-A3 | 4 |
| PB2 | TVHYPKVYK | SEQ ID NO: 280 | HLA-A3 | 5 |
| PB2 | KVYKTYFEK | SEQ ID NO: 281 | HLA-A3 | 3 |
| PB2 | GTFGPVHFR | SEQ ID NO: 282 | HLA-A3 | 5 |
| PB2 | SFSFGGFTFK | SEQ ID NO: 283 | HLA-A3 | 5 |
| PB2 | FSFGGFTFK | SEQ ID NO: 284 | HLA-A3 | 5 |
| PB2 | FSFGGFTFKR | SEQ ID NO: 285 | HLA-A3 | 5 |
| PB2 | SFGGFTFKR | SEQ ID NO: 286 | HLA-A3 | 4 |
| PB2 | VLTGNLQTLK | SEQ ID NO: 287 | HLA-A3 | 2 |
| PB2 | HQLLRHFQK | SEQ ID NO: 288 | HLA-A3 | 3 |
| PB2 | VVSIDRFLR | SEQ ID NO: 289 | HLA-A3 | 4 |
| PB2 | SQDPTMLYNK | SEQ ID NO: 290 | HLA-A3 | 2 |
| PB2 | GTFDTVQIIK | SEQ ID NO: 291 | HLA-A3 | 3 |
| PB2 | LLPFAAAPPK | SEQ ID NO: 292 | HLA-A3 | 4 |
| PB2 | VLRGFLILGK | SEQ ID NO: 293 | HLA-A3 | 3 |
| PB2 | SINELSNLAK | SEQ ID NO: 294 | HLA-A3 | 3 |
| PB2 | WMMAMKYPI | SEQ ID NO: 295 | HLA-A24 | 2 |
| PB2 | HYPKVYKTYF | SEQ ID NO: 296 | HLA-A24 | 2 |
| PB2 | LYNKMEFEPF | SEQ ID NO: 297 | HLA-A24 | 2 |
| PB2 | QYSGFVRTLF | SEQ ID NO: 298 | HLA-A24 | 2 |
| PB2 | NPALRMKWM | SEQ ID NO: 299 | HLA-B7 | 1 |
| PB2 | YPKVYKTYF | SEQ ID NO: 300 | HLA-B7 | 2 |
| PB2 | GPVHFRNQV | SEQ ID NO: 301 | HLA-B7 | 1 |
| PB2 | FPNEVGARIL | SEQ ID NO: 302 | HLA-B7 | 5 |
| PB2 | SPLMVAYML | SEQ ID NO: 303 | HLA-B7 | 4 |
| PB2 | APPKQSRMQF | SEQ ID NO: 304 | HLA-B7 | 1 |
| PB2 | APPEQSRMQF | SEQ ID NO: 305 | HLA-B7 | 1 |
| PB2 | GPALSINEL | SEQ ID NO: 306 | HLA-B7 | 1 |
| PB2 | RELVRKTRFL | SEQ ID NO: 307 | HLA-B44 | 4 |
| PB2 | MEFEPFQSL | SEQ ID NO: 308 | HLA-B44 | 5 |
| PB2 | KEDKRYGPAL | SEQ ID NO: 309 | HLA-B44 | 6 |

[a] See footnote (a) to Table 2.

In certain embodiments, the first heterologous sequence encodes a plurality of HTL epitopes listed in Table 1 (i.e., SEQ ID NOs: 1-61), wherein the plurality of HTL epitopes includes epitopes from a plurality of Influenza proteins. The encoded sequence can, for example, encode a multimer of HTL epitopes from different Influenza proteins. In certain embodiments, the plurality of HTL epitopes are selected, in part, based on percent conservation of the sequence, number and type of HLA class II alleles bound (e.g., to ensure binding to a broad spectrum of HLA class II alleles), IFN-γ response upon ELISPOT assay analysis using human PBMC, or any combination thereof. In certain embodiments, the first heterologous sequence encodes one or more HTL epitopes selected from the group listed in Table 13. In certain embodiments, the first heterologous sequence encodes a multimer of all of the HTL epitopes listed in Table 13.

TABLE 13

| Influenza Protein | HTL Peptide | SEQ ID NO. | Cons. (%)[a] | # Alleles Bound[b] | Recall[c] |
|---|---|---|---|---|---|
| M1 | KGILGFVFTLTVPSE | SEQ ID NO: 13 | 94 | 11 | 6 |
| M1 | YRKLKREITFHGAKE | SEQ ID NO: 14 | 61 | 11 | 10 |
| M1 | MGTVTTEVALGLVCA | SEQ ID NO: 15 | 22 | 7 | 5 |
| M1 | NPLIRHENRMVLAST | SEQ ID NO: 16 | 98 | 11 | 5 |
| M1 | AMEVASQARQMVQAM | SEQ ID NO: 17 | 75 | 8 | 3 |
| NP | IGRFYIQMCTELKLSDYEG | SEQ ID NO: 20 | 67 | 12 | 4 |
| NP | QNSITIERMVLSAFD | SEQ ID NO: 21 | 69 | 8 | 5 |

TABLE 13-continued

| Influenza Protein | HTL Peptide | SEQ ID NO. | Cons. (%)[a] | # Alleles Bound[b] | Recall[c] |
|---|---|---|---|---|---|
| NP | VGTMVMELIRMIKRG | SEQ ID NO: 22 | 73 | 10 | 8 |
| NP | DLIFLARSALILRGS | SEQ ID NO: 23 | 92 | 12 | 4 |
| NP | RSALILRGSVAHKSC | SEQ ID NO: 24 | 100 | 12 | 2 |
| NP | KSQLVWMACHSAAFE | SEQ ID NO: 25 | 71 | 11 | 2 |
| NP | AGQISVQPTFSVQRN | SEQ ID NO: 26 | 61 | 10 | 5 |
| NS1 | EGAIVGEISPLPSLPGHTD | SEQ ID NO: 28 | 27 | 8 | 5 |
| NS2 | SLKLYRDSLGEAVMR | SEQ ID NO: 30 | 46 | 8 | 3 |
| NS2 | IRWLIEEVRHRLRIT | SEQ ID NO: 31 | 8 | 7 | 4 |
| NS2 | FEQITFMQALQLLLE | SEQ ID NO: 32 | 58 | 10 | 1 |
| NS2 | ITFMQALQLLLEVEQ | SEQ ID NO: 33 | 58 | 10 | 1 |
| PA | RREVHIYYLEKANKI | SEQ ID NO: 34 | 76 | 11 | 4 |
| PA | LFTIRQEMASRGLWD | SEQ ID NO: 35 | 71 | 11 | 3 |
| PA | EPFLKTTPRPLRLPD | SEQ ID NO: 36 | 35 | 10 | 2 |
| PA | RSKFLLMDALKLSIED | SEQ ID NO: 37 | 90 | 13 | 2 |
| PA | VAPIEHIASMRRNYF | SEQ ID NO: 38 | 75 | 11 | 4 |
| PA | EYIMKGVYINTALLN | SEQ ID NO: 39 | 98 | 7 | 4 |
| PA | RPMFLYVRTNGTSKI | SEQ ID NO: 40 | 90 | 12 | 3 |
| PB1 | PTLLFLKVPAQNAIST | SEQ ID NO: 41 | 71 | 11 | 2 |
| PB1 | SYLIRALTLNTMTKD | SEQ ID NO: 42 | 88 | 12 | 2 |
| PB1 | FLAMITYITRNQPEW | SEQ ID NO: 43 | 76 | 11 | 3 |
| PB1 | QPEWFRNVLSIAPIMF | SEQ ID NO: 44 | 76 | 12 | 2 |
| PB1 | FRNVLSIAPIMFSNKM | SEQ ID NO: 45 | 76 | 12 | 1 |
| PB1 | IAPIMFSNKMARLGK | SEQ ID NO: 46 | 84 | 10 | 1 |
| PB1 | KGYMFESKSMKLRTQI | SEQ ID NO: 47 | 76 | 13 | 2 |
| PB1 | MMGMFNMLSTVLGVS | SEQ ID NO: 49 | 100 | 12 | 10 |
| PB1 | DFALIVNAPNHEGIQ | SEQ ID NO: 50 | 84 | 11 | 3 |
| PB1 | YGFVANFSMELPSFG | SEQ ID NO: 51 | 90 | 9 | 3 |
| PB1 | GVTVIKNNMINNDLGP | SEQ ID NO: 52 | 92 | 8 | 2 |
| PB1 | PNLYNIRNLHIPEVC | SEQ ID NO: 53 | 80 | 9 | 2 |
| PB1 | ISSMVEAMVSRARID | SEQ ID NO: 54 | 78 | 8 | 1 |
| PB2 | KWMMAMKYPITADKR | SEQ ID NO: 55 | 82 | 8 | 1 |
| PB2 | GARILTSESQLTITK | SEQ ID NO: 56 | 82 | 8 | 2 |
| PB2 | KAAMGLRISSSFSFG | SEQ ID NO: 57 | 78 | 13 | 3 |
| PB2 | IKAVRGDLNFVNRAN | SEQ ID NO: 58 | 90 | 9 | 4 |
| PB2 | LRHFQKDAKVLFQNW | SEQ ID NO: 59 | 88 | 8 | 1 |
| PB2 | QWIIRNWETVKIQWS | SEQ ID NO: 60 | 76 | 11 | 3 |
| PB2 | RMQFSSLTVNVRGSG | SEQ ID NO: 61 | 96 | 11 | 2 |

[a] See footnote (a) to Table 1.
[b] See footnote (b) to Table 1.
[c] See footnote (c) to Table 1.

In other embodiments, the first heterologous sequence encodes a plurality of CTL epitopes listed in Tables 2-3 and 5-12 (i.e., SEQ ID NOs: 62-309), wherein the plurality of CTL epitopes includes epitopes from a plurality of Influenza proteins. The encoded sequence can, for example, encode a multimer of CTL epitopes from different Influenza proteins. In certain embodiments, the plurality of CTL epitopes are selected, in part, based on percent conservation of the sequence, number and type of HLA class I alleles bound (e.g., to ensure binding to a broad spectrum of HLA class I alleles), IFN-γ response upon ELISPOT assay analysis using human PBMC, or any combination thereof. In certain embodiments, the first heterologous sequence encodes one or more CTL epitopes selected from the group listed in Table 14. In certain embodiments, the first heterologous sequence encodes a multimer of all the CTL epitopes listed in Table 14.

TABLE 14

| Protein | CTL Peptide | SEQ ID NO. | HLA Super type | # Alleles Bound[a] |
|---|---|---|---|---|
| NP | CTELKLSDY | SEQ ID NO: 111 | HLA-A1 | 1 |
| NP | HSNLNDATY | SEQ ID NO: 112 | HLA-A1 | 2 |
| NP | KSCLPACVY | SEQ ID NO: 113 | HLA-A1 | 2 |
| PB1 | YSHGTGTGY | SEQ ID NO: 206 | HLA-A1 | 4 |
| PB1 | LVSDGGPNLY | SEQ ID NO: 213 | HLA-A1 | 3 |
| PB2 | KISPLMVAY | SEQ ID NO: 266 | HLA-A1 | 2 |
| PB2 | GTEKLTITY | SEQ ID NO: 268 | HLA-A1 | 1 |
| M1 | GILGFVFTL | SEQ ID NO: 70 | HLA-A2 | 4 |
| M1 | RMGTVTTEV | SEQ ID NO: 72 | HLA-A2 | 4 |
| NS1 | FQVDCFLWHV | SEQ ID NO: 141 | HLA-A2 | 5 |
| NS2 | MQALQLLLEV | SEQ ID NO: 155 | HLA-A2 | 5 |
| NP | CLPACVYGL | SEQ ID NO: 114 | HLA-A2 | 4 |
| NP | FQGRGVFEL | SEQ ID NO: 116 | HLA-A2 | 4 |
| PA | FMYSDFHFI | SEQ ID NO: 170 | HLA-A2 | 5 |
| PB1 | RLIDFLKDV | SEQ ID NO: 216 | HLA-A2 | 4 |
| PB1 | QIRGFVYFV | SEQ ID NO: 217 | HLA-A2 | 4 |
| PB1 | NMLSTVLGV | SEQ ID NO: 221 | HLA-A2 | 4 |
| PB1 | FVANFSMEL | SEQ ID NO: 222 | HLA-A2 | 5 |
| M1 | ASCMGLIYNR | SEQ ID NO: 74 | HLA-A3 | 4 |
| M2 | RLFFKCIYRR | SEQ ID NO: 82 | HLA-A3 | 5 |
| NP | SVQPTFSVQR | SEQ ID NO: 124 | HLA-A3 | 4 |
| NP | SVQRNLPFER | SEQ ID NO: 126 | HLA-A3 | 4 |
| NS1 | AIMDKNIILK | SEQ ID NO: 146 | HLA-A3 | 3 |
| NS2 | TQFESLKLYR | SEQ ID NO: 157 | HLA-A3 | 3 |
| PA | KFLPDLYDYK | SEQ ID NO: 177 | HLA-A3 | 2 |
| PB1 | KLVGINMSKK | SEQ ID NO: 234 | HLA-A3 | 2 |
| PB1 | GTFEFTSFFY | SEQ ID NO: 235 | HLA-A3 | 4 |
| PB2 | SFSFGGFTFK | SEQ ID NO: 283 | HLA-A3 | 5 |

TABLE 14-continued

| Protein | CTL Peptide | SEQ ID NO. | HLA Super type | # Alleles Bound[a] |
|---|---|---|---|---|
| PB2 | VLRGFLILGK | SEQ ID NO: 293 | HLA-A3 | 3 |
| NP | FYIQMCTEL | SEQ ID NO: 128 | HLA-A24 | 2 |
| PA | YYLEKANKI | SEQ ID NO: 191 | HLA-A24 | 2 |
| PB1 | FYRGFVANF | SEQ ID NO: 248 | HLA-A24 | 2 |
| NS1 | VPASRYLTDM | SEQ ID NO: 147 | HLA-B7 | 2 |
| NP | LPRRSGAAGA | SEQ ID NO: 132 | HLA-B7 | 2 |
| NP | LPFERATIM | SEQ ID NO: 134 | HLA-B7 | 5 |
| PB1 | QPEWFRNVL | SEQ ID NO: 253 | HLA-B7 | 1 |
| PB1 | IPKRNRSIL | SEQ ID NO: 259 | HLA-B7 | 1 |
| M1 | TEVETYVLSI | SEQ ID NO: 76 | HLA-B44 | 4 |
| M1 | SEQAAEAMEV | SEQ ID NO: 78 | HLA-B44 | 6 |
| NP | GERQNATEI | SEQ ID NO: 135 | HLA-B44 | 4 |
| NS1 | LETLILLRAF | SEQ ID NO: 150 | HLA-B44 | 4 |
| NS1 | GEISPLPSL | SEQ ID NO: 151 | HLA-B44 | 6 |
| NS2 | QEIRTFSFQL | SEQ ID NO: 163 | HLA-B44 | 4 |
| PA | CELTDSSWI[b] | SEQ ID NO: 310 | HLA-B44 | n/a |
| NP | YERMCNILKG[b] | SEQ ID NO: 311 | HLA-B44 | n/a |

[a]See footnote (a) to Table 2.
[b]Assarsson et al. (2008), J Virol 82: 12241.

The first heterologous sequence can encode an immunogenic protein or antigen from any infectious pathogen disclosed herein. For instance, in some embodiments, the first heterologous sequence encodes an immunogenic protein from a virus, a bacterium, a protist, and/or a fungus. In one embodiment, the first heterologous sequence encodes an immunogenic protein from influenza virus, poliovirus, human immunodeficiency virus (HIV), human papilloma virus (HPV), chikungunya virus, and/or Dengue Fever virus. In another embodiment, the first heterologous sequence encodes an immunogenic protein from *Bacillus* (e.g., *Bacillus anthracis*), *Mycobacterium* (e.g., *Mycobacterium tuberculosis*, *Mycobacterium Leprae*), *Shigella* (e.g., *Shigella sonnei, Shigella dysenteriae, Shigella flexneri*), *Streptococcus*, and/or *Escherichia* (e.g., enterotoxigenic, enterohemorrhagic or Shiga toxin-producing *E. coli*). In another embodiment, the first heterologous sequence encodes an immunogenic protein from enterotoxigenic *E. coli* (ETEC), enteropathogenic *E. coli* (EPEC), enteroinvasive *E. coli* (EIEC), enterohemorrhagic *E. coli* (EHEC), and/or enteroaggregative *E. coli* (EAEC). In still another embodiment, the first heterologous sequence encodes an immunogenic protein from *Burkholderia* (e.g., *Burkholderia cepacia* complex), *Pseudomonas* (e.g., *Pseudomonas aeruginosa*), *Clostridium* (e.g., *Clostridium botulinum, Clostridium tetani, Clostridium difficile*), *Staphylococcus* (e.g., methicillin resistant, multidrug resistant, or oxacillin resistant *Staphylococcus aureus*), *Enterococcus* (e.g., *Enterococcus faecalis, Enterococcus faecum*, Vancomycin-resistant *enterococcus* (VRE)), *Streptococcus* (e.g., *Streptococcus pneumoniae, Streptococcus pyogenes, Streptococcus agalactiae*), and/or *Vibrio* (e.g.,

*Vibrio cholerae*). In another embodiment, the first heterologous sequence encodes an immunogenic protein from *Camphylobacter* (e.g., *Camphylobacter jejuni*), *Bordetella* (e.g., *Bordetella pertussis*), *Chlamydia* (e.g., *Chlamydia pneumonia, Chlamydia trachomatis*), *Corynebacterium* (e.g., *Corynebacterium diphtheria*), *Legionella* (e.g., *Legionella pneumophila*), *Listeria* (e.g., *Listeria monocytogenes*), *Neisseria* (e.g., *Neisseria gonorrhoeae, Neisseria meningitidis*), *Salmonella* (e.g., *Salmonella enterica, Salmonella typhi, Salmonella typhimurium*), *Yersinia* (e.g., *Yersinia pestis*), *Haemophilus* (e.g., *Haemophilus influenzae*), *Helicobacter* (e.g., *Helicobacter pylori*), *Coxiella* (e.g., *Coxiella burnetti*), and/or *Francisella* (e.g., *Francisella tularensis*). In certain embodiments, the first heterologous sequence encodes an immunogenic protein from influenza, HIV, HPV, *Bacillus anthracis, Plasmodium* and/or *Shigella*. In still other embodiments, the first heterologous sequence encodes an immunogenic protein from influenza, HIV, and/or *Bacillus anthracis*.

Influenza antigens encoded by the first heterologous sequence can be from any influenza strain, presently existing or subsequently isolated, including, e.g., a strain associated with the Spanish flu of 1918 (H1N1), the Asian flu of 1957 (H2N2), the Hong Kong flu of 1968 (H3N2), the Hong Kong flu of 1997 (H5N1), the Vietnam flu of 2004 (H5N1), the swine flu of 2009 (H1N1) etc. Thus, for example, the HA antigen can be an H1, H2, H3, H4, H5, H6, H7, H8, H9, H10, H11, H12, H13, H14, H15, H16, or B HA antigen, while the NA antigen can, for example, be an N1, N2, N3, N4, N5, N6, N7, N8, or N9 NA antigen. In some embodiments, the HA antigen is an H1, H3, H5, or B HA antigen. Non-limiting examples of influenza strains that can be the basis for a heterologous sequence of the invention include: A/goose/Guangdong/1/96 (H5N1); A/Brevig Mission/1/1918 (H1N1); A/Wilson-Smith/33 (H1N1); A/Puerto Rico/8/34/Mount Sinai (H1N1); A/Fort Monmouth/1/47 (H1N1); A/USSR/90/1977 (H1N1); A/New Calcdonia/20/1999 (H1N1); A/Solomon Islands/3/2006 (H1N1); A/Brisbane/59/2007 (H1N1); A/California/7/2009 (H1N1); A/California/14/2009 (H1N1); A/California/08/2009 (H1N1); A/California/05/2009 (H1N1); A/Texas/04/2009 (H1N1); A/Mexico/InDRE4114/2009 (H1N1); A/New York/1669/2009 (H1N1); A/Canada-AB/RV1532/2009 (H1N1); A/Leningrad/134/47/57 (H2N2); A/Ann Arbor/6/60 (H2N2); A/Berlin/3/64 (H2N2); A/Tokyo/3/67 (H2N2); A/Singapore/1/57 (H2N2); A/Hong Kong/1/68 (H3N2); A/Albany/1/76 (H3N2); A/Panama/2007/99 (H3N2); A/Wisconsin/67/05 (H3N2); A/Hong Kong/1774/99 (H3N2); A/Moscow/10/99 (H3N2); A/Hiroshima/52/2005 (H3N2); A/California/7/2004 (H3N2); A/New York/55/2004 (H3N2); A/Brisbane/10/2007 (H3N2); A/Perth/16/2009 (H3N2); A/goose/Guiyang/337/2006 (H5N1) Glade 4; A/HK/156/97 (H5N1); A/HK/483/97 (H5N1); A/VietNam/1194/2004 (H5N1) Glade 1; A/VietNam/1203/2004 (H5N1) Glade 1; A/duck/NCVD1/07 (H5N1); A/chicken/VietNam/NCVD-21/07 (H5N1); A/Indonesia/5/05 (H5N1) Glade 2.1; A/Turkey/65-596/06 (H5N1) Glade 2.2; A/chicken/India/NIV33487/2006 (H5N1) Glade 2.2; A/turkey/Turkey/1/2005 (H5N1) Glade 2.2; A/Egypt/902782/2006 (H5N1); A/Egypt/2321/2007 (H5N1); A/Egypt/3300-NAMRU3/2008 (H5N1); A/Anhui/1/2005 (H5N1); A/China/GD01/2006 (H5N1); A/common magpie/Hong Kong/50525/07 (H5N1) Glade 2.3.2; A/Japanese white-eye/Hong Kong/1038/2006 (H5N1) Glade 2.3.4; A/chicken/VietNam/NCVD-15/2007 (H5N1); A/chicken/Italy/2335/2000 (H7N1); A/turkey/Italy/3675/99 (H7N1); A/chicken/New York/21211-2/05 (H7N2); A/New York/107/03 (H7N2); A/chicken/British Columbia/GSC human B/04 (H7N3); A/Canada/rv504/04 (H7N3); A/chicken/British Columbia/CN-6/04 (H7N3); A/equine/San Paulo/4/76 (H7N7); A/seal/Mass/1/1980 (H7N7); A/chicken/Victoria/1/1985 (H7N7); A/chicken/Netherlands/2586/2003 (H7N7); A/mallard/California/HKWF1971/2007 (H7N7); A/chicken/Beijing/1/94 (H9N2); A/quail/Hong Kong/G1/1997 (H9N2); A/Korea/KBNP-0028/2000 (H9N2); A/chicken/Hong Kong/G9/97 (H9N2); A/chicken/Hong Kong/CSW153/2003 (H9N2); A/chicken/Shantou/6781/2005 (H9N2); A/chicken/Jiangsu/L1/2004 (H9N2); A/Hong Kong/1073/99 (H9N2); A/Hong Kong/2108/2003 (H9N2); A/chicken/Shiraz/AIV-IR004/2007 (H9N2); A/chicken/Zibo/L2/2008 (H9N2); A/chicken/Henan/L1/2008 (H9N2); A/avian/Israel/313/2008 (H9N2) and B/Brisbane/60/2008. Additional influenza strains can be readily identified by persons skilled in the art. For example, Table 1 of WO 2008/054540 provides an extensive list of different influenza strains that have been isolated to date, as does the website for the National Center for Biotechnology Information (NCBI).

In certain embodiments, the first heterologous sequence encodes an influenza HA antigen selected from H1, H3, H5, or B influenza virus. The HA antigen may, in some embodiments, be derived from one or more of the strains selected from the group consisting of A/Vietnam/1194/2004, A/Vietnam/1203/2004, A/Anhui/1/2005, A/Egypt/2321/2007, A/Egypt/3300-NAMRU3/2008, A/Perth/16/2009, A/California/05/2009, or B/Brisbane/60/2008. In some embodiments, the first heterologous sequence encodes an influenza NP or M1 antigen. In one embodiment, the NP or M1 antigen is derived from A/Texas/04/2009 or A/California/08/2009 influenza strains.

In other embodiments, the first heterologous sequence encodes an antigen from human papilloma virus (HPV). The HPV can be of any known or later discovered strain (e.g., HPV-1, HPV-2, HPV-6, HPV-11, HPV-16, HPV-18, HPV-31, HPV-45, etc.). In one embodiment, the first heterologous sequence encodes an antigen from a HPV-16 or HPV-18 strain. In certain embodiments, the HPV antigen is a surface antigen, such as full-length L1 protein or a fragment thereof (e.g., an evolutionarily conserved epitope and/or a HTL or CTL epitope). In one embodiment, the first heterologous sequence encodes a full-length L1 protein that is fully or partially codon-optimized. In other embodiments, the HPV antigen is full-length L2 or a fragment thereof (e.g., a evolutionarily conserved epitope and/or a HTL or CTL epitope). In other embodiments, the HPV antigen is a L1 hybrid polypeptide or a L1/L2 hybrid polypeptide. For instance, in one particular embodiment, the HPV antigen is a L1 polypeptide comprising a fragment of the L2 polypeptide (e.g., an L2 fragment can be inserted into a loop of the L1 polypeptide). In still other embodiments, the HPV antigen is a full-length E6 or E7 protein, or a fragment thereof (e.g., an evolutionarily conserved epitope and/or a HTL or CTL epitope). In still other embodiments, the HPV antigen is a fusion protein comprising L1, L2 and/or E6 and E7 proteins. For example, in some embodiments, the HPV antigen is a fusion protein comprising a L1/L2 hybrid polypeptide fused to an E7 protein. In other embodiments, the HPV antigen is a fusion protein comprising a L1/L2 hybrid polypeptide fused to an E6 protein.

In other embodiments, the first heterologous sequence encodes an antigen from human immunodeficiency virus (HIV). The HIV can be of any known or later discovered strain (e.g., HIV-1, HIV-2, etc.). In certain embodiments, the HIV antigen is a surface antigen, such as full-length Env protein (e.g., gp160) or a fragment or oligomer thereof (e.g., gp140, gp120, gp41, an evolutionarily conserved epitope, and/or a HTL or CTL epitope). In other embodiments, the HIV antigen is a full-length capsid protein (p24), matrix protein (p17), or a fragment thereof (e.g., a evolutionarily conserved epitope and/or a HTL or CTL epitope). In other embodiments, the HIV antigen is a Tat (e.g., p16 or p14), Rev (p19), Vif (p23), Vpr (p14), Nef (p27), Vpu (p16), or Gag protein. The HIV antigen can be any HIV protein, full-length or otherwise, such as a HTL or CTL epitope, and can be any evolutionarily conserved sequence. In some embodiments, the HIV antigen sequence can be engineered to contain heterologous trimerization domains (e.g., from yeast GCN, such as from GCN4, and T4 bacteriophage fibritin-FT motifs) or certain signal sequences for post-translational modifications, such as glycosylphosphatidylinisotol (GPI) anchor sites. For instance, in one embodiment, an HIV envelope protein, such as gp140 or gp120, can be modified to contain a GPI anchor site. In another embodiment, an HIV gp140 sequence can be modified to contain a heterologous GCN trimerization domain and/or a GPI anchor site. In some embodiments, the GCN trimerization domain or GPI anchor site is fused to the carboxyl terminus of an HIV envelope protein sequence (e.g., HIV gp140 sequence).

In other embodiments, the first heterologous sequence encodes an antigen from a *Bacillus* bacterium. The *Bacillus* can be any of a number of pathogenic species (e.g., *B. anthracis, B. cereus*, etc.) and can be any known or later discovered isolate of such a species. In certain embodiments, the *Bacillus* antigen is a surface antigen, such as protein resident in the cellular membrane, or a fragment thereof (e.g., an evolutionarily conserved epitope, and/or a HTL or CTL epitope). In other embodiments, the *Bacillus* antigen is an intracellular protein or a fragment thereof (e.g., an evolutionarily conserved epitope, and/or a HTL or CTL epitope). In certain embodiments, the *Bacillus* antigen is associated with host cell entry. For example, the antigen can be a target cell-binding protein (e.g., protective antigen (PrAg or PA)), a metallopeptidase (e.g., lethal factor (LF)), an adenylate cyclase (e.g., edema factor (EF)), or fragment thereof (e.g., an evolutionarily conserved epitope, and/or a HTL or CTL epitope). In some embodiments, the *Bacillus* antigen can be modified to delete a thermolysin cleavage site or contain a GPI anchor. In one embodiment, the first heterologous sequence encodes protective antigen or a modified protective antigen which has been modified to remove a thermolysin cleavage site or contain a GPI anchor.

In other embodiments, the first heterologous sequence encodes an antigen from a *Shigella* bacterium. The *Shigella* can be any of a number of pathogenic species (e.g., *S. sonnei, S. dysenteriae, S. flexneri*, etc.) and can be any known or later discovered isolate of such a species. In certain embodiments, the *Shigella* antigen is a surface antigen, such as protein resident in or associated with the cellular membrane, such as an integral membrane protein or a peripheral membrane protein, or a fragment thereof (e.g., an evolutionarily conserved epitope, and/or a HTL or CTL epitope). For example, the antigen can be an outer membrane protein, such as Karp strain p56. In other embodiments, the *Shigella* antigen is an intracellular protein or a fragment thereof (e.g., an evolutionarily conserved epitope, and/or a HTL or CTL epitope). In certain embodiments, the *Shigella* antigen is associated with host cell entry, such as invasion proteins IpaB, IpaC, or IpaD protein. In another embodiment, the *Shigella* antigens are universal antigens comprising IcsP and/or SigA polypeptides.

In other embodiments, the first heterologous sequence encodes an antigen from a *Mycobacterium*. The *Mycobacterium* can be any of a number of pathogenic species (e.g., *M. tuberculosis, M. leprae, M. lepromatosis*, etc.) and can be any known or later discovered isolate of such a species. In certain embodiments, the *Mycobacterium* antigen is a surface antigen, such as protein resident in or associated with the cellular membrane, such as an integral membrane protein or a peripheral membrane protein, or a fragment thereof (e.g., an evolutionarily conserved epitope, and/or a HTL or CTL epitope). In other embodiments, the *Mycobacterium* antigen is an intracellular protein or a fragment thereof (e.g., an evolutionarily conserved epitope, and/or a HTL or CTL epitope). In certain embodiments, the *Mycobacterium* antigen is selected from the group consisting of Ag85A, Ag85B, Ag85C, ESAT-6, CFP-10, HspX, and combinations thereof.

In other embodiments, the first heterologous sequence encodes an antigen from a *Plasmodium*. The *Plasmodium* can be any of a number of pathogenic species (e.g., *P. falciparum, P. vivax, P. ovale, P. malariae*, etc.) and can be any known or later discovered isolate of such a species. In certain embodiments, the *Plasmodium* antigen is a surface antigen, such as protein resident in or associated with the cellular membrane, such as an integral membrane protein or a peripheral membrane protein, or a fragment thereof (e.g., an evolutionarily conserved epitope, and/or a HTL or CTL epitope). In other embodiments, the *Plasmodium* antigen is an intracellular protein or a fragment thereof (e.g., an evolutionarily conserved epitope, and/or a HTL or CTL epitope). In certain embodiments, the *Plasmodium* antigen is selected from the group consisting of CS, CSP (uncleaved), MSP1, MSP2 (c-terminal p42), LSA1, EBA-175, AMA1, FMP1, Pfs48/45, and MSPS.

In certain embodiments, the first heterologous sequence encodes an antigen from *Streptococcus pneumoniae* (e.g. *Pneumococcus*). In certain embodiments, the *Streptococcus pneumoniae* antigen is a surface antigen, such as protein resident in or associated with the cellular membrane, such as an integral membrane protein or a peripheral membrane protein, or a fragment thereof (e.g., an evolutionarily conserved epitope, and/or a HTL or CTL epitope). In other embodiments, the *Streptococcus pneumoniae* antigen is an intracellular protein or a fragment thereof (e.g., an evolutionarily conserved epitope, and/or a HTL or CTL epitope). In certain embodiments, the *Streptococcus pneumoniae* antigen is selected from the group consisting of pneumococcal surface proteins (e.g., PspA, PspC), pneumolysin (Ply), neuraminidase enzymes (e.g., NanA, NanB), autolysin A (LytA), pneumococcal histidine-triad proteins, PiaA, PiuA, fructose-bisphosphate aldolase (FBA), adhesin A, and pneumolysoid.

In still other embodiments, the first heterologous sequence encodes a surface antigen, internal protein, toxin, invasion-associated protein, protease or other enzymes, heat shock protein, or other antigen from any other infectious pathogen. For example, the surface antigen can be from an infectious pathogen selected from the group consisting of *Bordetalla pertussis, Chlamydia pneumonia* (e.g., membrane protein D, outer membrane protein), *Chlamydia trachomatis* (e.g., membrane protein D, outer membrane protein), *Legionella pneumophilia, Staphylococcus aureus*, including methicillin-resistant, multi-drug-resistant, and oxacillin-resistant strains (e.g., IsdA, IsdB, SdrD, SdrE), *Streptococcus pneumoniae* (e.g., PsPA), *Streptococcus aeruginosa* (e.g., flagellar Ag, porins), *Streptococcus pyogenes* (e.g., M protein, Fibronectin-binding protein Sfb1), *Streptococcus agalactiae*, Enterohemorrhagic *E. coli* (e.g., Intimin, FimH adhesin), *Haemophilis influenzae* (e.g., Pili, P1, P2, P4, P6), *Candida* (e.g., A1s1p, A1s3p), *Coccidioides immitis* (e.g., Ag2), *Pseudomonas aeruginosa* (e.g., flagellar antigen, porins), Rous sarcoma virus (e.g., F protein, G protein), human endogenous retrovirus K (e.g., melanoma antigen HERV-K-MEL), herpes virus (e.g., glycoprotein D2), Dengue Fever virus (e.g., DEN1, DEN2, DEN3, DEN4 envelope proteins, tetravalent 4×EDIII domain protein), etc. The toxin can be selected from the group consisting of labile toxin of *Camphylobacter jejuni*, Toxins A and B of *Clostridium difficile*, pyrogenic exotoxins and endotoxins from *Streptococcus pyogenes*, Toxin B of *Vibrio cholerae*, Shiga toxin (e.g., Stx-1, Stx-2) of enterohemorrhagic *E. coli*, the exotoxin A from *Pseudomonas aeruginosa* etc. The protease or other enzymes can be selected from the group consisting of secreted protease factor of *Chlamydia*, pneumolysin, autolysin, or neuraminidase of *Streptococcus pneumoniae*, cystein protease or C5a peptidase from *Streptococcus pyogenes*, urease from *Helicobacter pylori*, urease of *Coccidioides immitis*, His-62, H antigen, and hsp70 of *Histoplasma capsulatum*, etc.

In certain embodiments, the first heterologous sequence encodes all or part of a protein produced by a cancer cell. The protein, or fragment thereof (e.g., cleavage product, structural domain, unit(s) of secondary structure, B-cell epitope, cytotoxic T lymphocyte (CTL) epitope, helper T lymphocyte (HTL) epitope, etc.), can be located on the surface of the cancer cell. For example, the protein or fragment thereof can be highly antigenic and/or a marker for the cancer cell (e.g., a cancer cell-specific marker or an antigen highly enriched on the cancer cells). Alternatively, the protein, or fragment thereof (e.g., cleavage product, structural domain, unit(s) of secondary structure, HTL or CTL epitope, etc.), can be located internal to the cancer cell. For example, the protein or fragment thereof can be a cytosolic protein, a nuclear protein, etc.

In certain embodiments, the first heterologous sequence comprises at least one complete open reading frame (ORF), wherein the at least one complete ORF encodes a discrete polypeptide capable of being expressed in a host cell infected by the adenoviral vector. In certain embodiments, the first heterologous sequence comprises two or more complete ORFs, each of which encodes a discrete polypeptide capable of being expressed in a host cell infected by the adenoviral vector. One or more of the discrete polypeptides can be a full-length protein or fragment thereof, as described above. Likewise, one or more of the discrete polypeptides can be a multimer of protein domains, structural motifs, or epitopes (e.g., B-cell, HTL or CTL epitopes), as described above. For example, in certain embodiments, the first heterologous sequence comprises a first ORF that encodes a full-length protein (e.g., influenza HA) and a second ORF that encodes a multimer of protein domains, structural motifs, or epitopes (e.g., a multimer of one or more influenza M2 sequences selected from Table 4, a multimer of one or more influenza B-cell epitopes, a multimer of one or more influenza HTL epitopes selected from Table 1 or Table 13, or a multimer of one or more influenza CTL epitopes selected from Tables 2-3 and 5-12 or Table 14, etc.).

Thus, in some embodiments, the first heterologous sequence encodes a fusion protein. The fusion protein can comprise one or more epitopes or fragments from antigenic proteins or full-length proteins from the same infectious pathogen or a different infectious pathogen. For instance, in one embodiment, the fusion protein comprises a L1/L2 hybrid polypeptide of HPV as described herein fused to the E6 or E7 proteins of HPV. In some embodiments, the fusion protein comprises a L1/L2 hybrid polypeptide derived from HPV-16 (e.g., full length HPV-16 L1 protein with a HPV-16 L2 fragment inserted into a L1 loop) fused to an E7 protein. In other embodiments, the fusion protein comprises a L1/L2 hybrid polypeptide derived from HPV-18 (e.g., full length HPV-18 L1 protein with a HPV-18 L2 fragment inserted into a L1 loop) fused to an E6 protein. In another embodiment, the fusion protein comprises immunogenic fragments from influenza HA and NA proteins fused together (e.g., neutralization epitopes of influenza HA or NA proteins as described herein). In another embodiment, the fusion protein comprises one or more neutralization epitopes of influenza HA proteins as described herein fused to full-length influenza NA proteins. In still another embodiment, the fusion protein can be a multimer of various epitopes as described herein. For instance, the fusion protein can be a multimer of HTL epitopes, wherein each epitope is connected by a linker sequence (see Example 13 for a representative multimer). In some embodiments, the fusion protein encoded by the first heterologous sequence comprises an antigen from two or more species or serotypes of an infectious pathogen. For instance, the fusion protein can comprise EDIII domains from the envelope proteins from each of the four Dengue Fever virus serotypes 1-4.

In certain embodiments, the first heterologous sequence comprises two complete ORFs, wherein the first and second ORFs are oriented in parallel (e.g., head to tail). In certain related embodiments, the first heterologous sequence further comprises an internal ribosomal entry sequence (IRES) located 3' to the stop codon of the first ORF and 5' to the start codon of the second ORF, thereby allowing the polypeptides encoded by the first and second ORFs to be translated from a single mRNA transcript. Persons skilled in the art can readily identify suitable IRES sequences that are functional in mammalian (e.g., human) cells and how such sequences should be positioned to ensure sufficient translation of the second ORF.

In certain related embodiments, the first heterologous sequence comprises two complete ORFs, wherein the first and second ORFs are oriented in parallel (e.g., head to tail), and further comprises a splice acceptor located 3' to the stop codon of the first ORF and 5' to the start codon of the second ORF, thereby allowing the polypeptides encoded by the first and second ORFs to be translated from a single mRNA transcript or as two separate mRNA transcripts. Persons skilled in the art can identify splicing elements and incorporate them in the correct fashion. Splicing acceptors can be either consensus sequences (such as SV40 splice sites) or non-consensus sequences (such as the Ad5 ADP splice acceptor), depending upon the desired outcome. For example, in the adenovirus major late transcription unit, 3' splice sites having atypical polypyrimidine tracts are preferred late in viral infection. See, e.g., Muhlemann et al. (1995), J. Virology 69(11):7324.

In certain related embodiments, the first heterologous sequence comprises two complete ORFs, wherein the first and second ORFs are oriented in parallel (e.g., head to tail), and further comprises a 2A skipping element (intra-ribosomal self-processing) located in frame between the 3' end of the first ORF (stop codon removed) and 5' in frame to the start codon of the second ORF, thereby allowing the polypeptides encoded by the first and second ORFs to be translated from a single mRNA transcript as a single peptide that "skips" a peptide bond at the location of the A2 element and thereby generates two polypeptides. Persons skilled in the art can identify 2A skipping elements such those derived from the foot and mouth disease virus (FMDV) and picornavirus, and organize them such that the two ORFs form a single continuous peptide.

In certain embodiments, the first heterologous sequence comprises two complete ORFs, wherein the first and second ORFs are oriented end-to-end. For example, the 3' end of the first ORF can be adjacent to the 3' end of the second ORF. Alternatively, the 5' end of the first ORF can be adjacent to the 5' end of the second ORF.

In general, the first heterologous sequence is part of a transcriptional unit that minimally contains a transcriptional enhancer and/or promoter and a poly adenylation sequence. In certain embodiments, the transcriptional unit further comprises one or more introns, one or more splice enhancers, a leader sequence, a consensus Kozak sequence, one or more elements that increase RNA stability and/or processing, or any combination thereof.

In certain embodiments, the first heterologous sequence is under the control of or operably linked to an adenoviral transcriptional and/or translational control sequence. As used herein in this context, "under the control of" and "operably linked to" mean that the transcription and/or translation of an ORF contained in a heterologous sequence is affected by the control sequence. Thus, for example, the transcription and/or translation of the ORF can be increased as a result of the adenoviral transcriptional and/or translational control sequence. In certain embodiments, "operably linked to" indicates that the control sequence and the heterologous sequence are in close proximity to one another. For example, in certain embodiments, an adenoviral control sequence that is operably linked to a heterologous sequence is located within about 100 bps, between about 100 and about 200 bps, between about 200 and about 300 bps, between about 300 and about 400 bps, or between about 400 and about 500 bps from one end of the heterologous sequence.

As used herein, an "adenoviral transcriptional and/or translational control sequence" is a nucleic acid sequence involved in transcriptional and/or translational regulation that is derived from an adenovirus. Such sequences include, but are not limited to, adenoviral promoters (e.g., the Major Late Promoter (MLP) or promoter within the Major Late transcription unit (MLTU)), adenoviral transcriptional enhancers, adenoviral splice acceptor sites (e.g., the native splice acceptor site for MLP-driven transcription of the Ad4 E3 24.8 k ORF or the Ad5 ADP splice acceptor sequence), adenoviral splice enhancers, adenoviral leader sequences (e.g., tripartite leader (TPL) sequences), adenoviral elements that increase RNA stability and/or processing (e.g., cis-acting RNA export elements), and adenoviral poly A signal sequences (e.g., Ad5 E3A polyadenylation signal sequence). The adenoviral transcriptional and/or translational control sequence can be from any adenoviral strain. Thus, an adenoviral vector (e.g., an Ad4 vector) of the invention can comprise an adenoviral transcriptional and/or translational control sequence derived from a different adenoviral strain (i.e., a non-Ad4 strain). The adenoviral transcriptional and/or translational control sequence can have a wild-type sequence (i.e., a sequence found in a naturally-occurring adenovirus) or variant sequence thereof. Adenoviral transcriptional and/or translational control sequences have been described in the art. For example, adenoviral TPL sequences are described in U.S. Patent Application 2006/0115456; enhancers are described in Massie et al. (1995), Biotechnology 13(6):602; and polyadenylation sequences are discussed in Bhat and Wold (1986), J. Virology 57(3):1155. Additional adenoviral transcriptional and/or translational control sequences can be identified by persons skilled in the art.

In certain embodiments, the first heterologous sequence is under (i.e., under the control of) an adenoviral MLP. As used herein, "Major Late Promoter (MLP)" is used interchangeably with Major Late transcription unit (MLTU) promoter. In other embodiments, the first heterologous sequence is under an adenoviral MLP and adenoviral TPL. In other embodiments, the first heterologous sequence is under an adenoviral MLP and operably linked to an adenoviral splice acceptor sequence. In still other embodiments, the first heterologous sequence is under an adenoviral MLP and adenoviral TLP, and operably linked to an adenoviral splice acceptor sequence. In certain embodiments, the adenoviral splice acceptor sequence is a non-consensus sequence. Without intending to be limited by theory, it is believed that non-consensus splice acceptors perform better than consensus splice acceptors when they are used in conjunction with the adenoviral MLP. In any of the foregoing embodiments, the first heterologous sequence can further be operably linked to an adenoviral poly A signal sequence.

In certain embodiments, the first heterologous sequence is under (i.e., under the control of) an endogenous adenoviral transcriptional and/or translational control sequence. As used herein, an "endogenous" adenoviral transcriptional and/or translational control sequence is a nucleic acid sequence involved in transcriptional and/or translational regulation that is native to an adenoviral vector and has not been introduced or moved to a new location by means of recombinant technologies. For example, any Ad4 transcriptional and/or translational control sequence present in an Ad4 adenoviral vector is endogenous to the Ad4 adenoviral vector providing that the location of the sequence has not been modified by recombinant technologies.

In certain embodiments, the first heterologous sequence comprises an exogenous transcriptional and/or translational control sequence. As used herein, an "exogenous" transcriptional and/or translational control sequence refers to either a non-adenoviral transcriptional and/or translational control sequence or an adenoviral transcriptional and/or translational control sequence taken out of its wild-type context and placed into a new context within the heterologous sequence. Examples of exogenous transcriptional and/or translational control sequences include, but are not limited to, promoters functional in mammalian cells (e.g., constitutive promoters, such as a CMV promoter, the Rous sarcoma virus (RSV) LTR promoter, the SV40 promoter, the dihydrofolate reductase (DHFR) promoter, the β-actin promoter, the phosphoglycerol kinase (PGK) promoter, the EF1α promoter (Invitrogen), etc.), enhancer sequences functional in mammalian cells (e.g., CMV or RSV enhancer sequences), splicing signals, splice enhancers, leader sequences, Kozak sequences, sequences that increase RNA stability and/or processing (e.g., cis-acting RNA export elements, Woodchuck Hepatitis Virus posttranslational regulatory element (WPRE)), poly A signal sequences (e.g., bovine growth hormone (BGH) or SV40 poly A signal sequence), etc. Various suitable transcriptional and/or translational control sequences have been described in the prior art. A suitable CMV promoter has been described, for example, in U.S. Patent Application 2006/0115456. WPRE elements have been described, e.g., in Donello et al. (1998), J. Virology 72(6):5085. WPRE elements must be located within the ORF message, typically between the 3' end of the gene and the 5' polyadenylation sequence. Without intending to be limited by theory, it is believed that WPREs function by increasing the efficiency of mRNA translocation from the nucleus, as well as increasing RNA translation and stability. Kozak sequences have also been described, for example, in Kozak, *Nucleic Acid Res* 15(20), 8125-48 (1987).

Suitable transcriptional and/or translational control sequences, whether adenoviral or otherwise, include naturally-occurring sequences as well as modified forms of such sequences. Such modified forms can include one or more base changes (e.g., deletions, insertions, substitutions) designed to enhance a desirable activity associated with the transcriptional and/or translational control sequence or reduce or eliminate an undesirable activity associated with the endogenous adenoviral transcriptional and/or translational control sequence.

In certain embodiments, the first heterologous sequence comprises multiple transcriptional or translational control sequences. For example, the first heterologous sequence can comprise sufficient transcriptional or translational control sequences to ensure expression of an ORF in the first heterologous sequence upon infection of an appropriate cell (e.g., a human cell) by the adenoviral vector. In certain embodiments, the first heterologous sequence comprises a promoter (e.g., a CMV promoter) and an adenoviral TPL sequence. In other embodiments, the first heterologous sequence comprises a promoter (e.g., a CMV promoter), an adenoviral TPL, and an adenoviral poly A signal sequence (e.g., an Ad5 E3A poly A signal sequence). In connection with any of the foregoing embodiments, the first heterologous sequence can further comprise a Kozak sequence.

In certain embodiments, the first heterologous sequence comprises one or more transcriptional or translational control sequences for each of two or more ORFs. For example, the first heterologous sequence can comprise sufficient transcriptional or translational control sequences to ensure expression of each of two or more ORFs. Accordingly, in certain embodiments, the first heterologous sequence comprises a promoter and a poly A signal sequence for each of two ORFs. The first heterologous sequence can further comprise an adenoviral TPL and/or a Kozak sequence for each of the ORFs. Alternatively, in certain embodiments, the first heterologous sequence can comprise sufficient transcriptional or translational control sequences to ensure expression of one ORF (e.g., a promoter and/or enhancer and a poly A signal sequence) while comprising a second ORF that is under the control of or operably linked to endogenous adenoviral transcriptional or translational control sequences.

In certain embodiments, the first heterologous sequence has been optimized to increase or maximize expression and/or translation of at least one ORF. For example, in certain embodiments, an ORF in the first heterologous sequence has been codon optimized (e.g., for expression in mammalian cells, such as human cells). In one embodiment, the first heterologous sequence has been codon optimized and is under the control of a non-adenoviral promoter, such as a CMV promoter. In other embodiments, a Kozak sequence operably linked to an ORF is the first heterologous sequence has been optimized to create, for example, a consensus Kozak sequence. In still other embodiments, the first heterologous sequence has been optimized to remove potential inhibitory sequences, such as exonic splice silencers or insulator sequences (e.g., sequences that function to organize chromatin and block the long range effects of promoters and/or enhancers). Codon optimization and other types of sequence optimization are routine in the art and skilled persons will readily understand how to perform such optimizations.

In some embodiments in which the first heterologous sequence is under the control of a MLP promoter, the first heterologous sequence is not codon optimized—i.e., the first heterologous sequence is the native sequence from the infectious pathogen. For instance, in one embodiment, the adenoviral vector comprises a non-codon optimized first heterologous sequence under the control of an adenoviral MLP promoter, wherein the adenoviral vector is replication competent and has a partial E3 deletion. In another embodiment, the adenoviral vector is derived from Ad4.

The first heterologous sequence can be inserted into a variety of different locations in the adenoviral vector, including the E1, E2, E3, E4, L3, and L5 regions or the E4-ITR boundary. In certain embodiments, the first heterologous sequence is inserted into an E1, E2B, E3, L3, or L5 region, or an E4-ITR boundary. In other embodiments, the first heterologous sequence is inserted into an E3 region, L3 region, or an E4-ITR boundary. In still other embodiments, the first heterologous sequence is inserted into an E3 region. In certain embodiments, a suitable E3 region insertion site is located downstream of the E3B polyA signal sequence. In certain embodiments, a suitable L3 region insertion site is located downstream of the L3 23k protease gene (e.g., the 23k protease gene of an Ad5 vector, or the equivalent sequence in any other adenoviral vector). The precise insertion site within the adenoviral regions or boundaries can be selected such that the first heterologous sequence is under the control of or operably attached to one or more endogenous adenoviral transcriptional and/or translational control sequences. Alternatively, or in addition, the precise insertion site can be selected so as to minimize any impact upon the ability of the resulting recombinant adenoviral vector to replicate in mammalian (e.g., human) cells.

The adenoviral vectors of the invention can comprise deletions in the adenoviral genome. Such deletions can, for example, provide space for the insertion of heterologous sequences (e.g., a first heterologous sequence) and help to minimize any impact of the insertion upon the ability of the resulting recombinant adenoviral vector to replicate in mammalian (e.g., human) cells. The adenoviral vector can be deleted in a variety of different locations, including the E1, E2, E3, E4, L3, and L5 regions or the E4-ITR boundary. In certain embodiments, the adenoviral vector is deleted in an E1, E2B, E3, L3, or L5 region, or an E4-ITR boundary. In other embodiments, the adenoviral vector is deleted in an E3 region, L3 region, or an E4-ITR boundary. In still other embodiments, the adenoviral vector is deleted in an E3 region. In certain embodiments, the first heterologous sequence is inserted into or proximal to any of the foregoing deletions. For example, the first heterologous sequence can be inserted into an E3 partial deletion or proximal to an E3 full deletion.

Figure 2:
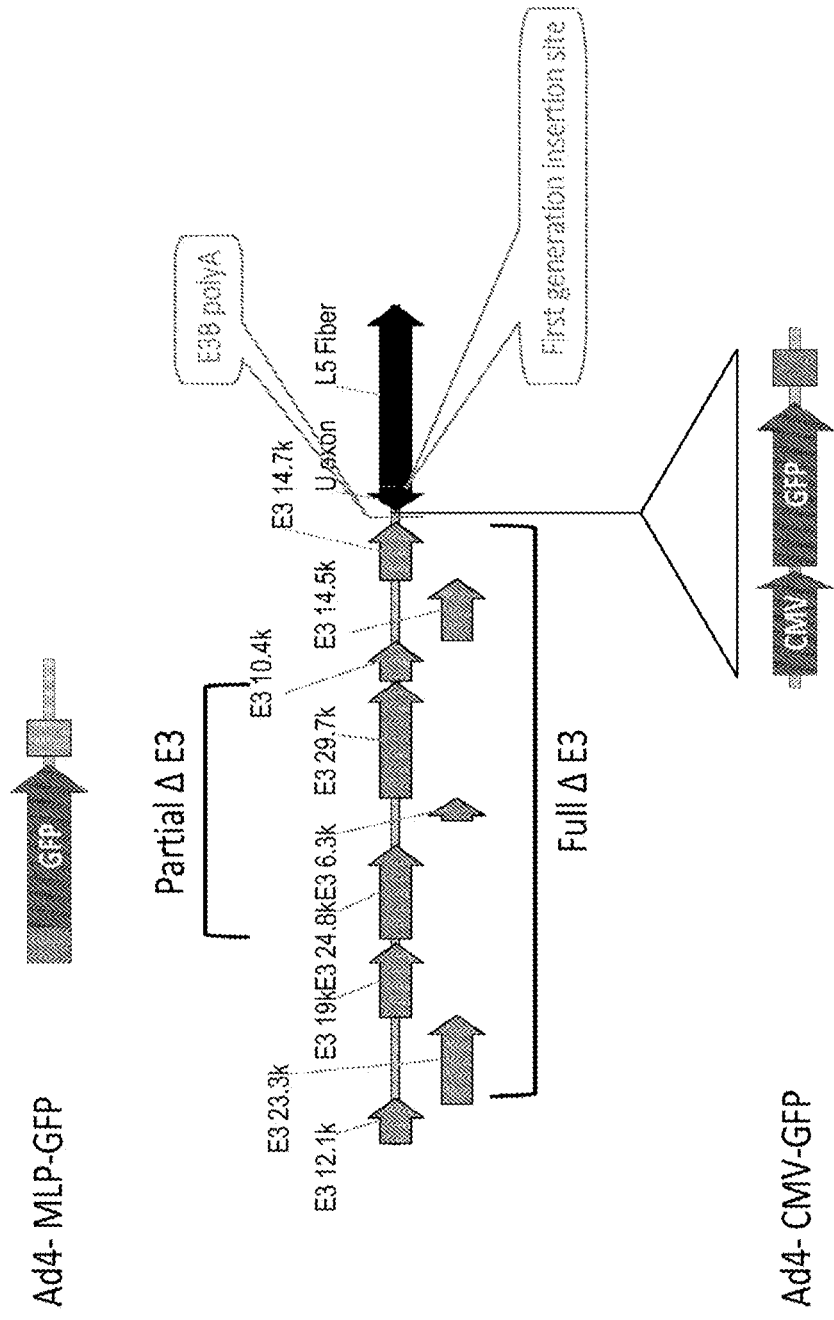
FIG. 2 is a diagram of the Ad4 E3 region that illustrates the location of various open reading frames, the endpoints of exemplary partial and full deletions of E3, and representative locations of where heterologous sequences can be inserted into the region.
Figure 3:
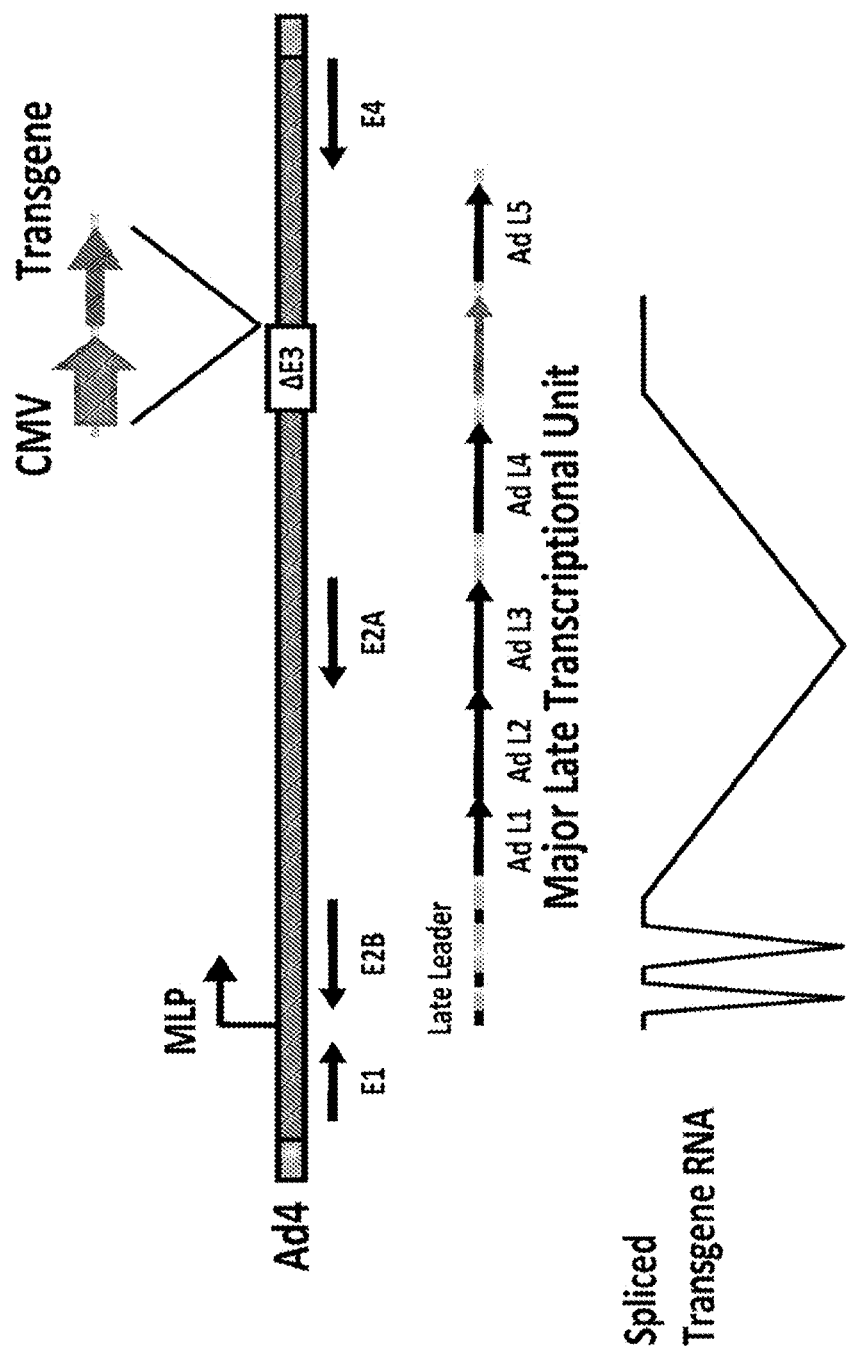
FIG. 3 is a diagram showing the location of various transcription units in the adenoviral genome.

In certain embodiments, a deletion in the adenoviral vector deletes one or more open reading frames. For example, one, two, three, or more open reading frames can be deleted. The open reading frames have either a known or an unknown function. In certain embodiments, the deletion is in the E3 region and comprises deletion of one, two, three, or more ORFs in the E3 region (e.g., E3 ORFs having an unknown function). The deletion in an E3 region can be a partial deletion. Alternatively, the deletion in an E3 region can be a full deletion. FIG. 2 shows exemplary partial and full deletions in the E3 region of Ad4. The exemplary Ad4 partial E3 deletion removes the 24.8 k, 6.3 k, and 29.7 k ORFs, all of which currently have no known function, while the Ad4 full E3 deletion removes the 23.3 k, 19 k, 24.8 k, 6.3 k, 29.7 k, 10.4 k, 14.5 k, and 14.7 k ORFs. One alternative partial E3 deletion removes the 24.8 k, 6.3 k, 29.7 k, 10.4 k, 14.5 k, and 14.7 k ORFs.

Thus, in certain embodiments, the adenoviral vector of the invention is an Ad4 vector that comprises a deletion of one or more (e.g., all) of the E3 24.8 k, 6.3 k, and 29.7 k ORFs. In related embodiments, the adenoviral vector is an Ad4 vector that comprises a deletion corresponding to nucleotides about 28,446 to about 30,226 of GenBank sequence AY594254. In other embodiments, the adenoviral vector of the invention is an Ad4 vector that comprises a deletion in the E3 region but retains one or more E3 ORFs selected from the group consisting of 23.3 k, 19k, 24.8 k, 6.3 k, 29.7 k, 10.4 k, 14.5 k, and 14.7 k (e.g., the 23.3 k and 19k ORFs can be retained, the 10.4 k, 14.5 k, and 14.7 k ORFs can be retained, or the 23.3 k, 19k, 10.4 k, 14.5 k, and 14.7 k ORFs can be retained). In related embodiments, the adenoviral vector is an Ad4 vector that comprises a deletion corresponding to nucleotides about 28,446 to about 31,282, or about 17,356 to about 30,226 of GenBank sequence AY594254. In still other embodiments, the adenoviral vector of the invention is an Ad4 vector that retains none of the E3 ORFs in the group consisting of 23.3 k, 19k, 24.8 k, 6.3 k, 29.7 k, 10.4 k, 14.5 k, and 14.7 k. In certain related embodiments, the adenoviral vector is an Ad4 vector that comprises a deletion corresponding to nucleotides about 27,356 to about 31,282 of GenBank sequence AY594254.

In certain embodiments, an ORF is deemed deleted even if part of the nucleic acid sequences that comprises the ORF remains present in the adenoviral vector (i.e., even if the ORF is only partially deleted). In certain embodiments, expression from a partially deleted ORF can be eliminated by further manipulation the sequence of the ORF. For example, in certain embodiments, the start codon of the ORF can be eliminated. In certain embodiments, a partial or full deletion of the Ad4 E3 region results in partial deletion of the E3 23.3 k ORF. In certain embodiments, an Ad4 vector having a partially deleted E3 23.3 k ORF further comprises a mutation that removes the start codon of the E3 23.3 k ORF (e.g., a mutation in the ATG codon present at position 27279 of GenBank sequence AY594254).

In still other embodiments, the adenoviral vectors of the invention can comprise a partial deletion in the E3 region that corresponds to the ADP region of the Ad5 genome (e.g., the region between the Ad5 E3 pg19k ORF and the Ad5 E3 RID-alpha ORF). For example, the partial E3 deletion of Ad4 shown in FIG. 2 corresponds to a deletion of the ADP region from the E3 region of Ad5. Similarly, the region between the Ad7 E3 18.3 k ORF and the Ad7 E3 10.3 k ORF (i.e., the region encompassing the Ad7 E3 20.1 k, 20.6 k, and 7.7 k ORFs) corresponds to the ADP region from the Ad5 E3 region. Persons skilled in the art can readily determine which regions in an adenoviral vector, from a serotype other than Ad4 or Ad7, correspond to the ADP region of Ad5.

A first heterologous sequence can be inserted into a deletion in the adenoviral vector (e.g., a deletion as described above). Alternatively, the first heterologous sequence can be inserted into the adenoviral vector in a location proximal to a deletion (e.g., a deletion as described above). For example, in certain embodiments, the first heterologous sequence is inserted into a partial E3 deletion (e.g., a partial E3 deletion in an Ad4 vector). In other embodiments, the first heterologous sequence is inserted into a full E3 deletion (e.g., a full E3 deletion in an Ad4 vector). In still other embodiments, the first heterologous sequence is inserted into a region proximal to a partial or full E3 deletion (e.g., between the E3B polyA signal sequence a downstream sequence, such as the L5 fiber gene or the U exon). In certain embodiments, the first heterologous sequence is inserted into a partial E3 deletion such that it is under the control of an endogenous promoter (e.g., a LTP). In certain embodiments, the first heterologous sequence comprises an exogenous promoter and, optionally, other transcriptional or translational control sequences and is inserted into a partial or full E3 deletion. In certain embodiments, the first heterologous sequence is not integrated into an ORF that encodes an adenoviral protein. As used herein in this context, the term "integrated" means that a heterologous sequence is inserted into an adenoviral ORF such that the resulting sequence encodes a chimeric protein, wherein part of the chimeric protein is encoded by the adenoviral ORF and part of the chimeric protein is encoded by the heterologous sequence.

In some embodiments, an adenoviral vector of the invention comprises a first heterologous sequence under the control of an adenoviral promoter (e.g., Major Late Promoter), wherein the first heterologous sequence encodes an antigen from influenza, *Bacillus*, HIV, HPV, togavirus (e.g. Dengue Fever virus), *Shigella, Mycobacterium, Streptococcus*, or *Plasmodium*. In one embodiment, the first heterologous sequence encodes H1 HA, H3 HA, H5 HA, or B HA antigen from influenza. In another embodiment, the first heterologous sequence encodes protective antigen or a modified protective antigen from *Bacillus anthracis*. In another embodiment, the first heterologous sequence encodes an envelope protein (e.g. gp160, gp140, gp120), modified envelope protein, or a gag protein from HIV. In yet another embodiment, the first heterologous sequence encodes a L1 protein, L2 protein, E6 protein, E7 protein or fusions thereof from HPV, including HPV16 and HPV18. In still another embodiment, the first heterologous sequence encodes CSP, Pfs48/45, MSP1, MSP (C-term, p42), or LSA1 from *Plasmodium*. In some embodiments, the first heterologous sequence encodes Ag85, ESAT, HspX, or combinations thereof from *Mycobacterium*. In other embodiments, the first heterologous sequence encodes PSSP, r56Karp protein, or an invasion protein (e.g., IpaB, IpaC, or IpaD protein) from *Shigella*. In still further embodiments, the adenoviral vector can further comprise an adenoviral tripartite leader sequence. For instance, the first heterologous sequence can be under the control of an adenoviral MLP and tripartite leader, wherein the first heterologous sequence encodes an antigen from influenza, *Bacillus*, HIV, HPV, togavirus (e.g. Dengue Fever virus), *Shigella, Mycobacterium, Streptococcus*, or *Plasmodium*.

In other embodiments, an adenoviral vector of the invention comprises a first heterologous sequence under the control of a non-adenoviral promoter (e.g., CMV promoter, RSV LTR promoter, SV40 promoter, DHFR promoter, β-actin promoter, PGK promoter, the EF1α promoter), wherein the first heterologous sequence encodes an antigen from influenza, *Bacillus*, HIV, HPV, togavirus (e.g. Dengue Fever virus), *Shigella, Mycobacterium, Streptococcus*, or *Plasmodium*. For instance, in one embodiment, the first heterologous sequence is under the control of a CMV promoter and encodes an antigen from influenza, *Bacillus*, or HIV. In one particular embodiment, the first heterologous sequence is codon-optimized sequence from influenza, *Bacillus*, or HIV. In another embodiment, the first heterologous sequence is a native sequence from influenza, *Bacillus*, or HIV. In another embodiment, the first heterologous sequence encodes H1 HA, H3 HA, H5 HA, B HA, NP, or M1 antigen from influenza. In another embodiment, the first heterologous sequence encodes protective antigen or a modified protective antigen from *Bacillus anthracis*. In yet another embodiment, the first heterologous sequence encodes an envelope protein (e.g. gp160, gp140, gp120), modified envelope protein, or a gag protein from HIV. In some embodiments, the adenoviral vector can further comprise an adenoviral tripartite leader sequence. For instance, the first heterologous sequence can be under the control of a CMV promoter and adenoviral tripartite leader, wherein the first heterologous sequence encodes an antigen from influenza, *Bacillus*, HIV, HPV, togavirus (e.g. Dengue Fever virus), *Shigella, Mycobacterium, Streptococcus*, or *Plasmodium*.

In certain embodiments, an adenoviral vector of the invention comprises a second heterologous sequence. Thus, in certain embodiments, the adenoviral vector of invention comprises both a first heterologous sequence and a second heterologous sequence. Alternatively, the adenoviral vector of the invention can comprise a second heterologous sequence in lieu of the first heterologous sequence.

The second heterologous sequence can have a structure as described above for the first heterologous sequence and can be inserted into the adenoviral genome in any manner described above. Thus, in certain embodiments, the second heterologous sequence can encode a full length antigen or a fragment thereof (e.g., a domain, unit(s) of secondary structure, conserved epitope, B-cell, HTL, or CTL epitope, or combinations thereof). In some embodiments, the second heterologous sequence encodes a therapeutic protein, such as a cytokine or growth factor or other protein that stimulates the immune system. For instance, in one embodiment, the second heterologous sequence encodes a protein that stimulates white blood cells, such as granulocyte macrophage colony stimulating factor (GM-CSF). In some embodiments, the first heterologous sequence encodes an antigen from an infectious pathogen and the second heterologous sequence encodes a therapeutic protein. In one particular embodiment, the first heterologous sequence encodes an influenza antigen (e.g., H1 HA, H3 HA, H5 HA, or B HA antigen) and the second heterologous sequence encodes a protein that stimulates white blood cells (e.g., GM-CSF). In certain embodiments, the second heterologous sequence is inserted into the same region of the adenoviral vector as the first heterologous sequence (e.g., such that the first and second heterologous sequences are located proximal to one another). In other embodiments, the first and second heterologous sequences are inserted into different regions of the adenoviral vector.

The second heterologous sequence can also be integrated into an adenoviral ORF. In certain embodiments, the adenoviral ORF encodes an adenoviral structural protein (e.g., a capsid protein, such as hexon protein or fiber protein). Thus, in certain embodiments, the second heterologous sequence is integrated into an adenoviral hexon ORF, wherein the resulting fusion of hexon ORF and heterologous sequences encodes a chimeric hexon protein. In other embodiments, the second heterologous sequence is integrated into an adenoviral fiber ORF, wherein the resulting fusion of fiber ORF and heterologous sequences encodes a chimeric fiber protein. In general, a chimeric hexon or fiber protein of the invention will retain hexon or fiber function (e.g., form hexon capsomeres or fibers and contribute to capsid formation) while presenting new antigens of the surface of the resulting adenoviruses. The presentation of new antigens of the surface of recombinant adenoviruses of the invention is advantageous because it helps to avoid problems with pre-existing adenovirus immunity in the general population, which can reduce the efficacy of the adenoviral-based vaccines. In addition, the presentation of antigens from infectious pathogens on the surface of the recombinant adenoviruses can broaden the immune response stimulated by the adenoviral-based vaccines of the invention by presenting a greater variety of infectious pathogen antigens to the immune system of a subject taking the vaccine.

In some embodiments, the second heterologous sequence encodes a fiber protein from a different adenoviral serotype and the second heterologous sequence replaces the sequence encoding the native fiber protein of the adenovirus. Thus, the resulting recombinant adenovirus expresses fibers from another adenoviral serotype. For instance, in one embodiment, an Ad5 adenovirus expresses fiber proteins from an Ad4, Ad7, Ad2, etc. adenovirus.

Accordingly, in certain embodiments, the second heterologous sequence is integrated into the ORF of an adenoviral structural protein (e.g., a capsid protein, such as hexon or protein), wherein the second heterologous sequence encodes an antigen from an infectious pathogen. The infectious pathogen and antigen thereof can be as described above. In certain embodiments, the antigen is from an influenza surface protein, such as M2 (e.g., an external domain, fragment, or epitope of M2). In certain embodiments, the M2 antigen is selected from the set of M2 peptide sequences listed in Table 4 (e.g., SEQ ID NO. 312, 318, 321, or 327). In certain embodiments, the second heterologous sequence encodes more than one of the M2 peptide sequences listed in table 4. For example, the second heterologous sequence can encode at least two M2 sequences from H1, H2, and/or H3 influenza strains (e.g., at least two sequences selected from the group consisting of SEQ ID NOs: 312-317), H5 influenza strains (e.g., at least two sequences selected from the group consisting of SEQ ID NOs: 318-320), H7 influenza strains (e.g., at least two sequences selected from the group consisting of SEQ ID NOs: 321-326), or H9 influenza strains (e.g., at least two sequences selected from the group consisting of SEQ ID NOs: 327-335). Alternatively, the second heterologous sequence can encode M2 sequences from a plurality of different influenza serotypes (e.g., at least one sequence selected from the group consisting of SEQ ID NOs: 312-317 in combination with at least one sequence selected from the group consisting of SEQ ID NOs: 318-320, at least one sequence selected from the group consisting of SEQ ID NOs: 321-326, at least one sequence selected from the group consisting of SEQ ID NOs: 327-335, or any combination thereof). In other embodiments, the second heterologous sequence can encode one or more copies of an influenza Matrix sequence (e.g., GAAAGILGFVFTLNAA—SEQ ID NO: 336) or influenza NP sequence (e.g., LELRSRYWAIRTRSGGNT-NQQRAS—SEQ ID NO: 337). In still other embodiments, the influenza antigen is a HTL or CTL epitope. For example, the second heterologous sequence can encode one or more HTL epitopes selected from Tables 1 or 13 or one or more CTL epitopes selected from Tables 2-3 and 5-12 or Table 14.

In other embodiments, the second heterologous sequence encodes one or more portions of an adenoviral hexon protein from an adenoviral serotype for which pre-existing immunity (e.g., in the human population) is not significant. For example, there is minimal pre-existing immunity against adenoviral serotype Ad35 in the human population. See, e.g., Vogels et al. (2003), J. Virology 77(15):8263. Other adenoviral serotypes for which there is minimal pre-existing immunity include, for example, Ad11, Ad34, Ad43, Ad48, Ad50, Ad26, Ad28, Ad45, and Ad49. Adenoviral serotypes having slightly higher but still low levels of pre-existing immunity include, for example, Ad22, Ad24, Ad36, Ad37, Ad38, Ad46, Ad47, and Ad10. Thus, an adenoviral-based vaccine of the invention can be derived, e.g., from an Ad4 serotype, and can comprise a second heterologous sequence encoding one or more fragments from an Ad35 hexon protein, such that the recombinant adenovirus encodes a hexon protein that is chimeric for Ad4 and Ad35 sequences. Alternatively, an adenoviral-based vaccine of the invention can be derived, e.g., from an Ad25 serotype, and can comprise a second heterologous sequence encoding one or more fragments from an Ad68 hexon protein, such that the recombinant adenovirus encodes a hexon protein that is chimeric for Ad25 and Ad68 sequences. Of course, the concern about pre-existing immunity depends upon the target population for the disease—whether or not a particular adenoviral serotype is not associated with pre-existing immunity in the target population will depend upon the target population. Persons skilled in the art can readily evaluate this issue and select appropriate hexon sequences for the second heterologous sequence accordingly. The integration of heterologous sequences into adenoviral structural proteins such as hexon has been described, for example, in U.S. Pat. No. 6,127,525.

Figure 13:
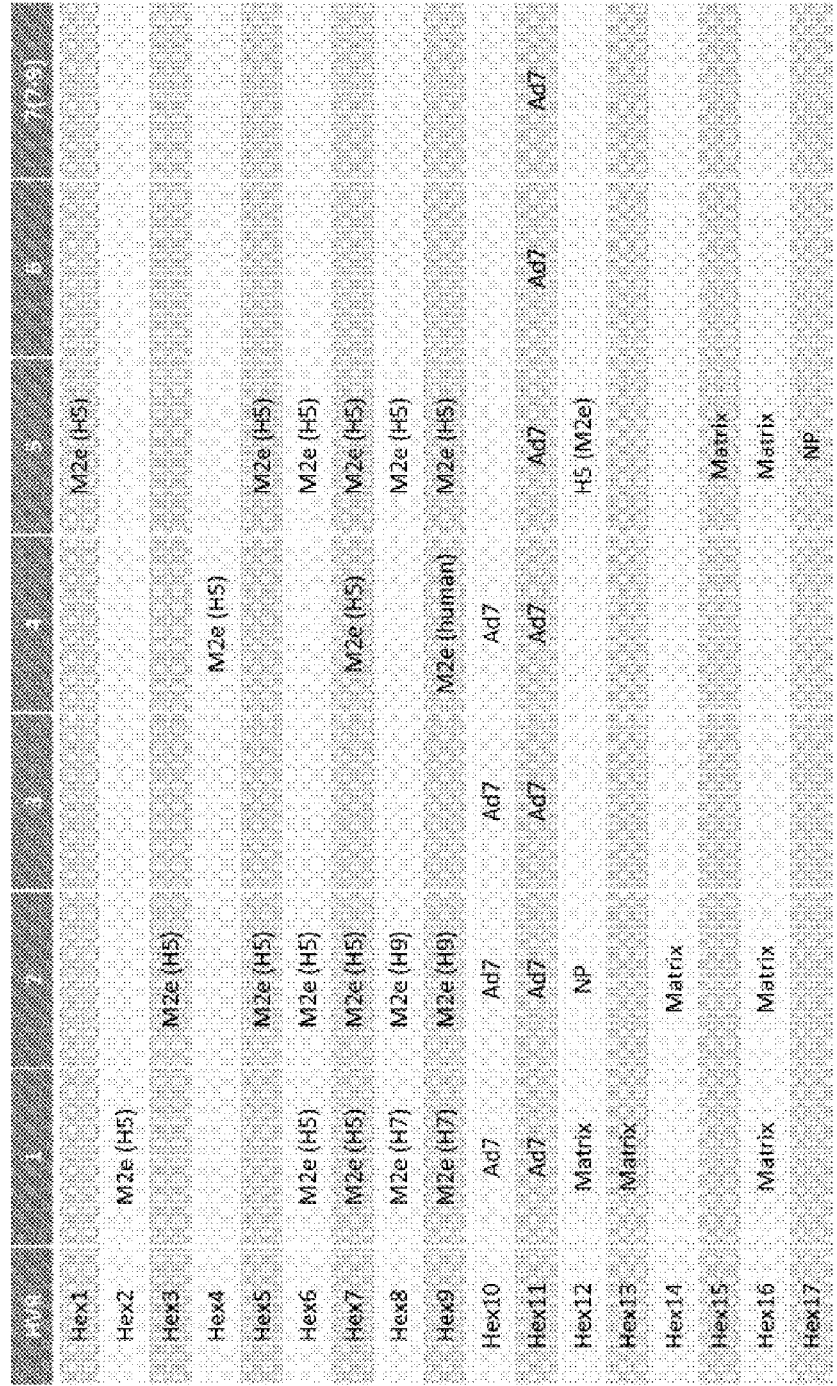
FIG. 13 depicts a series of chimeric Ad4 hexon constructs and indicates which HVRs can be replaced with influenza M2, Matrix, and/or NP sequences, or other Ad7 hexon HVR sequences.

In certain embodiments, the second heterologous sequence is integrated into a portion of a hexon ORF that encodes a hypervariable region (HVR). For example, the second heterologous sequence can be integrated as an insertion or such that it replaces all or a portion of the ORF encoding the hexon HVR. Any hexon HVR can be altered or replaced in this manner. In certain embodiments, the second heterologous sequence is integrated into (and, optionally, replaces) the hexon HVR5 coding region. In other embodiments, the second heterologous sequence is integrated into (and, optionally, replaces) the hexon HVR1, HVR2, or HVR4 coding region. Selection of which HVR to alter can be based upon the relative diversity of the different HVRs. For example, HVR5 of Ad5 has the greatest diversity for Ad5 hexon HVRs. In still other embodiments, more than one hexon HVR can have an insertion or substitution. Thus, in certain embodiments, the second heterologous sequence encodes a chimeric fragment of the hexon coding region wherein at least two of the HVR coding regions have insertions or have been replaced. As discussed above, the second heterologous sequence can encode antigens from infectious pathogens and/or other adenovirus serotypes. Accordingly, one or more of the hexon HVRs can contain an insertion of an antigen from an infectious pathogen or can be replaced by such an antigen or a HVR from another adenovirus serotype. In certain embodiments, one or more of the hexon HVRs can contain an insertion or an antigen or can be replaced by such an antigen, while one or more of the other hexon HVRs can be replaced by a HVR from another adenovirus serotype (e.g., a serotype for which there is minimal pre-existing immunity in the target population). A schematic diagram of chimeric hexon constructs that can be used in the adenoviral vectors of the invention are shown in FIG. 13.

Persons skilled in the art can readily identify the boundaries of hexon HVRs. Hexon HVRs have been identified, e.g., for Ad5 hexon. See, e.g., U.S. Pat. No. 6,127,525. Accordingly, alignment of hexon proteins from other serotypes with the Ad5 hexon can be used to identify the hexon HVRs in such other serotypes. Alternatively, an alignment of the hexon proteins from a diverse set of adenovirus serotypes can be used to identify HVR boundaries. For Ad4, for example, the HVR boundaries correspond to amino acid residues 136-172 (HVR1), 192-208 (HVR2), 227-235 (HVR3), 268-278 (HVR4), 300-305 (HVR5), 329-334 (HVR6), and 442-480 (HVR7-9) of the L5 hexon sequence of GenBank sequence AY594254.

The amount of sequence that can be inserted into a single hexon HVR depends upon the particular HVR (e.g., HVR1, HVR2, etc.) and the length of the HVR. In general, the insertion can code for a polypeptide sequence corresponding to the length of the HVR polypeptide sequence (if the HVR sequence is being replaced) plus an additional 0 to 75, 1 to 70, 2 to 65, 3 to 60, 4 to 55, or 5 to 50 amino acids. Hexon HVR insertions have been described, e.g., for Ad5 in Matthews et al. (2008), Virology Journal 5:98.

Sequences encoding antigens from infectious pathogens can replace hexon HVRs such that the hexon sequences and antigen sequences are adjacent to one another. As used herein in this context, the term "adjacent" refers to an in-frame fusion between the hexon coding sequences and the antigen coding sequences wherein there is no linker sequence connecting the hexon and antigen sequences. Alternatively, a linker sequence can be used to connect the hexon and antigen sequences. In certain embodiments, the linker sequence is a sequence encoding the tri-peptide "LGS." The linker sequence can be included, e.g., at the beginning and end of the antigen sequence, as shown in FIG. 12. Without intending to be bound by theory, it is believed that the LGS linker sequences provide structural flexibility, improve the stability of the resulting hexon fusion protein, and/or reduce the immunogenicity of the junctions between the hexon protein sequences and the protein sequences encoded by the heterologous sequence. In other embodiments, the linker sequence encodes the peptide sequence "GAAA" (SEQ ID NO: 352) or "NAA." Such linker sequences can be used in combination, e.g., with the GAAA sequence on the N-terminal end and the "NAA" sequence on the C-terminal end of the protein encoded by the heterologous sequence. Other appropriate linker sequences can be identified by persons skilled in the art.

In certain embodiments, an adenoviral vector of the invention comprises a third heterologous sequence. Thus, in certain embodiments, the adenoviral vector of invention comprises a first, second, and third heterologous sequence. Alternatively, the adenoviral vector of the invention can comprise a second and a third heterologous sequence. The third heterologous sequence can have a structure as described above for the first heterologous sequence or the second heterologous sequence, and can be inserted into the adenoviral genome in any manner described above.

Adenoviral vectors of the invention can be derived from any adenoviral serotype or isolate currently known or later discovered. For example, in certain embodiments, the adenoviral vector is derived from an Ad4 serotype. In other embodiments, the adenoviral vector is derived from an Ad7 serotype. In still other embodiments, the adenoviral vector is derived from an Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, or Ad50 serotype. In certain embodiments, the adenoviral vector is derived from a chimpanzee adenovirus. For instance, in some embodiments, the adenoviral vector is derived from an Ad C1, Ad C3, Ad C6, Ad C7, or Ad68.

Adenoviral vectors of the invention can vary in size from the corresponding size (i.e., genome size) of the wild-type adenovirus from which the vector is derived. In general, however, significant deviations in size are associated with defective adenovirus replication. For example, deleting large portions of the adenoviral genome can lead to the removal of genomic regions necessary for proper viral replication and function. Alternatively, adding large insertions can result in a genome that is too large to be effectively packaged in the adenovirus capsid, thereby also disrupting proper viral replication and function. Accordingly, in certain embodiments, the adenoviral vectors of the invention have a length of about 95% to about 110%, about 97% to about 105%, about 99% to about 103%, about 99.5% to about 102%, or about 100% to about 101% of the length of the wild-type adenovirus genome from which the vector was derived. In other embodiments, the adenoviral vectors of the invention have a length of about 34,000 bps to about 38,000 bps, about 34,500 bps to about 37,500 bps, about 35,000 bps to about 37,000 bps, about 35,500 bps to about 36,500 bps, about 35,750 bps to about 36,250 bps, or about 36,000 bps.

Regardless of the specific alterations that have been introduced (e.g., number and type of heterologous sequences, number and type of deletions, etc.), the adenoviral vectors of the invention are typically replication competent. The term "replication competent" refers to the ability of an adenoviral vector to replicate within a subject. In certain embodiments, the replication competent adenoviral vectors of the invention are able to replicate within a human subject. In other embodiments, the replication competent adenoviral vectors of the invention are able to replicate within a mammalian subject (e.g., a farm animal, such as a pig, cattle, horse, sheep, goat, etc.; a zoo animal, such as a lion, tiger, elephant, rhinoceros, hippo, giraffe, zebra, monkey, ape, etc.; or a pet, such as a dog, cat, rabbit, guinea pig, hamster, gerbil, rat, mouse, etc.). In certain embodiments, the in vitro burst size (e.g., as measured in cell culture) of a replication competent adenoviral vector of the invention is at least 1000, 2000, 3000, 4000, 5000, 7500, 10k, 15k, 20k, 25k, 30k, 35k, 40k, 45k, 50k, 75k, 100k, 150k, 200k, 300k, 400k, or more. In other embodiments, the in vivo burst size (e.g., in a subject) of a replication competent adenoviral vector of the invention is at least 1000, 2000, 3000, 4000, 5000, 7500, 10k, 15k, 20k, 25k, 30k, 35k, 40k, 45k, 50k, 75k, 100k, 150k, 200k, 300k, 400k, or more. In certain embodiments, the replication competent adenoviral vectors of the invention are able to stimulate an immune response (e.g., a humoral immune response, cellular immune response, or both) in a subject. In certain embodiments, the immune response includes a measurable response (e.g., a measurable humoral or cellular immune response, or combination thereof) to an epitope encoded by a heterologous sequence inserted or integrated into the adenoviral vector. Replication competent adenoviral vectors of the invention are particularly useful for overcoming the problems associated with pre-existing immunity to adenovirus in target subjects. For instance, in certain embodiments, an effective immune response to a heterologous antigen can be induced in a subject with pre-existing immunity to adenovirus with a lower dose of a replication competent adenoviral vector expressing the heterologous antigen as described herein as compared to a dose of a replication incompetent adenoviral vector expressing the same antigen. Thus, in some embodiments, an effective dose of a replication competent adenoviral vector of the invention is two-fold, three-fold, four-fold, five-fold, or ten-fold lower than an effective dose of a replication incompetent adenoviral vector.

Techniques for constructing, genetically manipulating, and propagating recombinant adenoviral vectors are disclosed in the Examples set forth below. See also, e.g., WO 2008/010864, U.S. Patent Application 2006/0115456, and U.S. Pat. No. 6,127,525, the contents of which are incorporated herein by reference.

In another aspect, the present invention provides vaccines comprising one or more adenoviral vectors of the invention. As used herein, the term "vaccine" refers to a composition that comprises an adenoviral vector of the invention and a carrier. In certain embodiments, the adenoviral vector is a virus. In other embodiments, the adenoviral vector is the genome alone and does not include the adenoviral capsid. In certain embodiments, the carrier is an adjuvant. Examples of such adjuvants include, but are not limited to, salts, such as calcium phosphate, aluminum phosphate, calcium hydroxide and aluminum hydroxide; natural polymers such as algal glucans (e.g., beta glucans), chitosan or crystallized inulin; synthetic polymers such as poly-lactides, poly-glycolides, poly lactide-co-glycolides or methylacrylate polymers; micelle-forming cationic or non-ionic block copolymers or surfactants such as Pluronics, L121, 122 or 123, Tween 80, or NP-40; fatty acid, lipid or lipid and protein based vesicles such as liposomes, proteoliposomes, ISCOM and cochleate structures; and surfactant stabilized emulsions composed of synthetic or natural oils and aqueous solutions. In certain embodiments, a vaccine of the invention, upon administration to a subject, is capable of stimulating an immune response (e.g., a humoral immune response, cellular immune response, or both) in the subject. In certain embodiments, the immune response includes a measurable response (e.g., a measurable humoral or cellular immune response, or combination thereof) to an epitope encoded by a heterologous sequence inserted or integrated into an adenoviral vector of the vaccine. In certain embodiments, a vaccine of the invention is capable of providing protection against an infectious pathogen or against cancer. For example, in certain embodiments, the vaccine is capable of stimulating an immune response against one or more antigens (e.g., encoded by a heterologous sequence) such that, upon later encountering such an antigen, the subject receiving the vaccine has an immune response that is stronger than it would have been if the vaccine had not been administered previously. In some embodiments, a vaccine of the invention is capable of providing protection against an infectious pathogen or cancer in a subject with pre-existing immunity to adenovirus. In other embodiments, a vaccine of the invention is capable of ameliorating a pathogen infection or cancer and/or reducing at least one symptom of a pathogen infection or cancer. For instance, in one embodiment, the vaccine of the invention induces a therapeutic immune response against one or more antigens encoded by a heterologous sequence such that symptoms and/or complications of a pathogen infection or cancer will be alleviated, reduced, or improved in a subject suffering from such an infection or cancer.

The adenoviral vectors used for the vaccines can be prepared and formulated for administration to a mammal in accordance with techniques well known in the art. Formulations for oral administration can consist of capsules or tablets containing a predetermined amount of a recombinant adenoviral vector of the invention; liquid solutions, such as an effective amount of the pharmaceutical dissolved in ingestible diluents, such as water, saline, orange juice, and the like; suspensions in an appropriate liquid; and suitable emulsions.

The adenoviral vectors of the invention can, for example, be formulated as enteric coated capsules for oral administration, as previously described, in order to bypass the upper respiratory tract and allow viral replication in the gut. See, e.g., Tacket et al., Vaccine 10:673-676, 1992; Horwitz, in Fields et al., eds., Fields Virology, third edition, vol. 2, pp. 2149-2171, 1996; Takafuji et al., J. Infec. Dis. 140:48-53, 1979; and Top et al., J. Infec. Dis. 124:155-160, 1971. Alternatively, the adenoviral vectors can be formulated in conventional solutions, such as sterile saline, and can incorporate one or more pharmaceutically acceptable carriers or excipients. The pharmaceutical composition can further comprise other active agents.

In certain embodiments, formulations of the invention comprise a buffered solution comprising adenoviral vectors (e.g., viruses) in a pharmaceutically acceptable carrier. A variety of carriers can be used, such as buffered saline, water and the like. Such solutions are generally sterile and free of undesirable matter. These compositions can be sterilized by conventional, well known sterilization techniques, or can be sterile filtered. The compositions may contain pharmaceutically acceptable auxiliary substances as required to approximate physiological conditions such as pH adjusting and buffering agents, tonicity adjusting agents and the like, for example, sodium acetate, sodium chloride, potassium chloride, calcium chloride, sodium lactate and the like.

Pharmaceutically acceptable carriers can contain a physiologically acceptable compound that acts, e.g., to stabilize the composition or to increase or decrease the absorption of the virus and/or pharmaceutical composition. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of any co-administered agents, or excipient, or other stabilizers and/or buffers. Detergents can also be used to stabilize the composition or to increase or decrease absorption. One skilled in the art will appreciate that the choice of a pharmaceutically acceptable carrier, including a physiologically acceptable compound depends, e.g., on the route of administration of the adenoviral preparation and on the particular physio-chemical characteristics of any co-administered agent.

The adenoviral vectors can also be administered in a lipid formulation, more particularly either complexed with liposomes or to lipid/nucleic acid complexes or encapsulated in liposomes. The vectors of the current invention, alone or in combination with other suitable components, can also be made into aerosol formulations to be administered via inhalation. The vaccines can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. In some embodiments, the adenoviral vectors of the invention can be formulated as suppositories, for example, for rectal or vaginal administration.

Vaccines can have a unit dosage comprising between about $10^3$ to about $10^{13}$ (e.g., about $10^3$ to about $10^4$, about $10^4$ to about $10^5$, about $10^5$ to about $10^6$, about $10^6$ to about $10^7$, about $10^7$ to about $10^8$, about $10^8$ to about $10^9$, about $10^9$ to about $10^{10}$, about $10^{10}$ to about $10^{11}$, about $10^{11}$ to about $10^{12}$, about $10^{12}$ to about $10^{13}$) recombinant adenoviruses in a single dose. The dosages can vary based on the route of administration. For instance, vaccines formulated for sublingual or intranasal administration may contain a lower dosage of adenovirus per single dose than vaccines formulated for oral administration. One of skill in the art can determine the appropriate dosage for a particular patient depending on the type of infection or cancer, and the route of administration to be used without undue experimentation.

In another aspect, the invention provides methods of inducing an immune response to any infectious pathogen described herein in a subject comprising administering to the subject a vaccine of the invention. In one embodiment, the invention provides a method of vaccinating a subject against an infectious pathogen comprising administering a sufficient amount of a vaccine of the invention to a subject at risk for being infected by an infectious pathogen. In another embodiment, the subject has an infection induced by the infectious pathogen. Thus, for instance, in one embodiment, the present invention provides a method of inducing a therapeutic immune response in a subject experiencing an infection induced by an infectious pathogen. In some embodiments, one or more symptoms or complications of the infection is reduced or alleviated in the subject following administration of the vaccine. The vaccines of the invention can be used to vaccinate human or veterinary subjects.

The vaccines of the invention can be administered alone, or can be co-administered or sequentially administered with other immunological, antigenic, vaccine, or therapeutic compositions. Such compositions can include other agents to potentiate or broaden the immune response, e.g., IL-2 or other cytokines which can be administered at specified intervals of time, or continuously administered (see, e.g., Smith et al., N Engl J Med 1997 Apr. 24; 336(17):1260-1; and Smith, Cancer J Sci Am. 1997 December; 3 Suppl 1:S137-40). The vaccines or vectors can also be administered in conjunction with other vaccines or vectors. For example, an adenovirus of the invention can be administered either before or after administration of an adenovirus of a different serotype. An adenovirus preparation may also be used, for example, for priming in a vaccine regimen using an additional vaccine agent.

The adenoviral formulations can be delivered systemically, regionally, or locally. Regional administration refers to administration into a specific anatomical space, such as intraperitoneal, intrathecal, subdural, or to a specific organ, and the like. Local administration refers to administration of a composition into a limited, or circumscribed, anatomic space such as an intratumor injection into a tumor mass, subcutaneous injections, intramuscular injections, and the like. One of skill appreciates that local administration or regional administration can also result in entry of the viral preparation into the circulatory system. Typical delivery routes include parenteral administration, e.g., intradermal, intramuscular or subcutaneous routes. Other routes include oral administration, including administration to the oral mucosa (e.g., tonsils), intranasal, sublingual, intravesical (e.g., within the bladder), rectal, and intravaginal routes. For delivery of adenovirus, administration can often be performed via inhalation. Aerosol formulations can, for example, be placed into pressurized, pharmaceutically acceptable propellants, such as dichlorodifluoro-methane, nitrogen and the like. They can also be formulated as pharmaceuticals for non-pressurized preparations such as in a nebulizer or an atomizer. Typically, such administration is in an aqueous pharmacologically acceptable buffer as described above. Delivery to the lung can also be accomplished, for example, using a bronchoscope.

The vaccines of the invention can be administered in a variety of unit dosage forms, depending upon the intended use, e.g., prophylactic vaccine or therapeutic regimen, and the route of administration. With regard to therapeutic use, the particular condition or disease and the general medical condition of each patient will influence the dosing regimen. The concentration of adenovirus in the pharmaceutically acceptable excipient can be, e.g., from about $10^3$ to about $10^{13}$ virus particles per dose, between about $10^4$ to about $10^{11}$ virus particles per dose, between about $10^6$ to about $10^{10}$ virus particles per dose, between about $10^7$ to about $10^9$ virus particles per dose, or between about $10^9$ to about $10^{11}$ virus particles per dose. In other embodiments, the concentration of adenovirus in the pharmaceutically acceptable excipient can be, e.g., from about $10^3$ to about $10^9$, about $10^4$ to about $10^8$, or about $10^5$ to about $10^7$ infectious units per dose.

The replication-competent adenoviral vectors of the invention are typically administered at much lower doses than would be needed to achieve equivalent expression levels of the encoded transgene by a replication-defective adenovirus recombinant administered in vivo. Replication competent adenovirus vectors can be administered at a range of dosages (see, e.g., U.S. Pat. No. 4,920,209; Smith et al., J. Infec. Dis. 122:239-248, 1970; Top et al., J. Infect. Dis. 124:155-160, 1971; Takafuji et al., J. Infec. Dis. 140:48-53, 1979; Tacket et al., Vaccine 10:673-676, 1992). For example, $10^4$ to $10^9$ 50% tissue culture infective doses (or plaque forming units) can be administered. Typically an oral dosage for a replication-competent adenovirus is about $10^7$ 50% tissue culture infective doses or $10^7$ plaque forming units. In some embodiments, an oral dosage for a replication-competent adenovirus is about $10^{11}$ plaque forming units. Typical intranasal administration of adenovirus recombinants is often in dosages of about $10^3$ to about $10^5$ plaque forming units. The exact concentration of virus, the amount of formulation, and the frequency of administration can also be adjusted depending on the levels of in vivo, e.g., in situ transgene expression and vector retention after an initial administration.

The amount and concentration of virus and the formulation of a given dose, or a "therapeutically effective" dose can be determined by the clinician. A therapeutically effective dose of a vaccine is an amount of adenovirus that will stimulate an immune response to the protein(s) encoded by the heterologous nucleic acid included in the viral vector. The dosage schedule, i.e., the dosing regimen, will depend upon a variety of factors, e.g., the general state of the patient's health, physical status, age and the like. The state of the art allows the clinician to determine the dosage regimen for each individual patient. Adenoviruses have been safely used for many years for human vaccines. See, e.g., Franklin et al., supra; Jag-Ahmade et al., J. Virol., 57:267, 1986; Ballay et al., EMBO J. 4:3861, 1985; PCT publication WO 94/17832. These illustrative examples can also be used as guidance to determine the dosage regimen when practicing the methods of the invention.

Single or multiple administrations of adenoviral formulations can be administered as prophylactic or therapeutic vaccines. In one embodiment, multiple doses (e.g., two or more, three or more, four or more, or five or more doses) are administered to a subject to induce or boost a protective or therapeutic immune response. The two or more doses can be separated by periodic intervals, for instance, one week, two week, three week, one month, two month, three month, or six month intervals.

In yet another aspect, the invention also provides kits that contain the vectors, vector systems or vaccines of the invention. The kits can, for example, also contain cells for growing the adenoviruses of the invention. The kits can also include instructional material teaching methodologies for generating adenoviruses using the kits and, for vaccines, can include instruction for indication of dosages, routes and methods of administration and the like.

The following examples illustrate various aspects of the present invention. The examples should, of course, be understood to be merely illustrative of only certain embodiments of the invention and not to constitute limitations upon the scope of the invention which is defined by the claims that are appended at the end of this description.

EXAMPLES

Example 1

Construction of Recombinant Adenoviral Vectors

Homologous recombination in *E. coli* was used to rapidly and reliably produce recombinant adenovirus vectors. As an example, wild-type Ad4 viral DNA was isolated from a military Ad4 tablet (from Lot. No. 4958221, Wyeth Labs, US Gov't License No. 3) and cloned by homologous recombination into a bacterial plasmid capable of replication in *E. coli*. The resulting vector was designated pPV-Ad4vax.

The starting construct for the pPV-Ad4vax vector was created by synthetic gene synthesis of the left arm of wild-type Ad4 and insertion of the synthetic fragment into a bacterial plasmid. The resulting plasmid was designated pPV-Ad4 Left Arm™. An XbaI/EcoRI polylinker added at the 3' end of the Ad4 synthetic gene fragment was provided to allow for subsequent insertion of the Ad4 right arm fragment. See FIG. 1. The right arm fragment of Ad4 was generated by high fidelity PCR from the Ad4 genomic DNA isolated from the military Ad4 tablet, and then cloned into the XbaI/EcoRI polylinker sites. The resulting plasmid, designated pPV-Ad4 RHT & LFT Arm™, includes the left arm and right arm fragments of Ad4 separated by unique XbaI, ClaI, and SpeI restriction sites. See FIG. 1. Following linearization with XbaI and SpeI and dephosphorylation, the linearized pPV-Ad4 RHT & LFT Arm™ vector was co-transfected with the wild-type Ad4 genomic DNA into BJ1583 recombination-competent bacteria. Clones were screened by restriction enzyme digestion before retransformation into TOP10 cells. Final validation of pPV-Ad4pax was performed by sequencing.

Heterologous sequences and modifications of the Ad4 genome were introduced into the pPV-Ad4pax vector using shuttle plasmids. The shuttle plasmids were engineered to contain a heterologous sequence flanked by sufficient wild-type Ad4 DNA to allow homologous recombination between the shuttle vector and pPV-Ad4vax. Heterologous sequences included genes encoding Green Fluorescent Protein (GFP) and influenza hemagglutinin (HA). Separate full-length HA genes were artificially synthesized from HA Bbn (GenBank sequence EU199366-"Influenza A virus (A/Brisbane/10/2007 (H3N2)) segment 4 hemagglutinin (HA) gene, complete cds."), HA VT/1203 (GenBank sequence EF541403-A/Vietnam/1203/2004 (H5N1)), and HA VT/1194 (GenBank sequence EF541402-A/Vietnam/1194/2004 (H5N1)). Homologous recombination between the shuttle plasmid and pPV-Ad4pax resulted in the production of recombinant adenoviral vectors containing the desired modifications. The identify of the recombinant adenoviral vectors was confirmed by multiple enzyme restriction analysis and DNA sequencing.

Example 2

Recombinant Adenoviral Vectors that Express Heterologous Sequences Under the Control of an Adenoviral MLTU To accommodate heterologous sequences and support their expression via an adenoviral Major Late transcription unit (MLTU), a partial deletion in the E3 region of the Ad4 genome was generated. The partial deletion consisted of 1780 base pairs and was located at nucleotide positions 28446-30226 of GenBank sequence AY594254. The partial deletion was designed to preserve the known function of the E3 region while removing three open reading frames of unknown function (E3 24.8 k, E3 6.3 k, and E3 29.7 k). See FIG. 2. The deleted region is analogous to the ADP region of Ad5, although Ad4 does not encode an ADP-like gene.

Expression of various heterologous sequences (e.g., HA Bbn, HA VT/1194, or GFP) was linked to the endogenous adenoviral MLTU by cloning the heterologous sequence into the partial E3 deletion such that the heterologous sequence became operably linked to the native E3 24.8 k splice acceptor for MLP-driven expression. The native E3 24.8 k splice acceptor is close to consensus, so the sequence did not require modification. To promote the strongest initiation of translation, the sequence immediately preceding the ATG start codon of the heterologous sequence was optimized to a consensus Kozak sequence. In the resulting recombinant viral vectors, some early low-level expression may occur through the endogenous E3 promoter at early stages of virus replication, but expression is greatly boosted when the MLP becomes active upon the initiation of DNA replication in infected cells. In order to better define the boundary between early and late E3 gene products, a small piece of DNA comprising 29 bps of the Ad5 E3A poly A signal sequence was incorporated downstream of the heterologous sequences. A potentially similar sequence to the Ad5 E3A poly A sequence can be found further downstream in Ad4 and may help to control transcription at the early stages and maximize expression of the heterologous sequences.

Different recombinant adenoviral vectors featuring MTLU-driven expression of heterologous sequences are listed in Table 15. For the Ad-4-HA-Bbn vector, the genome size is 22 base pairs smaller than the wild-type Ad4 military strain, as indicated below:

a) −1780 bps Partial deletion with the E3 region (nt 28446-30226 of AY594254);
b) +10 bps 5' addition of consensus Kozak sequence;
c) +1701 bps full length HA gene (A/Brisbane/10/2007 (H3N2))
d) +18 bps remaining polylinker
e) +29 bps Ad5 E3A poly A signal sequence

TABLE 15

Recombinant Adenoviral Vectors Expressing Influenza Antigens

| Antigen | Virus Name | Strain | Promoter | Gene[1] |
|---|---|---|---|---|
| H5HA | PXVX0116 | A/Vietnam/1194/2004 | CMV | Opt. |
|  | PXVX0103 | A/Vietnam/1194/2004 | MLTU | Native |
|  | PXVX0113 | A/Vietnam/1194/2004 | CMV | Native |
|  | PXVX0117 | A/Vietnam/1203/2004 | CMV | Opt. |
|  | PXVX0107 | A/Vietnam/1203/2004 | MLTU | Native |
|  | PXVX0252 | A/Anhui/1/2005 | MLTU | Native |
|  | PXVX0250 | A/Egypt/2321/2007 | MLTU | Native |
|  | PXVX0251 | A/Egypt/3300-NAMRU3/2008 | MLTU | Native |
| H3HA | PXVX0101 | A/Brisbane/10/2007 | MLTU | Native |
|  | PXVX0102 | A/Brisbane/10/2007 | CMV | Opt. |
|  | PXVX0253 | A/Perth/16/2009 | MLTU | Native |
| BHA | PXVX0254 | B/Brisbane/60/2008 | MLTU | Native |
| H1HA | PXVX0201 | A/California/05/2009 | MLTU | Native |
|  | PXVX0204 | A/California/05/2009 | CMV | Opt. |
| H1NP | PXVX0205 | A/Texas/04/2009 | MLTU | Native |
|  | PXVX0206 | A/Texas/04/2009 | CMV | Native |
| H1M1 | PXVX0207 | A/California/08/2009 | MLTU | Native |
|  | PXVX0208 | A/California/08/2009 | CMV | Native |

[1]Gene Description of either native or codon-optimized sequence.

Example 3

Recombinant Adenoviral Vectors that Express Heterologous Sequences Under the Control of an Exogenous Promoter Another set of recombinant adenoviral vectors were generated wherein heterologous sequences of interest were integrated into the polylinker of an expression cassette consisting of a CMV promoter, an Ad4 tripartite leader sequence, a polylinker, and a bovine growth hormone (BGH) poly A signal sequence. The resulting expression cassettes were integrated into Ad4 vectors containing either a partial or full E3 deletion. The partial E3 deletion was as described in Example 2. The full E3 deletion consisted of 3926 base pairs, was located at nucleotide positions 27,356 to 31,282 of GenBank sequence AY594254, and further comprised a mutation in the ATG start codon of the 23.3 k ORF, which was only partially deleted. See FIG. 2. Regardless of the type of E3 deletion, the expression cassettes were inserted into the Ad4 vector between the E3 poly A signal sequence and the L5 fiber gene. See FIG. 2.

Different recombinant adenoviral vectors featuring CMV-driven expression of heterologous sequences are listed in Table 15. "Opt." refers to codon optimization of the antigen sequence.

Example 4

Production of Recombinant Adenoviruses

Recombinant adenoviruses were created by transfecting A549 (MCB) cells with a linear DNA fragment corresponding to a recombinant adenoviral genome. The linear DNA fragments were cleaved so as to remove all extraneous bacterial plasmid sequences. Once cytopathic effect was observed in the A549 cells (typically after 7-10 days), viruses were harvested and serial passaged for higher yields. To ensure that the identify of the virus was correct, the viral DNA was isolated using a modified Hirt protocol and analyzed by PCR, restriction digest, and sequencing of the heterologous inserts and flanking regions. The sequence confirmed that the heterologous inserts and flanking regions were correct at the nucleotide level.

Example 5

Expression of Heterologous Sequences from Recombinant Adenoviruses

Figure 4:
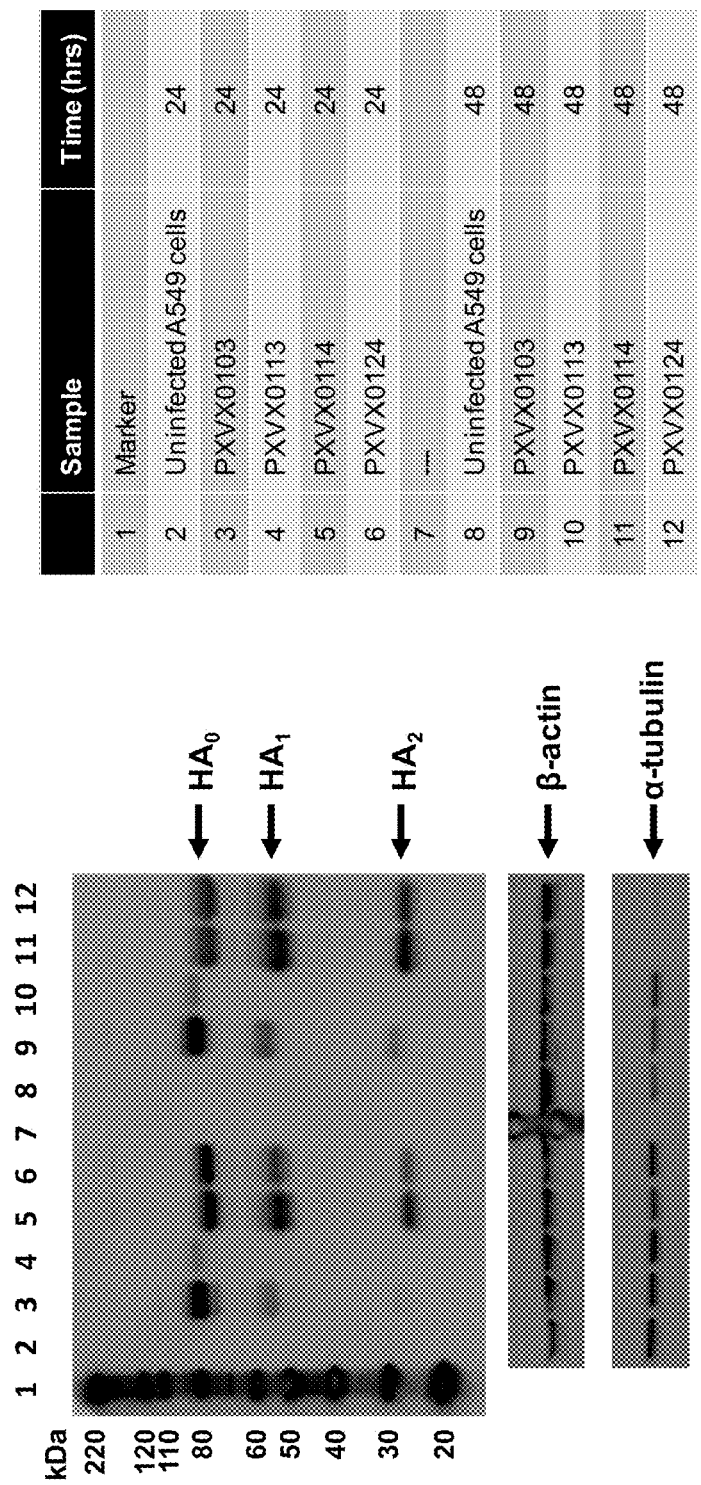
FIG. 4. Detection by western blot of hemagglutinin expression from A549 cells infected with 4 different Ad4 H5-HA viruses. A549 cells (50-70% confluent in 6-well plate) were infected with $2.5 \times 10^7$ vp/mL of each virus and incubated at 37° C. in a CO2 incubator. After either 24 or 48 hours whole cell lysates were prepared. Proteins were separated by SDS-PAGE, transferred to nitrocellulose and blots probed with antibodies to detect HA, β-actin and α-tubulin as indicated. Marker lanes and controls, both uninfected and non-relevant recombinant virus, are also identified. All recombinant viruses express HA robustly except for the non-optimized CMV virus, PXVX0113, which expressed a substantially lower level of HA.
Figure 5:
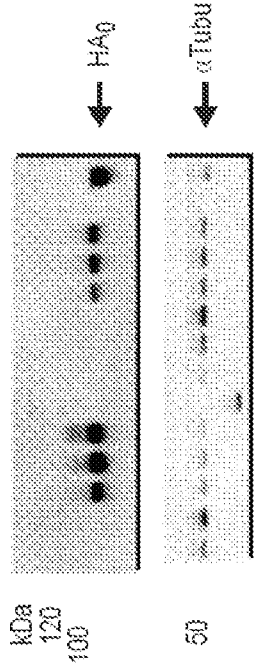
FIG. 5 demonstrates the expression of a influenza HA protein from two different adenoviral vectors of the invention as detected by Western blot analysis. The PXVX0101 vector contains a partial E3 deletion and a heterologous sequence encoding HA, wherein the heterologous sequence is inserted into the partial E3 deletion and under the control of the endogenous MLP. The PXVX0111 vector contains a full E3 deletion and a heterologous sequence encoding HA, wherein the heterologous sequence is inserted proximal to the E3 deletion and comprises a CMV promoter.
Figure 6:
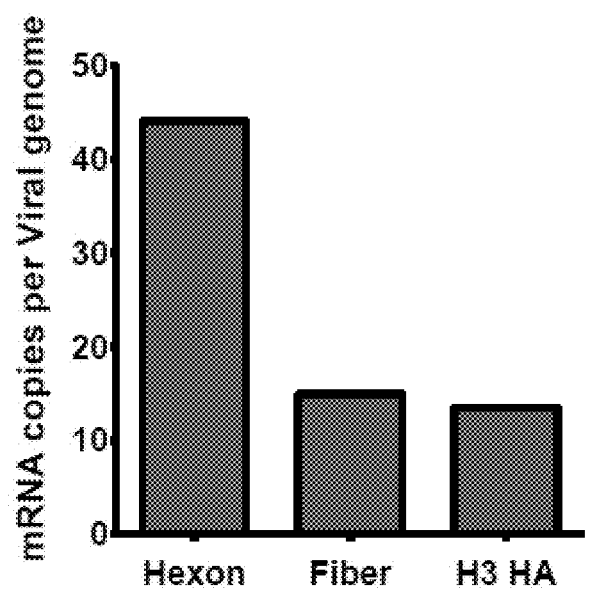
FIG. 6 shows mRNA expression by real time PCR analysis for H3 HA antigen and adenoviral proteins of A549 cells infected with PXVX0101.
Figure 7:
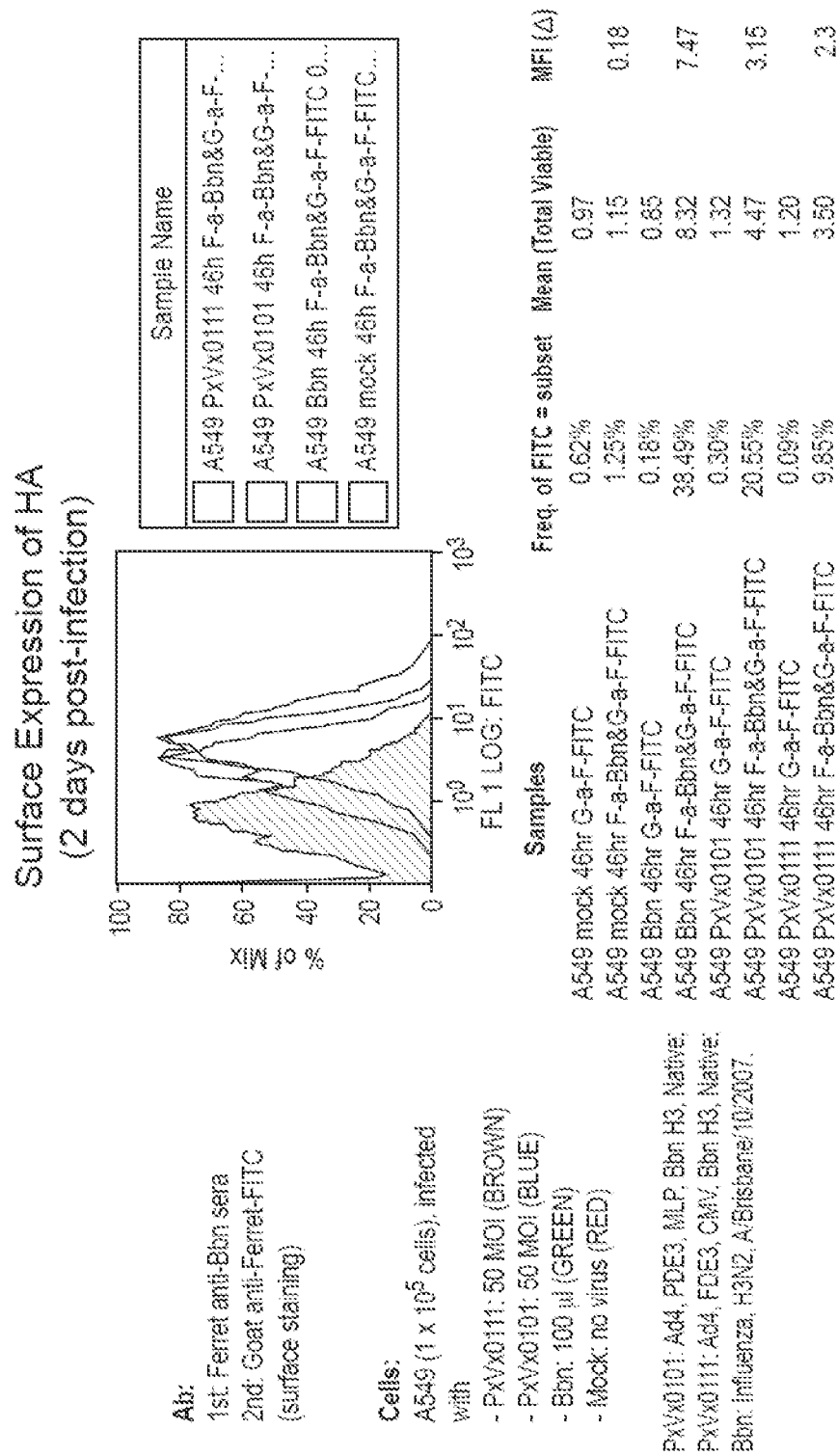
FIG. 7 demonstrates surface expression of HA in a FACS assay wherein A549 cells were infected with PXVX0101 and PXVX0111.
Figure 8A:
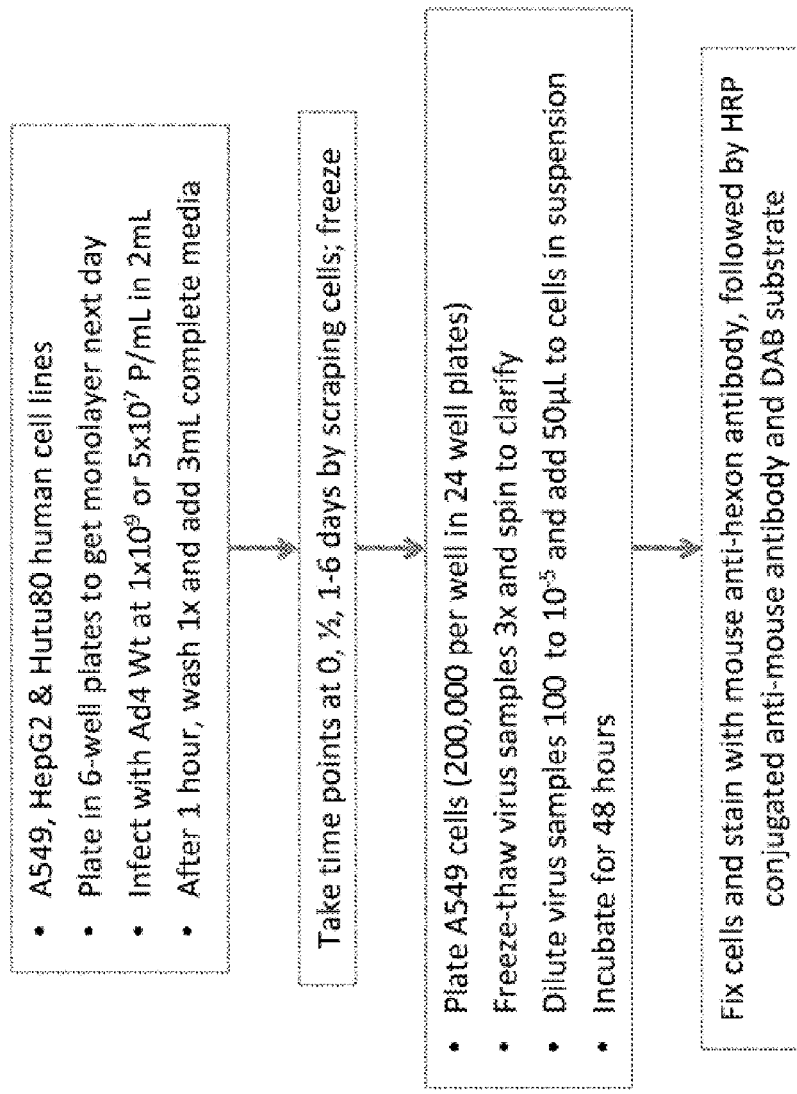
FIGS. 8A and 8B show a flow chart describing a one-step growth assay that can be used to test the production of adenoviral vectors of the invention and the results of the assay for PXVX0101 and PXVX0111 in three different cell lines.
Figure 8B:
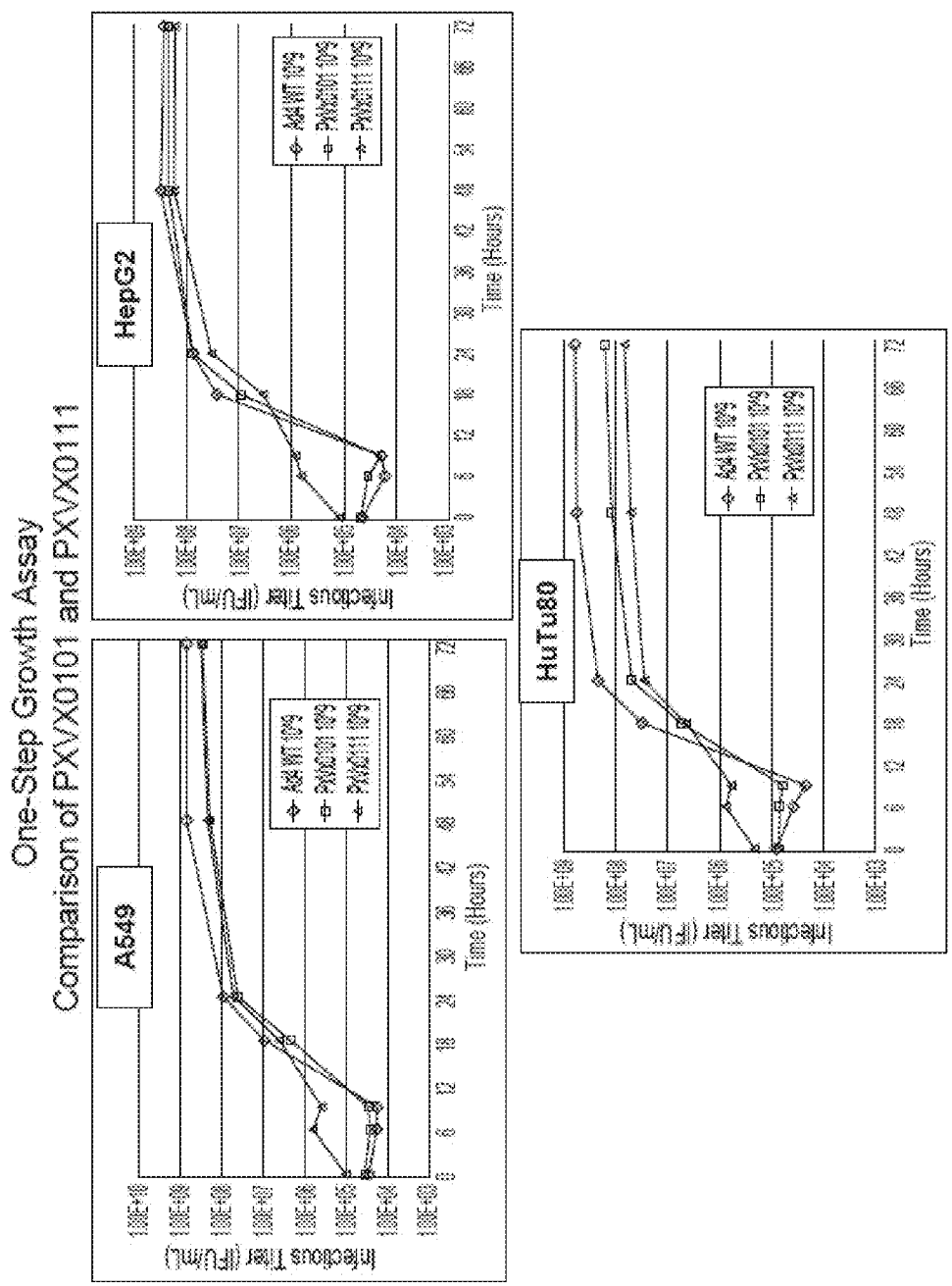
Figure 9A:
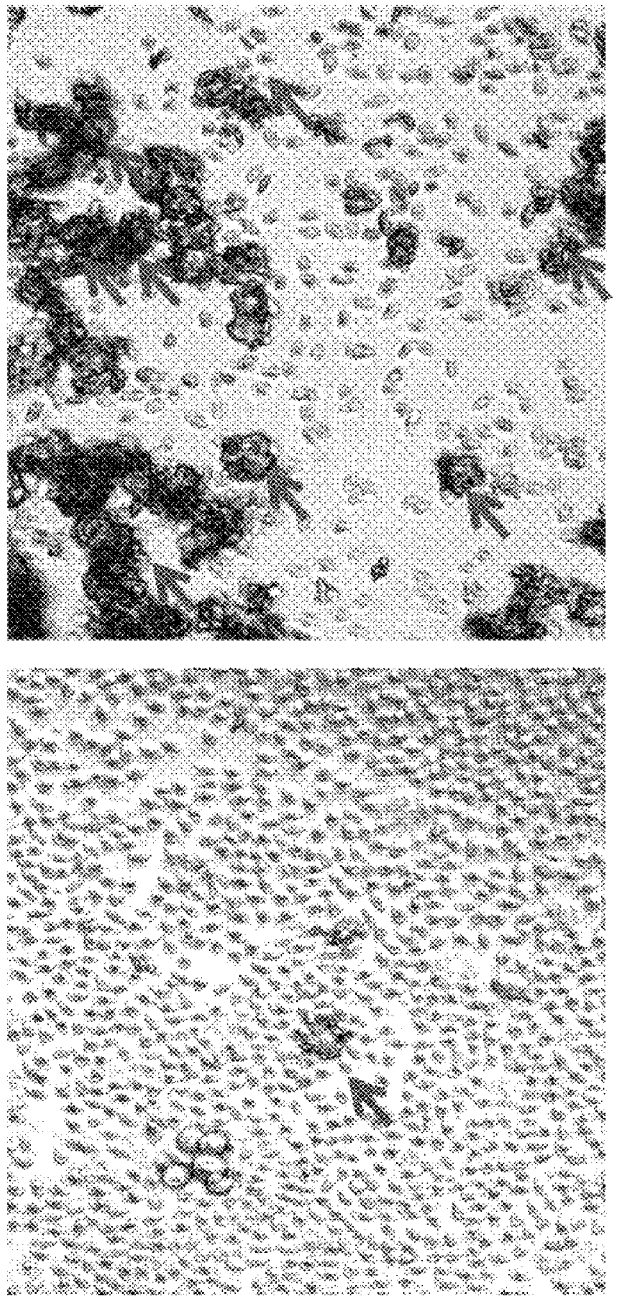
FIGS. 9A and 9B show agglutination of red blood cells on A549 cells infected with influenza virus (A) or PVXV0101 (B).
Figure 9B:
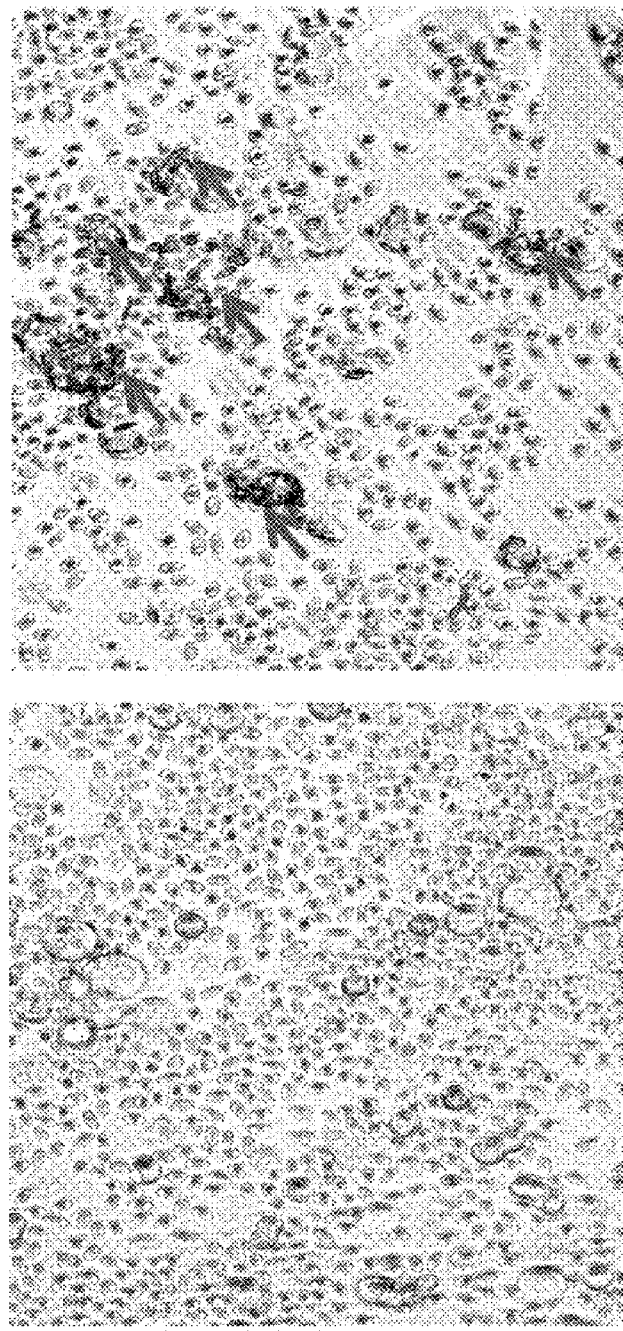

A549 cells infected with recombinant adenoviruses were analyzed for expression of heterologous sequences. FIG. 4 shows expression of HA from four different recombinant Ad4H5HA adenoviruses: H5HA from A/Vietnam/1194/2004 under the control of the endogenous MLP promoter (PVXV0103); H5HA from A/Vietnam/1194/2004 under the control of the CMV promoter (PVXV0113); H5HA from A/Vietnam/1203/2004 under the control of the CMV promoter, full deletion of E3 (PVXV0114); and H5HA from A/Vietnam/1203/2004 under the control of the CMV promoter, partial E3 deletion (PVXV0124). FIG. 5 shows expression of HA from the endogenous MLP of adenoviral vector PXVX0101 and from a CMV promoter in adenoviral vector PXVX0111. Real time PCR analysis confirmed that the expression levels of H3 HA from the adenoviral vector PXVX0101 were similar to the distal adenoviral protein Fiber. See FIG. 6. Two days after infection with these constructs, HA antigen is present on the surface of A549 cells, as shown in the FACS results of FIG. 7. Consistent with these results, A549 cells infected with PVXV0101 were shown to agglutinate with red blood cells. See FIGS. 9A and 9B. Using a one-step growth assay (FIG. 8A), PXVX0101 and PXVX0111 exhibited near-wild type growth in A549, HepG2, and HuTu80 cells (FIG. 8B).

Example 6

Integration of Antigens from Influenza in the HVRs of Ad4 Hexon

Figure 10:
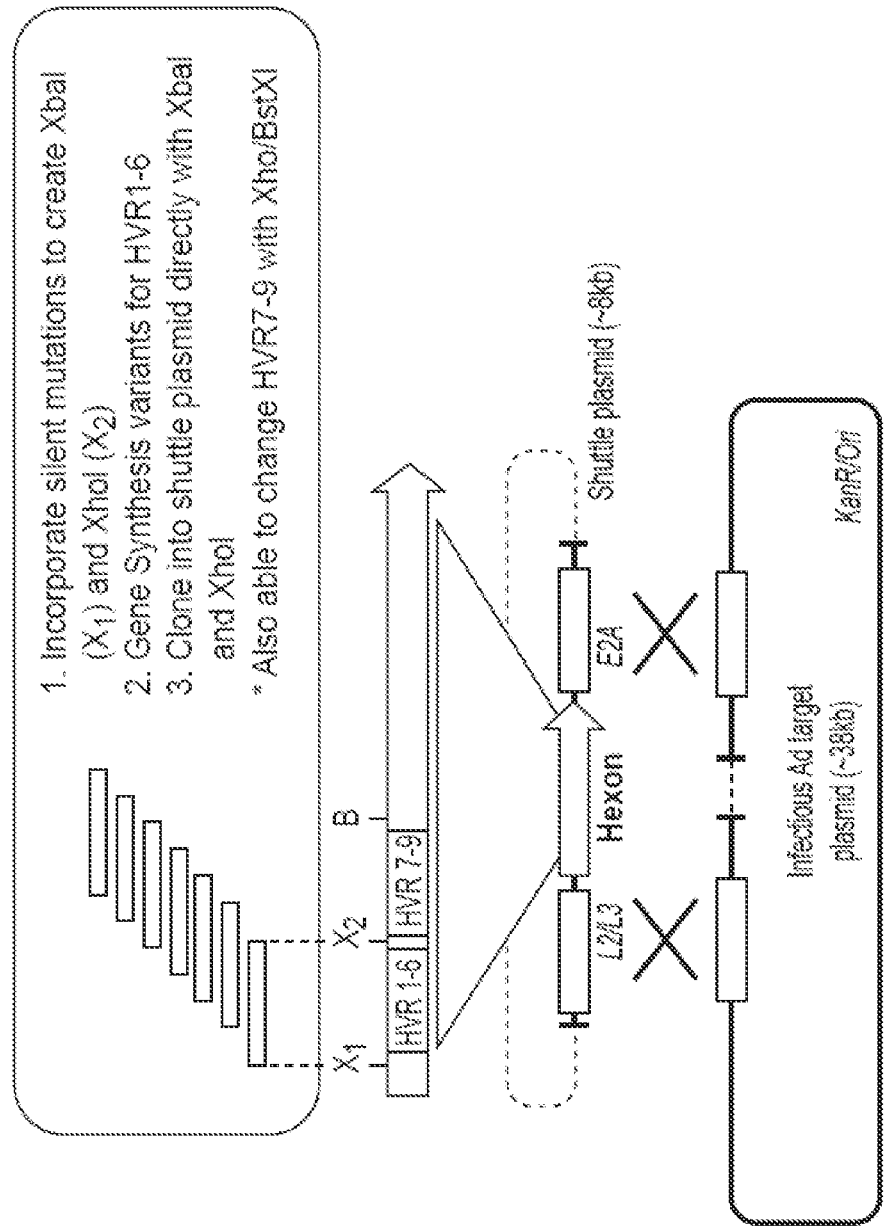
FIG. 10 is a diagram of various cloning steps involved in creating a hexon sequence that can be used for generating chimeric hexon coding sequences.
Figure 11:
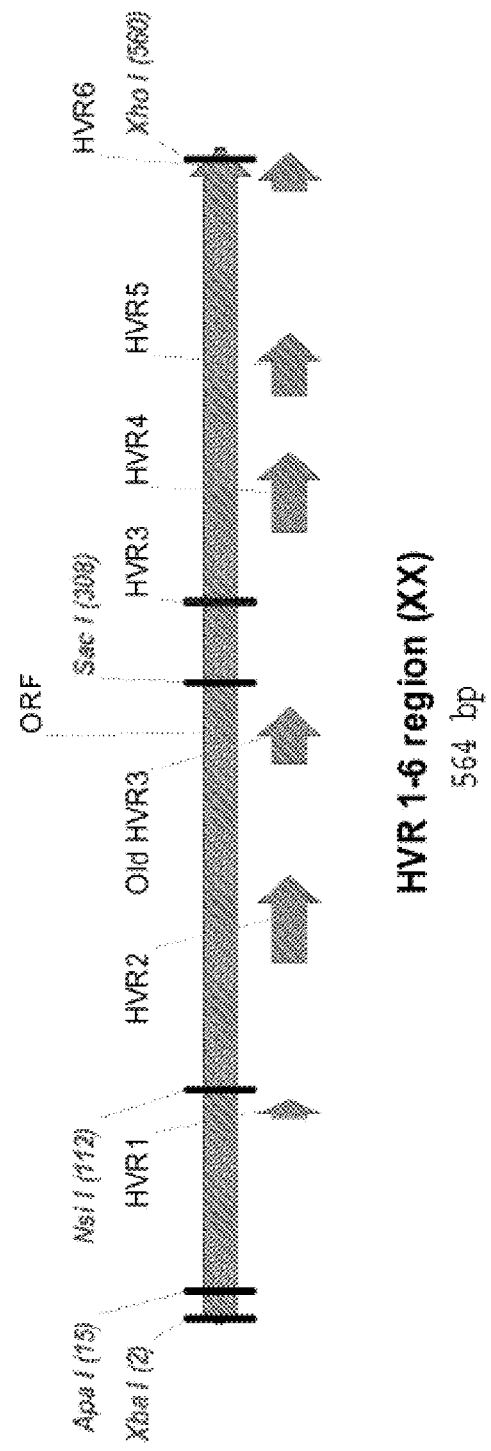
FIG. 11 is a diagram of the location of the hexon HVR 1-6 regions in a fragment of the hexon coding sequence being used to construct chimeric sequences.

FIG. 10 depicts one strategy for generating hexon modified vectors. The strategy relies upon incorporation of silent mutations into the Ad4 hexon sequence such that a DNA fragment containing HVR regions. 1-6 can be replaced in a single step. The strategy incorporates both XbaI and XhoI cloning sites into the Ad4 hexon coding region. Each XbaI/XhoI fragment is then generated by synthetic gene synthesis. FIG. 11 shows the location of the restriction sites in relation to the HVR regions. In addition, the XhoI site and an endogenous BstXI site can be used to replace HVR7 or HVR7-9, as needed. A series of epitopes were designed around the M2e sequence of different influenza viruses (see FIG. 12). The sequences provide a consensus for M2 proteins from H5, H7, and H9 strains of influenza. Human M2E represents a consensus sequence for H1 and H3 M2e. Spacer sequences are included to position the integrated sequences in an optimal immunoreactive manner. The sequences are designed to prevent antibodies from being raised to the boundaries between epitopes. FIG. 13 describes a series of 17 hexon modification that can be generated.

Example 7

Ad-4-H5-Vtn Purified Virus from A549 Cells Induces HA-Specific Antibodies in Mice The immunogenicity of purified Ad-4-H5-Vtn PXVX0103 and PXVX0116 viruses in mice was tested as shown in Table 16. Controls were wt Ad4 virus (negative control) and H5 HA protein (positive control).

A549 cells were infected with Ad-4-H5-Vtn PXVX0103 (MLTU promoter) and PXVX0116 (CMV promoter) viruses. Viruses were subsequently isolated and purified by ion exchange chromatography. For each group in the immunogenicity studies, six C57B1/6×Balb/c F1 female mice between 6 and 8 weeks of age were used. Mice were immunized once on Day 0 (prime) then again on Day 14 (boost) using the dose titrations of $1 \times 10^{10}$, $1 \times 10^9$, $1 \times 10^8$ vp/mouse and an intramuscular (i.m.) route of administration. After 10 and 27 days, 0.2 mL of blood were collected by retro-orbital bleeding and serum antibody titers determined by HA endpoint ELISA and hemagglutination inhibition (HAI).

Briefly, for the ELISA assay, high-binding 96-well ELISA plates were coated with either 1.5 ug/ml ($5 \times 10^9$ particles/ml) adenovirus or 5 ug/ml purified HA protein (Immune Technologies) and incubated overnight at 4° C. ELISA plates were then washed and blocked with PBS+3% BSA for 2 hours. Serial dilutions of sera were added to the plates and incubated for 2 hours. After thorough washing, antigen-specific serum antibodies were detected using HRP-coupled secondary antibody. The plates were developed with an HRP substrate reagent, stopped with acid, and absorbance measured on a PolarStar plate reader at 450 nm. End-point ELISA titers are expressed as the reciprocal of the highest dilution that gives a reading three standard deviations above the mean background. In the case of HAI titers, serial dilutions of sera are allowed to react with a fixed dose (4HAU) of influenza virus or HA protein, followed by the addition of chicken RBC. In the presence of neutralizing antibody, the ability of the virus to agglutinate the RBC is inhibited. Antibody HAI titer is the reciprocal of the last dilution of serum capable of inhibiting agglutination.

TABLE 16

Immunogens, Dose, Route

| Groups | Description | Particles/Dose | Volume | Route |
|---|---|---|---|---|
| 1 | Ad4-H5-Vtn virus PXVX0103[a,b] | $1 \times 10^{10}$ | 0.1 mL | IM |
| 2 | Ad4-H5-Vtn virus PXVX0103 | $1 \times 10^9$ | 0.1 mL | IM |
| 3 | Ad4-H5-Vtn virus PXVX0103 | $1 \times 10^8$ | 0.1 mL | IM |
| 4 | Ad4-H5-Vtn virus PXVX0116[c] | $1 \times 10^{10}$ | 0.1 mL | IM |
| 5 | Ad4-H5-Vtn virus PXVX0116 | $1 \times 10^9$ | 0.1 mL | IM |
| 6 | Ad4-H5-Vtn virus PXVX0116 | $1 \times 10^8$ | 0.1 mL | IM |
| 7 | wt Ad4 virus | $1 \times 10^{10}$ | 0.1 mL | IM |
| 8 | H5 recombinant protein | 5 µg | 0.2 mL | SC |

[a]H5-Vtn (hemagglutinin (HA) from A/Viet Nam/1194/2004 strain)
[b]PXVX0103 - Ad4 with HA transgene driven by MLTU promoter
[c]PXVX0116 - Ad4 vector with HA transgene driven by CMV promoter As shown in FIGS. 14, A, B and C, mice immunized with high dose ($1 \times 10^{10}$ vp), purified Ad-4-H5-Vtn (PXVX0103) virus produced a strong HA-specific antibody titer when measured by ELISA of approximately $2.5 \times 10^4$ and $7 \times 10^4$ following one and two immunizations, respectively. Lower but significant HA-specific responses of approximately $2.5 \times 10^3$ and $2 \times 10^4$ were also induced using a lower dose of virus ($1 \times 10^9$ vp) following one and two immunizations, respectively. At the lowest viral dose used ($1 \times 10^8$ vp), a significant response of $8 \times 10^3$ antibody endpoint titer was observed following two immunizations. When the H5 transgene was driven by CMV (PXVX0116), approximately 3-fold higher antibody responses were induced. As expected, mice immunized with wt Ad4 purified virus ($1 \times 10^{10}$ vp), which does not contain a HA transgene, did not induce a detectable HA-specific antibody response. Following two immunizations, the H5 protein induced HA antibody endpoint responses of approximately $7 \times 10^4$. In regard to HAI titers, mice immunized with $1 \times 10^{10}$ vp of purified Ad-4-H5-Vtn (PXVX0103) virus produced a significant HAI antibody titer of 1:20 and 1:40 following one and two immunizations, respectively. Following the second immunization, Ad-4-H5-Vtn (PXVX0103) at the lower dose of $1 \times 10^9$ vp induced a significant HAI response of 1:20. HA-specific responses were not detected for the wt Ad4 virus. Again, Ad-4-H5-Vtn (PXVX0116) induced approximately 4-fold higher HAI titers. Purified H5 protein induced a significant response of 1:40 following the second immunization. These result are consistent with the study using infected cells where it was demonstrated that two immunizations of purified H5 protein were required to induce a measurable HAI antibody titer.

These immunogenicity studies using purified Ad-4-H5-Vtn viruses shows that, in spite of the lack of viral replication in mice, the viruses entered cells in vivo and the transgene was expressed sufficiently to induce an H5-specific antibody response.

Example 8

Figure 15:
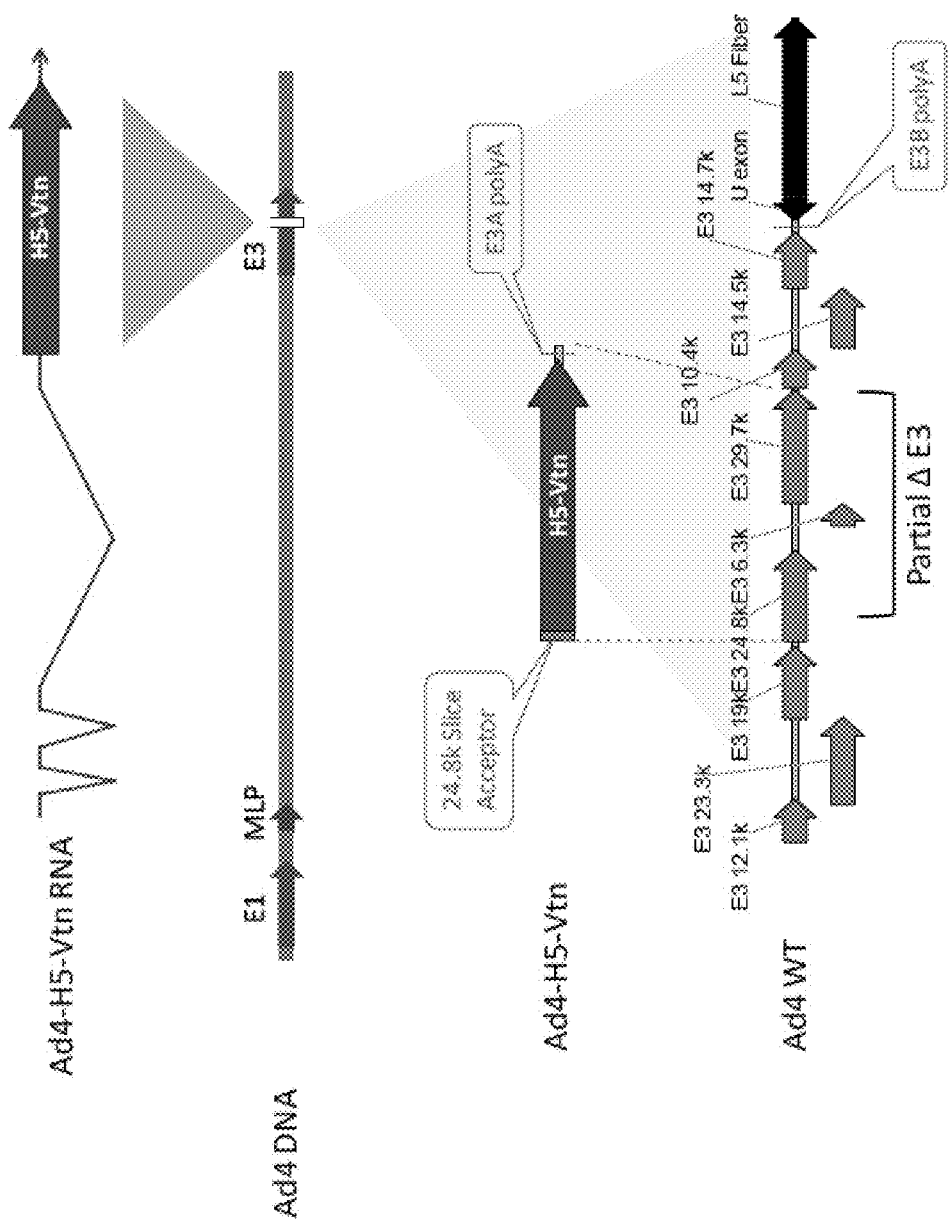
FIG. 15. Schematic representation of Ad-4-H5-Vtn vector design (PXVX0103). The H5 HA native coding sequence, with the polybasic domain removed, was derived from A/VietNam/1194/2004 influenza virus and inserted into the Ad4 virus E3 gene region. The Ad4 virus E3 24.8K, E3 6.8K and E3 29.7K genes were deleted to accommodate the HA transgene and the splice acceptor site of E3 24.8K was retained to drive expression of the HA transgene. The E3A polyadenylation signal sequence, derived from Ad5, was placed downstream of the HA coding sequence.
Figure 16:
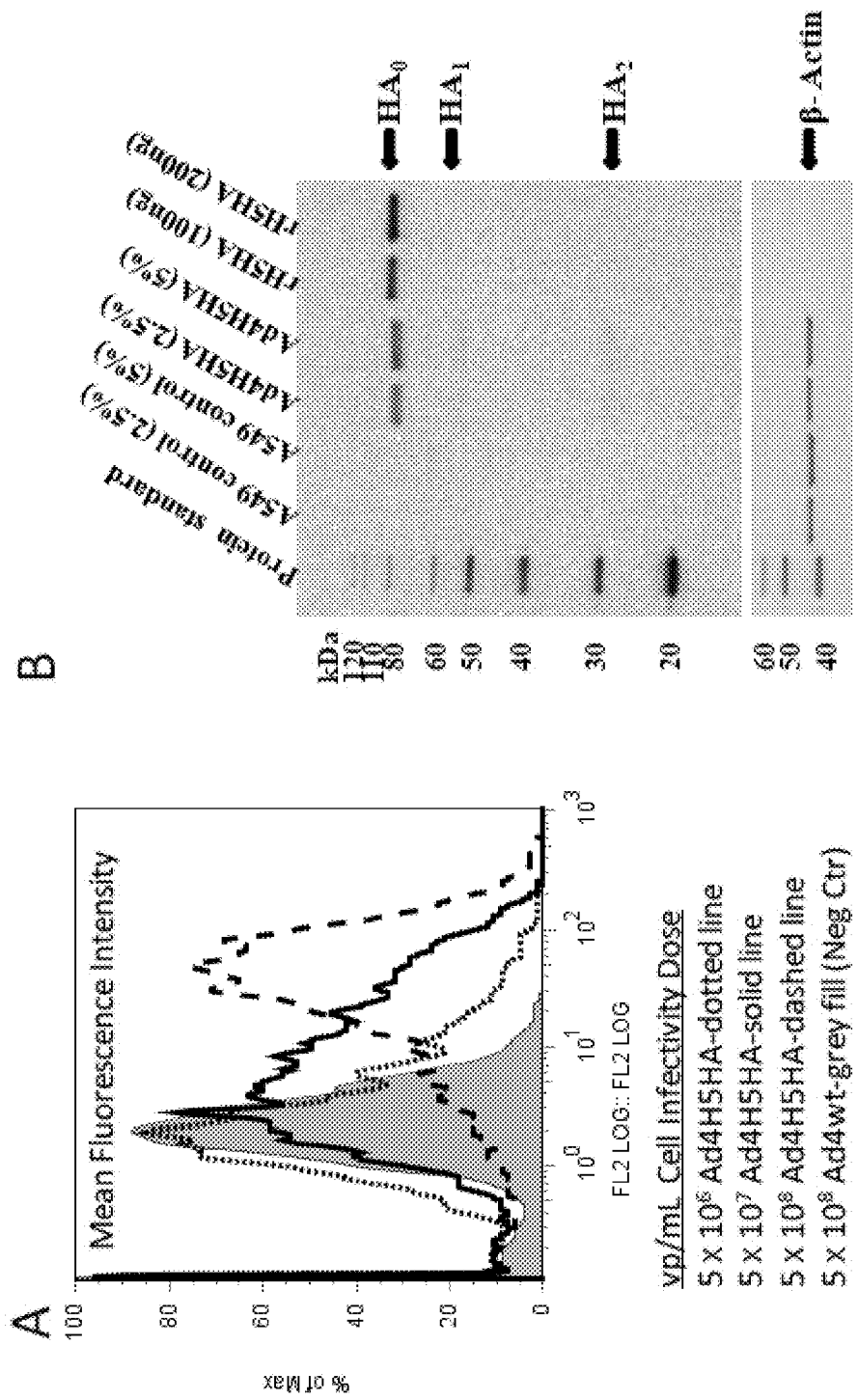
FIG. 16. (A) Characterization of PXVX0103 demonstrating cell surface expression of H5 HA. HA (H5-Vtn) surface expression was confirmed by infecting $1 \times 10^6$ A549 cells with different levels of PXVX0103 (as indicated) for 48 hours before surface staining with a mouse anti-avian H5 monoclonal antibody (clone 19C11, Advanced ImmunoChemical). Detection was with a goat anti-mouse IgG-PE secondary antibody. Ad4 wild-type was used as the control (shaded area) for comparison to the Ad-4-H5-Vtn infected cells (lines). With increasing amounts of Ad-4-H5-Vtn a significant shift to the right indicates that cells are expressing robust levels of H5 protein on the cell surface. (B) Western analysis of the same samples used for flow cytometry in (A).
Figure 17:
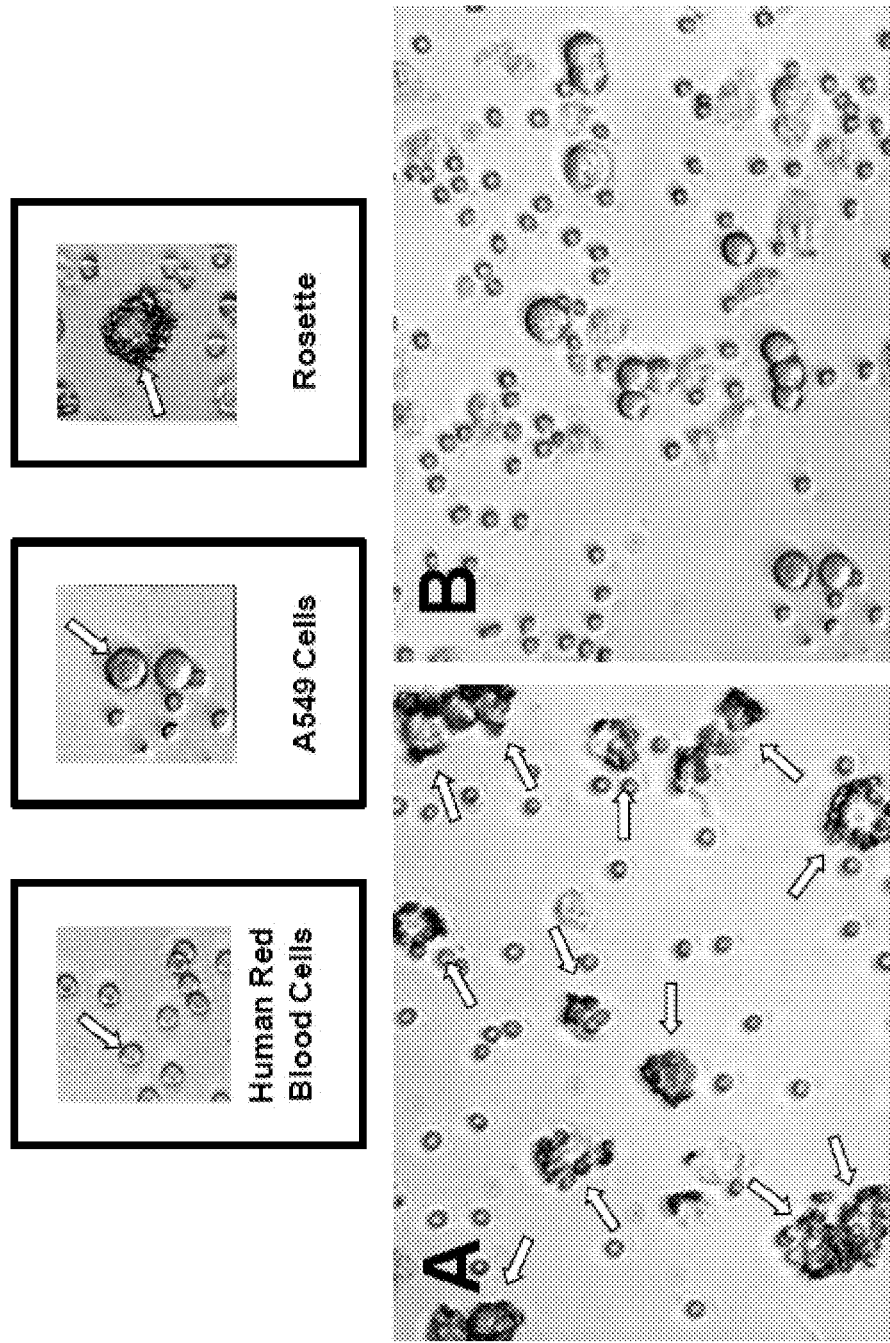
FIG. 17. The recombinant HA (Vtn) expressed from PXVX0103 is functional as demonstrated by red blood cell rosetting of virus-infected A549 cells. Representative pictures of A549 cells infected with (A) PXVX0103 or (B) Ad-4-wt for 24 hours, washed, and then incubated in the presence of human donor red blood cells (RBCs). Rosettes are indicated by white arrows as a sign of interaction between the virus-expressed HA on the A549 cell surface (larger cells) and the N-acetylneuraminic acid (the predominant sialic acid found in cells) found on the surface of the RBCs (smaller cells). This will only occur if the HA is correctly folded.
Figure 18:
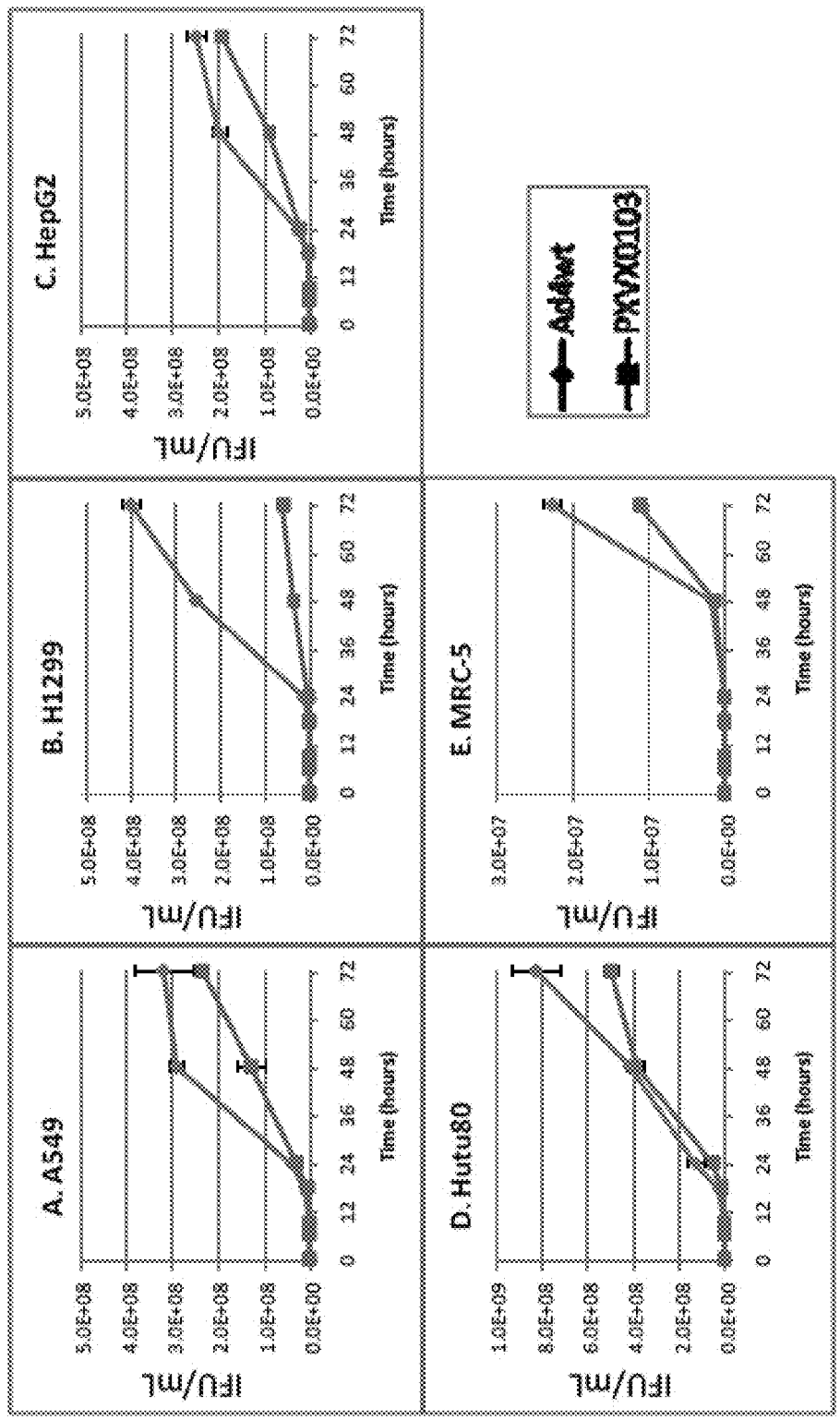
FIG. 18. Ad4-H5-Vtn (PXVX0103) virus growth is attenuated in various human cell lines versus Ad4 wild type virus. Growth of Ad-4-H5-Vtn virus was compared to growth of Ad4 WT virus in several human cell lines; A549 (lung carcinoma; A), H1299 (lung carcinoma; B), HepG2 (hepatocellular carcinoma; C), HuTu 80 (duodenum adenocarcinoma; D) and MRC-5 (embryonic lung fibroblast; E).
Figure 19:
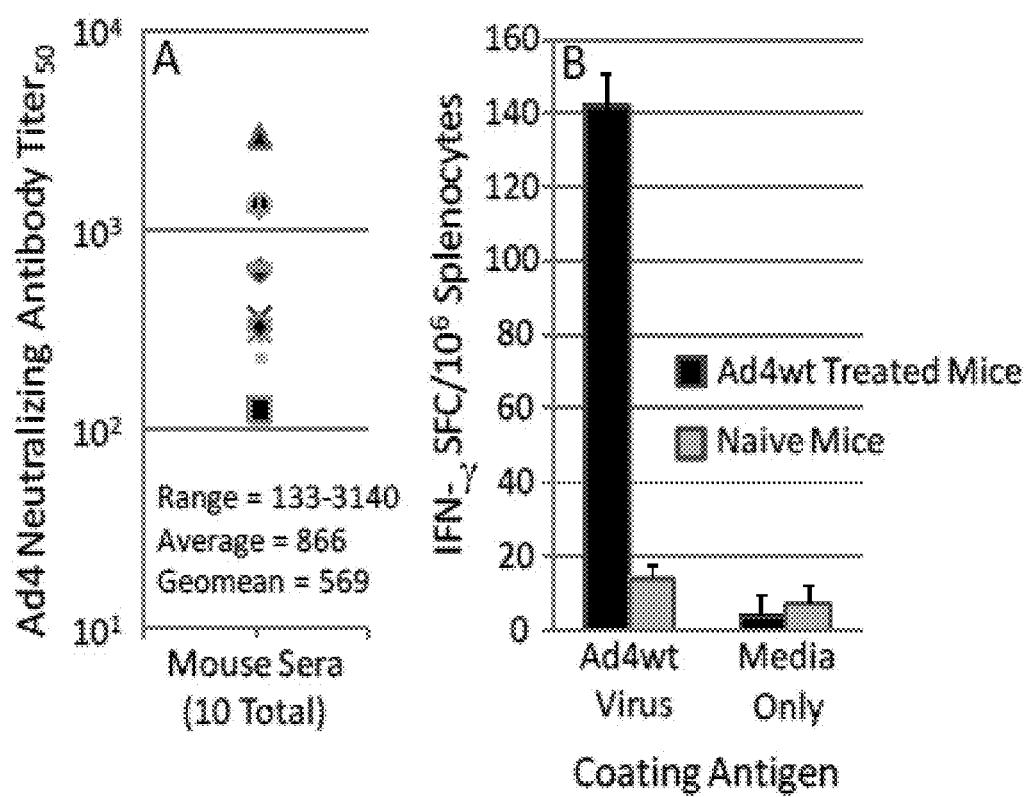
FIG. 19. Ad4-specific neutralizing antibody titers (A) and Ad-4-specific cellular immunity following Ad4 wt immunization (B). Mice were immunized intranasally with $1 \times 10^9$ vp of Ad4 wt virus per mouse to establish pre-existing immunity to the vector. Four weeks following the immunization, ten individual mice were bled and Ad-4-specific neutralizing antibody titers were determined (A). Two m (with a combination of 120 µg PA and 60 µg lethal factor) after 46 days post immunization. Survival was monitored for 30 days post challenge.
Figure 20:
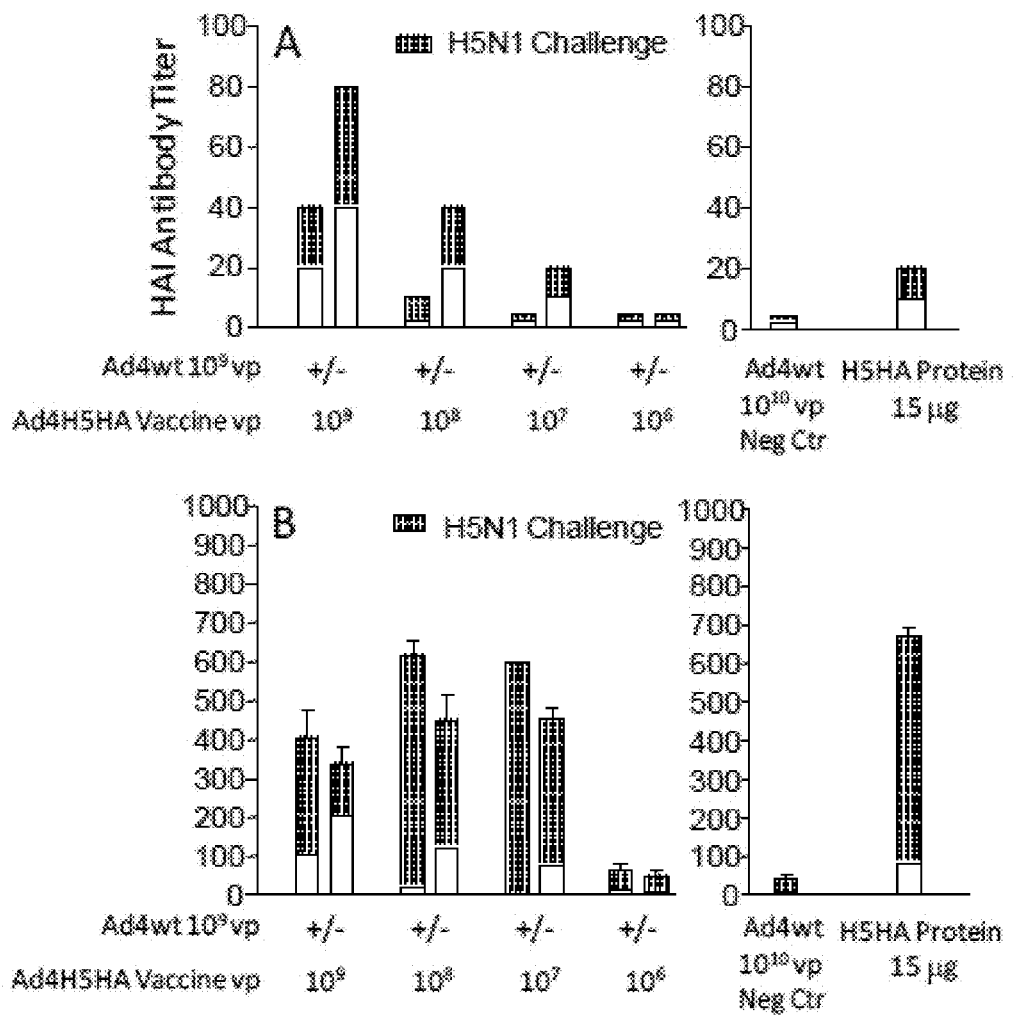

Evaluation of an Adenovirus Serotype 4 Influenza H5 Hemagglutinin Vaccine in Mice Design of an Adenovirus Serotype 4 HSHA Vaccine The Ad-4-H5-Vtn (PXVX0103) recombinant adenovirus described in Example 7 was evaluated for safety, immunogenicity and efficacy as a vaccine in a murine model. As depicted in FIG. 15, the Ad4H5HA vaccine was constructed with the Ad4 virus E3 24.8K, 6.8K and 29.7K genes deleted to accommodate the HA gene from A/VietNam/1194/2004 H5N1 influenza virus. The splice acceptor site of E3 24.8K gene was retained to drive expression of the HA transgene. The HA native coding sequence was used with the polybasic cleavage site removed. The E3A polyadenylation signal sequence, derived from Ad5, was placed downstream of the HA coding sequence. Direct sequencing of DNA confirmed the integrity of the HA transgene and flanking vector sequences. Once the correct recombinant was identified and isolated it was digested with the appropriate restriction enzymes to remove extraneous bacterial plasmid sequences but retain the complete recombinant Ad4 genomic DNA encoding the HA transgene.

To produce virus for characterization, transfection of this linear Ad4H5HA DNA sequence into the mammalian A549 cells (ATCC, Manassas, Va.) was performed. One day before transfection, $3\times10^{5}$ A549 cells were plated into each well of a 6-well plate (BD Biosciences San Jose, Calif.) in DMEM (Hyclone, Logan, Utah/10% fetal calf serum (FBS) (Hyclone) and plates incubated at 37° C. in a humidified atmosphere of 5% $CO_2$. The following day, cells were 50-90% confluent and subsequently transfected with 2 μg of linearized Ad4H5HA DNA per well using Fugene HD transfection reagent at 8 μL per well per manufacturer's instructions (Roche, Indianapolis, Ind.). Once a cytopathic effect (CPE) was observed, generally 7-10 days after transfection, virus was harvested from at least 3 of the 6 wells by dislodging infected cells using 16 cm cell scrapers (VWR, West Chester, Pa.) followed by 3 cycles of freeze-thaw cell disruption (liquid nitrogen and a 37° C. water bath). The lysate was clarified by centrifugation at 4° C. at 1,800 g for 10 min and approximately 6 mL of supernatant was collected for a two-step viral expansion procedure. Three mL of the supernatant was used to infect $1.5 \times 10^6$ A549 cells in suspension in a 75 cm² flask (BD Biosciences) with a final volume of 15 mL DMEM/10% FCS. In 3 to 7 days following observation of CPE, cells were removed using 16 cm cell scrapers and subjected to the freeze-thaw and clarification procedure to obtain virus supernatant.

To assess HA expression from Ad4H5HA recombinant virus, HA protein expression was evaluated by flow cytometry in vitro. A549 cells were infected with a dose titration of Ad4H5HA viral particles (vp) and analyzed 48 h later using a primary H5-specific and secondary PE labeled antibody. As shown in FIG. 16A, A549 cells infected with the Ad4H5HA vaccine expressed HA protein in a dose-dependent manner. The mean fluorescence intensity (MFI) of the detected HA protein corresponding to the highest vaccine dose used was approximately 34.0 compared to Ad4 wt-infected cells used as a negative control where a MFI of approximately 2.0 was detected.

To confirm the Ad4H5HA recombinant virus induction of HA protein in vitro and to insure stable expression after 15 serial passages in A549 cells, western blot analysis was used. Ad4H5HA recombinant virus-infected A549 cells were harvested and whole cell extracts prepared. Varying amounts of infected cell extracts were separated by SDS-PAGE gels and transferred to nitrocellulose. HSHA-specific antiserum was used to detect the HA protein while anti-β-actin antibody was used as a protein loading control. As shown in FIG. 16B, HA protein derived from Ad4H5HA recombinant virus-infected cell lysates (2.5 and 5%) was detected at the appropriate size, 80 kDa, relative to purified recombinant (r)H5 protein positive controls (100 and 200 ng). HA-specific protein was not detected using protein from uninfected A549 cells (2.5 and 5%), negative control. Minor bands of HA1 and HA2 fragments corresponding to cleaved HA0 were also observed in Ad4H5HA-infected A549 cell lysates. The western analysis also confirmed that the Ad4H5HA recombinant virus stably expressed H5HA even after 15 passages in A549 cells. Consistent with these results, A549 cells infected with PVXV0103 were shown to agglutinate with red blood cells. See FIG. 17.

Efficacy of Ad4H5HA Recombinant Adenovirus as a Vaccine

To address safety of the recombinant virus, the growth of Ad4H5HA virus to Ad4 wt virus was compared in several human cell lines; A549, H1299, HepG2, HuTu 80 and MRC-5. Although Ad5 viruses can be assessed by spread assay methodology, Ad4 does not behave in a similar manner and does not readily lyse cells in vitro. Thus, a traditional one-step growth assay was used to evaluate growth kinetics (see FIG. 8A). Growth of Ad4H5HA virus was similar or attenuated relative to Ad4 wt virus. See FIG. 18. Specifically, when evaluating the 48 and 72 h time points following infection, the infectious particles measured following cell lysis was 1.1 to 2.3-fold higher for Ad4 wt virus versus Ad4H5HA virus in 4 of the 5 cell lines tested, FIG. 18. For the fifth cell line, H1299, the infectious particles measured for Ad4 wt relative to Ad4H5HA was 7 to 6.5-fold higher for the 48 and 72 h time points, respectively. In no case was growth of Ad4H5HA vector higher than Ad4 wt virus.

The initial phase of the immunogenicity and efficacy evaluation process was to establish pre-existing immunity to Ad4 wt virus to evaluate effect on vaccine potency. Thus, mice were immunized i.n. with $1\times10^9$ vp of Ad4 wt virus and one month later Ad-4-specific neutralizing antibody titers and cellular immunity were determined. Immune sera from 10 immunized mice were collected and Ad-4-specific neutralizing antibody titers measured ranged from 133 to 3140 with arithmetic and geometric means of 866 and 569, respectively, FIG. 19A. Significant Ad-4-specific cellular immunity was also induced. Unpurified splenocytes from two mice were pooled and used in an ELISPOT assay. Upon incubation with heat-inactivated Ad4 wt virus, 140 IFN-γ spot forming cells (SFC) per $1\times10^6$ splenocytes were detected from Ad4 wt immunized mice versus 18 IFN-γ SFC using splenocytes from unimmunized mice, FIG. 19B. These mice and naïve mice with no pre-existing Ad4 wt immunity were subsequently used for Ad4H5HA vaccine immunizations.

Significant hemagglutination inhibition (HAI) antibody titers were measured 6 weeks following a single immunization of Ad4H5HA vaccine. As shown in FIG. 20A, a dose response was observed; $10^9$ vp (40 HAI), $10^8$ vp (20 HAI), and $10^7$ vp (10 HAI). The lowest dose of vaccine, $10^6$ vp was not immunogenic. There was an effect of Ad4 wt pre-existing immunity on vaccine potency whereby a HAI antibody titer of 20 was measured at the $10^9$ vp dose but lower doses were not immunogenic. Following the H5N1 reassortant virus challenge, HA1 responses were typically higher by one dilution, e.g., 40 to 80 and 20 to 40 at the $10^9$ vp vaccine doses. Again, the lowest dose of vaccine, $10^6$ vp, was not immunogenic. For comparator negative and positive controls, mice were immunized with $1\times10^{10}$ vp of Ad4 wt virus and 15 μg of recombinant H5HA protein, respectively. As expected, Ad4 wt virus did not induce a detectable HAI antibody titer response. The recombinant protein induced HAI antibody titer responses pre- and post-influenza challenge of 10 and 20 HAI antibody titers, respectively.

Vaccine induction of H5HA-specific cellular immunity was evaluated specific for a pool of four 15-mer peptides derived from the A/Vietnam/1194/2004 HA protein, FIG. 20B. The peptides in the pool consisted of: HA.156, seq KSSFFRNVVWLIKKN (SEQ ID NO: 2); HA.241 seq RMEFFWTILKPNDAI (SEQ ID NO: 5); HA.325 seq NRLVLATGLRNSPQR (SEQ ID NO: 8); and HA.529 seq IYQILSIYSTVASSLALAI (SEQ ID NO: 338). IFN-γ responses were measured of greater than 80 SFC when mice were immunized with doses of $10^7$, $10^8$ and $10^9$ vp of Ad4H5HA vaccine. Pre-existing Ad4 wt immunity also affected vaccine induction of cellular immunity in that only the $10^9$ vp dose of Ad4H5HA vaccine was immunogenic inducing approximately 100 IFN-γ SFC. Cellular responses were augmented 5 days following H5N1 reassortant virus challenge. In the presence or absence of pre-existing Ad4 wt immunity, $10^7$, $10^8$ and $10^9$ vp dose of Ad4H5HA vaccine induced between 300 and 600 IFN-γ SFC. It should be noted that in the case of pre-existing Ad4 wt immunity and vaccine doses of $10^7$ and $10^8$ vp, minimal IFN-γ responses of less than 50 SFC were boosted to greater than 500 SFC suggesting that even the lower vaccine doses primed for cellular responses. In all cases the $10^6$ vp dose was not immunogenic. As comparator controls, mice immunized with 15 μg of recombinant H5HA protein induced 80 and 680 IFN-γ SFC pre- and post-H5N1 reassortant virus challenge. Significant HA-specific cellular responses, 5 days post virus challenge, were not detected in mice immunized with only Ad4 wt virus and subsequently challenged with H5N1 reassortant virus.

Weight loss, survival and reduction of lung influenza virus titers were vaccine dose dependent following lethal H5N1 reassortant virus challenge. Weights of the animals were measured for 14 days following H5N1 reassortant challenge, FIG. 21A. If animals were recorded to have lost 20% or more of their original weight for two days in a row then they were euthanized. Typically, it was necessary to sacrifice animals at days 6-12 following challenge. In animals without pre-treatment of Ad4 wt virus little to no weight loss was observed at the $10^7$, $10^8$ and $10^9$ vp vaccine doses. In the case of Ad4 wt pretreatment, only the high vaccine dose of $10^9$ vp prevented any weight loss. More severe weight loss was recorded at the lower vaccine doses when animals were pre-treated with Ad4 wt, $10^8$ vp vaccine dose (max average of 6% weight loss) and $10^7$ vp vaccine dose (max average of 17% weight loss). Animals receiving a vaccine dose of $10^6$ vp did not prevent severe weight loss. Mice immunized with recombinant H5HA protein lost no weight while Ad4 wt immunized mice succumbed to disease.

Figure 21:
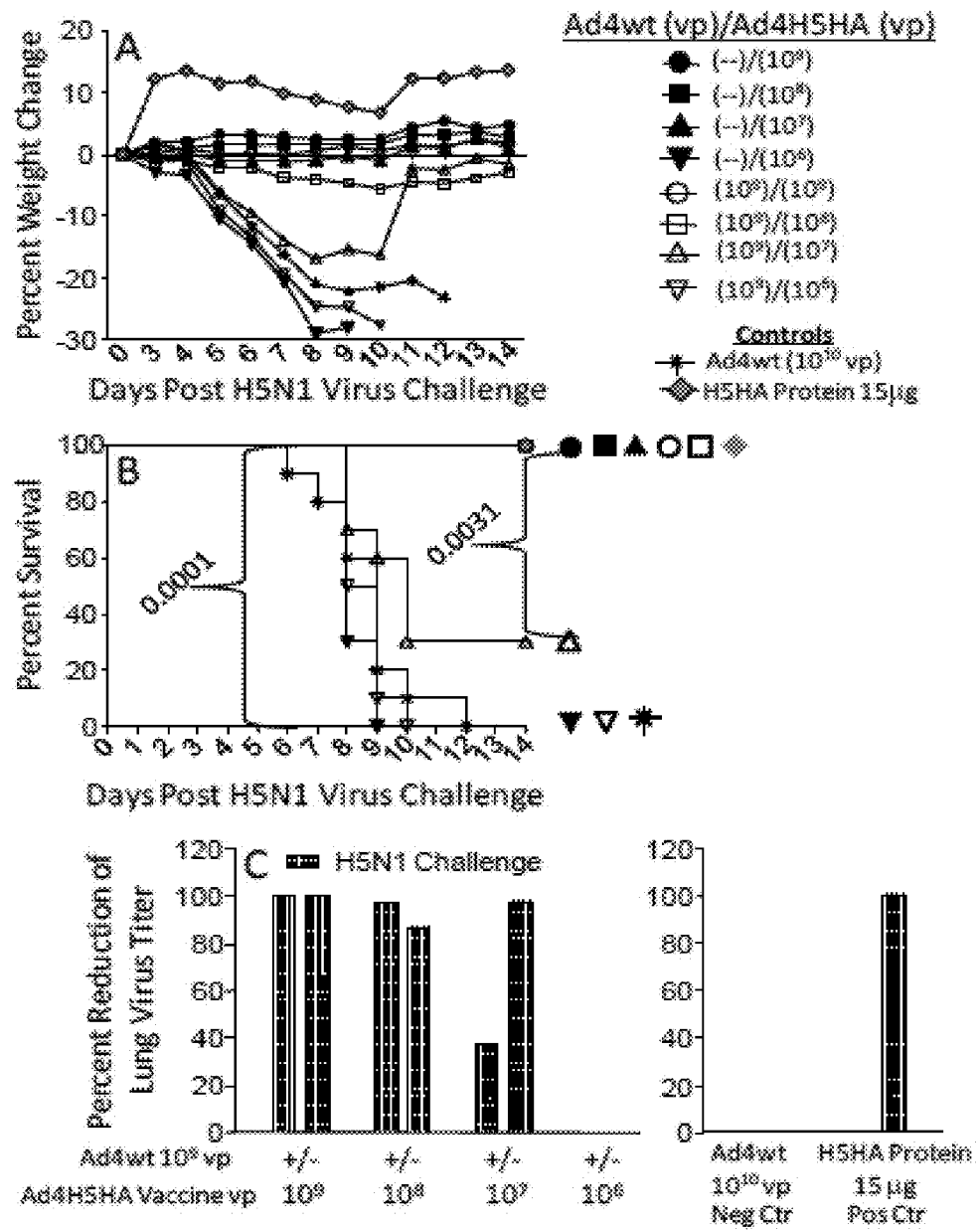
Figure 22:
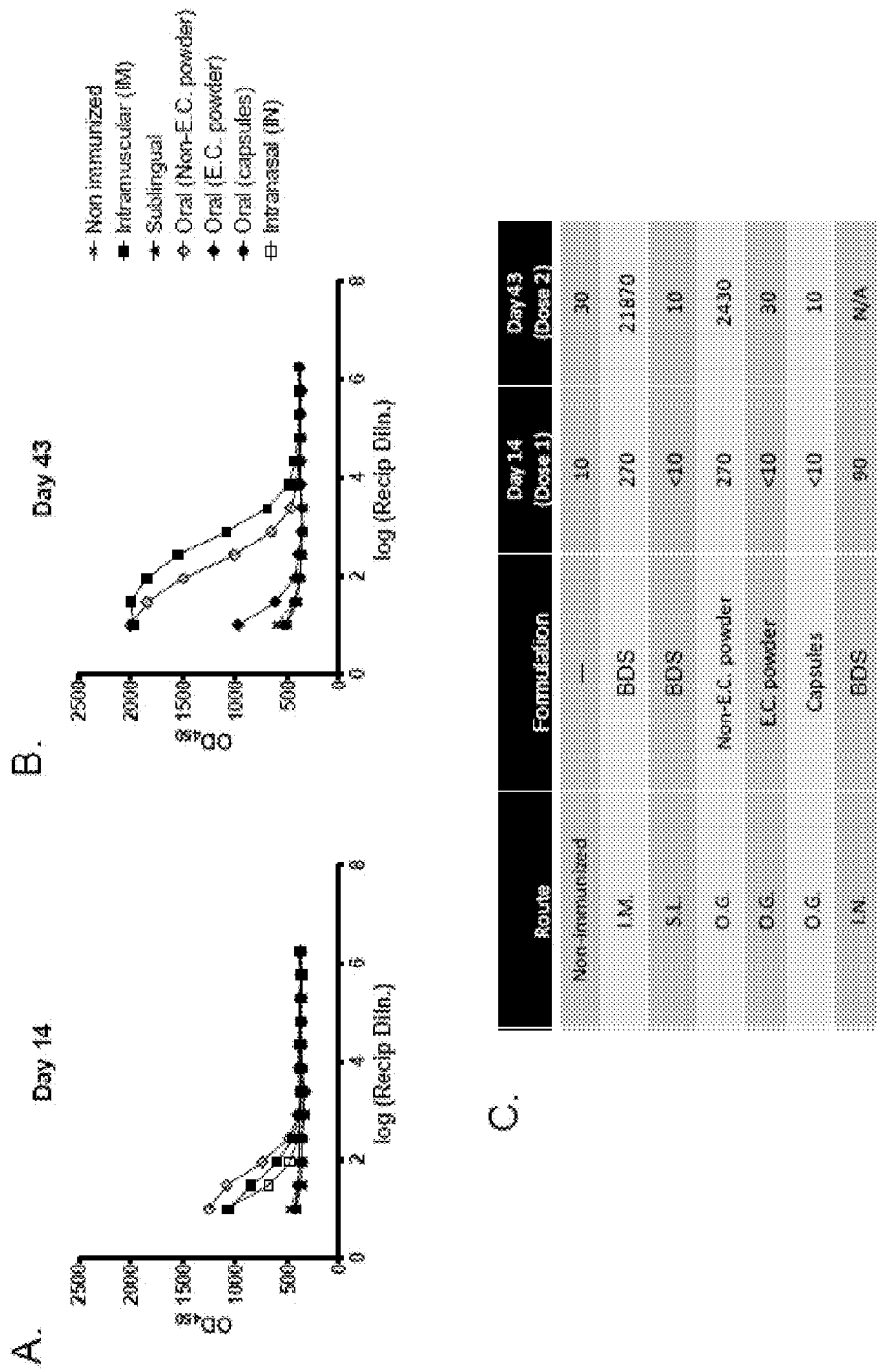
Figure 23:
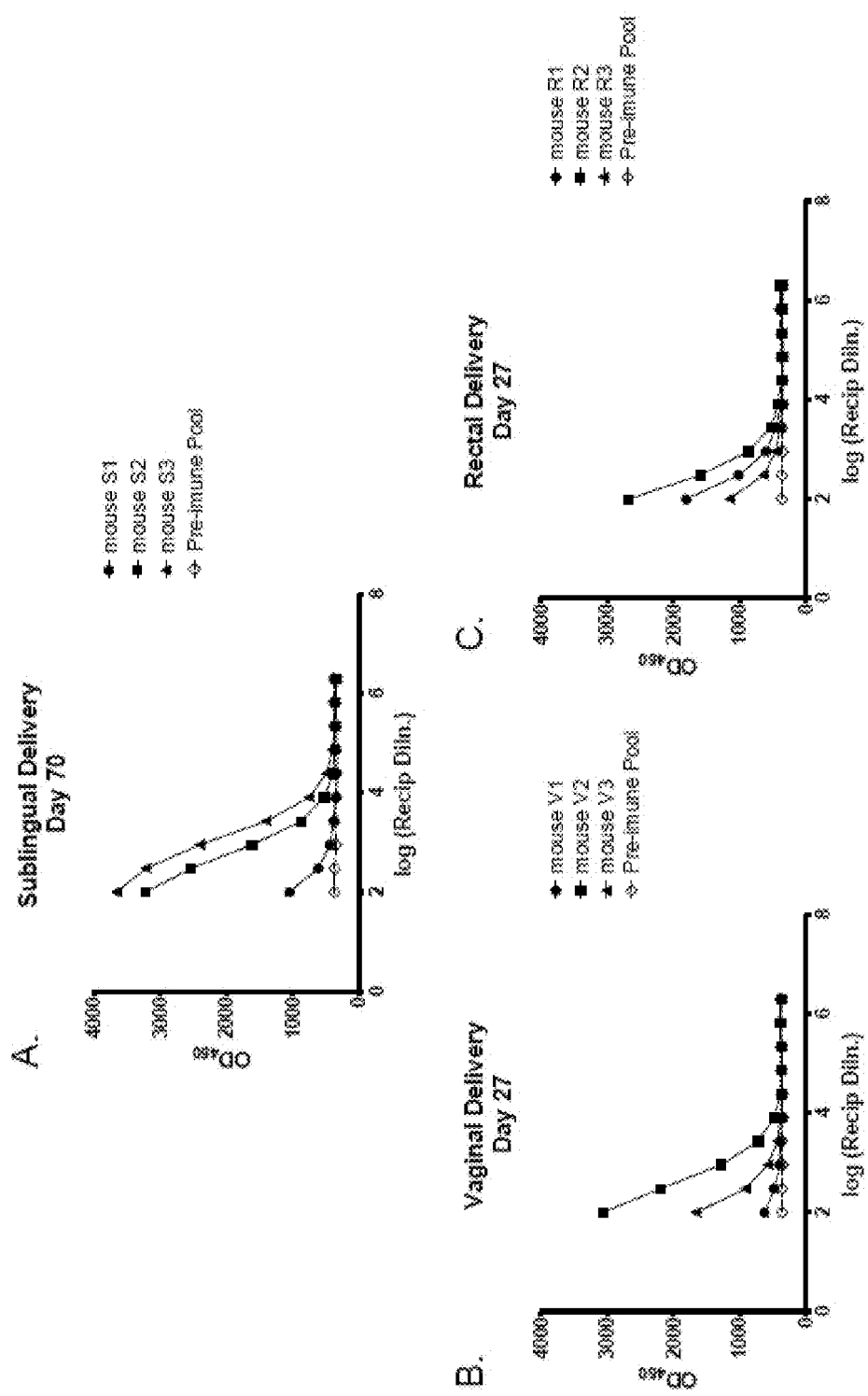

Survival of mice following lethal H5N1 reassortant virus challenge is shown in FIG. 21B. Groups of mice receiving $10^8$ and $10^9$ vp of vaccine were completely protected, 10 of 10 mice survived. Pre-treatment of mice with Ad4 wt to establish pre-existing immunity to vector did not affect animal survival at these doses. However, at lower vaccine doses of $10^7$ and $10^6$ vp, the vaccine was not as effective. Pre-existing immunity to Ad4 wt virus affected the $10^7$ vp vaccine dose in that only 3 of 10 mice survived in the presence of Ad4 wt-specific immunity versus 10 of 10 animals surviving when mice were not pre-treated with Ad4 wt virus. The lowest vaccine dose of $10^6$ vp was not protective. Immunization with Ad4 wt virus, did not protect animals, 0 of 10 survived. Immunization of mice with recombinant H5HA protein completely protected mice, 10 of 10 survived.

Lastly, as a measure of efficacy, lungs from two mice representing each group were obtained 5 days post H5N1 reassortant virus challenge to evaluate influenza virus titer, FIG. 21C. Greater than 85% reduction of influenza virus titer was observed at the higher Ad4H5HA vaccine doses of $10^7$, $10^8$ and $10^9$ vp. The exception being the vaccine dose of $10^7$ vp where the animal group was pre-treated with Ad4 wt resulting in a reduction of influenza virus titer of approximately 40%, thus indicating an effect of pre-existing Ad4 wt immunity on vaccine potency. No reduction of influenza virus titers was observed when immunizing with a vaccine dose of $10^6$ vp or with the Ad4 wt $10^{10}$ vp negative control. Mice immunized with recombinant H5HA protein also exhibited a greater than 85% reduction of challenge virus in the lungs.

In summary, Ad4H5HA vaccine induction of H5HA-specific humoral and cellular immunity generally predicted efficacy of the vaccine. Pre-existing immunity to the Ad4 wt vector did have an effect on both immunogenicity and efficacy but the effect was more pronounced at the lower vaccine doses suggesting that pre-existing immunity to the Ad vector may be overcome by using higher vaccine doses.

Example 9

Ad-4-H5-Vtn (PXVX0103) Induced Immune Responses to the H5 HA Transgene in Mammals when Delivered by Multiple Routes To evaluate the efficacy of recombinant Ad-4-H5 adenovirus in inducing immune responses when delivered by various routes of administration, rabbits were immunized with different formulations comprising Ad-4-H5-Vtn (PXVX0103) viral particles by one of four different routes of administration. The Ad-4-H5-Vtn virus vaccine was amplified in MRC-5 cells and purified for use in animal studies by anion exchange chromatography and ultra filtration. The bulk drug substance (BDS) and enteric-coated capsules were produced at PaxVax, with additional BDS used for spray dried powders production at Niro (Copenhagen, Denmark). The components of the various formulations are described below:

BDS in liquid form: $5\times10^{10}$ Ad-4-H5-Vtn viral particles, Sucrose, Magnesium Chloride hexa-hydrate, Potassium phosphate, glycerin Spray-dried powder: $5\times10^{10}$ Ad-4-H5-Vtn viral particles, Maltodextrin, Beta cyclodextrin, Sucrose, Magnesium Chloride hexa-hydrate, Potassium phosphate, glycerin, tween 80

Enteric-coated, Spray-dried powder: $5\times10^{10}$ Ad-4-H5-Vtn viral particles, Eudragit L30D55, Maltodextrin, Beta cyclodextrin, Sucrose, Magnesium Chloride hexa-hydrate, Potassium phosphate, glycerin, tween 80

Enteric-coated capsules: $1\times10^{10}$ Ad-4-H5-Vtn viral particles (per capsule), AcrylEZE white, HPMC capsules, Maltodextrin, Beta cyclodextrin, Sucrose, Magnesium Chloride hexa-hydrate, Potassium phosphate, glycerin, tween 80

Adult New Zealand White male rabbits were immunized (3 per group) with $5\times10^{10}$ vp using one of the different Ad-4-H5-Vtn vaccine formulations described above; bulk drug substance (BDS), enteric-coated (E.C.) and non-enteric coated (non-E.C.) powders, and enteric-coated capsules (5 capsules of $1\times10^{10}$vp/capsule). Animals were immunized twice, 30 days apart. Multiple routes of administration were used as indicated; intramuscular (I.M.), intranasal (I.N.), sublingual (S.L.) or oral gavage (O.G.). Rabbits were bled for ELISA immune assays two weeks following the second immunization. The exception being that data shown for BDS delivered I.N. was from immune sera taken two weeks following only one immunization.

ELISA plates were coated with 2 μg/mL purified rHA protein (eEnzyme) and incubated overnight at 4° C. before being washed and blocked with PBS with 10% goat serum for 2 hours. A 3-fold serial dilution series was generated from each pooled sera and added to the plates before a 2 hour incubation. After thorough washing, antigen-specific serum antibodies were detected using a HRP-coupled secondary antibody. The plates were developed with a HRP substrate reagent, stopped with acid, and absorbance measured at 450 nm. End-point titers are expressed as the reciprocal of the highest dilution that gave a reading three standard deviations above the mean background. The results show that the Ad-4-H5-Vtn vaccine was immunogenic in rabbits when delivered by various routes. See FIG. 22.

In another series of experiments, the efficacy of a recombinant Ad-4-H5 adenovirus in inducing immune responses when delivered by sublingual, vaginal, and rectal routes of administration was examined. Mice were immunized with Ad-4-H5-Vtn (PXVX0103) viral particles by sublingual, vaginal, or rectal administration. For sublingual administration, anesthetized mice were immunized at day 0 (prime) and boosted at day 43 (boost) with $1\times10^{10}$ Ad-4-H5-Vtn viral particles in 7 μL bulk drug substance (BDS) formulation buffer placed under the tongue and volume allowed to sit, typically 1 minute recovery time. For vaginal administration, five days prior to immunization, 2.5 mg Depo-Provera was administered S.C. to thin the vaginal wall. Anesthetized mice were immunized vaginally at day 0 (prime) and boosted at day 14 (boost), by first clearing mucus with a Q-tip, then administering $1\times10^{10}$ vp of Ad-4-H5-Vtn in 20 μL volume of BDS formulation buffer into the vagina. Mice were kept facing upward for 10 minutes under anesthesia. For rectal administration, anesthetized mice were immunized rectally at day 0 (prime) and boosted at day 14 (boost) by administering $1\times10^{10}$ vp of Ad-4-H5-Vtn in 20 μL BDS formulation buffer into the rectum. Mice were kept facing upward for 10 minutes under anesthesia. All mice were anesthetized using isoflurane and were fasted by removing food the night before immunization.

Mice were bled 2-4 weeks following the second immunization (e.g., boost immunization) and ELISA was performed as described above using recombinant H5 (ANN/1203/04). The results show that Ad-4-H5-Vtn influenza vaccine (PXVX0103) induces significant H5HA-specific antibody responses in mice when delivered by sublingual, vaginal and rectal routes of administration. See FIG. 23.

Example 10

Phase 1 Clinical Safety Study for Ad-4-H5-Vtn Vaccine

A Phase 1 double blind, placebo-controlled, ascending dose study was initiated. Four dosage cohorts, $10^7$, $10^8$, $10^9$, and $10^{10}$ viral particles (vp) have been sequentially enrolled. Each cohort consists of approximately 24 vaccinees and 8 placebo recipients, and all their household contacts (HHCs). In each dosage cohort, vaccinees or placebo recipients receive three vaccinations, 56 days apart (Days 0, 56, and 112). Measurements of immune function include antibody to H5 HA by HAI and microneutralization; Ad4 neutralizing antibody; assessment of IgG and IgA to HA and Ad4 in nasal, rectal, and cervical secretions; and CMI response to HA and to Ad4. Replication and excretion of the Ad-4-H5-Vtn vaccine virus are evaluated by PCR and culture from rectal and throat swabs and from blood. The immunological and virological parameters are analyzed with stratification by baseline Ad4 neutralizing antibody titer. Currently 132 vaccine/placebo recipients and 67 HHCs have been enrolled. Cohorts 1-3 have received all three doses, and Cohort 4 has received its first dose. Currently Cohort 4 is receiving dose 2 and Cohort 5 ($10^{11}$ vp) is undergoing enrollment.

The primary safety parameters are reactogenicity, serious or severe adverse events, and clinical safety lab abnormalities. These have been evaluated formally prior to each of 5 DMC reviews, and are evaluated in "real time" on an ongoing basis. At the most recent DMC review, the safety data following all three dose administrations from Cohorts 1, 2, & 3, and following first dose from Cohort 4 were reviewed. No safety concerns or dose limiting toxicity were identified. There were no significant laboratory abnormalities or serious or severe adverse events. Reactogenicity remained generally mild to moderate. Shedding of the vaccine virus, monitored by PCR, has been detected in rectal swabs at days 7 and/or 14 following vaccination. There has been no evidence of systemic or respiratory spread of the vaccine virus. All throat swabs and blood specimens have been negative for the Ad-4-H5-Vtn virus, except for a single instance of a PCR positive throat swab from a vaccinee (whose rectal swabs and bloods were negative by PCR). That vaccinee has remained entirely asymptomatic. Based on these data, the DMC approved administering dose 2 to Cohort 4, and enrolling Cohort 5. Baseline Ad4 antibody status for each of the cohorts at different time points during the study are shown in Table 17.

Example 11

Construction and Evaluation of Recombinant Adenovirus Expressing Anthrax Antigens Recombinant Ad4 virus with full or partial deletions of the E3 region expressing protective antigen (PA) from *Bacillus anthracis* were generated with methods similar to those described in Examples 1-3. Modifications of the PA transgene included codon modification for optimized expression in human cells, addition of glycosylphosphatidylinisotol (GPI) anchor for cell surface expression, and two phenylalanine deletions to remove the thermolysin cleavage site. Transgene expression was driven by a human CMV or native MLTU promoter. Different recombinant adenoviral vectors featuring MLTU-driven or CMV-driven expression of heterologous sequences are listed in Table 18.

TABLE 18

Recombinant Adenoviral Vectors Expressing Anthrax Antigens

| | Construct | Transgene | Promoter |
|---|---|---|---|
| 1 | Ad4-FDE3-CMV-PA (PXVX0212) | Codon optimized PA | CMV |
| 2 | Ad4-FDE3-CMV-PA-GPI (PXVX0214) | Codon optimized PA with GPI anchor | CMV |
| 3 | Ad4-PDE3-MLTU-PA-GPI | Native PA with GPI anchor | MLTU |
| 4 | Ad4-FDE3-CMV-PA-GPI | Native PA with GPI anchor | CMV |
| 5 | Ad4-FDE3-CMV-PAΔFF | Thermolysin cleavage site deleted | CMV |
| 6 | Ad4-FDE3-CMV-PA-GPIΔFF | Thermolysin cleavage site deleted | CMV |

FDE3 = full deletion of E3 region except for E3 12.1k;
PDE = partial deletion of E3 region.

Figure 24:
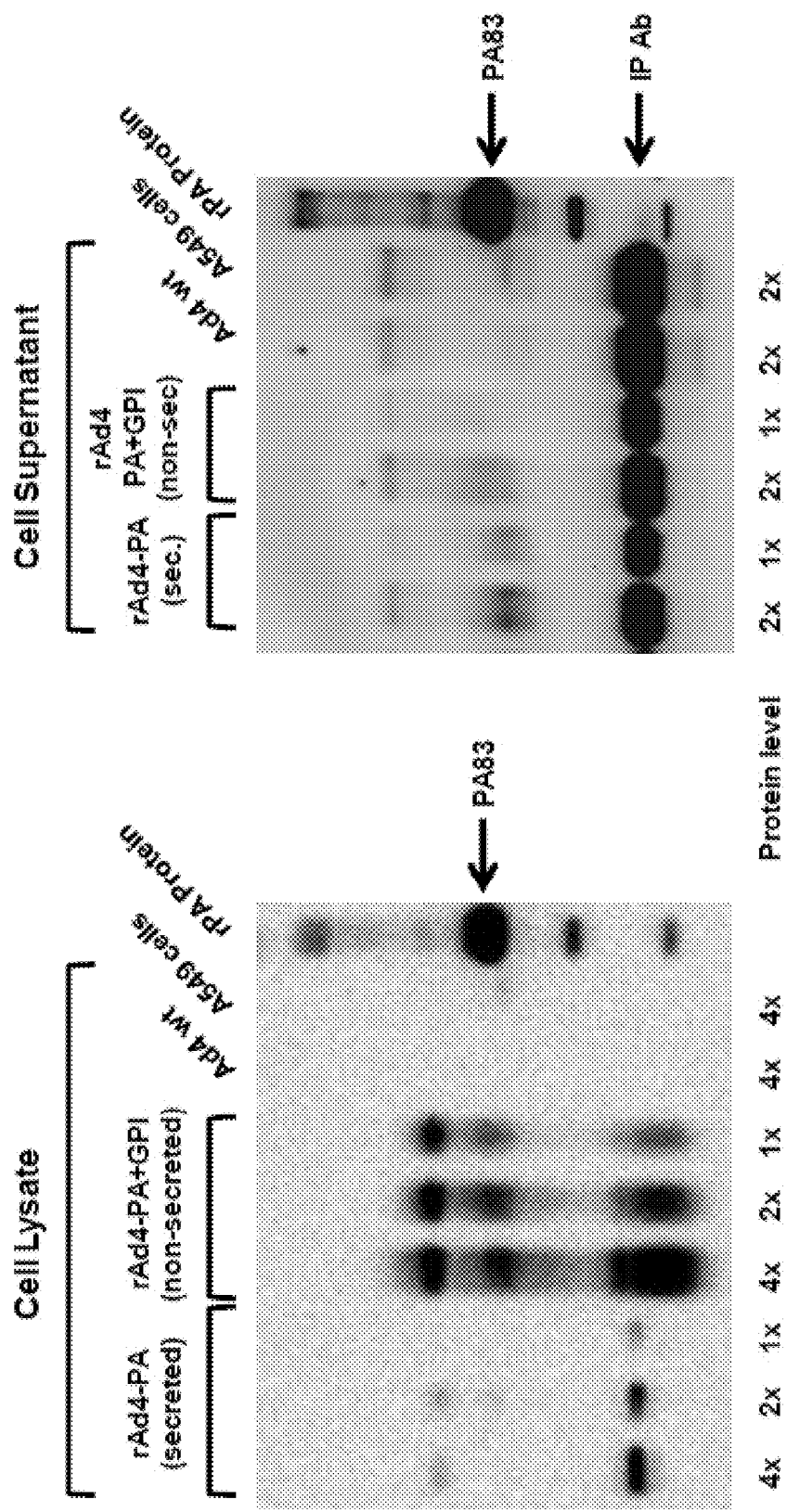

A549 cells ($5 \times 10^5$) infected with $2.5 \times 10^7$ recombinant Ad-4-PA adenoviruses were analyzed for expression of protective antigen. The cells were incubated at 37° C. for 48 hours before harvest. Either whole cell lysate (FIG. 24, left panel) or cell culture supernatant (FIG. 24, right panel) from each sample was analyzed by western blot following separation on SDS-PAGE gel. Nitrocellulose membranes were probed with an anti-PA mouse monoclonal antibody. Confirmation of recombinant protein expression was made by reference to commercially available recombinant PA loaded in parallel as a positive control. A549 and A549 infected with Ad4 WT represent the negative controls, demonstrating the specificity to rPA. Protein levels are shown as relative amounts by total protein levels. See FIG. 24.

TABLE 17

Phase 1 Clinical Safety Study of Ad4-H5-Vtn Vaccine

| | Dosage | | | | | | | | |
|---|---|---|---|---|---|---|---|---|---|
| | $10^7$ vp | | | $10^8$ vp | | | $10^9$ vp | | |
| Ad4 Baseline Antibody Status | Ad4 neg | Ad4 pos* | All | Ad4 neg | Ad4 pos | All | Ad4 neg | Ad4 pos | All |
| Post-Dose 1 | 6/21 (29%) | 0/3 (0%) | 6/24 (25%) | 8/15 (53%) | 1/10 (10%) | 9/25 (36%) | 12/17 (71%) | 3/10 (30%) | 15/27 (56%) |
| Post-Dose 2 | 11/21 (52%) | 0/3 (0%) | 11/24 (46%) | 12/15 (80%) | 2/10 (20%) | 14/25 (56%) | 15/17 (88%) | 6/10 (60%) | 21/27 (78%) |
| Post-Dose 3 | 11/21 (52%) | 1/3 (33%) | 12/24 (50%) | 12/15 (80%) | 2/10 (20%) | 14/25 (56%) | 15/17 (88%) | 6/10 (60%) | 21/27 (78%) |

*Cohort 1 had a statistical anomaly resulting in a lower number of Ad4 positive patients.

Figure 25:
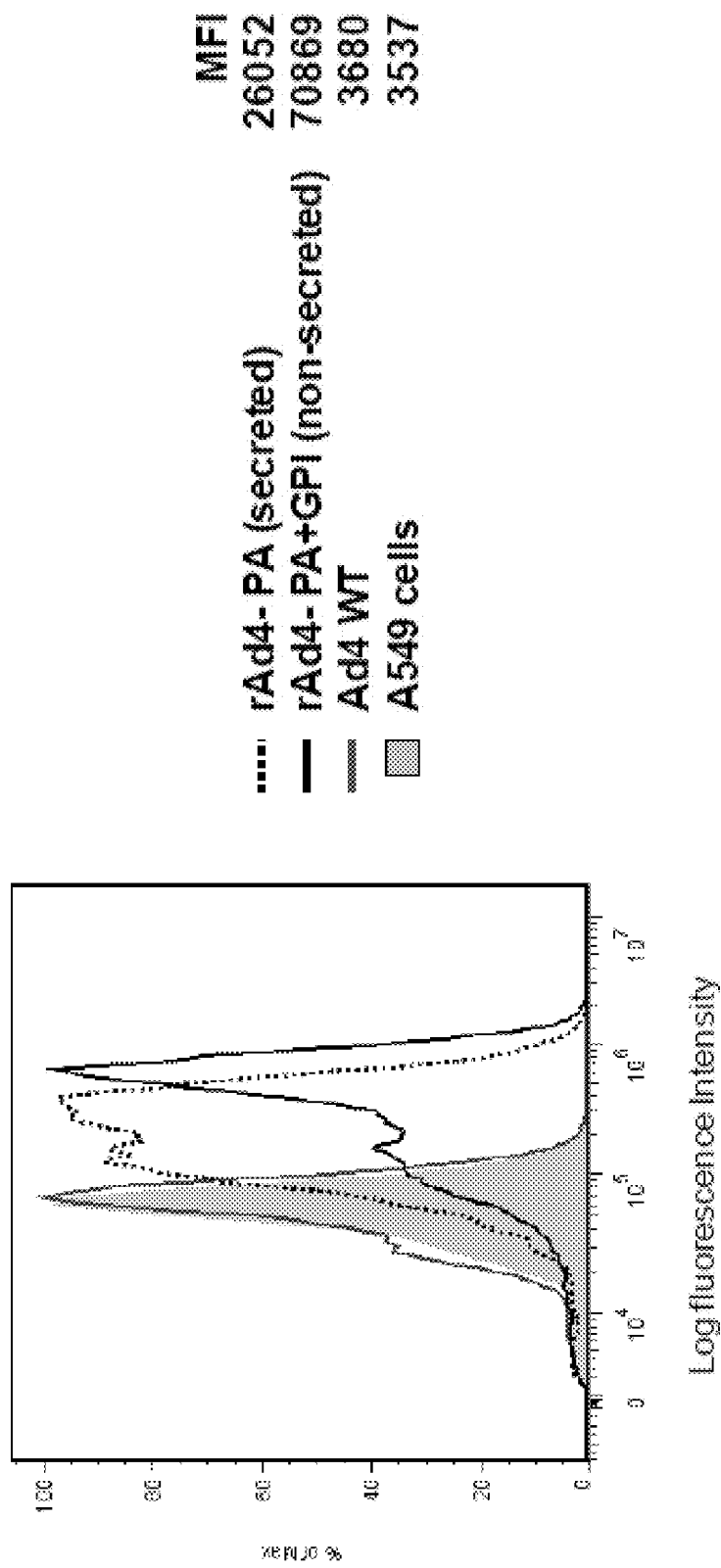
Figure 26:
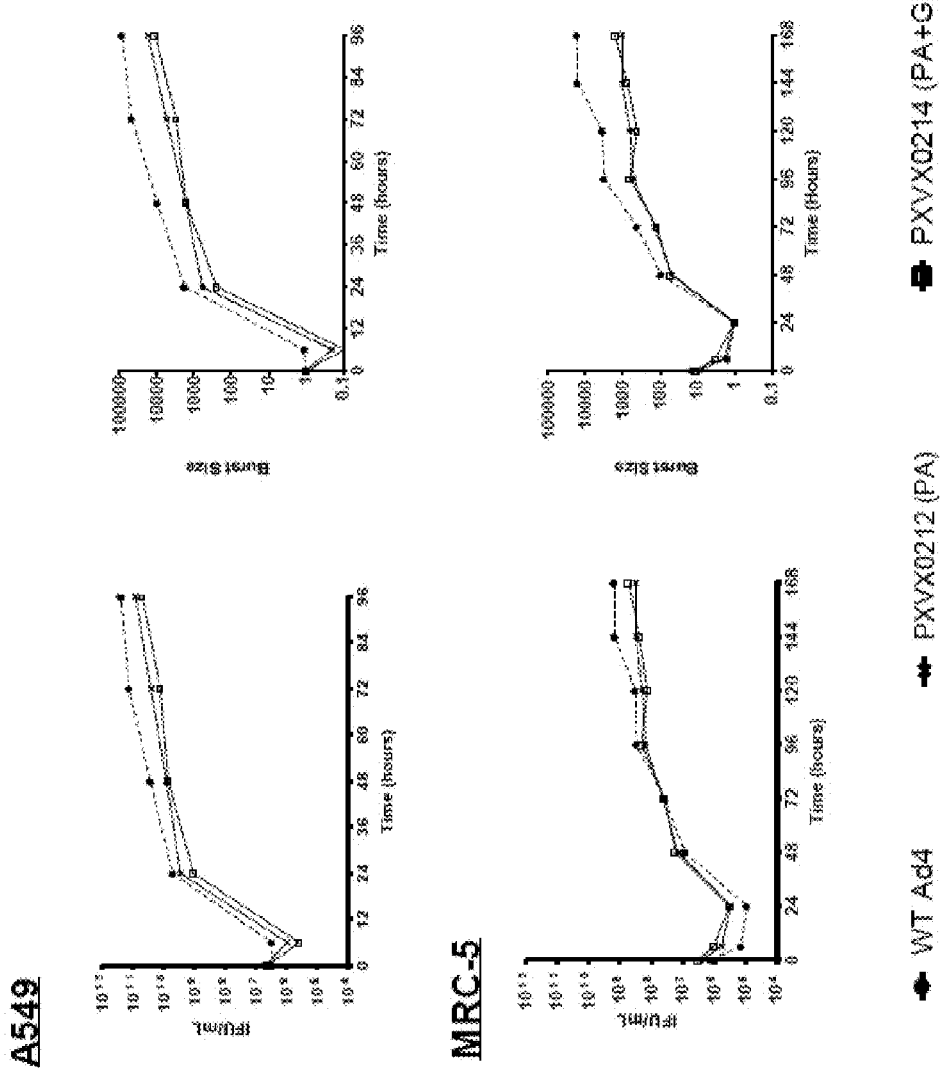

One day after infection with these constructs, PA antigen was present on the surface of A549 cells, as shown by the FACS analysis presented in FIG. 25. The mean fluorescent intensity (MFI), which represents a measure of fluorescent intensity that is an indication of expression level per cell, is shown for each of the groups. A one-step growth assay was used to evaluate growth kinetics of PXVX0212 and PXVX0214 recombinant adenoviruses in A549 (lung carcinoma) and MRC-5 (embryonic lung fibroblast, diploid) cells (see FIG. 8A). Time courses of rAd4 levels were measured by $TCID_{50}$ following rAd-4-PA virus infection of either A549 or MRC-5 cells. Cell burst size was calculated using the minimum infectivity level (1 hour for A549 and 24 hours for MRC-5) as reference, thus correcting for differences in infection. Burst size confirms that both PXVX0212 and PXVX0214 show reduced rates of growth compared to Ad4 Wt and also result in lower yields per cell. See FIG. 26.

Example 12

Figure 27:
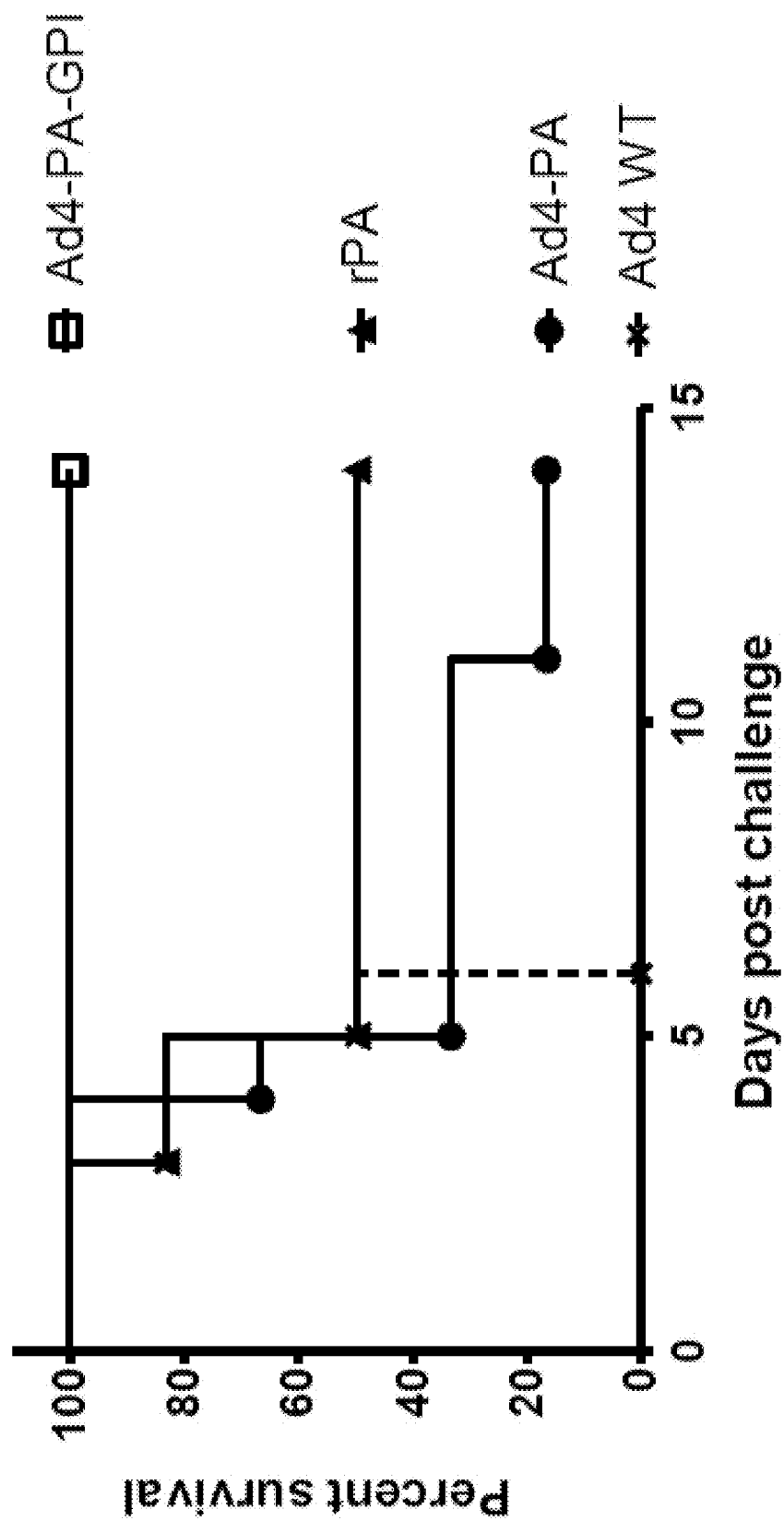

Efficacy of Ad-4-PA Recombinant Adenovirus as a Protective Vaccine Against Anthrax Challenge To determine whether recombinant adenovirus expressing protective antigen (PA) from *B. anthracis* could induce a protective immune response against anthrax challenge, mice were immunized with whole cell lysates from cells infected with one of the recombinant adenoviral vectors described in Example 11. Specifically, mice (6 animals/group) were immunized by intraperitoneal injection (IP) of whole cell lysates equivalent to $5 \times 10^6$ A549 cells infected with $5 \times 10^8$ viral particles of Ad4 wild-type (Ad4 WT), Ad-4-PA (PXVX0212), or Ad-4-PA-GPI (PXVX0214). As a positive control, 10 µg recombinant protective antigen (rPA) was administered subcutaneously (S.C.). Five weeks post-immunization, mice were challenged intravenously with lethal toxin (combination of 120 µg PA with 60 µg lethal factor (LF)) and monitored daily. The results of the experiments are shown in FIG. 27. An Ad4-PA-GPI cell lysate completely protected mice against lethal toxin challenge.

Figure 28:
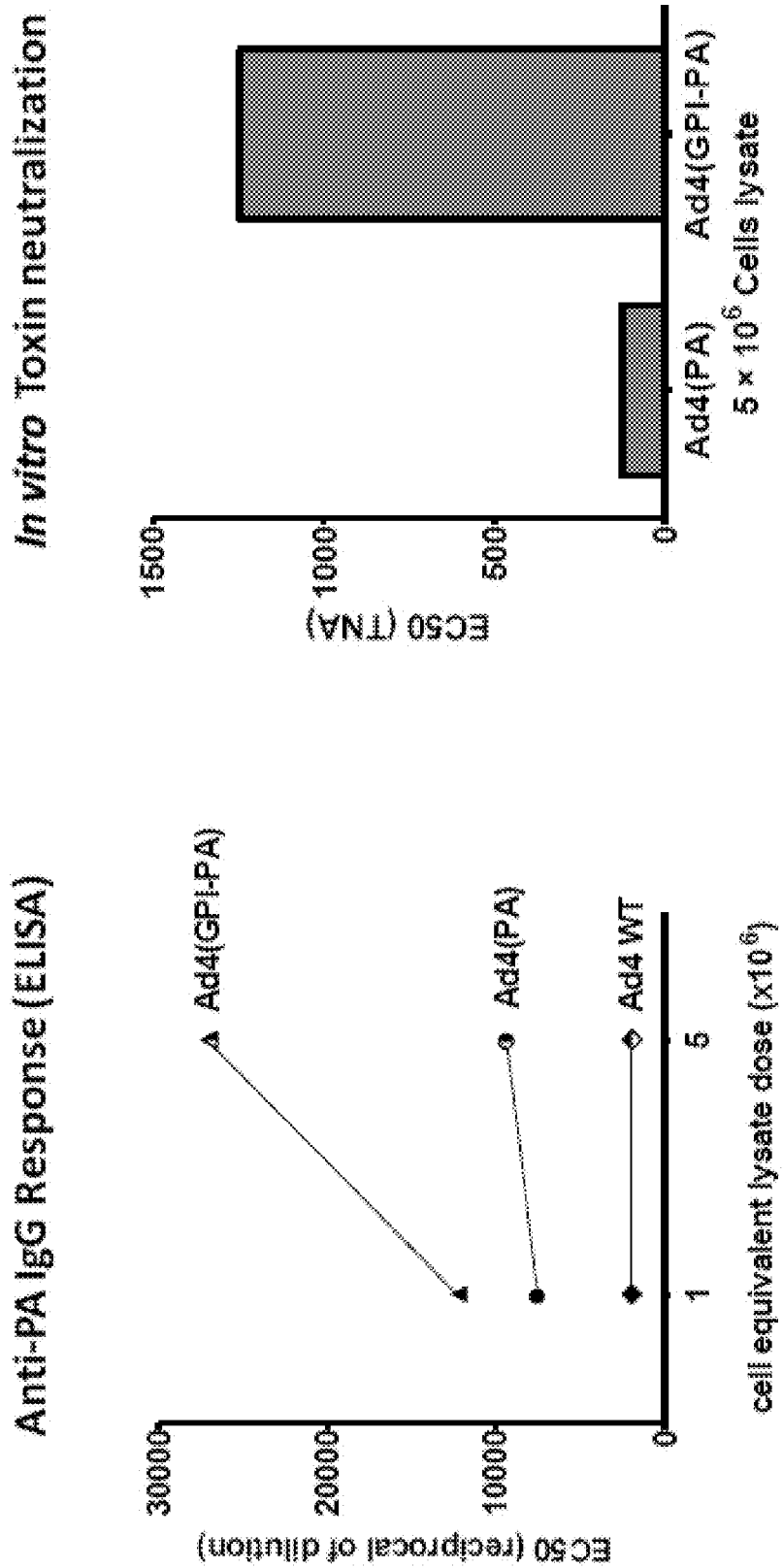

Antibody responses were measured in the immunized mice from serum obtained 21 days following IP immunization. Antibody responses were analyzed by both ELISA (FIG. 28, left panel) and in vitro macrophage based toxin neutralization assay (FIG. 28, right panel). An $EC_{50}$ was calculated from 6 animals/group. PA-specific IgG responses were detectable three weeks following immunization with whole cell lysate from A549 cells infected with recombinant adenovirus.

In another series of experiments, the efficacy of purified recombinant adenovirus in inducing protective immune responses was examined. Mice (n=25/group) were immunized with one of five different antigens (Ad4 wild-type, Ad-4-CMV-PA (PXVX0212), Ad-4-CMV-PA-GPI (PXVX0214), rPA, and rPA+alum) at day 0 as indicated in the schematic in FIG. 29. rAd4 viruses were administered intranasally (I.N.) as $1 \times 10^{10}$ viral particles (vp) in 50-62.5 µL PBS per animal. Wild-type Ad4 virus served as a negative control. Positive controls, injected subcutaneously, in a final volume of 100 µL PBS contained either 10 µg recombinant protective antigen (rPA) alone or 10 µg of rPA adsorbed to 1 mg of aluminum hydroxide gel (Rehydragel HPA). Cell mediated immune responses (IFN-γ ELISPOT and IL-4 ELISPOT) were measured 27 days post immunization in splenocytes pooled from 2 mice/group. Mice that survived toxin challenge #1 (day 20 post immunization, n=10/group) were assayed for cellular immune responses on day 54. The same 9 animals/group (5 groups) were bled for both ELISA and toxin neutralization assays after 14 and 40 days post immunization. A total of 10 mice per group, including 7 mice from the 9 mice that were bled, were also lethal toxin challenged (with a combination of 120 µg PA and 60 µg lethal factor) after 46 days post immunization. Survival was monitored for 30 days post challenge.

Figure 29:
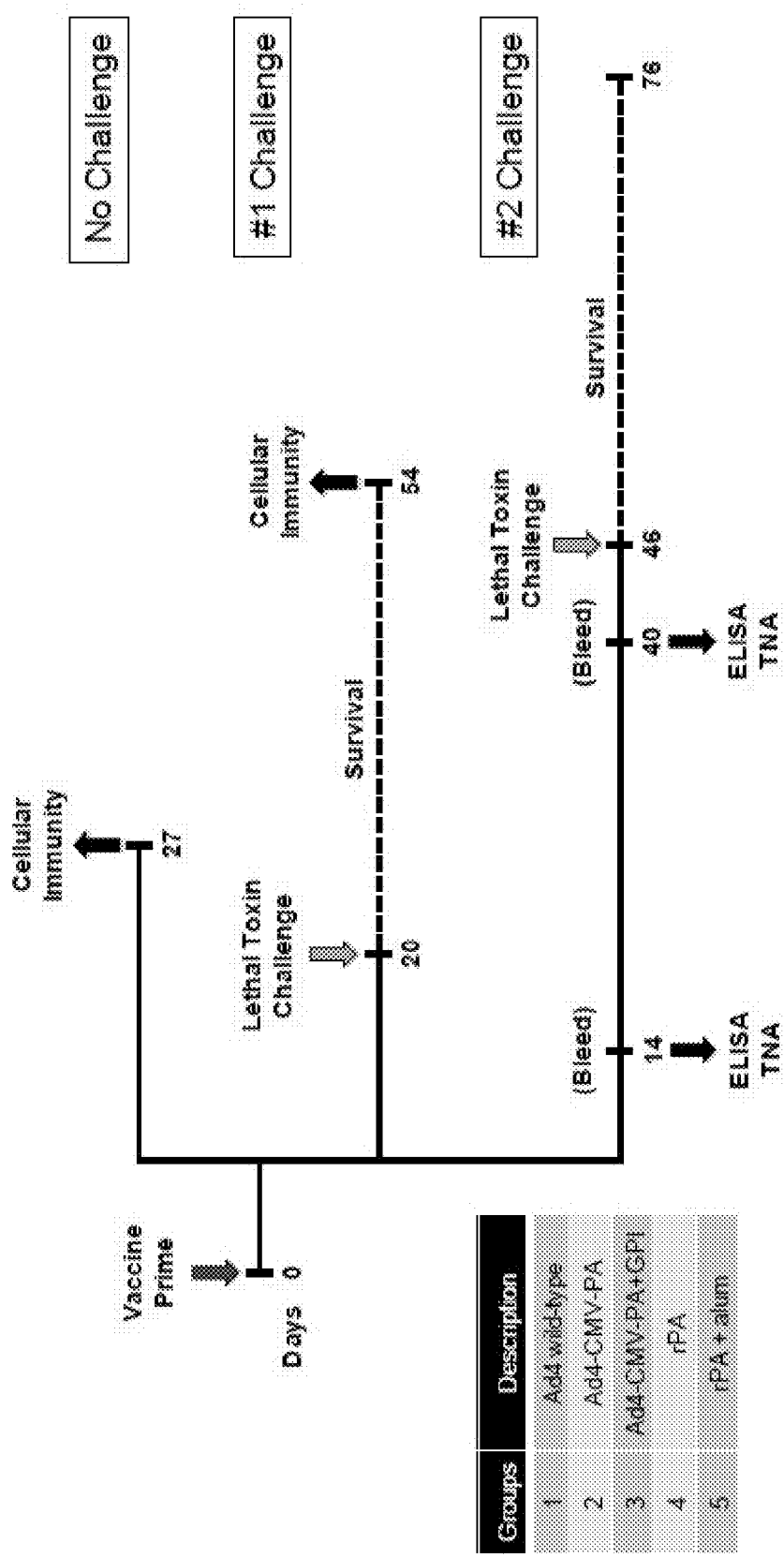
Figure 30:
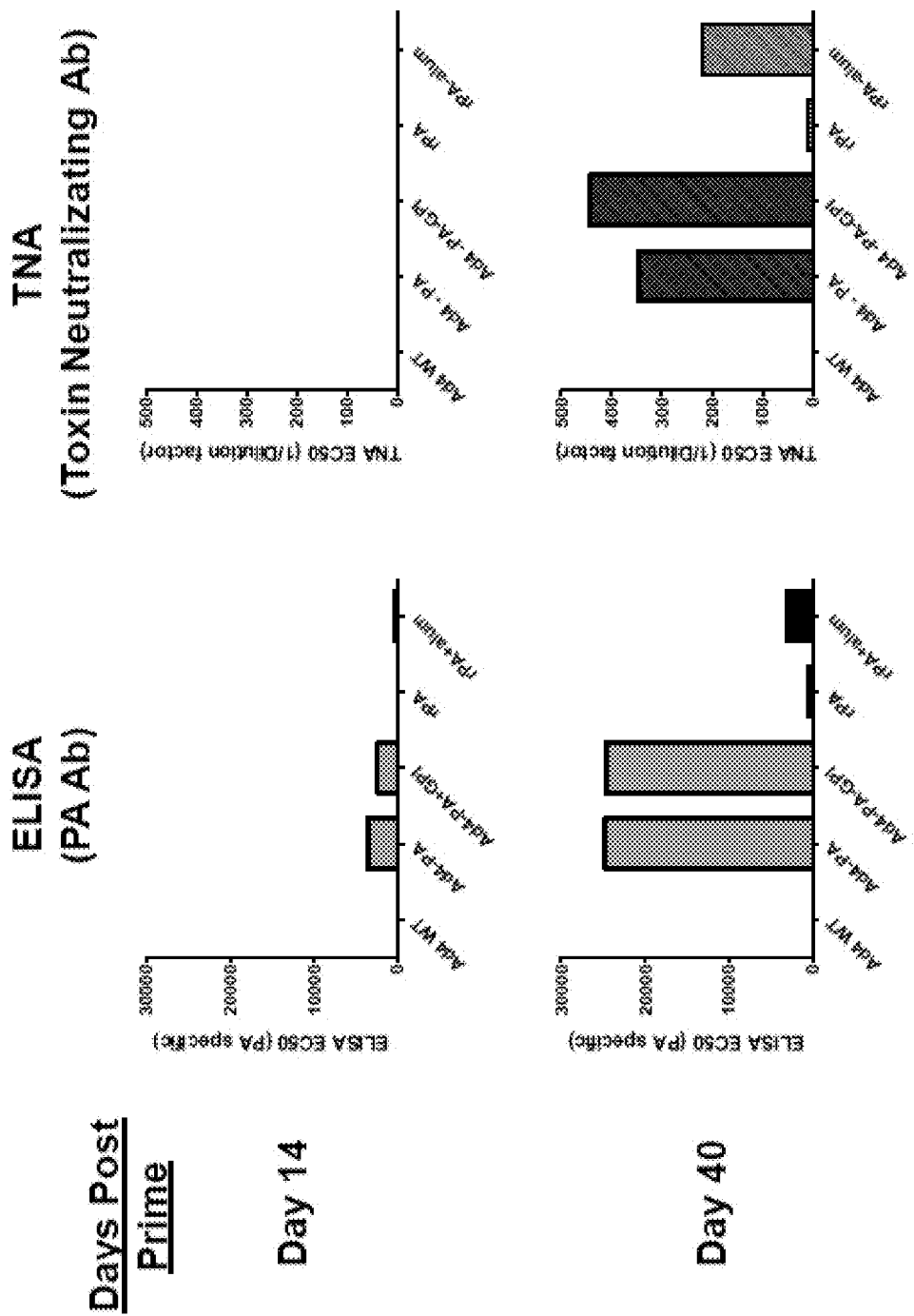
FIG. 30. Antibody responses were measured in serum at 14 and 40 days post intranasal immunization with purified Ad-4-PA and Ad-4-PA-GPI viruses. Anti-PA IgG responses analyzed by ELISA are shown in the left panels, and toxin neutralizing antibodies (TNA) measured by in vitro murine macrophage based toxin neutralization assay are shown in the right panels. $EC_{50}$ was calculated using sigmoidal dose-response curve fit to data from serial dilution of samples.

Antibody responses were measured in serum at 14 and 40 days post intranasal immunization with purified Ad-4-PA and Ad-4-PA-GPI viruses (see FIG. 29). Anti-PA IgG responses were analyzed by ELISA (FIG. 30, left panels), while toxin neutralizing antibodies (TNA) were measured by in vitro murine macrophage based toxin neutralization assay (FIG. 30, right panels). $EC_{50}$ was calculated using sigmoidal dose-response curve fit to data from serial dilution of samples. Only a minimal anti-PA IgG response and no measurable TNA responses were observed after 14 days post immunization (FIG. 30). After 40 days post immunization, significant anti-PA IgG and TNA responses were observed with both Ad-4-PA (PXVX0212) and Ad-4-PA-GPI (PXVX0214) compared to rPA or rPA with alum (FIG. 30). Both recombinant PA adenoviruses (Ad-4-PA and Ad-4-PA-GPI viruses) induced comparable immune responses.

Figure 31:
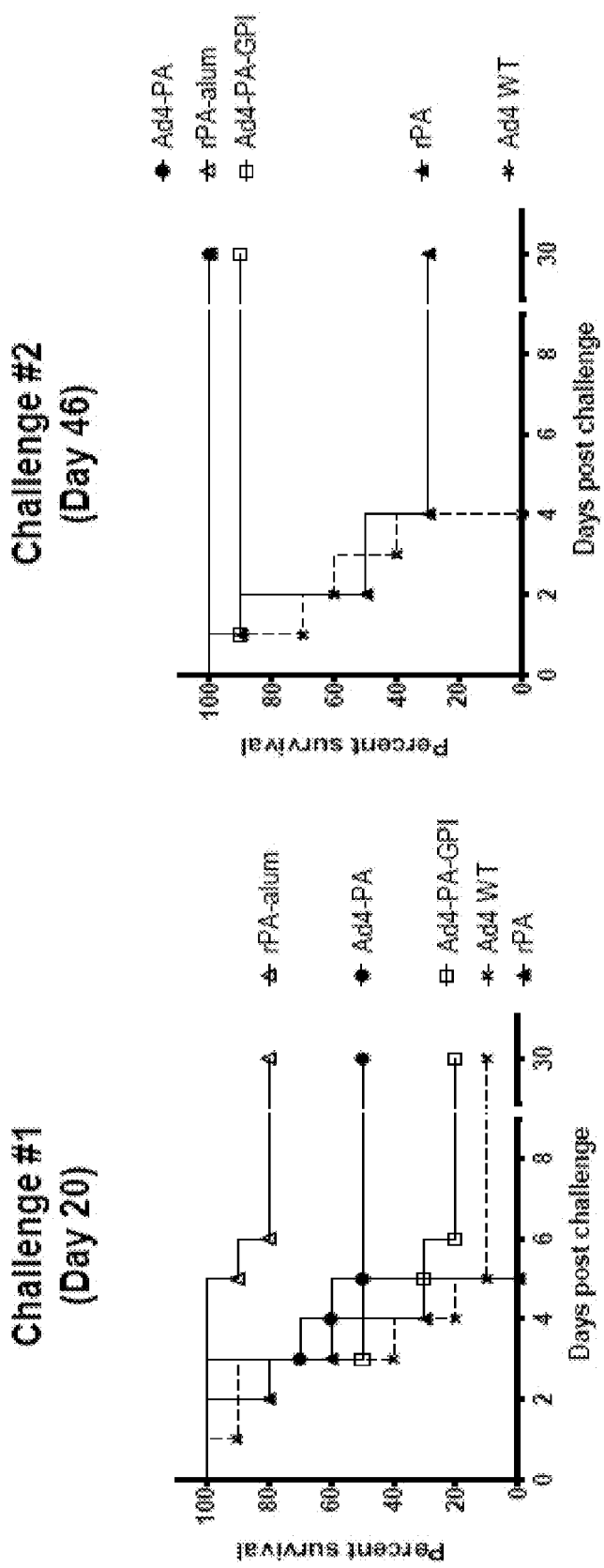
FIG. 31. Survival curves show protection of mice from lethal toxin challenge when immunized with rAd-4-PA viruses. Mice (n=10/group) were immunized with one of five different immunogens (rPA, rPA+alum, Ad4 wild-type, Ad-4-PA, and Ad-4-PA-GPI) at day 0 and were challenged with lethal toxin (60 µg PA and 30 µg LF in a total volume of 100 µL PBS) at 20 and 46 days post immunization. Survival was monitored for 30 days. Left panel shows the survival following challenge at 20 days post immunization. Right panel shows the survival following challenge at 46 days post immunization.

Mice were immunized with one of five different immunogens (n=10/group) as indicated in FIG. 29 at day 0 and were challenged with lethal toxin (60 µg PA and 30 µg LF in a total volume of 100 µL PBS) at 20 and 46 days post immunization. Survival was monitored for 30 days. The results are shown in FIG. 31. Following the challenge 20 days post immunization, 80% survival was observed with mice immunized with rPA-alum, while Ad-4-PA and Ad-4-PA-GPI immunized groups had 50% and 20% survival, respectively (FIG. 31, left panel). One mouse in the Ad4 wild-type immunized group survived and none survived in the rPA immunized group. Following the challenge 46 days post immunization, 100% survival was observed in the rPA+alum and Ad-4-PA immunized groups, while 90% and 30% survival was observed in the Ad-4-PA-GPI and rPA immunized groups, respectively (FIG. 31, right panel). None survived in the Ad4 wild-type-treated group. The results indicate that in a lethal toxin challenge, the two Ad-4-PA vector viruses confer partial protection at 20 days post immunization and complete protection at 46 days post immunization. There was no statistical difference in the protection afforded by Ad-4-PA or Ad-4-PA-GPI recombinant adenoviruses.

Figure 32:
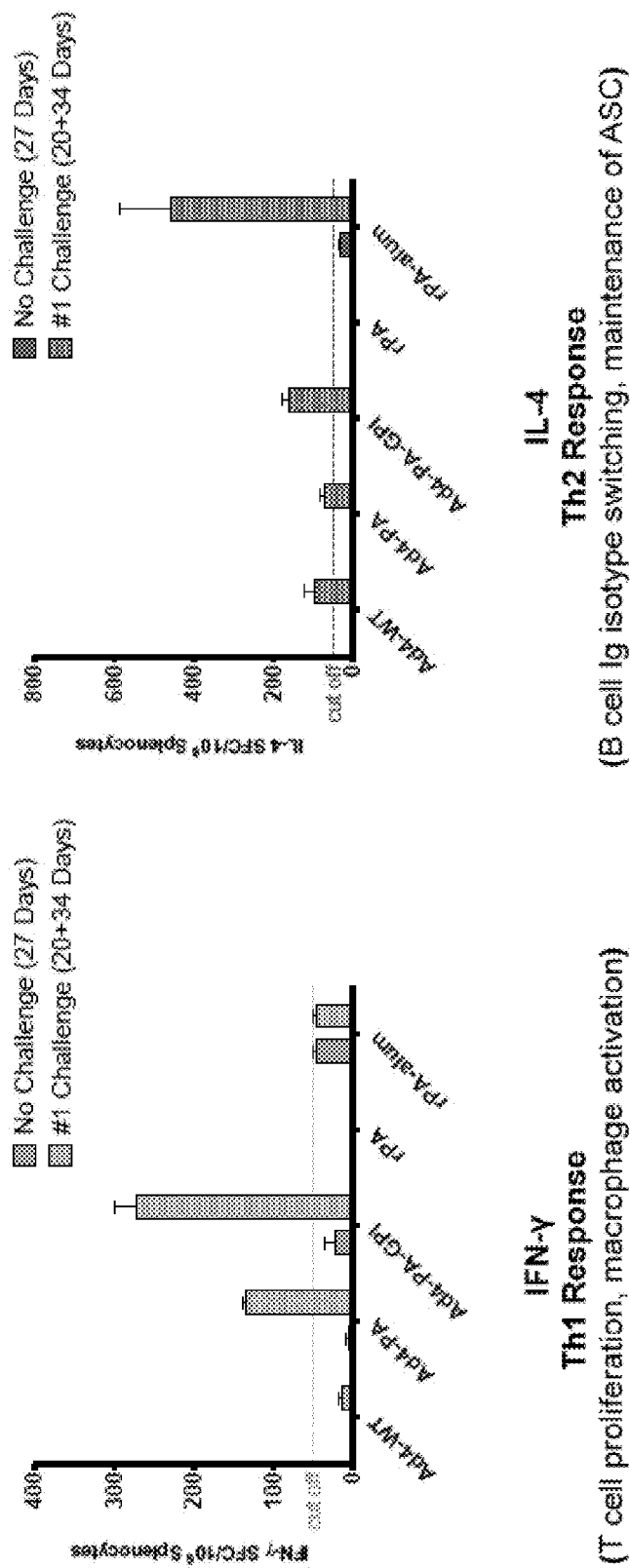
FIG. 32. Immunization of mice with rAd-4-PA viruses induce cell mediated immune responses that are detected following lethal toxin challenge. Cell mediated immune responses (IFN-γ ELISPOT and IL-4 ELISPOT) were measured 27 days post immunization in splenocytes pooled from mice (2 mice/group) immunized with one of five different immunogens (rPA, rPA+alum, Ad4 wild-type, Ad-4-PA, and Ad-4-PA-GPI) at day 0. Mice that survived toxin challenge #1 (day 20 post immunization, n=10/group) were assayed for cellular immune response on day 54 (34 days post challenge). Left panel: Th1 responses measured by IFN-γ ELISPOT. Right panel: Th2 responses measured by IL-4 ELISPOT.

Cell mediated immune responses (IFN-γ ELISPOT and IL-4 ELISPOT) were measured 27 days post immunization in splenocytes pooled from mice immunized with one of the five different antigens (2 mice/group) as indicated in FIG. 29. Mice that survived toxin challenge #1 (day 20 post immunization, n=10/group) were assayed for cellular immune responses on day 54 (34 days post challenge). Both recombinant Ad-4-PA and Ad-4-PA-GPI adenoviruses induced Th1 and Th2 responses to PA indicated by IFN-γ and IL-4 responses, responses (FIG. 32).

In summary, the results of the experiments described in this Example demonstrate that recombinant adenoviruses expressing protective antigen induce both humoral and cell-mediated immunity in mice and provide protection against lethal anthrax challenge.

Example 13

Expression of a Multiple HTL Epitope Polypeptide from Recombinant Adenovirus

Figure 33A:
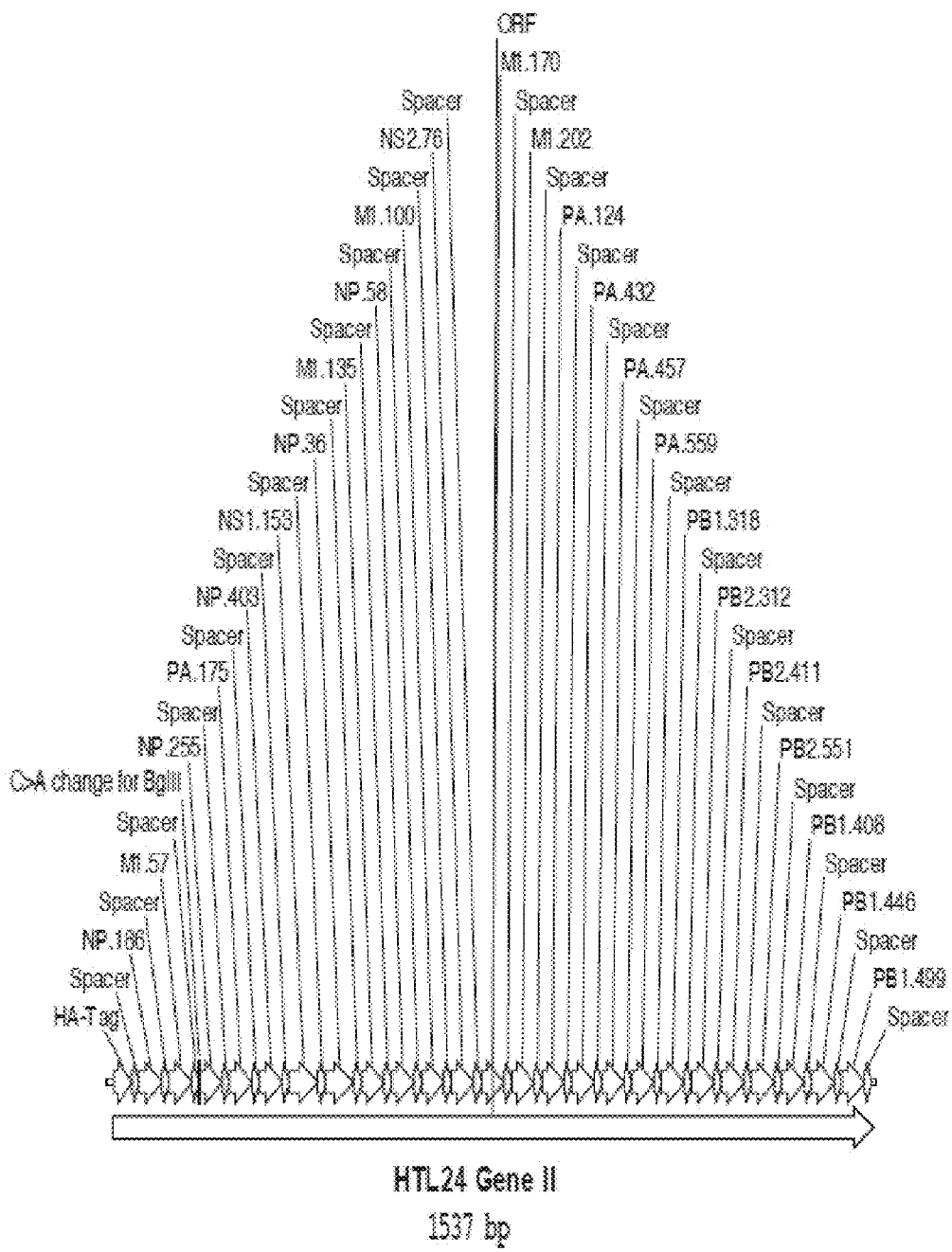
FIG. 33. Ad4-CMV-HTL24 (PXVX0109) Expression of the 52.5K polypeptide. (A) A schematic representation of the HTL24 polypeptide gene containing 24 influenza helper epitopes each separated by a GPGPG spacer sequence (SEQ ID NO: 353). (B) Western blot analysis of cell lysates from A549 cells infected with a recombinant Ad4 virus with a full deletion of the E3 region and with HTL24 expression driven by the CMV promoter (PXVX0109). As a positive control, A549 cells were infected with A/Uruguay/716/2007 (A/Brisbane/10/2007-like) influenza (NYMC X-175C reassortant, NIBSC). The PVXV0109 recombinant adenovirus efficiently express the HTL24 polypeptide as shown by the bands migrating at 52.5 kDa.
Figure 33B:
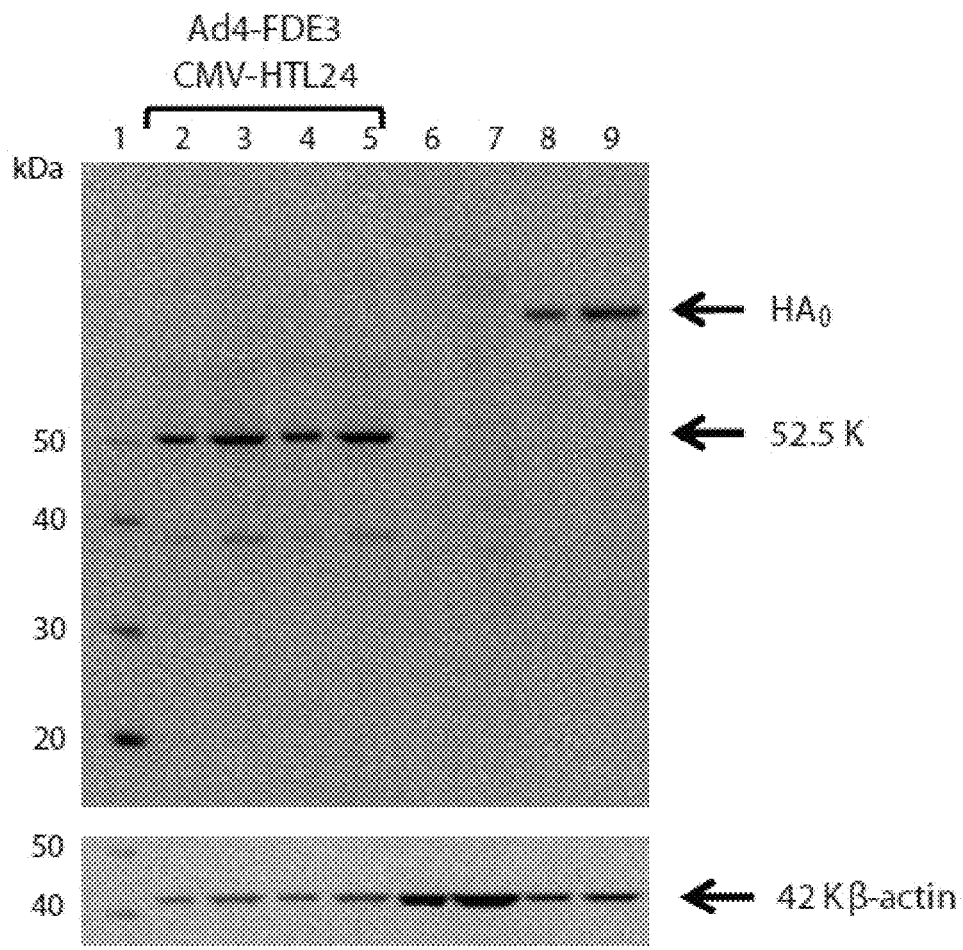

A synthetic influenza antigen sequence was designed that contained 24 influenza helper T lymphocyte (HTL) epitopes each separated by a GPGPG spacer sequence (SEQ ID NO: 353). See FIG. 33A. A recombinant Ad4 virus with a full deletion of the E3 region expressing this HTL24 polypeptide under the control of a CMV promoter (PXVX0109) was generated with methods similar to those described in Example 3. A549 cells were infected with PXVX0109 following transfection to generate virus from two identical plasmid clones (15-4 and 19-1). Infected cells were harvested at >90% cytopathic effect (CPE) and cell lysates prepared at $1\times10^6$ cells per 100 μL of RIPA buffer containing protease inhibitors. As a positive control, A549 cells were infected with A/Uruguay/716/2007 (A/Brisbane/10/2007-like) influenza (NYMC X-175C reassortant, NIBSC). Following separation on an SDS-PAGE gel and subsequent transfer to blotting membrane, proteins were detected with an anti-HA tag monoclonal antibody and a HRP Goat anti-Mouse IgG secondary antibody. For loading control, a parallel membrane was probed with an anti-beta-actin rabbit polyclonal antibody and a HRP Goat anti-rabbit IgG secondary antibody. Protein bands were visualized by Chemiluminescence (Supersignal West Femto, Thermoscientific). As shown by the results of the Western blot analysis in FIG. 33B, the recombinant Ad4 adenovirus expressed high levels of the HTL24 polypeptide.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

```
                        SEQUENCE LISTING

<160> NUMBER OF SEQ ID NOS: 353

<210> SEQ ID NO 1
<211> LENGTH: 17
<212> TYPE: PRT
<213> ORGANISM: Influenza Virus

<400> SEQUENCE: 1

Met Glu Lys Ile Val Leu Leu Phe Ala Ile Val Ser Leu Val Lys Ser
 1               5                  10                  15

Asp

<210> SEQ ID NO 2
<211> LENGTH: 15
<212> TYPE: PRT
<213> ORGANISM: Influenza Virus

<400> SEQUENCE: 2

Lys Ser Ser Phe Phe Arg Asn Val Val Trp Leu Ile Lys Lys Asn
 1               5                  10                  15

<210> SEQ ID NO 3
<211> LENGTH: 16
<212> TYPE: PRT
<213> ORGANISM: Influenza Virus

<400> SEQUENCE: 3

Val Val Trp Leu Ile Lys Lys Asn Ser Thr Tyr Pro Thr Ile Lys Arg
 1               5                  10                  15

<210> SEQ ID NO 4
<211> LENGTH: 16
<212> TYPE: PRT
<213> ORGANISM: Influenza Virus

<400> SEQUENCE: 4

Pro Thr Thr Tyr Ile Ser Val Gly Thr Ser Thr Leu Asn Gln Arg Leu
 1               5                  10                  15

<210> SEQ ID NO 5
<211> LENGTH: 15
```

```
<212> TYPE: PRT
<213> ORGANISM: Influenza Virus

<400> SEQUENCE: 5

Arg Met Glu Phe Phe Trp Thr Ile Leu Lys Pro Asn Asp Ala Ile
1               5                   10                  15

<210> SEQ ID NO 6
<211> LENGTH: 15
<212> TYPE: PRT
<213> ORGANISM: Influenza Virus

<400> SEQUENCE: 6

Trp Thr Ile Leu Lys Pro Asn Asp Ala Ile Asn Phe Glu Ser Asn
1               5                   10                  15

<210> SEQ ID NO 7
<211> LENGTH: 16
<212> TYPE: PRT
<213> ORGANISM: Influenza Virus

<400> SEQUENCE: 7

Cys Pro Lys Tyr Val Lys Ser Asn Arg Leu Val Leu Ala Thr Gly Leu
1               5                   10                  15

<210> SEQ ID NO 8
<211> LENGTH: 15
<212> TYPE: PRT
<213> ORGANISM: Influenza Virus

<400> SEQUENCE: 8

Asn Arg Leu Val Leu Ala Thr Gly Leu Arg Asn Ser Pro Gln Arg
1               5                   10                  15

<210> SEQ ID NO 9
<211> LENGTH: 17
<212> TYPE: PRT
<213> ORGANISM: Influenza Virus

<400> SEQUENCE: 9

Glu Leu Leu Val Leu Met Glu Asn Glu Arg Thr Leu Asp Phe His Asp
1               5                   10                  15

Ser

<210> SEQ ID NO 10
<211> LENGTH: 17
<212> TYPE: PRT
<213> ORGANISM: Influenza Virus

<400> SEQUENCE: 10

Ile Ser Gly Val Lys Leu Glu Ser Ile Gly Ile Tyr Gln Ile Leu Ser
1               5                   10                  15

Ile

<210> SEQ ID NO 11
<211> LENGTH: 16
<212> TYPE: PRT
<213> ORGANISM: Influenza Virus

<400> SEQUENCE: 11

Ile Tyr Gln Ile Leu Ser Ile Tyr Ser Thr Val Ala Ser Ser Leu Ala
1               5                   10                  15
```

```
<210> SEQ ID NO 12
<211> LENGTH: 16
<212> TYPE: PRT
<213> ORGANISM: Influenza Virus

<400> SEQUENCE: 12

Ile Leu Ser Ile Tyr Ser Thr Val Ala Ser Ser Leu Ala Leu Ala Ile
1               5                   10                  15

<210> SEQ ID NO 13
<211> LENGTH: 15
<212> TYPE: PRT
<213> ORGANISM: Influenza Virus

<400> SEQUENCE: 13

Lys Gly Ile Leu Gly Phe Val Phe Thr Leu Thr Val Pro Ser Glu
1               5                   10                  15

<210> SEQ ID NO 14
<211> LENGTH: 15
<212> TYPE: PRT
<213> ORGANISM: Influenza Virus

<400> SEQUENCE: 14

Tyr Arg Lys Leu Lys Arg Glu Ile Thr Phe His Gly Ala Lys Glu
1               5                   10                  15

<210> SEQ ID NO 15
<211> LENGTH: 15
<212> TYPE: PRT
<213> ORGANISM: Influenza Virus

<400> SEQUENCE: 15

Met Gly Thr Val Thr Thr Glu Val Ala Leu Gly Leu Val Cys Ala
1               5                   10                  15

<210> SEQ ID NO 16
<211> LENGTH: 15
<212> TYPE: PRT
<213> ORGANISM: Influenza Virus

<400> SEQUENCE: 16

Asn Pro Leu Ile Arg His Glu Asn Arg Met Val Leu Ala Ser Thr
1               5                   10                  15

<210> SEQ ID NO 17
<211> LENGTH: 15
<212> TYPE: PRT
<213> ORGANISM: Influenza Virus

<400> SEQUENCE: 17

Ala Met Glu Val Ala Ser Gln Ala Arg Gln Met Val Gln Ala Met
1               5                   10                  15

<210> SEQ ID NO 18
<211> LENGTH: 15
<212> TYPE: PRT
<213> ORGANISM: Influenza Virus

<400> SEQUENCE: 18

Asp Pro Leu Val Val Ala Ala Ser Ile Ile Gly Ile Leu His Leu
1               5                   10                  15

<210> SEQ ID NO 19
<211> LENGTH: 17
```

```
<212> TYPE: PRT
<213> ORGANISM: Influenza Virus

<400> SEQUENCE: 19

Ser Leu Met Leu Gln Ile Gly Asn Met Ile Ser Ile Trp Val Ser His
1               5                   10                  15

Ser

<210> SEQ ID NO 20
<211> LENGTH: 19
<212> TYPE: PRT
<213> ORGANISM: Influenza Virus

<400> SEQUENCE: 20

Ile Gly Arg Phe Tyr Ile Gln Met Cys Thr Glu Leu Lys Leu Ser Asp
1               5                   10                  15

Tyr Glu Gly

<210> SEQ ID NO 21
<211> LENGTH: 15
<212> TYPE: PRT
<213> ORGANISM: Influenza Virus

<400> SEQUENCE: 21

Gln Asn Ser Ile Thr Ile Glu Arg Met Val Leu Ser Ala Phe Asp
1               5                   10                  15

<210> SEQ ID NO 22
<211> LENGTH: 15
<212> TYPE: PRT
<213> ORGANISM: Influenza Virus

<400> SEQUENCE: 22

Val Gly Thr Met Val Met Glu Leu Ile Arg Met Ile Lys Arg Gly
1               5                   10                  15

<210> SEQ ID NO 23
<211> LENGTH: 15
<212> TYPE: PRT
<213> ORGANISM: Influenza Virus

<400> SEQUENCE: 23

Asp Leu Ile Phe Leu Ala Arg Ser Ala Leu Ile Leu Arg Gly Ser
1               5                   10                  15

<210> SEQ ID NO 24
<211> LENGTH: 15
<212> TYPE: PRT
<213> ORGANISM: Influenza Virus

<400> SEQUENCE: 24

Arg Ser Ala Leu Ile Leu Arg Gly Ser Val Ala His Lys Ser Cys
1               5                   10                  15

<210> SEQ ID NO 25
<211> LENGTH: 15
<212> TYPE: PRT
<213> ORGANISM: Influenza Virus

<400> SEQUENCE: 25

Lys Ser Gln Leu Val Trp Met Ala Cys His Ser Ala Ala Phe Glu
1               5                   10                  15
```

```
<210> SEQ ID NO 26
<211> LENGTH: 15
<212> TYPE: PRT
<213> ORGANISM: Influenza Virus

<400> SEQUENCE: 26

Ala Gly Gln Ile Ser Val Gln Pro Thr Phe Ser Val Gln Arg Asn
1               5                   10                  15

<210> SEQ ID NO 27
<211> LENGTH: 15
<212> TYPE: PRT
<213> ORGANISM: Influenza Virus

<400> SEQUENCE: 27

Ser Leu Cys Ile Arg Met Asp Gln Ala Ile Met Asp Lys Asp Ile
1               5                   10                  15

<210> SEQ ID NO 28
<211> LENGTH: 19
<212> TYPE: PRT
<213> ORGANISM: Influenza Virus

<400> SEQUENCE: 28

Glu Gly Ala Ile Val Gly Glu Ile Ser Pro Leu Pro Ser Leu Pro Gly
1               5                   10                  15

His Thr Asp

<210> SEQ ID NO 29
<211> LENGTH: 15
<212> TYPE: PRT
<213> ORGANISM: Influenza Virus

<400> SEQUENCE: 29

Val Gly Glu Ile Ser Pro Leu Pro Ser Leu Pro Gly His Thr Asp
1               5                   10                  15

<210> SEQ ID NO 30
<211> LENGTH: 15
<212> TYPE: PRT
<213> ORGANISM: Influenza Virus

<400> SEQUENCE: 30

Ser Leu Lys Leu Tyr Arg Asp Ser Leu Gly Glu Ala Val Met Arg
1               5                   10                  15

<210> SEQ ID NO 31
<211> LENGTH: 15
<212> TYPE: PRT
<213> ORGANISM: Influenza Virus

<400> SEQUENCE: 31

Ile Arg Trp Leu Ile Glu Glu Val Arg His Arg Leu Arg Ile Thr
1               5                   10                  15

<210> SEQ ID NO 32
<211> LENGTH: 15
<212> TYPE: PRT
<213> ORGANISM: Influenza Virus

<400> SEQUENCE: 32

Phe Glu Gln Ile Thr Phe Met Gln Ala Leu Gln Leu Leu Leu Glu
1               5                   10                  15
```

```
<210> SEQ ID NO 33
<211> LENGTH: 15
<212> TYPE: PRT
<213> ORGANISM: Influenza Virus

<400> SEQUENCE: 33

Ile Thr Phe Met Gln Ala Leu Gln Leu Leu Glu Val Glu Gln
1               5                   10                  15

<210> SEQ ID NO 34
<211> LENGTH: 15
<212> TYPE: PRT
<213> ORGANISM: Influenza Virus

<400> SEQUENCE: 34

Arg Arg Glu Val His Ile Tyr Tyr Leu Glu Lys Ala Asn Lys Ile
1               5                   10                  15

<210> SEQ ID NO 35
<211> LENGTH: 15
<212> TYPE: PRT
<213> ORGANISM: Influenza Virus

<400> SEQUENCE: 35

Leu Phe Thr Ile Arg Gln Glu Met Ala Ser Arg Gly Leu Trp Asp
1               5                   10                  15

<210> SEQ ID NO 36
<211> LENGTH: 15
<212> TYPE: PRT
<213> ORGANISM: Influenza Virus

<400> SEQUENCE: 36

Glu Pro Phe Leu Lys Thr Thr Pro Arg Pro Leu Arg Leu Pro Asp
1               5                   10                  15

<210> SEQ ID NO 37
<211> LENGTH: 16
<212> TYPE: PRT
<213> ORGANISM: Influenza Virus

<400> SEQUENCE: 37

Arg Ser Lys Phe Leu Leu Met Asp Ala Leu Lys Leu Ser Ile Glu Asp
1               5                   10                  15

<210> SEQ ID NO 38
<211> LENGTH: 15
<212> TYPE: PRT
<213> ORGANISM: Influenza Virus

<400> SEQUENCE: 38

Val Ala Pro Ile Glu His Ile Ala Ser Met Arg Arg Asn Tyr Phe
1               5                   10                  15

<210> SEQ ID NO 39
<211> LENGTH: 15
<212> TYPE: PRT
<213> ORGANISM: Influenza Virus

<400> SEQUENCE: 39

Glu Tyr Ile Met Lys Gly Val Tyr Ile Asn Thr Ala Leu Leu Asn
1               5                   10                  15

<210> SEQ ID NO 40
<211> LENGTH: 15
```

```
<212> TYPE: PRT
<213> ORGANISM: Influenza Virus

<400> SEQUENCE: 40

Arg Pro Met Phe Leu Tyr Val Arg Thr Asn Gly Thr Ser Lys Ile
1               5                   10                  15

<210> SEQ ID NO 41
<211> LENGTH: 16
<212> TYPE: PRT
<213> ORGANISM: Influenza Virus

<400> SEQUENCE: 41

Pro Thr Leu Leu Phe Leu Lys Val Pro Ala Gln Asn Ala Ile Ser Thr
1               5                   10                  15

<210> SEQ ID NO 42
<211> LENGTH: 15
<212> TYPE: PRT
<213> ORGANISM: Influenza Virus

<400> SEQUENCE: 42

Ser Tyr Leu Ile Arg Ala Leu Thr Leu Asn Thr Met Thr Lys Asp
1               5                   10                  15

<210> SEQ ID NO 43
<211> LENGTH: 15
<212> TYPE: PRT
<213> ORGANISM: Influenza Virus

<400> SEQUENCE: 43

Phe Leu Ala Met Ile Thr Tyr Ile Thr Arg Asn Gln Pro Glu Trp
1               5                   10                  15

<210> SEQ ID NO 44
<211> LENGTH: 16
<212> TYPE: PRT
<213> ORGANISM: Influenza Virus

<400> SEQUENCE: 44

Gln Pro Glu Trp Phe Arg Asn Val Leu Ser Ile Ala Pro Ile Met Phe
1               5                   10                  15

<210> SEQ ID NO 45
<211> LENGTH: 16
<212> TYPE: PRT
<213> ORGANISM: Influenza Virus

<400> SEQUENCE: 45

Phe Arg Asn Val Leu Ser Ile Ala Pro Ile Met Phe Ser Asn Lys Met
1               5                   10                  15

<210> SEQ ID NO 46
<211> LENGTH: 15
<212> TYPE: PRT
<213> ORGANISM: Influenza Virus

<400> SEQUENCE: 46

Ile Ala Pro Ile Met Phe Ser Asn Lys Met Ala Arg Leu Gly Lys
1               5                   10                  15

<210> SEQ ID NO 47
<211> LENGTH: 16
<212> TYPE: PRT
<213> ORGANISM: Influenza Virus
```

<400> SEQUENCE: 47

Lys Gly Tyr Met Phe Glu Ser Lys Ser Met Lys Leu Arg Thr Gln Ile
1               5                   10                  15

<210> SEQ ID NO 48
<211> LENGTH: 15
<212> TYPE: PRT
<213> ORGANISM: Influenza Virus

<400> SEQUENCE: 48

Ile Arg Pro Leu Leu Val Glu Gly Thr Ala Ser Leu Ser Pro Gly
1               5                   10                  15

<210> SEQ ID NO 49
<211> LENGTH: 15
<212> TYPE: PRT
<213> ORGANISM: Influenza Virus

<400> SEQUENCE: 49

Met Met Gly Met Phe Asn Met Leu Ser Thr Val Leu Gly Val Ser
1               5                   10                  15

<210> SEQ ID NO 50
<211> LENGTH: 15
<212> TYPE: PRT
<213> ORGANISM: Influenza Virus

<400> SEQUENCE: 50

Asp Phe Ala Leu Ile Val Asn Ala Pro Asn His Glu Gly Ile Gln
1               5                   10                  15

<210> SEQ ID NO 51
<211> LENGTH: 15
<212> TYPE: PRT
<213> ORGANISM: Influenza Virus

<400> SEQUENCE: 51

Tyr Gly Phe Val Ala Asn Phe Ser Met Glu Leu Pro Ser Phe Gly
1               5                   10                  15

<210> SEQ ID NO 52
<211> LENGTH: 16
<212> TYPE: PRT
<213> ORGANISM: Influenza Virus

<400> SEQUENCE: 52

Gly Val Thr Val Ile Lys Asn Asn Met Ile Asn Asn Asp Leu Gly Pro
1               5                   10                  15

<210> SEQ ID NO 53
<211> LENGTH: 15
<212> TYPE: PRT
<213> ORGANISM: Influenza Virus

<400> SEQUENCE: 53

Pro Asn Leu Tyr Asn Ile Arg Asn Leu His Ile Pro Glu Val Cys
1               5                   10                  15

<210> SEQ ID NO 54
<211> LENGTH: 15
<212> TYPE: PRT
<213> ORGANISM: Influenza Virus

<400> SEQUENCE: 54

```
Ile Ser Ser Met Val Glu Ala Met Val Ser Arg Ala Arg Ile Asp
1               5                   10                  15

<210> SEQ ID NO 55
<211> LENGTH: 15
<212> TYPE: PRT
<213> ORGANISM: Influenza Virus

<400> SEQUENCE: 55

Lys Trp Met Met Ala Met Lys Tyr Pro Ile Thr Ala Asp Lys Arg
1               5                   10                  15

<210> SEQ ID NO 56
<211> LENGTH: 15
<212> TYPE: PRT
<213> ORGANISM: Influenza Virus

<400> SEQUENCE: 56

Gly Ala Arg Ile Leu Thr Ser Glu Ser Gln Leu Thr Ile Thr Lys
1               5                   10                  15

<210> SEQ ID NO 57
<211> LENGTH: 15
<212> TYPE: PRT
<213> ORGANISM: Influenza Virus

<400> SEQUENCE: 57

Lys Ala Ala Met Gly Leu Arg Ile Ser Ser Ser Phe Ser Phe Gly
1               5                   10                  15

<210> SEQ ID NO 58
<211> LENGTH: 15
<212> TYPE: PRT
<213> ORGANISM: Influenza Virus

<400> SEQUENCE: 58

Ile Lys Ala Val Arg Gly Asp Leu Asn Phe Val Asn Arg Ala Asn
1               5                   10                  15

<210> SEQ ID NO 59
<211> LENGTH: 15
<212> TYPE: PRT
<213> ORGANISM: Influenza Virus

<400> SEQUENCE: 59

Leu Arg His Phe Gln Lys Asp Ala Lys Val Leu Phe Gln Asn Trp
1               5                   10                  15

<210> SEQ ID NO 60
<211> LENGTH: 15
<212> TYPE: PRT
<213> ORGANISM: Influenza Virus

<400> SEQUENCE: 60

Gln Trp Ile Ile Arg Asn Trp Glu Thr Val Lys Ile Gln Trp Ser
1               5                   10                  15

<210> SEQ ID NO 61
<211> LENGTH: 15
<212> TYPE: PRT
<213> ORGANISM: Influenza Virus

<400> SEQUENCE: 61

Arg Met Gln Phe Ser Ser Leu Thr Val Asn Val Arg Gly Ser Gly
```

<210> SEQ ID NO 62
<211> LENGTH: 9
<212> TYPE: PRT
<213> ORGANISM: Influenza Virus

<400> SEQUENCE: 62

Leu Thr Ile Gly Glu Cys Pro Lys Tyr
1               5

<210> SEQ ID NO 63
<211> LENGTH: 9
<212> TYPE: PRT
<213> ORGANISM: Influenza Virus

<400> SEQUENCE: 63

Gly Met Ile Asp Gly Trp Tyr Gly Tyr
1               5

<210> SEQ ID NO 64
<211> LENGTH: 10
<212> TYPE: PRT
<213> ORGANISM: Influenza Virus

<400> SEQUENCE: 64

Gly Leu Phe Gly Ala Ile Ala Gly Phe Ile
1               5                   10

<210> SEQ ID NO 65
<211> LENGTH: 9
<212> TYPE: PRT
<213> ORGANISM: Influenza Virus

<400> SEQUENCE: 65

Phe Leu Asp Ile Trp Thr Tyr Asn Ala
1               5

<210> SEQ ID NO 66
<211> LENGTH: 10
<212> TYPE: PRT
<213> ORGANISM: Influenza Virus

<400> SEQUENCE: 66

Thr Ile Gly Glu Cys Pro Lys Tyr Val Lys
1               5                   10

<210> SEQ ID NO 67
<211> LENGTH: 9
<212> TYPE: PRT
<213> ORGANISM: Influenza Virus

<400> SEQUENCE: 67

Leu Pro Phe His Asn Val His Pro Leu
1               5

<210> SEQ ID NO 68
<211> LENGTH: 9
<212> TYPE: PRT
<213> ORGANISM: Influenza Virus

<400> SEQUENCE: 68

Asn Met Asp Arg Ala Val Lys Leu Tyr
1               5

```
<210> SEQ ID NO 69
<211> LENGTH: 9
<212> TYPE: PRT
<213> ORGANISM: Influenza Virus

<400> SEQUENCE: 69

Leu Leu Thr Glu Val Glu Thr Tyr Val
1               5

<210> SEQ ID NO 70
<211> LENGTH: 9
<212> TYPE: PRT
<213> ORGANISM: Influenza Virus

<400> SEQUENCE: 70

Gly Ile Leu Gly Phe Val Phe Thr Leu
1               5

<210> SEQ ID NO 71
<211> LENGTH: 10
<212> TYPE: PRT
<213> ORGANISM: Influenza Virus

<400> SEQUENCE: 71

Ile Leu Gly Phe Val Phe Thr Leu Thr Val
1               5                   10

<210> SEQ ID NO 72
<211> LENGTH: 9
<212> TYPE: PRT
<213> ORGANISM: Influenza Virus

<400> SEQUENCE: 72

Arg Met Gly Thr Val Thr Thr Glu Val
1               5

<210> SEQ ID NO 73
<211> LENGTH: 9
<212> TYPE: PRT
<213> ORGANISM: Influenza Virus

<400> SEQUENCE: 73

Ala Leu Met Glu Trp Leu Lys Thr Arg
1               5

<210> SEQ ID NO 74
<211> LENGTH: 10
<212> TYPE: PRT
<213> ORGANISM: Influenza Virus

<400> SEQUENCE: 74

Ala Ser Cys Met Gly Leu Ile Tyr Asn Arg
1               5                   10

<210> SEQ ID NO 75
<211> LENGTH: 9
<212> TYPE: PRT
<213> ORGANISM: Influenza Virus

<400> SEQUENCE: 75

Glu Trp Leu Lys Thr Arg Pro Ile Leu
1               5

<210> SEQ ID NO 76
```

<211> LENGTH: 10
<212> TYPE: PRT
<213> ORGANISM: Influenza Virus

<400> SEQUENCE: 76

Thr Glu Val Glu Thr Tyr Val Leu Ser Ile
1 5 10

<210> SEQ ID NO 77
<211> LENGTH: 10
<212> TYPE: PRT
<213> ORGANISM: Influenza Virus

<400> SEQUENCE: 77

His Glu Asn Arg Met Val Leu Ala Ser Thr
1 5 10

<210> SEQ ID NO 78
<211> LENGTH: 10
<212> TYPE: PRT
<213> ORGANISM: Influenza Virus

<400> SEQUENCE: 78

Ser Glu Gln Ala Ala Glu Ala Met Glu Val
1 5 10

<210> SEQ ID NO 79
<211> LENGTH: 10
<212> TYPE: PRT
<213> ORGANISM: Influenza Virus

<400> SEQUENCE: 79

Met Glu Val Ala Ser Gln Ala Arg Gln Met
1 5 10

<210> SEQ ID NO 80
<211> LENGTH: 9
<212> TYPE: PRT
<213> ORGANISM: Influenza Virus

<400> SEQUENCE: 80

Ser Ile Ile Gly Ile Leu His Leu Ile
1 5

<210> SEQ ID NO 81
<211> LENGTH: 9
<212> TYPE: PRT
<213> ORGANISM: Influenza Virus

<400> SEQUENCE: 81

Arg Leu Phe Phe Lys Cys Ile Tyr Arg
1 5

<210> SEQ ID NO 82
<211> LENGTH: 10
<212> TYPE: PRT
<213> ORGANISM: Influenza Virus

<400> SEQUENCE: 82

Arg Leu Phe Phe Lys Cys Ile Tyr Arg Arg
1 5 10

<210> SEQ ID NO 83
<211> LENGTH: 9
<212> TYPE: PRT

<213> ORGANISM: Influenza Virus

<400> SEQUENCE: 83

Leu Phe Phe Lys Cys Ile Tyr Arg Arg
1               5

<210> SEQ ID NO 84
<211> LENGTH: 9
<212> TYPE: PRT
<213> ORGANISM: Influenza Virus

<400> SEQUENCE: 84

Leu Trp Ile Leu Asp Arg Leu Phe Phe
1               5

<210> SEQ ID NO 85
<211> LENGTH: 9
<212> TYPE: PRT
<213> ORGANISM: Influenza Virus

<400> SEQUENCE: 85

Ile Tyr Arg Arg Phe Lys Tyr Gly Leu
1               5

<210> SEQ ID NO 86
<211> LENGTH: 9
<212> TYPE: PRT
<213> ORGANISM: Influenza Virus

<400> SEQUENCE: 86

Gly Thr Val Lys Asp Arg Ser Pro Tyr
1               5

<210> SEQ ID NO 87
<211> LENGTH: 9
<212> TYPE: PRT
<213> ORGANISM: Influenza Virus

<400> SEQUENCE: 87

Val Ser Phe Asp Gln Asn Leu Asp Tyr
1               5

<210> SEQ ID NO 88
<211> LENGTH: 10
<212> TYPE: PRT
<213> ORGANISM: Influenza Virus

<400> SEQUENCE: 88

Ile Val Ala Ile Thr Asp Trp Ser Gly Tyr
1               5                   10

<210> SEQ ID NO 89
<211> LENGTH: 9
<212> TYPE: PRT
<213> ORGANISM: Influenza Virus

<400> SEQUENCE: 89

Lys Ser Cys Ile Asn Arg Cys Phe Tyr
1               5

<210> SEQ ID NO 90
<211> LENGTH: 9
<212> TYPE: PRT
<213> ORGANISM: Influenza Virus

```
<400> SEQUENCE: 90

Ala Leu Ser Thr Leu Cys Leu Leu Ile
1               5

<210> SEQ ID NO 91
<211> LENGTH: 9
<212> TYPE: PRT
<213> ORGANISM: Influenza Virus

<400> SEQUENCE: 91

His Leu Glu Cys Arg Thr Phe Phe Leu
1               5

<210> SEQ ID NO 92
<211> LENGTH: 9
<212> TYPE: PRT
<213> ORGANISM: Influenza Virus

<400> SEQUENCE: 92

Cys Ile Asn Gly Ser Cys Phe Thr Val
1               5

<210> SEQ ID NO 93
<211> LENGTH: 9
<212> TYPE: PRT
<213> ORGANISM: Influenza Virus

<400> SEQUENCE: 93

Ile Thr Gly Phe Ala Pro Phe Ser Lys
1               5

<210> SEQ ID NO 94
<211> LENGTH: 9
<212> TYPE: PRT
<213> ORGANISM: Influenza Virus

<400> SEQUENCE: 94

Ile Thr Gly Trp Ala Ile Phe Ser Lys
1               5

<210> SEQ ID NO 95
<211> LENGTH: 10
<212> TYPE: PRT
<213> ORGANISM: Influenza Virus

<400> SEQUENCE: 95

Ala Ser Tyr Lys Ile Phe Lys Ile Glu Lys
1               5                   10

<210> SEQ ID NO 96
<211> LENGTH: 10
<212> TYPE: PRT
<213> ORGANISM: Influenza Virus

<400> SEQUENCE: 96

Val Val Phe Cys Gly Thr Ser Gly Thr Tyr
1               5                   10

<210> SEQ ID NO 97
<211> LENGTH: 9
<212> TYPE: PRT
<213> ORGANISM: Influenza Virus

<400> SEQUENCE: 97
```

```
Val Phe Val Ile Arg Glu Pro Phe Ile
1               5
```

<210> SEQ ID NO 98
<211> LENGTH: 9
<212> TYPE: PRT
<213> ORGANISM: Influenza Virus

<400> SEQUENCE: 98

```
Phe Phe Leu Thr Gln Gly Ala Leu Leu
1               5
```

<210> SEQ ID NO 99
<211> LENGTH: 10
<212> TYPE: PRT
<213> ORGANISM: Influenza Virus

<400> SEQUENCE: 99

```
Trp Trp Thr Ser Asn Ser Ile Ile Val Phe
1               5                   10
```

<210> SEQ ID NO 100
<211> LENGTH: 10
<212> TYPE: PRT
<213> ORGANISM: Influenza Virus

<400> SEQUENCE: 100

```
Ser Trp Pro Asp Gly Ala Asn Ile Pro Phe
1               5                   10
```

<210> SEQ ID NO 101
<211> LENGTH: 10
<212> TYPE: PRT
<213> ORGANISM: Influenza Virus

<400> SEQUENCE: 101

```
Ser Trp Pro Asp Gly Ala Asn Ile Asn Phe
1               5                   10
```

<210> SEQ ID NO 102
<211> LENGTH: 9
<212> TYPE: PRT
<213> ORGANISM: Influenza Virus

<400> SEQUENCE: 102

```
Ala Pro Phe Ser Lys Asp Asn Ser Ile
1               5
```

<210> SEQ ID NO 103
<211> LENGTH: 9
<212> TYPE: PRT
<213> ORGANISM: Influenza Virus

<400> SEQUENCE: 103

```
Ala Pro Ser Pro Tyr Asn Ser Arg Phe
1               5
```

<210> SEQ ID NO 104
<211> LENGTH: 10
<212> TYPE: PRT
<213> ORGANISM: Influenza Virus

<400> SEQUENCE: 104

```
Ser Pro Tyr Asn Ser Arg Phe Glu Ser Val
1               5                   10
```

<210> SEQ ID NO 105
<211> LENGTH: 10
<212> TYPE: PRT
<213> ORGANISM: Influenza Virus

<400> SEQUENCE: 105

Arg Pro Trp Val Ser Phe Asn Gln Asn Leu
1               5                   10

<210> SEQ ID NO 106
<211> LENGTH: 9
<212> TYPE: PRT
<213> ORGANISM: Influenza Virus

<400> SEQUENCE: 106

Arg Pro Cys Phe Trp Val Glu Leu Ile
1               5

<210> SEQ ID NO 107
<211> LENGTH: 9
<212> TYPE: PRT
<213> ORGANISM: Influenza Virus

<400> SEQUENCE: 107

Glu Glu Cys Ser Cys Tyr Pro Asp Tyr
1               5

<210> SEQ ID NO 108
<211> LENGTH: 9
<212> TYPE: PRT
<213> ORGANISM: Influenza Virus

<400> SEQUENCE: 108

Glu Glu Cys Ser Cys Tyr Pro Arg Tyr
1               5

<210> SEQ ID NO 109
<211> LENGTH: 9
<212> TYPE: PRT
<213> ORGANISM: Influenza Virus

<400> SEQUENCE: 109

Phe Glu Met Ile Trp Asp Pro Asn Gly
1               5

<210> SEQ ID NO 110
<211> LENGTH: 9
<212> TYPE: PRT
<213> ORGANISM: Influenza Virus

<400> SEQUENCE: 110

Ala Ser Gln Gly Thr Lys Arg Ser Tyr
1               5

<210> SEQ ID NO 111
<211> LENGTH: 9
<212> TYPE: PRT
<213> ORGANISM: Influenza Virus

<400> SEQUENCE: 111

Cys Thr Glu Leu Lys Leu Ser Asp Tyr
1               5

<210> SEQ ID NO 112
<211> LENGTH: 9
<212> TYPE: PRT
<213> ORGANISM: Influenza Virus

<400> SEQUENCE: 112

His Ser Asn Leu Asn Asp Ala Thr Tyr
1               5

<210> SEQ ID NO 113
<211> LENGTH: 9
<212> TYPE: PRT
<213> ORGANISM: Influenza Virus

<400> SEQUENCE: 113

Lys Ser Cys Leu Pro Ala Cys Val Tyr
1               5

<210> SEQ ID NO 114
<211> LENGTH: 9
<212> TYPE: PRT
<213> ORGANISM: Influenza Virus

<400> SEQUENCE: 114

Cys Leu Pro Ala Cys Val Tyr Gly Leu
1               5

<210> SEQ ID NO 115
<211> LENGTH: 9
<212> TYPE: PRT
<213> ORGANISM: Influenza Virus

<400> SEQUENCE: 115

Leu Gln Asn Ser Gln Val Phe Ser Leu
1               5

<210> SEQ ID NO 116
<211> LENGTH: 9
<212> TYPE: PRT
<213> ORGANISM: Influenza Virus

<400> SEQUENCE: 116

Phe Gln Gly Arg Gly Val Phe Glu Leu
1               5

<210> SEQ ID NO 117
<211> LENGTH: 9
<212> TYPE: PRT
<213> ORGANISM: Influenza Virus

<400> SEQUENCE: 117

Ile Gln Asn Ser Ile Thr Ile Glu Arg
1               5

<210> SEQ ID NO 118
<211> LENGTH: 9
<212> TYPE: PRT
<213> ORGANISM: Influenza Virus

<400> SEQUENCE: 118

Met Val Leu Ser Ala Phe Asp Glu Arg
1               5

<210> SEQ ID NO 119
<211> LENGTH: 10

```
<212> TYPE: PRT
<213> ORGANISM: Influenza Virus

<400> SEQUENCE: 119

Ser Leu Met Gln Gly Ser Thr Leu Pro Arg
1               5                   10

<210> SEQ ID NO 120
<211> LENGTH: 9
<212> TYPE: PRT
<213> ORGANISM: Influenza Virus

<400> SEQUENCE: 120

Met Gln Gly Ser Thr Leu Pro Arg Arg
1               5

<210> SEQ ID NO 121
<211> LENGTH: 9
<212> TYPE: PRT
<213> ORGANISM: Influenza Virus

<400> SEQUENCE: 121

Gly Thr Met Val Met Glu Leu Ile Arg
1               5

<210> SEQ ID NO 122
<211> LENGTH: 10
<212> TYPE: PRT
<213> ORGANISM: Influenza Virus

<400> SEQUENCE: 122

Met Val Met Glu Leu Ile Arg Met Ile Lys
1               5                   10

<210> SEQ ID NO 123
<211> LENGTH: 10
<212> TYPE: PRT
<213> ORGANISM: Influenza Virus

<400> SEQUENCE: 123

Ala Val Ala Ser Gly Tyr Asp Phe Glu Arg
1               5                   10

<210> SEQ ID NO 124
<211> LENGTH: 10
<212> TYPE: PRT
<213> ORGANISM: Influenza Virus

<400> SEQUENCE: 124

Ser Val Gln Pro Thr Phe Ser Val Gln Arg
1               5                   10

<210> SEQ ID NO 125
<211> LENGTH: 9
<212> TYPE: PRT
<213> ORGANISM: Influenza Virus

<400> SEQUENCE: 125

Val Gln Pro Thr Phe Ser Val Gln Arg
1               5

<210> SEQ ID NO 126
<211> LENGTH: 10
<212> TYPE: PRT
<213> ORGANISM: Influenza Virus
```

<400> SEQUENCE: 126

Ser Val Gln Arg Asn Leu Pro Phe Glu Arg
1               5                   10

<210> SEQ ID NO 127
<211> LENGTH: 9
<212> TYPE: PRT
<213> ORGANISM: Influenza Virus

<400> SEQUENCE: 127

Gly Val Phe Glu Leu Ser Asp Glu Lys
1               5

<210> SEQ ID NO 128
<211> LENGTH: 9
<212> TYPE: PRT
<213> ORGANISM: Influenza Virus

<400> SEQUENCE: 128

Phe Tyr Ile Gln Met Cys Thr Glu Leu
1               5

<210> SEQ ID NO 129
<211> LENGTH: 9
<212> TYPE: PRT
<213> ORGANISM: Influenza Virus

<400> SEQUENCE: 129

His Met Met Ile Trp His Ser Asn Leu
1               5

<210> SEQ ID NO 130
<211> LENGTH: 9
<212> TYPE: PRT
<213> ORGANISM: Influenza Virus

<400> SEQUENCE: 130

Ile Phe Leu Ala Arg Ser Ala Leu Ile
1               5

<210> SEQ ID NO 131
<211> LENGTH: 9
<212> TYPE: PRT
<213> ORGANISM: Influenza Virus

<400> SEQUENCE: 131

Trp Met Ala Cys His Ser Ala Ala Phe
1               5

<210> SEQ ID NO 132
<211> LENGTH: 10
<212> TYPE: PRT
<213> ORGANISM: Influenza Virus

<400> SEQUENCE: 132

Leu Pro Arg Arg Ser Gly Ala Ala Gly Ala
1               5                   10

<210> SEQ ID NO 133
<211> LENGTH: 10
<212> TYPE: PRT
<213> ORGANISM: Influenza Virus

<400> SEQUENCE: 133

-continued

Leu Pro Ala Cys Val Tyr Gly Leu Ala Val
1               5                   10

<210> SEQ ID NO 134
<211> LENGTH: 9
<212> TYPE: PRT
<213> ORGANISM: Influenza Virus

<400> SEQUENCE: 134

Leu Pro Phe Glu Arg Ala Thr Ile Met
1               5

<210> SEQ ID NO 135
<211> LENGTH: 9
<212> TYPE: PRT
<213> ORGANISM: Influenza Virus

<400> SEQUENCE: 135

Gly Glu Arg Gln Asn Ala Thr Glu Ile
1               5

<210> SEQ ID NO 136
<211> LENGTH: 9
<212> TYPE: PRT
<213> ORGANISM: Influenza Virus

<400> SEQUENCE: 136

Arg Glu Ser Arg Asn Pro Gly Asn Ala
1               5

<210> SEQ ID NO 137
<211> LENGTH: 9
<212> TYPE: PRT
<213> ORGANISM: Influenza Virus

<400> SEQUENCE: 137

Phe Glu Asp Leu Arg Val Ser Ser Phe
1               5

<210> SEQ ID NO 138
<211> LENGTH: 9
<212> TYPE: PRT
<213> ORGANISM: Influenza Virus

<400> SEQUENCE: 138

Phe Glu Arg Ala Thr Ile Met Ala Ala
1               5

<210> SEQ ID NO 139
<211> LENGTH: 10
<212> TYPE: PRT
<213> ORGANISM: Influenza Virus

<400> SEQUENCE: 139

Phe Glu Arg Ala Thr Ile Met Ala Ala Phe
1               5                   10

<210> SEQ ID NO 140
<211> LENGTH: 10
<212> TYPE: PRT
<213> ORGANISM: Influenza Virus

<400> SEQUENCE: 140

Thr Ile Ala Ser Val Pro Ala Pro Arg Tyr

```
1               5                   10
```

```
<210> SEQ ID NO 141
<211> LENGTH: 10
<212> TYPE: PRT
<213> ORGANISM: Influenza Virus

<400> SEQUENCE: 141

Phe Gln Val Asp Cys Phe Leu Trp His Val
1               5                   10

<210> SEQ ID NO 142
<211> LENGTH: 9
<212> TYPE: PRT
<213> ORGANISM: Influenza Virus

<400> SEQUENCE: 142

Gln Val Asp Cys Phe Leu Trp His Val
1               5

<210> SEQ ID NO 143
<211> LENGTH: 9
<212> TYPE: PRT
<213> ORGANISM: Influenza Virus

<400> SEQUENCE: 143

Phe Leu Trp His Val Arg Lys Gln Val
1               5

<210> SEQ ID NO 144
<211> LENGTH: 9
<212> TYPE: PRT
<213> ORGANISM: Influenza Virus

<400> SEQUENCE: 144

Ile Ile Leu Lys Ala Asn Phe Ser Val
1               5

<210> SEQ ID NO 145
<211> LENGTH: 9
<212> TYPE: PRT
<213> ORGANISM: Influenza Virus

<400> SEQUENCE: 145

Lys Gln Ile Val Glu Arg Ile Leu Lys
1               5

<210> SEQ ID NO 146
<211> LENGTH: 10
<212> TYPE: PRT
<213> ORGANISM: Influenza Virus

<400> SEQUENCE: 146

Ala Ile Met Asp Lys Asn Ile Ile Leu Lys
1               5                   10

<210> SEQ ID NO 147
<211> LENGTH: 10
<212> TYPE: PRT
<213> ORGANISM: Influenza Virus

<400> SEQUENCE: 147

Val Pro Ala Ser Arg Tyr Leu Thr Asp Met
1               5                   10
```

<210> SEQ ID NO 148
<211> LENGTH: 9
<212> TYPE: PRT
<213> ORGANISM: Influenza Virus

<400> SEQUENCE: 148

Asp Glu Ala Leu Lys Met Thr Ile Ala
1               5

<210> SEQ ID NO 149
<211> LENGTH: 10
<212> TYPE: PRT
<213> ORGANISM: Influenza Virus

<400> SEQUENCE: 149

Leu Glu Glu Met Ser Arg Asp Trp Leu Met
1               5                   10

<210> SEQ ID NO 150
<211> LENGTH: 10
<212> TYPE: PRT
<213> ORGANISM: Influenza Virus

<400> SEQUENCE: 150

Leu Glu Thr Leu Ile Leu Leu Arg Ala Phe
1               5                   10

<210> SEQ ID NO 151
<211> LENGTH: 9
<212> TYPE: PRT
<213> ORGANISM: Influenza Virus

<400> SEQUENCE: 151

Gly Glu Ile Ser Pro Leu Pro Ser Leu
1               5

<210> SEQ ID NO 152
<211> LENGTH: 9
<212> TYPE: PRT
<213> ORGANISM: Influenza Virus

<400> SEQUENCE: 152

Ser Glu Thr Leu Gln Arg Phe Ala Trp
1               5

<210> SEQ ID NO 153
<211> LENGTH: 10
<212> TYPE: PRT
<213> ORGANISM: Influenza Virus

<400> SEQUENCE: 153

Ile Thr Gln Phe Glu Ser Leu Lys Leu Tyr
1               5                   10

<210> SEQ ID NO 154
<211> LENGTH: 9
<212> TYPE: PRT
<213> ORGANISM: Influenza Virus

<400> SEQUENCE: 154

Phe Met Gln Ala Leu Gln Leu Leu Leu
1               5

<210> SEQ ID NO 155

```
<211> LENGTH: 10
<212> TYPE: PRT
<213> ORGANISM: Influenza Virus

<400> SEQUENCE: 155

Met Gln Ala Leu Gln Leu Leu Leu Glu Val
1               5                   10

<210> SEQ ID NO 156
<211> LENGTH: 9
<212> TYPE: PRT
<213> ORGANISM: Influenza Virus

<400> SEQUENCE: 156

Met Ile Thr Gln Phe Glu Ser Leu Lys
1               5

<210> SEQ ID NO 157
<211> LENGTH: 10
<212> TYPE: PRT
<213> ORGANISM: Influenza Virus

<400> SEQUENCE: 157

Thr Gln Phe Glu Ser Leu Lys Leu Tyr Arg
1               5                   10

<210> SEQ ID NO 158
<211> LENGTH: 9
<212> TYPE: PRT
<213> ORGANISM: Influenza Virus

<400> SEQUENCE: 158

Lys Phe Glu Glu Ile Arg Trp Leu Ile
1               5

<210> SEQ ID NO 159
<211> LENGTH: 9
<212> TYPE: PRT
<213> ORGANISM: Influenza Virus

<400> SEQUENCE: 159

Phe Met Gln Ala Leu Gln Leu Leu Phe
1               5

<210> SEQ ID NO 160
<211> LENGTH: 9
<212> TYPE: PRT
<213> ORGANISM: Influenza Virus

<400> SEQUENCE: 160

Glu Glu Val Arg His Arg Leu Lys Ile
1               5

<210> SEQ ID NO 161
<211> LENGTH: 9
<212> TYPE: PRT
<213> ORGANISM: Influenza Virus

<400> SEQUENCE: 161

Phe Glu Gln Ile Thr Phe Met Gln Ala
1               5

<210> SEQ ID NO 162
<211> LENGTH: 9
<212> TYPE: PRT
```

<213> ORGANISM: Influenza Virus

<400> SEQUENCE: 162

Leu Glu Val Glu Gln Glu Ile Arg Thr
1               5

<210> SEQ ID NO 163
<211> LENGTH: 10
<212> TYPE: PRT
<213> ORGANISM: Influenza Virus

<400> SEQUENCE: 163

Gln Glu Ile Arg Thr Phe Ser Phe Gln Leu
1               5                   10

<210> SEQ ID NO 164
<211> LENGTH: 10
<212> TYPE: PRT
<213> ORGANISM: Influenza Virus

<400> SEQUENCE: 164

Cys Thr His Leu Glu Val Cys Phe Met Tyr
1               5                   10

<210> SEQ ID NO 165
<211> LENGTH: 9
<212> TYPE: PRT
<213> ORGANISM: Influenza Virus

<400> SEQUENCE: 165

Val Thr Arg Arg Glu Val His Ile Tyr
1               5

<210> SEQ ID NO 166
<211> LENGTH: 9
<212> TYPE: PRT
<213> ORGANISM: Influenza Virus

<400> SEQUENCE: 166

Ser Ser Leu Glu Asn Phe Arg Ala Tyr
1               5

<210> SEQ ID NO 167
<211> LENGTH: 10
<212> TYPE: PRT
<213> ORGANISM: Influenza Virus

<400> SEQUENCE: 167

Tyr Val Asp Gly Phe Glu Pro Asn Gly Tyr
1               5                   10

<210> SEQ ID NO 168
<211> LENGTH: 9
<212> TYPE: PRT
<213> ORGANISM: Influenza Virus

<400> SEQUENCE: 168

His Ile Ala Ser Met Arg Arg Asn Tyr
1               5

<210> SEQ ID NO 169
<211> LENGTH: 9
<212> TYPE: PRT
<213> ORGANISM: Influenza Virus

<400> SEQUENCE: 169

Val Ser His Cys Arg Ala Thr Glu Tyr
1 5

<210> SEQ ID NO 170
<211> LENGTH: 9
<212> TYPE: PRT
<213> ORGANISM: Influenza Virus

<400> SEQUENCE: 170

Phe Met Tyr Ser Asp Phe His Phe Ile
1 5

<210> SEQ ID NO 171
<211> LENGTH: 9
<212> TYPE: PRT
<213> ORGANISM: Influenza Virus

<400> SEQUENCE: 171

Ala Leu Leu Lys His Arg Phe Glu Ile
1 5

<210> SEQ ID NO 172
<211> LENGTH: 9
<212> TYPE: PRT
<213> ORGANISM: Influenza Virus

<400> SEQUENCE: 172

Met Ala Trp Thr Val Val Asn Ser Ile
1 5

<210> SEQ ID NO 173
<211> LENGTH: 10
<212> TYPE: PRT
<213> ORGANISM: Influenza Virus

<400> SEQUENCE: 173

Leu Leu Met Asp Ala Leu Lys Leu Ser Ile
1 5 10

<210> SEQ ID NO 174
<211> LENGTH: 9
<212> TYPE: PRT
<213> ORGANISM: Influenza Virus

<400> SEQUENCE: 174

Leu Leu Ala Trp Lys Gln Val Leu Ala
1 5

<210> SEQ ID NO 175
<211> LENGTH: 9
<212> TYPE: PRT
<213> ORGANISM: Influenza Virus

<400> SEQUENCE: 175

Tyr Ile Asn Thr Ala Leu Leu Asn Ala
1 5

<210> SEQ ID NO 176
<211> LENGTH: 10
<212> TYPE: PRT
<213> ORGANISM: Influenza Virus

<400> SEQUENCE: 176

Ser Ile Cys Asn Thr Thr Gly Val Glu Lys
1               5                   10

<210> SEQ ID NO 177
<211> LENGTH: 10
<212> TYPE: PRT
<213> ORGANISM: Influenza Virus

<400> SEQUENCE: 177

Lys Phe Leu Pro Asp Leu Tyr Asp Tyr Lys
1               5                   10

<210> SEQ ID NO 178
<211> LENGTH: 10
<212> TYPE: PRT
<213> ORGANISM: Influenza Virus

<400> SEQUENCE: 178

His Ile Tyr Tyr Leu Glu Lys Ala Asn Lys
1               5                   10

<210> SEQ ID NO 179
<211> LENGTH: 9
<212> TYPE: PRT
<213> ORGANISM: Influenza Virus

<400> SEQUENCE: 179

Lys Phe Leu Leu Met Asp Ala Leu Lys
1               5

<210> SEQ ID NO 180
<211> LENGTH: 10
<212> TYPE: PRT
<213> ORGANISM: Influenza Virus

<400> SEQUENCE: 180

Arg Thr Phe Phe Gly Trp Lys Glu Pro Tyr
1               5                   10

<210> SEQ ID NO 181
<211> LENGTH: 10
<212> TYPE: PRT
<213> ORGANISM: Influenza Virus

<400> SEQUENCE: 181

Lys Ile Pro Lys Thr Lys Asn Met Lys Lys
1               5                   10

<210> SEQ ID NO 182
<211> LENGTH: 9
<212> TYPE: PRT
<213> ORGANISM: Influenza Virus

<400> SEQUENCE: 182

Phe Gln Leu Ile Pro Met Ile Ser Lys
1               5

<210> SEQ ID NO 183
<211> LENGTH: 10
<212> TYPE: PRT
<213> ORGANISM: Influenza Virus

<400> SEQUENCE: 183

Lys Thr Asn Leu Tyr Gly Phe Ile Ile Lys
1               5                   10

<210> SEQ ID NO 184
<211> LENGTH: 10
<212> TYPE: PRT
<213> ORGANISM: Influenza Virus

<400> SEQUENCE: 184

Asn Leu Tyr Gly Phe Ile Ile Lys Gly Arg
1               5                   10

<210> SEQ ID NO 185
<211> LENGTH: 9
<212> TYPE: PRT
<213> ORGANISM: Influenza Virus

<400> SEQUENCE: 185

Ser Val Lys Glu Lys Asp Met Thr Lys
1               5

<210> SEQ ID NO 186
<211> LENGTH: 9
<212> TYPE: PRT
<213> ORGANISM: Influenza Virus

<400> SEQUENCE: 186

Met Thr Lys Glu Phe Phe Glu Asn Lys
1               5

<210> SEQ ID NO 187
<211> LENGTH: 9
<212> TYPE: PRT
<213> ORGANISM: Influenza Virus

<400> SEQUENCE: 187

Lys Val Cys Arg Thr Leu Leu Ala Lys
1               5

<210> SEQ ID NO 188
<211> LENGTH: 10
<212> TYPE: PRT
<213> ORGANISM: Influenza Virus

<400> SEQUENCE: 188

Lys Leu Leu Leu Ile Val Gln Ala Leu Arg
1               5                   10

<210> SEQ ID NO 189
<211> LENGTH: 9
<212> TYPE: PRT
<213> ORGANISM: Influenza Virus

<400> SEQUENCE: 189

Lys Phe Ala Ala Ile Cys Thr His Leu
1               5

<210> SEQ ID NO 190
<211> LENGTH: 9
<212> TYPE: PRT
<213> ORGANISM: Influenza Virus

<400> SEQUENCE: 190

Cys Phe Met Tyr Ser Asp Phe His Phe
1               5

-continued

```
<210> SEQ ID NO 191
<211> LENGTH: 9
<212> TYPE: PRT
<213> ORGANISM: Influenza Virus

<400> SEQUENCE: 191

Tyr Tyr Leu Glu Lys Ala Asn Lys Ile
1               5

<210> SEQ ID NO 192
<211> LENGTH: 9
<212> TYPE: PRT
<213> ORGANISM: Influenza Virus

<400> SEQUENCE: 192

Glu Tyr Ile Met Lys Gly Val Tyr Ile
1               5

<210> SEQ ID NO 193
<211> LENGTH: 9
<212> TYPE: PRT
<213> ORGANISM: Influenza Virus

<400> SEQUENCE: 193

Phe Phe Glu Asn Lys Ser Glu Thr Trp
1               5

<210> SEQ ID NO 194
<211> LENGTH: 10
<212> TYPE: PRT
<213> ORGANISM: Influenza Virus

<400> SEQUENCE: 194

Leu Tyr Ala Ser Pro Gln Leu Glu Gly Phe
1               5                   10

<210> SEQ ID NO 195
<211> LENGTH: 9
<212> TYPE: PRT
<213> ORGANISM: Influenza Virus

<400> SEQUENCE: 195

Ala Pro Ile Glu His Ile Ala Ser Met
1               5

<210> SEQ ID NO 196
<211> LENGTH: 9
<212> TYPE: PRT
<213> ORGANISM: Influenza Virus

<400> SEQUENCE: 196

Ser Pro Gln Leu Glu Gly Phe Ser Ala
1               5

<210> SEQ ID NO 197
<211> LENGTH: 9
<212> TYPE: PRT
<213> ORGANISM: Influenza Virus

<400> SEQUENCE: 197

Ser Glu Lys Thr His Ile His Ile Phe
1               5

<210> SEQ ID NO 198
<211> LENGTH: 9
```

```
<212> TYPE: PRT
<213> ORGANISM: Influenza Virus

<400> SEQUENCE: 198

Gly Glu Glu Thr Ile Glu Glu Arg Phe
1               5

<210> SEQ ID NO 199
<211> LENGTH: 10
<212> TYPE: PRT
<213> ORGANISM: Influenza Virus

<400> SEQUENCE: 199

Pro Glu Leu Arg Ser Leu Ser Ser Trp Ile
1               5                   10

<210> SEQ ID NO 200
<211> LENGTH: 10
<212> TYPE: PRT
<213> ORGANISM: Influenza Virus

<400> SEQUENCE: 200

Ser Glu Phe Asn Lys Ala Cys Glu Leu Thr
1               5                   10

<210> SEQ ID NO 201
<211> LENGTH: 10
<212> TYPE: PRT
<213> ORGANISM: Influenza Virus

<400> SEQUENCE: 201

Met Glu Phe Ser Leu Thr Asp Pro Arg Leu
1               5                   10

<210> SEQ ID NO 202
<211> LENGTH: 9
<212> TYPE: PRT
<213> ORGANISM: Influenza Virus

<400> SEQUENCE: 202

Trp Glu Lys Tyr Cys Val Leu Glu Ile
1               5

<210> SEQ ID NO 203
<211> LENGTH: 9
<212> TYPE: PRT
<213> ORGANISM: Influenza Virus

<400> SEQUENCE: 203

Ala Glu Ser Arg Lys Leu Leu Leu Ile
1               5

<210> SEQ ID NO 204
<211> LENGTH: 10
<212> TYPE: PRT
<213> ORGANISM: Influenza Virus

<400> SEQUENCE: 204

Ala Glu Ser Arg Lys Leu Leu Leu Ile Val
1               5                   10

<210> SEQ ID NO 205
<211> LENGTH: 9
<212> TYPE: PRT
<213> ORGANISM: Influenza Virus
```

-continued

<400> SEQUENCE: 205

Tyr Glu Ala Ile Glu Glu Cys Leu Ile
1               5

<210> SEQ ID NO 206
<211> LENGTH: 9
<212> TYPE: PRT
<213> ORGANISM: Influenza Virus

<400> SEQUENCE: 206

Tyr Ser His Gly Thr Gly Thr Gly Tyr
1               5

<210> SEQ ID NO 207
<211> LENGTH: 9
<212> TYPE: PRT
<213> ORGANISM: Influenza Virus

<400> SEQUENCE: 207

Gly Met Gln Ile Arg Gly Phe Val Tyr
1               5

<210> SEQ ID NO 208
<211> LENGTH: 9
<212> TYPE: PRT
<213> ORGANISM: Influenza Virus

<400> SEQUENCE: 208

Arg Met Phe Leu Ala Met Ile Thr Tyr
1               5

<210> SEQ ID NO 209
<211> LENGTH: 9
<212> TYPE: PRT
<213> ORGANISM: Influenza Virus

<400> SEQUENCE: 209

Lys Met Ala Arg Leu Gly Lys Gly Tyr
1               5

<210> SEQ ID NO 210
<211> LENGTH: 9
<212> TYPE: PRT
<213> ORGANISM: Influenza Virus

<400> SEQUENCE: 210

Met Leu Ala Asn Ile Asp Leu Lys Tyr
1               5

<210> SEQ ID NO 211
<211> LENGTH: 9
<212> TYPE: PRT
<213> ORGANISM: Influenza Virus

<400> SEQUENCE: 211

Met Leu Ala Ser Ile Asp Leu Lys Tyr
1               5

<210> SEQ ID NO 212
<211> LENGTH: 9
<212> TYPE: PRT
<213> ORGANISM: Influenza Virus

<400> SEQUENCE: 212

Thr Phe Glu Phe Thr Ser Phe Phe Tyr
1               5

<210> SEQ ID NO 213
<211> LENGTH: 10
<212> TYPE: PRT
<213> ORGANISM: Influenza Virus

<400> SEQUENCE: 213

Leu Val Ser Asp Gly Gly Pro Asn Leu Tyr
1               5                   10

<210> SEQ ID NO 214
<211> LENGTH: 9
<212> TYPE: PRT
<213> ORGANISM: Influenza Virus

<400> SEQUENCE: 214

Ala Gln Thr Asp Cys Val Leu Glu Ala
1               5

<210> SEQ ID NO 215
<211> LENGTH: 9
<212> TYPE: PRT
<213> ORGANISM: Influenza Virus

<400> SEQUENCE: 215

Cys Val Leu Glu Ala Met Ala Phe Leu
1               5

<210> SEQ ID NO 216
<211> LENGTH: 9
<212> TYPE: PRT
<213> ORGANISM: Influenza Virus

<400> SEQUENCE: 216

Arg Leu Ile Asp Phe Leu Lys Asp Val
1               5

<210> SEQ ID NO 217
<211> LENGTH: 9
<212> TYPE: PRT
<213> ORGANISM: Influenza Virus

<400> SEQUENCE: 217

Gln Ile Arg Gly Phe Val Tyr Phe Val
1               5

<210> SEQ ID NO 218
<211> LENGTH: 9
<212> TYPE: PRT
<213> ORGANISM: Influenza Virus

<400> SEQUENCE: 218

Phe Val Tyr Phe Val Glu Thr Leu Ala
1               5

<210> SEQ ID NO 219
<211> LENGTH: 10
<212> TYPE: PRT
<213> ORGANISM: Influenza Virus

<400> SEQUENCE: 219

Arg Met Phe Leu Ala Met Ile Thr Tyr Ile

```
1               5               10
```

<210> SEQ ID NO 220
<211> LENGTH: 9
<212> TYPE: PRT
<213> ORGANISM: Influenza Virus

<400> SEQUENCE: 220

```
Leu Leu Ile Asp Gly Thr Ala Ser Leu
1               5
```

<210> SEQ ID NO 221
<211> LENGTH: 9
<212> TYPE: PRT
<213> ORGANISM: Influenza Virus

<400> SEQUENCE: 221

```
Asn Met Leu Ser Thr Val Leu Gly Val
1               5
```

<210> SEQ ID NO 222
<211> LENGTH: 9
<212> TYPE: PRT
<213> ORGANISM: Influenza Virus

<400> SEQUENCE: 222

```
Phe Val Ala Asn Phe Ser Met Glu Leu
1               5
```

<210> SEQ ID NO 223
<211> LENGTH: 9
<212> TYPE: PRT
<213> ORGANISM: Influenza Virus

<400> SEQUENCE: 223

```
Ala Gln Met Ala Leu Gln Leu Phe Ile
1               5
```

<210> SEQ ID NO 224
<211> LENGTH: 10
<212> TYPE: PRT
<213> ORGANISM: Influenza Virus

<400> SEQUENCE: 224

```
Arg Leu Cys Asn Pro Leu Asn Pro Phe Val
1               5                   10
```

<210> SEQ ID NO 225
<211> LENGTH: 9
<212> TYPE: PRT
<213> ORGANISM: Influenza Virus

<400> SEQUENCE: 225

```
Gln Thr Tyr Asp Trp Thr Leu Asn Arg
1               5
```

<210> SEQ ID NO 226
<211> LENGTH: 10
<212> TYPE: PRT
<213> ORGANISM: Influenza Virus

<400> SEQUENCE: 226

```
Ala Leu Ala Asn Thr Ile Glu Val Phe Arg
1               5                   10
```

<210> SEQ ID NO 227
<211> LENGTH: 9
<212> TYPE: PRT
<213> ORGANISM: Influenza Virus

<400> SEQUENCE: 227

Met Val Thr Gln Arg Thr Ile Gly Lys
1               5

<210> SEQ ID NO 228
<211> LENGTH: 10
<212> TYPE: PRT
<213> ORGANISM: Influenza Virus

<400> SEQUENCE: 228

Met Val Thr Gln Arg Thr Ile Gly Lys Lys
1               5                   10

<210> SEQ ID NO 229
<211> LENGTH: 9
<212> TYPE: PRT
<213> ORGANISM: Influenza Virus

<400> SEQUENCE: 229

Ala Leu Thr Leu Asn Thr Met Thr Lys
1               5

<210> SEQ ID NO 230
<211> LENGTH: 9
<212> TYPE: PRT
<213> ORGANISM: Influenza Virus

<400> SEQUENCE: 230

Thr Leu Ala Arg Ser Ile Cys Glu Lys
1               5

<210> SEQ ID NO 231
<211> LENGTH: 10
<212> TYPE: PRT
<213> ORGANISM: Influenza Virus

<400> SEQUENCE: 231

Ser Ile Ala Pro Ile Met Phe Ser Asn Lys
1               5                   10

<210> SEQ ID NO 232
<211> LENGTH: 10
<212> TYPE: PRT
<213> ORGANISM: Influenza Virus

<400> SEQUENCE: 232

Ile Gln Ala Gly Val Asp Arg Phe Tyr Arg
1               5                   10

<210> SEQ ID NO 233
<211> LENGTH: 9
<212> TYPE: PRT
<213> ORGANISM: Influenza Virus

<400> SEQUENCE: 233

Lys Leu Val Gly Ile Asn Met Ser Lys
1               5

<210> SEQ ID NO 234

```
<211> LENGTH: 10
<212> TYPE: PRT
<213> ORGANISM: Influenza Virus

<400> SEQUENCE: 234

Lys Leu Val Gly Ile Asn Met Ser Lys Lys
1               5                   10

<210> SEQ ID NO 235
<211> LENGTH: 10
<212> TYPE: PRT
<213> ORGANISM: Influenza Virus

<400> SEQUENCE: 235

Gly Thr Phe Glu Phe Thr Ser Phe Phe Tyr
1               5                   10

<210> SEQ ID NO 236
<211> LENGTH: 10
<212> TYPE: PRT
<213> ORGANISM: Influenza Virus

<400> SEQUENCE: 236

Thr Phe Glu Phe Thr Ser Phe Phe Tyr Arg
1               5                   10

<210> SEQ ID NO 237
<211> LENGTH: 10
<212> TYPE: PRT
<213> ORGANISM: Influenza Virus

<400> SEQUENCE: 237

Ala Gln Met Ala Leu Gln Leu Phe Ile Lys
1               5                   10

<210> SEQ ID NO 238
<211> LENGTH: 9
<212> TYPE: PRT
<213> ORGANISM: Influenza Virus

<400> SEQUENCE: 238

Leu Gln Leu Phe Ile Lys Asp Tyr Arg
1               5

<210> SEQ ID NO 239
<211> LENGTH: 9
<212> TYPE: PRT
<213> ORGANISM: Influenza Virus

<400> SEQUENCE: 239

Ala Thr Thr His Ser Trp Ile Pro Lys
1               5

<210> SEQ ID NO 240
<211> LENGTH: 10
<212> TYPE: PRT
<213> ORGANISM: Influenza Virus

<400> SEQUENCE: 240

Ala Thr Thr His Ser Trp Ile Pro Lys Arg
1               5                   10

<210> SEQ ID NO 241
<211> LENGTH: 10
<212> TYPE: PRT
```

<213> ORGANISM: Influenza Virus

<400> SEQUENCE: 241

Tyr Gln Lys Cys Cys Thr Leu Phe Glu Lys
1 5 10

<210> SEQ ID NO 242
<211> LENGTH: 10
<212> TYPE: PRT
<213> ORGANISM: Influenza Virus

<400> SEQUENCE: 242

Tyr Gln Lys Cys Cys Asn Leu Phe Glu Lys
1 5 10

<210> SEQ ID NO 243
<211> LENGTH: 9
<212> TYPE: PRT
<213> ORGANISM: Influenza Virus

<400> SEQUENCE: 243

Lys Phe Phe Pro Ser Ser Ser Tyr Arg
1 5

<210> SEQ ID NO 244
<211> LENGTH: 9
<212> TYPE: PRT
<213> ORGANISM: Influenza Virus

<400> SEQUENCE: 244

Ser Tyr Leu Ile Arg Ala Leu Thr Leu
1 5

<210> SEQ ID NO 245
<211> LENGTH: 9
<212> TYPE: PRT
<213> ORGANISM: Influenza Virus

<400> SEQUENCE: 245

Met Phe Leu Ala Met Ile Thr Tyr Ile
1 5

<210> SEQ ID NO 246
<211> LENGTH: 9
<212> TYPE: PRT
<213> ORGANISM: Influenza Virus

<400> SEQUENCE: 246

Arg Tyr Thr Lys Thr Thr Tyr Trp Trp
1 5

<210> SEQ ID NO 247
<211> LENGTH: 9
<212> TYPE: PRT
<213> ORGANISM: Influenza Virus

<400> SEQUENCE: 247

Ser Tyr Ile Asn Arg Thr Gly Thr Phe
1 5

<210> SEQ ID NO 248
<211> LENGTH: 10
<212> TYPE: PRT
<213> ORGANISM: Influenza Virus

```
<400> SEQUENCE: 248

Phe Tyr Arg Tyr Gly Phe Val Ala Asn Phe
1               5                   10

<210> SEQ ID NO 249
<211> LENGTH: 9
<212> TYPE: PRT
<213> ORGANISM: Influenza Virus

<400> SEQUENCE: 249

Leu Tyr Asn Ile Arg Asn Leu His Ile
1               5

<210> SEQ ID NO 250
<211> LENGTH: 9
<212> TYPE: PRT
<213> ORGANISM: Influenza Virus

<400> SEQUENCE: 250

Met Tyr Gln Lys Cys Cys Asn Leu Phe
1               5

<210> SEQ ID NO 251
<211> LENGTH: 9
<212> TYPE: PRT
<213> ORGANISM: Influenza Virus

<400> SEQUENCE: 251

Met Tyr Gln Lys Cys Cys Thr Leu Phe
1               5

<210> SEQ ID NO 252
<211> LENGTH: 9
<212> TYPE: PRT
<213> ORGANISM: Influenza Virus

<400> SEQUENCE: 252

Asn Pro Arg Met Phe Leu Ala Met Ile
1               5

<210> SEQ ID NO 253
<211> LENGTH: 9
<212> TYPE: PRT
<213> ORGANISM: Influenza Virus

<400> SEQUENCE: 253

Gln Pro Glu Trp Phe Arg Asn Val Leu
1               5

<210> SEQ ID NO 254
<211> LENGTH: 9
<212> TYPE: PRT
<213> ORGANISM: Influenza Virus

<400> SEQUENCE: 254

Ala Pro Ile Met Phe Ser Asn Lys Met
1               5

<210> SEQ ID NO 255
<211> LENGTH: 9
<212> TYPE: PRT
<213> ORGANISM: Influenza Virus

<400> SEQUENCE: 255
```

Ile Pro Ala Glu Met Leu Ala Ser Ile
1               5

<210> SEQ ID NO 256
<211> LENGTH: 9
<212> TYPE: PRT
<213> ORGANISM: Influenza Virus

<400> SEQUENCE: 256

Ser Pro Gly Met Met Met Gly Met Phe
1 5

<210> SEQ ID NO 257
<211> LENGTH: 9
<212> TYPE: PRT
<213> ORGANISM: Influenza Virus

<400> SEQUENCE: 257

Gly Pro Ala Thr Ala Gln Met Ala Leu
1 5

<210> SEQ ID NO 258
<211> LENGTH: 10
<212> TYPE: PRT
<213> ORGANISM: Influenza Virus

<400> SEQUENCE: 258

Met Pro Ala His Gly Pro Ala Lys Ser Met
1 5 10

<210> SEQ ID NO 259
<211> LENGTH: 9
<212> TYPE: PRT
<213> ORGANISM: Influenza Virus

<400> SEQUENCE: 259

Ile Pro Lys Arg Asn Arg Ser Ile Leu
1 5

<210> SEQ ID NO 260
<211> LENGTH: 10
<212> TYPE: PRT
<213> ORGANISM: Influenza Virus

<400> SEQUENCE: 260

Phe Pro Ser Ser Ser Tyr Arg Arg Pro Val
1 5 10

<210> SEQ ID NO 261
<211> LENGTH: 9
<212> TYPE: PRT
<213> ORGANISM: Influenza Virus

<400> SEQUENCE: 261

Arg Pro Val Gly Ile Ser Ser Met Val
1 5

<210> SEQ ID NO 262
<211> LENGTH: 9
<212> TYPE: PRT
<213> ORGANISM: Influenza Virus

<400> SEQUENCE: 262

Cys Glu Lys Leu Glu Gln Ser Gly Leu
1 5

<210> SEQ ID NO 263
<211> LENGTH: 9
<212> TYPE: PRT
<213> ORGANISM: Influenza Virus

<400> SEQUENCE: 263

Ile Glu Lys Ile Arg Pro Leu Leu Ile
1               5

<210> SEQ ID NO 264
<211> LENGTH: 9
<212> TYPE: PRT
<213> ORGANISM: Influenza Virus

<400> SEQUENCE: 264

Ile Glu Ser Val Asn Asn Ala Val Val
1               5

<210> SEQ ID NO 265
<211> LENGTH: 9
<212> TYPE: PRT
<213> ORGANISM: Influenza Virus

<400> SEQUENCE: 265

Ser Thr Val His Tyr Pro Lys Val Tyr
1               5

<210> SEQ ID NO 266
<211> LENGTH: 9
<212> TYPE: PRT
<213> ORGANISM: Influenza Virus

<400> SEQUENCE: 266

Lys Ile Ser Pro Leu Met Val Ala Tyr
1               5

<210> SEQ ID NO 267
<211> LENGTH: 10
<212> TYPE: PRT
<213> ORGANISM: Influenza Virus

<400> SEQUENCE: 267

Arg Val Ser Lys Met Gly Val Asp Glu Tyr
1               5                   10

<210> SEQ ID NO 268
<211> LENGTH: 9
<212> TYPE: PRT
<213> ORGANISM: Influenza Virus

<400> SEQUENCE: 268

Gly Thr Glu Lys Leu Thr Ile Thr Tyr
1               5

<210> SEQ ID NO 269
<211> LENGTH: 10
<212> TYPE: PRT
<213> ORGANISM: Influenza Virus

<400> SEQUENCE: 269

Gln Trp Ser Gln Glu Pro Thr Met Leu Tyr
1               5                   10

```
<210> SEQ ID NO 270
<211> LENGTH: 9
<212> TYPE: PRT
<213> ORGANISM: Influenza Virus

<400> SEQUENCE: 270

Trp Ser Gln Asp Pro Thr Met Leu Tyr
1               5

<210> SEQ ID NO 271
<211> LENGTH: 9
<212> TYPE: PRT
<213> ORGANISM: Influenza Virus

<400> SEQUENCE: 271

Leu Gln Asp Cys Lys Ile Ala Pro Leu
1               5

<210> SEQ ID NO 272
<211> LENGTH: 9
<212> TYPE: PRT
<213> ORGANISM: Influenza Virus

<400> SEQUENCE: 272

Phe Gln Asn Trp Gly Ile Glu His Ile
1               5

<210> SEQ ID NO 273
<211> LENGTH: 9
<212> TYPE: PRT
<213> ORGANISM: Influenza Virus

<400> SEQUENCE: 273

Phe Gln Asn Trp Gly Ile Glu Pro Ile
1               5

<210> SEQ ID NO 274
<211> LENGTH: 9
<212> TYPE: PRT
<213> ORGANISM: Influenza Virus

<400> SEQUENCE: 274

Arg Met Gln Phe Ser Ser Leu Thr Val
1               5

<210> SEQ ID NO 275
<211> LENGTH: 10
<212> TYPE: PRT
<213> ORGANISM: Influenza Virus

<400> SEQUENCE: 275

Thr Thr Val Asp His Met Ala Ile Ile Lys
1               5                   10

<210> SEQ ID NO 276
<211> LENGTH: 9
<212> TYPE: PRT
<213> ORGANISM: Influenza Virus

<400> SEQUENCE: 276

Thr Val Asp His Met Ala Ile Ile Lys
1               5

<210> SEQ ID NO 277
<211> LENGTH: 9
```

```
<212> TYPE: PRT
<213> ORGANISM: Influenza Virus

<400> SEQUENCE: 277

Arg Ile Met Glu Met Ile Pro Glu Arg
1               5

<210> SEQ ID NO 278
<211> LENGTH: 9
<212> TYPE: PRT
<213> ORGANISM: Influenza Virus

<400> SEQUENCE: 278

Thr Thr Ser Thr Val His Tyr Pro Lys
1               5

<210> SEQ ID NO 279
<211> LENGTH: 10
<212> TYPE: PRT
<213> ORGANISM: Influenza Virus

<400> SEQUENCE: 279

Ser Thr Val His Tyr Pro Lys Val Tyr Lys
1               5                   10

<210> SEQ ID NO 280
<211> LENGTH: 9
<212> TYPE: PRT
<213> ORGANISM: Influenza Virus

<400> SEQUENCE: 280

Thr Val His Tyr Pro Lys Val Tyr Lys
1               5

<210> SEQ ID NO 281
<211> LENGTH: 9
<212> TYPE: PRT
<213> ORGANISM: Influenza Virus

<400> SEQUENCE: 281

Lys Val Tyr Lys Thr Tyr Phe Glu Lys
1               5

<210> SEQ ID NO 282
<211> LENGTH: 9
<212> TYPE: PRT
<213> ORGANISM: Influenza Virus

<400> SEQUENCE: 282

Gly Thr Phe Gly Pro Val His Phe Arg
1               5

<210> SEQ ID NO 283
<211> LENGTH: 10
<212> TYPE: PRT
<213> ORGANISM: Influenza Virus

<400> SEQUENCE: 283

Ser Phe Ser Phe Gly Gly Phe Thr Phe Lys
1               5                   10

<210> SEQ ID NO 284
<211> LENGTH: 9
<212> TYPE: PRT
<213> ORGANISM: Influenza Virus
```

<400> SEQUENCE: 284

Phe Ser Phe Gly Gly Phe Thr Phe Lys
1               5

<210> SEQ ID NO 285
<211> LENGTH: 10
<212> TYPE: PRT
<213> ORGANISM: Influenza Virus

<400> SEQUENCE: 285

Phe Ser Phe Gly Gly Phe Thr Phe Lys Arg
1               5                   10

<210> SEQ ID NO 286
<211> LENGTH: 9
<212> TYPE: PRT
<213> ORGANISM: Influenza Virus

<400> SEQUENCE: 286

Ser Phe Gly Gly Phe Thr Phe Lys Arg
1               5

<210> SEQ ID NO 287
<211> LENGTH: 10
<212> TYPE: PRT
<213> ORGANISM: Influenza Virus

<400> SEQUENCE: 287

Val Leu Thr Gly Asn Leu Gln Thr Leu Lys
1               5                   10

<210> SEQ ID NO 288
<211> LENGTH: 9
<212> TYPE: PRT
<213> ORGANISM: Influenza Virus

<400> SEQUENCE: 288

His Gln Leu Leu Arg His Phe Gln Lys
1               5

<210> SEQ ID NO 289
<211> LENGTH: 9
<212> TYPE: PRT
<213> ORGANISM: Influenza Virus

<400> SEQUENCE: 289

Val Val Ser Ile Asp Arg Phe Leu Arg
1               5

<210> SEQ ID NO 290
<211> LENGTH: 10
<212> TYPE: PRT
<213> ORGANISM: Influenza Virus

<400> SEQUENCE: 290

Ser Gln Asp Pro Thr Met Leu Tyr Asn Lys
1               5                   10

<210> SEQ ID NO 291
<211> LENGTH: 10
<212> TYPE: PRT
<213> ORGANISM: Influenza Virus

<400> SEQUENCE: 291

```
Gly Thr Phe Asp Thr Val Gln Ile Ile Lys
1               5                   10

<210> SEQ ID NO 292
<211> LENGTH: 10
<212> TYPE: PRT
<213> ORGANISM: Influenza Virus

<400> SEQUENCE: 292

Leu Leu Pro Phe Ala Ala Ala Pro Pro Lys
1               5                   10

<210> SEQ ID NO 293
<211> LENGTH: 10
<212> TYPE: PRT
<213> ORGANISM: Influenza Virus

<400> SEQUENCE: 293

Val Leu Arg Gly Phe Leu Ile Leu Gly Lys
1               5                   10

<210> SEQ ID NO 294
<211> LENGTH: 10
<212> TYPE: PRT
<213> ORGANISM: Influenza Virus

<400> SEQUENCE: 294

Ser Ile Asn Glu Leu Ser Asn Leu Ala Lys
1               5                   10

<210> SEQ ID NO 295
<211> LENGTH: 9
<212> TYPE: PRT
<213> ORGANISM: Influenza Virus

<400> SEQUENCE: 295

Trp Met Met Ala Met Lys Tyr Pro Ile
1               5

<210> SEQ ID NO 296
<211> LENGTH: 10
<212> TYPE: PRT
<213> ORGANISM: Influenza Virus

<400> SEQUENCE: 296

His Tyr Pro Lys Val Tyr Lys Thr Tyr Phe
1               5                   10

<210> SEQ ID NO 297
<211> LENGTH: 10
<212> TYPE: PRT
<213> ORGANISM: Influenza Virus

<400> SEQUENCE: 297

Leu Tyr Asn Lys Met Glu Phe Glu Pro Phe
1               5                   10

<210> SEQ ID NO 298
<211> LENGTH: 10
<212> TYPE: PRT
<213> ORGANISM: Influenza Virus

<400> SEQUENCE: 298

Gln Tyr Ser Gly Phe Val Arg Thr Leu Phe
```

```
<210> SEQ ID NO 299
<211> LENGTH: 9
<212> TYPE: PRT
<213> ORGANISM: Influenza Virus

<400> SEQUENCE: 299

Asn Pro Ala Leu Arg Met Lys Trp Met
1               5

<210> SEQ ID NO 300
<211> LENGTH: 9
<212> TYPE: PRT
<213> ORGANISM: Influenza Virus

<400> SEQUENCE: 300

Tyr Pro Lys Val Tyr Lys Thr Tyr Phe
1               5

<210> SEQ ID NO 301
<211> LENGTH: 9
<212> TYPE: PRT
<213> ORGANISM: Influenza Virus

<400> SEQUENCE: 301

Gly Pro Val His Phe Arg Asn Gln Val
1               5

<210> SEQ ID NO 302
<211> LENGTH: 10
<212> TYPE: PRT
<213> ORGANISM: Influenza Virus

<400> SEQUENCE: 302

Phe Pro Asn Glu Val Gly Ala Arg Ile Leu
1               5                   10

<210> SEQ ID NO 303
<211> LENGTH: 9
<212> TYPE: PRT
<213> ORGANISM: Influenza Virus

<400> SEQUENCE: 303

Ser Pro Leu Met Val Ala Tyr Met Leu
1               5

<210> SEQ ID NO 304
<211> LENGTH: 10
<212> TYPE: PRT
<213> ORGANISM: Influenza Virus

<400> SEQUENCE: 304

Ala Pro Pro Lys Gln Ser Arg Met Gln Phe
1               5                   10

<210> SEQ ID NO 305
<211> LENGTH: 10
<212> TYPE: PRT
<213> ORGANISM: Influenza Virus

<400> SEQUENCE: 305

Ala Pro Pro Glu Gln Ser Arg Met Gln Phe
1               5                   10
```

```
<210> SEQ ID NO 306
<211> LENGTH: 9
<212> TYPE: PRT
<213> ORGANISM: Influenza Virus

<400> SEQUENCE: 306

Gly Pro Ala Leu Ser Ile Asn Glu Leu
1               5

<210> SEQ ID NO 307
<211> LENGTH: 10
<212> TYPE: PRT
<213> ORGANISM: Influenza Virus

<400> SEQUENCE: 307

Arg Glu Leu Val Arg Lys Thr Arg Phe Leu
1               5                   10

<210> SEQ ID NO 308
<211> LENGTH: 9
<212> TYPE: PRT
<213> ORGANISM: Influenza Virus

<400> SEQUENCE: 308

Met Glu Phe Glu Pro Phe Gln Ser Leu
1               5

<210> SEQ ID NO 309
<211> LENGTH: 10
<212> TYPE: PRT
<213> ORGANISM: Influenza Virus

<400> SEQUENCE: 309

Lys Glu Asp Lys Arg Tyr Gly Pro Ala Leu
1               5                   10

<210> SEQ ID NO 310
<211> LENGTH: 9
<212> TYPE: PRT
<213> ORGANISM: Influenza Virus

<400> SEQUENCE: 310

Cys Glu Leu Thr Asp Ser Ser Trp Ile
1               5

<210> SEQ ID NO 311
<211> LENGTH: 10
<212> TYPE: PRT
<213> ORGANISM: Influenza Virus

<400> SEQUENCE: 311

Tyr Glu Arg Met Cys Asn Ile Leu Lys Gly
1               5                   10

<210> SEQ ID NO 312
<211> LENGTH: 23
<212> TYPE: PRT
<213> ORGANISM: Influenza Virus

<400> SEQUENCE: 312

Ser Leu Leu Thr Glu Val Glu Thr Pro Ile Arg Asn Glu Trp Gly Cys
1               5                   10                  15

Arg Cys Asn Asp Ser Ser Asp
            20
```

<210> SEQ ID NO 313
<211> LENGTH: 23
<212> TYPE: PRT
<213> ORGANISM: Influenza Virus

<400> SEQUENCE: 313

Ser Leu Leu Thr Glu Val Glu Thr Pro Thr Arg Asn Glu Trp Gly Cys
1               5                   10                  15

Arg Cys Asn Asp Ser Ser Asp
            20

<210> SEQ ID NO 314
<211> LENGTH: 23
<212> TYPE: PRT
<213> ORGANISM: Influenza Virus

<400> SEQUENCE: 314

Ser Leu Leu Thr Glu Val Glu Thr Pro Ile Arg Asn Glu Trp Gly Cys
1               5                   10                  15

Arg Cys Asn Gly Ser Ser Asp
            20

<210> SEQ ID NO 315
<211> LENGTH: 23
<212> TYPE: PRT
<213> ORGANISM: Influenza Virus

<400> SEQUENCE: 315

Ser Leu Leu Thr Glu Val Glu Thr Pro Thr Lys Asn Glu Trp Glu Cys
1               5                   10                  15

Arg Cys Asn Asp Ser Ser Asp
            20

<210> SEQ ID NO 316
<211> LENGTH: 23
<212> TYPE: PRT
<213> ORGANISM: Influenza Virus

<400> SEQUENCE: 316

Ser Leu Leu Thr Glu Val Glu Thr Pro Ile Arg Ser Glu Trp Gly Cys
1               5                   10                  15

Arg Cys Asn Asp Ser Ser Asp
            20

<210> SEQ ID NO 317
<211> LENGTH: 23
<212> TYPE: PRT
<213> ORGANISM: Influenza Virus

<400> SEQUENCE: 317

Ser Leu Leu Thr Glu Val Glu Thr Pro Thr Arg Asn Gly Trp Glu Cys
1               5                   10                  15

Arg Cys Ser Gly Ser Ser Asp
            20

<210> SEQ ID NO 318
<211> LENGTH: 23
<212> TYPE: PRT
<213> ORGANISM: Influenza Virus

<400> SEQUENCE: 318

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 319
<211> LENGTH: 23
<212> TYPE: PRT
<213> ORGANISM: Influenza Virus

<400> SEQUENCE: 319

Ser Leu Leu Thr Glu Val Glu Thr Pro Thr Lys Asn Glu Trp Glu Cys
1               5                   10                  15

Lys Cys Ser Asp Ser Ser Asp
            20

<210> SEQ ID NO 320
<211> LENGTH: 23
<212> TYPE: PRT
<213> ORGANISM: Influenza Virus

<400> SEQUENCE: 320

Ser Leu Leu Thr Glu Val Glu Thr Leu Thr Arg Asn Gly Trp Gly Cys
1               5                   10                  15

Arg Cys Ser Asp Ser Ser Asp
            20

<210> SEQ ID NO 321
<211> LENGTH: 23
<212> TYPE: PRT
<213> ORGANISM: Influenza Virus

<400> SEQUENCE: 321

Ser Leu Leu Thr Glu Val Glu Thr Pro Thr Arg Asn Gly Trp Glu Cys
1               5                   10                  15

Lys Cys Ser Asp Ser Ser Asp
            20

<210> SEQ ID NO 322
<211> LENGTH: 23
<212> TYPE: PRT
<213> ORGANISM: Influenza Virus

<400> SEQUENCE: 322

Ser Leu Leu Thr Glu Val Glu Thr Pro Thr Arg Asn Gly Trp Val Cys
1               5                   10                  15

Lys Cys Ser Asp Ser Ser Asp
            20

<210> SEQ ID NO 323
<211> LENGTH: 23
<212> TYPE: PRT
<213> ORGANISM: Influenza Virus

<400> SEQUENCE: 323

Ser Leu Leu Thr Glu Val Glu Thr Pro Ile Arg Lys Gly Trp Glu Cys
1               5                   10                  15

Asn Cys Ser Asp Ser Ser Asp
            20

<210> SEQ ID NO 324
<211> LENGTH: 23

```
<212> TYPE: PRT
<213> ORGANISM: Influenza Virus

<400> SEQUENCE: 324

Ser Leu Leu Thr Glu Val Glu Thr Pro Thr Lys Ser Glu Trp Glu Cys
1               5                   10                  15

Arg Cys Asn Asp Ser Ser Asp
            20

<210> SEQ ID NO 325
<211> LENGTH: 23
<212> TYPE: PRT
<213> ORGANISM: Influenza Virus

<400> SEQUENCE: 325

Ser Leu Leu Thr Glu Val Glu Thr Pro Ile Arg Asn Gly Trp Glu Cys
1               5                   10                  15

Lys Cys Ser Asp Ser Ser Asp
            20

<210> SEQ ID NO 326
<211> LENGTH: 23
<212> TYPE: PRT
<213> ORGANISM: Influenza Virus

<400> SEQUENCE: 326

Ser Leu Leu Thr Glu Val Glu Thr Pro Thr Arg Asn Gly Trp Glu Cys
1               5                   10                  15

Lys Cys Asn Asp Ser Ser Asp
            20

<210> SEQ ID NO 327
<211> LENGTH: 23
<212> TYPE: PRT
<213> ORGANISM: Influenza Virus

<400> SEQUENCE: 327

Ser Leu Leu Thr Glu Val Glu Thr Leu Thr Arg Asn Gly Trp Glu Cys
1               5                   10                  15

Arg Cys Ser Gly Ser Ser Asp
            20

<210> SEQ ID NO 328
<211> LENGTH: 23
<212> TYPE: PRT
<213> ORGANISM: Influenza Virus

<400> SEQUENCE: 328

Ser Leu Leu Thr Glu Val Glu Thr Pro Thr Arg Asn Gly Trp Gly Cys
1               5                   10                  15

Arg Cys Ser Asp Ser Ser Asp
            20

<210> SEQ ID NO 329
<211> LENGTH: 23
<212> TYPE: PRT
<213> ORGANISM: Influenza Virus

<400> SEQUENCE: 329

Ser Leu Leu Thr Glu Val Glu Thr Leu Thr Arg Asn Gly Trp Gly Cys
1               5                   10                  15

Arg Cys Ser Asp Ser Ser Asp
```

```
<210> SEQ ID NO 330
<211> LENGTH: 23
<212> TYPE: PRT
<213> ORGANISM: Influenza Virus

<400> SEQUENCE: 330

Ser Leu Le

Ser Leu Leu Thr Glu Val Glu Thr Leu Thr Arg Asn Gly Trp Glu Cys
1               5                   10                  15

Asn Cys Ser Asp Ser Ser Asp
            20

<210> SEQ ID NO 336
<211> LENGTH: 16
<212> TYPE: PRT
<213> ORGANISM: Influenza Virus

<400> SEQUENCE: 336

Gly Ala Ala Ala Gly Ile Leu Gly Phe Val Phe Thr Leu Asn Ala Ala
1               5                   10                  15

<210> SEQ ID NO 337
<211> LENGTH: 24
<212> TYPE: PRT
<213> ORGANISM: Influenza Virus

<400> SEQUENCE: 337

Leu Glu Leu Arg Ser Arg Tyr Trp Ala Ile Arg Thr Arg Ser Gly Gly
1               5                   10                  15

Asn Thr Asn Gln Gln Arg Ala Ser
            20

<210> SEQ ID NO 338
<211> LENGTH: 19
<212> TYPE: PRT
<213> ORGANISM: Influenza Virus

<400> SEQUENCE: 338

Ile Tyr Gln Ile Leu Ser Ile Tyr Ser Thr Val Ala Ser Ser Leu Ala
1               5                   10                  15

Leu Ala Ile

<210> SEQ ID NO 339
<211> LENGTH: 29
<212> TYPE: PRT
<213> ORGANISM: Influenza Virus

<400> SEQUENCE: 339

Leu Gly Ser Ser Leu Leu Thr Glu Val Glu Thr Pro Thr Arg Asn Glu
1               5                   10                  15

Trp Glu Cys Arg Cys Ser Asp Ser Ser Asp Leu Gly Ser
            20                  25

<210> SEQ ID NO 340
<211> LENGTH: 87
<212> TYPE: DNA
<213> ORGANISM: Influenza Virus

<400> SEQUENCE: 340
ctgggcagca gcctgctgac cgaggtggag accccacccc gcaacgagtg ggagtgccgc    60
tgcagcgaca gcagcgacct gggcagc                                       87

<210> SEQ ID NO 341
<211> LENGTH: 87
<212> TYPE: DNA
<213> ORGANISM: Influenza Virus

<400> SEQUENCE: 341
ctgggcagca gtcttctaac cgaggtcgaa acgcctacca gaaacgaatg ggagtgcaga    60
tgcagcgatt caagtgatct gggcagc    87

<210> SEQ ID NO 342
<211> LENGTH: 29
<212> TYPE: PRT
<213> ORGANISM: Influenza Virus

<400> SEQUENCE: 342

Leu Gly Ser Ser Leu Leu Thr Glu Val Glu Thr Pro Thr Arg Asn Gly
1               5                   10                  15

Trp Glu Cys Lys Cys Ser Asp Ser Ser Asp Leu Gly Ser
            20                  25

<210> SEQ ID NO 343
<211> LENGTH: 87
<212> TYPE: DNA
<213> ORGANISM: Influenza Virus

<400> SEQUENCE: 343
ctgggcagca gcctgctgac cgaggtggag accccaccc gcaacggctg ggagtgcaag    60
tgcagcgaca gcagcgacct gggcagc    87

<210> SEQ ID NO 344
<211> LENGTH: 29
<212> TYPE: PRT
<213> ORGANISM: Influenza Virus

<400> SEQUENCE: 344

Leu Gly Ser Ser Leu Leu Thr Glu Val Glu Thr Leu Thr Arg Asn Gly
1               5                   10                  15

Trp Glu Cys Arg Cys Ser Gly Ser Ser Asp Leu Gly Ser
            20                  25

<210> SEQ ID NO 345
<211> LENGTH: 87
<212> TYPE: DNA
<213> ORGANISM: Influenza Virus

<400> SEQUENCE: 345
ctgggcagca gcctgctgac cgaggtggag accctgaccc gcaacggctg ggagtgccgc    60
tgcagcggca gcagcgacct gggcagc    87

<210> SEQ ID NO 346
<211> LENGTH: 29
<212> TYPE: PRT
<213> ORGANISM: Homo sapiens

<400> SEQUENCE: 346

Leu Gly Ser Ser Leu Leu Thr Glu Val Glu Thr Pro Ile Arg Asn Glu
1               5                   10                  15

Trp Gly Cys Arg Cys Asn Asp Ser Ser Asp Leu Gly Ser
            20                  25

<210> SEQ ID NO 347
<211> LENGTH: 87
<212> TYPE: DNA
<213> ORGANISM: Homo sapiens

<400> SEQUENCE: 347
ctgggcagca gcctgctgac cgaggtggag accccatcc gcaacgagtg gggctgccgc    60
tgcaacgaca gcagcgacct gggcagc    87

<210> SEQ ID NO 348
<211> LENGTH: 30
<212> TYPE: PRT
<213> ORGANISM: Influenza Virus

<400> SEQUENCE: 348

Leu Gly Ser Leu Glu Leu Arg Ser Arg Tyr Trp Ala Ile Arg Thr Arg
1               5                   10                  15

Ser Gly Gly Asn Thr Asn Gln Gln Arg Ala Ser Leu Gly Ser
            20                  25                  30

<210> SEQ ID NO 349
<211> LENGTH: 90
<212> TYPE: DNA
<213> ORGANISM: Influenza Virus

<400> SEQUENCE: 349
ctgggcagcc ttgaactgag aagcagatat tgggctataa gaaccagaag cggaggaaac      60
accaaccagc agagggcatc tctgggcagc                                      90

<210> SEQ ID NO 350
<211> LENGTH: 22
<212> TYPE: PRT
<213> ORGANISM: Influenza Virus

<400> SEQUENCE: 350

Leu Gly Ser Gly Ala Ala Ala Gly Ile Leu Gly Phe Val Phe Thr Leu
1               5                   10                  15

Asn Ala Ala Leu Gly Ser
            20

<210> SEQ ID NO 351
<211> LENGTH: 66
<212> TYPE: DNA
<213> ORGANISM: Influenza Virus

<400> SEQUENCE: 351
ctgggcagcg gcgccgccgc cgggattttg ggatttgtat tcacgctcaa cgccgccctg      60
ggcagc                                                                66

<210> SEQ ID NO 352
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 352

Gly Ala Ala Ala
1

<210> SEQ ID NO 353
<211> LENGTH: 5
<212> TYPE: PRT
<213> ORGANISM: Artificial Sequence
<220> FEATURE:
<223> OTHER INFORMATION: Peptide spacer sequence

<400> SEQUENCE: 353

Gly Pro Gly Pro Gly
1               5

What is claimed:

1. A vaccine comprising an adenoviral vector comprising a first heterologous sequence, wherein said adenoviral vector is replication competent and has a partial E3 deletion, and wherein the first heterologous sequence is integrated into a location containing the partial E3 deletion and is operably linked to a native adenovirus splice acceptor site and is under the control of the endogenous Major Late Promoter.

2. The vaccine of claim 1, wherein the adenoviral vector is derived from Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, or Ad50.

3. The vaccine of claim 1, wherein the partial E3 deletion comprises deletion of at least 1, 2 or 3 open reading frames within the E3 region.

4. The vaccine of claim 1, wherein the partial E3 deletion does not alter the function of the E3 region.

5. The vaccine of claim 1, wherein the partial E3 deletion comprises deletion of a region corresponding to ADP region of Ad5.

6. The vaccine of claim 1, wherein the adenoviral vector is derived from Ad4 and the partial E3 deletion comprises a deletion of E3 24.8 k, E3 6.3 k, and E3 29.7 k.

7. The vaccine of claim 1, wherein the adenoviral vector is derived from Ad7 and the partial E3 deletion comprises a deletion of E3 20.1 k, E3 20.6 k, and E3 7.7 k.

8. The vaccine of claim 1, wherein the expression of the first heterologous sequence is under the control of the endogenous Major Late Promoter and tripartite leader sequence.

9. The vaccine of claim 1, wherein the first heterologous sequence is operably linked to a native E3 24.8 k splice acceptor.

10. The vaccine of claim 1, wherein the first heterologous sequence is operably linked to an adenoviral polyA signal sequence.

11. The vaccine of claim 10, wherein the first heterologous sequence is operably linked to an Ad5 E3 polyA signal sequence.

12. The vaccine of claim 1, wherein the first heterologous sequence encodes an immunogenic protein of an infectious pathogen.

13. The vaccine of claim 12, wherein the infectious pathogen is selected from the group consisting of a virus, a bacterium, a protist, and a fungus.

14. The vaccine of claim 13, wherein the infectious pathogen is influenza, human immunodeficiency virus, or human papilloma virus.

15. The vaccine of claim 13, wherein the infectious pathogen is Bacillus, Shigella, Mycobacterium, or Plasmodium.

16. The vaccine of claim 1, wherein the first heterologous sequence encodes influenza hemaglutinin, influenza neuraminidase, influenza M2, a multimer of M2e, a multimer of HTL epitopes, or a multimer of CTL epitopes.

17. The vaccine of claim 1, wherein the first heterologous sequence comprises a first ORF encoding an immunogenic protein of an infectious pathogen and a second ORF encoding a multimer of epitopes from said infectious pathogen.

18. A vaccine comprising an adenoviral vector comprising a first heterologous sequence, wherein said adenoviral vector is derived from Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, Ad50, Ad C1, Ad C3, Ad C6, Ad C7, or Ad68, is replication competent, and has a full E3 deletion, and wherein the first heterologous sequence is operably linked to a native adenovirus splice acceptor site under the control of the endogenous Major Late Promoter.

19. A vaccine comprising an adenoviral vector comprising a first heterologous sequence and a second heterologous sequence, wherein the second heterologous sequence is integrated into an adenoviral hexon region, wherein the first heterologous sequence is integrated into an adenoviral non-hexon region, and wherein the adenoviral vector is replication competent, and wherein the first heterologous sequence is operably linked to a native adenovirus splice acceptor site under the control of the endogenous Major Late Promoter.

20. The vaccine of claim 19, wherein the adenoviral vector is derived from Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, or Ad50.

21. The vaccine of claim 19, wherein the adenoviral vector comprises a partial E3 deletion and wherein the first heterologous sequence is integrated into a location containing the partial E3 deletion.

22. The vaccine of claim 19, wherein the second heterologous sequence is integrated into HVR1, HVR2, HVR4, or HVR5.

23. The vaccine of claim 19, wherein the second heterologous sequence encodes a region of a membrane protein of a virus.

24. The vaccine of claim 19, wherein the second heterologous sequence encodes an extracellular part of a conserved virus membrane protein.

25. The vaccine of claim 19, wherein the second heterologous sequence encodes a region of an influenza M2 protein, an influenza Matrix CTL, an influenza NP epitope, one or more HVRs from an adenovirus of another serotype, or a combination thereof.

26. The vaccine of claim 19, wherein the second heterologous sequence encodes one or more copies of M2e of influenza M2.

27. The vaccine of claim 19, wherein the second heterologous sequence encodes one or more copies of M2e of influenza M2, wherein each M2 copy is integrated into a different HVR, and wherein the one or more copies of M2e are integrated into HVR1, HVR2, HVR4, HVR5 or a combination thereof.

28. The vaccine of claim 19, wherein the second heterologous sequence comprises the sequence of SEQ ID NO. 318 (H5 M2e), SEQ ID NO. 321 (H7 M2e), SEQ ID NO. 327 (H9 M2e), SEQ ID NO. 312 (Human M2e), SEQ ID NO. 337 (NP), or SEQ ID NO. 336 (Matrix CTL).

29. The vaccine of claim 1, 18, or 19, which is formulated for oral, intranasal, sublingual, intravesical, rectal, or intravaginal administration.

30. A vaccine of claim 1, 18, or 19, further comprising an acceptable carrier.

31. A dosage unit of the vaccine of claim 1, 18, or 19, wherein a single dose comprises about $10^3$ to about $10^{13}$ adenoviral particles.

32. A method of inducing an immune response to an infectious pathogen in a subject comprising administering to the subject the vaccine of claim 1, 18, or 19.

33. The method of claim 32, wherein one or more doses of the vaccine is administered to the subject.

34. The method of claim 32, wherein the infectious pathogen is influenza, HIV, HPV, Bacillus, Plasmodium, Mycobacteria, or Shigella.

35. The method of claim 32, wherein the subject has an infection induced by said infectious pathogen.

* * * * *